United States Patent
Biannic et al.

(10) Patent No.: US 11,084,829 B2
(45) Date of Patent: Aug. 10, 2021

(54) UBIQUITIN-SPECIFIC-PROCESSING PROTEASE 7 (USP7) MODULATORS AND USES THEREOF

(71) Applicant: RAPT THERAPEUTICS, INC., South San Francisco, CA (US)

(72) Inventors: Berenger Biannic, San Mateo, CA (US); Xinping Han, Daly City, CA (US); Dennis X. Hu, San Mateo, CA (US); Paul Robert Leger, Oakland, CA (US); Jack Maung, Daly City, CA (US); Akinori Okano, San Mateo, CA (US); Jacob Bradley Schwarz, South San Francisco, CA (US); David Juergen Wustrow, Los Gatos, CA (US); Kyle Young, San Mateo, CA (US); Gene Cutler, San Francisco, CA (US); Yamini Ohol-Gupta, Belmont, CA (US)

(73) Assignee: RAPT THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 16/578,276

(22) Filed: Sep. 20, 2019

(65) Prior Publication Data
US 2020/0095260 A1  Mar. 26, 2020

Related U.S. Application Data

(60) Provisional application No. 62/735,749, filed on Sep. 24, 2018, provisional application No. 62/847,490, filed on May 14, 2019.

(51) Int. Cl.
C07D 495/04 (2006.01)
A61K 31/519 (2006.01)
A61P 35/02 (2006.01)

(52) U.S. Cl.
CPC ............ *C07D 495/04* (2013.01); *A61P 35/02* (2018.01)

(58) Field of Classification Search
CPC ........................... A61K 31/519; C07D 495/04
See application file for complete search history.

(56) References Cited

FOREIGN PATENT DOCUMENTS

| WO | WO-2008/144223 A2 | 11/2008 |
|---|---|---|
| WO | WO-2008/144223 A3 | 11/2008 |
| WO | WO-2013/117285 A1 | 8/2013 |
| WO | WO2014183850 * | 11/2014 |
| WO | WO-2016/126929 A1 | 8/2016 |
| WO | WO-2020/068600 A1 | 4/2020 |

OTHER PUBLICATIONS

International Search Report dated Dec. 12, 2019, for PCT Application No. PCT/US2019/052302, filed Sep. 20, 2019, 4 pages.
Written Opinion dated Dec. 12, 2019, for PCT Application No. PCT/US2019/052302, filed Sep. 20, 2019, 5 pages.

* cited by examiner

*Primary Examiner* — Karen Cheng
(74) *Attorney, Agent, or Firm* — Mintz, Levin, Cohn, Ferris, Glovsky and Popeo, P.C.

(57) ABSTRACT

Disclosed herein, inter alia, compounds and methods of use thereof for the modulation of USP7 activity.

55 Claims, 1 Drawing Sheet

UBIQUITIN-SPECIFIC-PROCESSING PROTEASE 7 (USP7) MODULATORS AND USES THEREOF

CROSS-REFERENCES TO RELATED APPLICATIONS

This application claims the benefit of U.S. Provisional Patent Application No. 62/735,749 filed Sep. 24, 2018 and U.S. Provisional Patent Application No. 62/847,490 filed May 14, 2019, which are incorporated herein by reference in their entireties.

BACKGROUND

Ubiquitination is an important form of post-translational modification that can determine a protein's fate. While ubiquitin itself is a small and conserved protein, its covalent conjugation to protein substrates and to other ubiquitin molecules is a tightly controlled process involving complex cellular machinery. Perhaps the most prominent and well-known function of ubiquitin is to target a protein for degradation by the 26S proteasome. This is done via isopeptide bond formation between the carboxy-terminal Gly on the ubiquitin and ε-amino group of lysine side chains of the protein substrate.

The ubiquitin-substrate system is further diversified via the process of polyubiquitination, during which a ubiquitin molecule's C-terminal Gly is conjugated with one of the seven Lys residues on another ubiquitin (Lys6, Lys11, Lys27, Lys29, Lys33, Lys48, or Lys63) or with the N-terminus to form linear chains. While Lys48-linked and Lys11-linked polyubiquitination has been shown mostly to target protein substrates for 26S-mediated degradation, other functions of ubiquitination continue to unfold. For example, Lys63-polyubiquitination is involved in DNA repair and endocytosis, while both Lys63-linked and linear polyubiquitination has been demonstrated to regulate immunity via NF-κB activation. Accordingly, the biological complexity of ubiquitination is complex and suggests that enzymes involved in this process must have remarkable specificity to correctly carry out their unique functions. E1, E2, and E3 are enzymes that together facilitate the multistep process of ubiquitin-substrate conjugation, and deubiquitinat-ing enzymes (deubiquitinases or DUBs) carry out the reverse steps of breaking the isopeptide bond.

There are approximately 100 DUBs known in the human genome, any of which could be playing a key role in the ubiquitin-proteasome system as well as other biological processes. The main functions for which DUBs are responsible include: (a) liberation of ubiquitin from protein substrates (e.g., to remove degradation signal), (b) editing of polyubiquitin signal on protein substrates to change the fate of the protein, (c) disassembling polyubiquitin chains to free up ubiquitin monomers, (d) cleaving ubiquitin precursors or adducts to regenerate active ubiquitin.

The DUBs are subdivided into five families: ubiquitin C-terminal hydrolases (UCHs), ubiquitin-specific proteases (USPs), ovarian tumor proteases (OTUs), Josephins and JAB1/MPN/MOV34 metalloenzymes (JAMM/MPN+). The first four families (UCH, USP, OTU, and Josephin) are cysteine proteases, while JAMM/MPN+ are zinc metalloproteases. Among these, UCHs and USPs are the best characterized, and USPs represent more than half of the known human DUBs. The reaction mechanism of the cysteine protease DUB families is the same as that of the cysteine protease superfamily. Each enzyme active site requires the interplay between three conserved residues forming the catalytic triad: a cysteine, a histidine, and an aspartic acid. The initial attack creates a negatively charged transition state stabilized by the oxy-anion hole. The intermediate is a thiohemiacetal stabilized through interactions with the active site residues as an incoming water molecule liberates the lysine side chain from the conjugated ubiquitin or substrate. A nucleophilic attack of the water creates another negatively charged transition state, which rearranges to free up the carboxylate terminus of the N-terminal ubiquitin and restores the enzyme to its apo form.

Recently, increased biological understanding has led to numerous DUBs being implicated in various diseases spanning oncology, neurodegeneration, hematology, and infectious diseases. Most recently, Bingol et al. carried out elegant experiments in vitro and in vivo to illustrate the role of USP30 as an antagonist of Parkin-mediated mitophagy, suggesting the inhibition of USP30 as a potential therapy for Parkinson's disease (PD). The search for DUB antagonists is thus actively carried out by academic and pharmaceutical companies alike. This is illustrated through chemically diverse small molecules that have been reported to inhibit one or more of the UCH and USP family members.

Indeed, the covalent attachment of ubiquitin to proteins is an important step in the degradation of proteins via the 26S proteasome. See e.g., Metzger M B et. al. [J Cell Sci. 2012; 125:531-7] Deubiquitinating enzymes (DUBs), also known as deubiquitinating peptidases, deubiquitinating isopeptidases, deubiquitinases, ubiquitin proteases, ubiquitin hydrolases, ubiquitin isopeptidases, are a large group of proteases that cleave ubiquitin from proteins and other molecules. [Nijman S M, et al. Cell. 2005; 123:773-86] DUBs can prevent the degradation of proteins by cleaving the peptide or isopeptide bond between ubiquitin and its substrate protein. In humans there are nearly 100 DUB genes, which can be classified into two main classes: cysteine proteases and metalloproteases. The cysteine proteases comprise ubiquitin-specific proteases (USPs), ubiquitin C-terminal hydrolases (UCHs), Machado-Josephin domain proteases (MJDs) and ovarian tumour proteases (OTU). The metalloprotease group contains only the Jab1/Mov34/Mpr1 Pad1 N-terminal+(MPN+) (JAMM) domain proteases.

Ubiquitin-specific-processing protease 7 (USP7), also known as ubiquitin carboxyl-terminal hydrolase 7 or herpesvirus-associated ubiquitin-specific protease (HAUSP), is an enzyme that in humans is encoded by the USP7 gene. USP7 or HAUSP is a DUB enzyme that cleaves ubiquitin from its substrates. Since ubiquitylation (polyubiquitination) is most commonly associated with the stability and degradation of cellular proteins, USP7 activity generally stabilizes its substrate proteins. Shi D et. al. Cancer Biology and Therapy 2010 10:8 737-747.

USP7 is most popularly known as a direct antagonist of Mdm2, the E3 ubiquitin ligase for the tumor suppressor protein, p53. Normally, p53 levels are kept low in part due to Mdm2-mediated ubiquitylation and degradation of p53. In response to oncogenic insults, USP7 can deubiquitinate p53 and protect p53 from Mdm2-mediated degradation, indicating that it may possess a tumor suppressor function for the immediate stabilization of p53 in response to stress.

In addition, USP7 also plays a key role in the immunoregulatory transcription factor protein FOXP3. By de-ubiquitylating and preserving FOXP3, USP7 increases T regulatory cell (Treg) mediated suppression of tumor-infiltrating T effector cells, the latter being associated with improved clinical outcome for many solid tumors. Thus, USP7 functions to limit immune cell-mediated antitumor defenses. The observation that the accumulation of FOXP3+ Treg cells at the tumor or in draining lymph nodes signals poor prognosis further highlights the significance of this recently described second oncogenic mechanism of USP7. Thus, inhibitors of USP7 can exert in vivo antitumor activity by: 1) directly inhibiting tumor cell proliferation via Hdm2 and other targets; and 2) suppressing T regulatory cells via FOXP3, thereby facilitating the antitumor function of T effector cells.

Another important role of USP7 function involves the oncogenic stabilization of p53. Oncogenes such as Myc and E1A are thought to activate p53 through a p19 alternative reading frame (p19ARF, also called ARF)-dependent pathway, although some evidence suggests ARF is not essential in this process. A possibility is that USP7 provides an alternative pathway for safeguarding the cell against oncogenic insults.

USP7 can deubiquitinate histone H2B and this activity is associated with gene silencing in Drosophila. USP7 associates with a metabolic enzyme, GMP synthetase (GMPS) and this association stimulates USP7 deubiquitinase activity towards H2B. The USP7-GMPS complex is recruited to the polycomb (Pc) region in Drosophila and contributes to epigenetic silencing of homeotic genes.

USP7 was originally identified as a protein associated with the ICP0 protein of herpes simplex virus (HSV), hence the alternate name Herpesvirus Associated USP (HAUSP). ICP0 is an E3-ubiquitin ligase that is involved in ubiquitination and subsequent degradation of itself and certain cellular proteins. USP7 has been shown to regulate the auto-ubiquitination and degradation of ICP0.

More recently, an interaction between USP7 and the EBNA1 protein of Epstein-Barr virus (EBV) (another herpes virus) was also discovered. This interaction is particularly interesting given the oncogenic potential (potential to cause cancer) of EBV, which is associated with several human cancers. EBNA1 can compete with p53 for binding USP7. Stabilization by USP7 is important for the tumor suppressor function of p53. In cells, EBNA1 can sequester USP7 from p53 and thus attenuate stabilization of p53, rendering the cells predisposed to turning cancerous. Compromising the function of p53 by sequestering USP7 is one way EBNA1 can contribute to the oncogenic potential of EBV. Additionally, human USP7 was also shown to form a complex with GMPS and this complex is recruited to EBV genome sequences. USP7 was shown to be important for histone H2B deubiquitination in human cells and for deubiquitination of histone H2B incorporated in the EBV genome. Thus, USP7 may also be important for regulation of viral gene expression. The fact that viral proteins have evolved so as to target USP7, underscores the significance of USP7 in tumor suppression and other cellular processes.

BRIEF SUMMARY

Disclosed herein are compounds that modulate USP7 function and methods of using the same.

In an aspect, provided is a compound of structural formula (I) or pharmaceutically acceptable salt thereof:

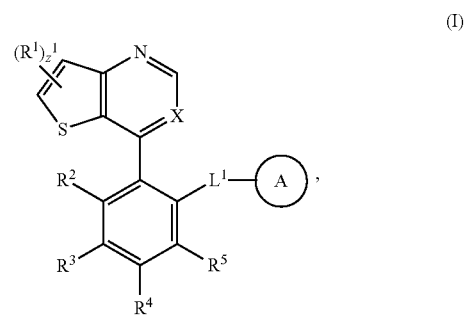

(I)

wherein: $z^1$ is 0 to 2; X is N or CH; $L^1$ is an substituted or unsubstituted alkylene, or a bond; Ring A is substituted or unsubstituted cycloalkyl, substituted or unsubstituted heterocycloalkyl, substituted or unsubstituted aryl, or substituted or unsubstituted heteroaryl; $R^1$ is independently halogen, $-CF_3$, $-CCl_3$, $-CBr_3$, $-Cl_3$, $-CHF_2$, $-CHCl_2$, $-CHBr_2$, $-CHI_2$, $-CH_2F$, $-CH_2Cl$, $-CH_2Br$, $-CH_2I$, $-CN$, $-N_3$, $-S(O)_{n1}R^{1A}$, $-S(O)_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCH_2R^{1A}$, $-OCF_3$, $-OCCl_3$, $-OCBr_3$, $-OCl_3$, $-OCHF_2$, $-OCHCl_2$, $-OCHBr_2$, $-OCHI_2$, $-OCH_2F$, $-OCH_2Cl$, $-OCH_2Br$, $-OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein if $z^1$ is 2, then the two $R^1$ substituents optionally join together to form a substituted or unsubstituted cycloalkyl, substituted or unsubstituted heterocycloalkyl, substituted or unsubstituted aryl, or substituted or unsubstituted heteroaryl;

$R^2$ is hydrogen, halogen, $-CF_3$, $-CCl_3$, $-CBr_3$, $-Cl_3$, $-CHF_2$, $-CHCl_2$, $-CHBr_2$, $-CHI_2$, $-CH_2F$, $-CH_2Cl$, $-CH_2Br$, $-CH_2I$, $-CN$, $-N_3$, $-S(O)_{n2}R^{2A}$, $-S(O)_{v2}NR^{2B}R^{2C}$, $-NHNR^{2B}R^{2C}$, $-ONR^{2B}R^{2C}$, $-NHC(O)NHNR^{2B}R^{2C}$, $-NHC(O)NR^{2B}R^{2C}$, $-N(O)_{m2}$, $-NR^{2B}R^{2C}$, $-C(O)R^{2D}$, $-C(O)OR^{2D}$, $-C(O)NR^{2B}R^{2C}$, $-OR^{2A}$, $-NR^{2B}SO_2R^{2A}$, $-NR^2BC(O)R^{2D}$, $-NR^2BC(O)OR^{2D}$, $-NR^{2B}OR^{2D}$, $-OCH_2R^{2A}$, $-OCF_3$, $-OCCl_3$, $-OCBr_3$, $-OCl_3$, $-OCHF_2$, $-OCHCl_2$, $-OCHBr_2$, $-OCHI_2$, $-OCH_2F$, $-OCH_2Cl$, $-OCH_2Br$, $-OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, $-CF_3$, $-CCl_3$, $-CBr_3$, $-Cl_3$, $-CHF_2$, $-CHCl_2$, $-CHBr_2$, $-CHI_2$, $-CH_2F$, $-CH_2Cl$, $-CH_2Br$, $-CH_2I$, $-CN$, $-N_3$, $-S(O)_{n3}R^{3A}$, $-S(O)_{v3}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m3}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^3BC(O)R^{3D}$, $-NR^3BC(O)OR^{3D}$, $-NR^{3B}OR^{3D}$, $-OCH_2R^{3A}$, $-OCF_3$, $-OCCl_3$, $-OCBr_3$, $-OCl_3$, $-OCHF_2$, $-OCHCl_2$, $-OCHBr_2$, $-OCHI_2$, $-OCH_2F$, $-OCH_2Cl$, $-OCH_2Br$, $-OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, $-CF_3$, $-CCl_3$, $-CBr_3$, $-Cl_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —S(O)$_{n4}$R$^{4A}$, —S(O)$_{v4}$NR$^{4B}$R$^{4C}$, —NHNR$^{4B}$R$^{4C}$, —ONR$^{4B}$R$^{4C}$, —NHC(O)NHNR$^{4B}$R$^{4C}$, —NHC(O)NR$^{4B}$R$^{4C}$, —N(O)$_{m4}$, —NR$^{4B}$R$^{4C}$, —C(O)R$^{4D}$, —C(O)OR$^{4D}$, —C(O)NR$^{4B}$R$^{4C}$, —OR$^{4A}$, —NR$^{4B}$SO$_2$R$^{4A}$, —NR$^{4B}$C(O)R$^{4D}$, —NR$^{4B}$C(O)OR$^{4D}$, —NR$^{4B}$OR$^{4D}$, —OCH$_2$R$^{4A}$, —OCH$_2$R$^{4A}$, —OCF$_3$, —OCCl$_3$, —OCBr$_3$, —OCl$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^5$ is hydrogen, halogen, —CF$_3$, —CCl$_3$, —CBr$_3$, —Cl$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —S(O)$_n$R$^{5A}$, —S(O)$_{v5}$NR$^{5B}$R$^{5C}$, —NHNR$^{5B}$R$^{5C}$, —ONR$^{5B}$R$^{5C}$, —NHC(O)NHNR$^{5B}$R$^{5C}$, —NHC(O)NR$^{5B}$R$^{5C}$, —N(O)$_{m5}$, —NR$^{5B}$R$^{5C}$, —C(O)R$^{5D}$, —C(O)OR$^{5D}$, —C(O)NR$^{5B}$R$^{5C}$, —OR$^{5A}$, —NR$^{5B}$SO$_2$R$^{5A}$, —NR$^{5B}$C(O)R$^{5D}$, —NR$^{5B}$C(O)OR$^{5D}$, —NR$^{5B}$OR$^{5D}$, —OCF$_3$, —OCH$_2$R$^{5A}$, —OCCl$_3$, —OCBr$_3$, —OCl$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, and R$^{5D}$ are hydrogen, halogen, —N$_3$, —CF$_3$, —CCl$_3$, —CBr$_3$, —Cl$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCl$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n1, n2, n3, n4, n5 are independently an integer from 0 to 4; v1, v2, v3, v4, v5 are independently 1 or 2; and m1, m2, m3, m4, and m5 are independently 1 or 2.

In an aspect provided is a pharmaceutical composition, including a compound as described herein, including embodiments (e.g., structural Formula (I)) and a pharmaceutically acceptable excipient.

In another aspect provided is a method of inhibiting ubiquitin-specific-processing protease 7 (USP7), the method including contacting USP7 with a compound as described herein, including embodiments (e.g., structural Formula (I)), or a pharmaceutically acceptable salt thereof.

In an aspect, provided is a method of treating or preventing a disease or disorder mediated by USP7, including administering to a subject in need thereof a therapeutically effective amount of a compound as described herein, including embodiments (e.g., structural Formulae (I)), or a pharmaceutically acceptable salt thereof.

In another aspect, provided herein is a kit including a compound described herein (e.g., a USP7 inhibitor) or pharmaceutical compositions thereof. The kits are generally in the form of a physical structure housing various components, as described below, and may be utilized, for example, in practicing the methods described herein.

BRIEF DESCRIPTION OF THE DRAWINGS

FIG. 1A depicts the effects of USP7 inhibition on tumor volume. FIG. 1B depicts the effects of USP7 inhibition on survival rates.

FIG. 2A depicts the effects of USP7 inhibition on tumor volume. FIG. 2B depicts the effects of USP7 inhibition on survival rates.

DETAILED DESCRIPTION

Figure 1A:
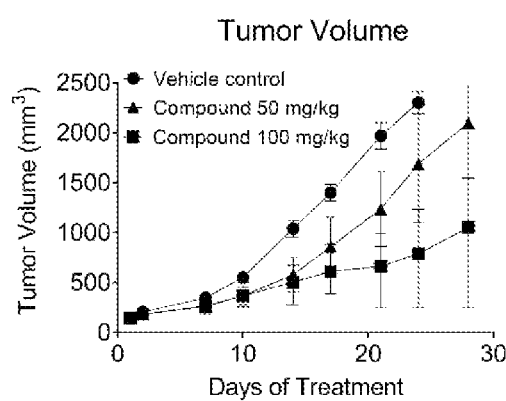
FIGS. 1A-1B Depicts the effects of USP7 inhibition in vivo (using 3-((7-(5-chloro-2-(((2S,6S)-2,6-dimethylpiperazin-1-yl)methyl)-3-methylphenyl)thieno[3,2-b]pyridin-2-yl)methyl)-3-azabicyclo[3.1.0]hexane-2,4-dione—the compound of Example 31).

Provided herein are, for example, compounds and compositions for inhibition of ubiquitin-specific-processing protease 7 (USP7), and pharmaceutical compositions comprising the same. Also provided herein are, for example, methods of treating or preventing a disease, disorder or condition, or a symptom thereof, defined by modulation (e.g., inhibition) of USP7.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'-represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. Cycloalkyl, heterocycloalkyl, cycloalkylene, or heterocycloalkylene may be bridged or fused. Bridged or fused rings may be substituted or unsubstituted cycloalkyl, substituted or unsubstituted cycloalkylene, substituted or unsubstituted heterocycloalkyl or substituted or unsubstituted heterocycloalkylene and individual rings within a bridged or fused ring group may be any of the immediately previous list, including having all rings of one type (e.g. all rings being substituted cycloalkyl, substituted heterocycloalkyl, substituted heterocycloalkylene or substituted cycloalkylene wherein each ring may be the same or different substituted heterocycloalkyl, substituted cycloalkyl, substituted heterocycloalkylene or substituted cycloalkylene).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring.

Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "~~" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

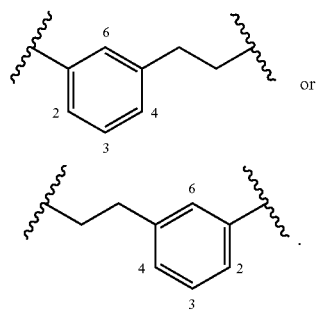

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$—SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"'R'''', —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$ H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_5$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C6-C10 aryl, C10 aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds may exist in tautomeric forms, all such tautomeric forms of the compounds being within the scope hereof.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope hereof.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope hereof.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the presentdisclosure, whether radioactive or not, are encompassed within the scope of the presentdisclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}R^{13B}$, $R^{13C}$, $R^{13D}$, etc., wherein each of $R^{13A}$, $R^{13B}$, $R^{13C}R^{13D}$, etc. is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radio-labeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In embodiments, compounds of the present disclosure contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of a compound to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "USP7 inhibitor" refers to a compound (e.g., a compound described herein) that reduces the function or activity of USP7 when compared to a control, such as, for example, the absence of the compound or a compound with known inactivity. As used herein, the terms "USP7 inhibitor" and "USP7 antagonist" and all other related art-accepted terms, many of which are set forth herein, refer to a compound capable of reducing (e.g., reducing relative to the absence of the inhibitor), either directly or indirectly, the activity and/or function USP7 receptor in an in vitro assay, an in vivo model, and/or other means indicative of therapeutic efficacy. The terms also refer to a compound that exhibits at least some therapeutic benefit in a human subject.

The term "USP7-mediated disease or disorder" refers to a disease or disorder that is characterized by involvement of activity and/or function of USP7 through USP7-mediated pathways in a body.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. In embodiments, the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences, with or without N-terminus methionine residues; immunologically tagged proteins; and the like.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway (e.g., USP7, p53, or Foxp3 pathway).

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein (e.g., decreased in a disease).

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In embodiments, an agonist is a molecule that interacts with a target to cause or promote an increase in the activation of the target. In embodiments, activators are molecules that increase, activate, facilitate, enhance activation, sensitize, or up-regulate, e.g., a gene, protein, ligand, receptor, or cell.

As defined herein, the term "inhibition," "inhibit," "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g., an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist. An antagonist prevents, reduces, inhibits, or neutralizes the activity of an agonist, and an antagonist can also prevent, inhibit, or reduce constitutive activity of a target, e.g., a target receptor, even where there is no identified agonist. In embodiments, inhibitors are molecules that decrease, block, prevent, delay activation, inactivate, desensitize, or down-regulate, e.g., a gene, protein, ligand, receptor, or cell. An inhibitor may also be defined as a molecule that reduces, blocks, or inactivates a constitutive activity. An "antagonist" is a molecule that opposes the action(s) of an agonist.

The terms "ubiquitin-specific-processing protease 7" or "USP7" or the like refer, in the usual and customary sense, to a protein (including homologs, isoforms, and functional fragments thereof) which can cleaves ubiquitin from a substrate, e.g., a ubiquitinated protein. Exemplary substrates include FOXO4, p53/TP53, MDM2, ERCC6, DNMT1, UHRF1, PTEN, and DAXX, as known in the art. USP7 catalyzes the thiol-dependent hydrolysis of ester, thioester, amide, peptide and isopeptide bonds formed by the C-terminal Gly of ubiquitin (a 76-residue protein attached to proteins as an intracellular targeting signal). USP7 can be referred to by a number of different names in the scientific literature, including "uniquitin specific peptidase 7," "ubiquitin-specific processing protease 7," "deubiquitinating enzyme 7," "unibuitin thioesterase 7," "HAUSP," "Herpes Virus-associated uniquitin specific protease," "ubiquitincarboxyl terminal hydroxylase 7," "EC 3.4.19.12," "EC 3.1.2.15" or "TEF1." The term includes any recombinant or naturally-occurring form of USP7 variants thereof that maintain USP7 activity (e.g. within at least 30%, 40%, 50%, 60%, 70%, 80%, 90%, 95%, or 100% activity compared to wildtype USP7). The term includes any mutant form of USP7 variants (e.g., frameshift mutations) thereof that maintain USP& activity (e.g. within at least 30%, 40%, 50%, 60%, 70%, 80%, 90%, 95%, or 100% activity compared to wildtype USP7). In embodiments, the USP7 protein encoded by the USP7 gene has the amino acid sequence set forth in or corresponding to Entrez 7874, UniProt Q93009, or NCBI Accession NP:_001308787.1, NP01273386.1, NP003461.2, NP001273387.1, or EAW85194.1. In embodiments, the amino acid sequence or nucleic acid sequence is the sequence known at the time of filing of the present application.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including MDS, AML, ALL, ATLL and CML), or multiple myeloma.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis. Such conditions are frequently inextricably intertwined with other diseases, disorders and conditions. A non-limiting list of inflammatory-related diseases, disorders and conditions which may, for example, be caused by inflammatory cytokines, include, arthritis, kidney failure, lupus, asthma, psoriasis, colitis, pancreatitis, allergies, fibrosis, surgical complications (e.g., where inflammatory cytokines prevent healing), anemia, and fibromyalgia. Other diseases and disorders, which may be associated with chronic inflammation include Alzheimer's disease, congestive heart failure, stroke, aortic valve stenosis, arteriosclerosis, osteoporosis, Parkinson's disease, infections, inflammatory bowel disease (IBD), allergic contact dermatitis and other eczemas, systemic sclerosis, transplantation and multiple sclerosis. Some of the aforementioned diseases, disorders and conditions for which a compound (e.g., USP7 inhibitor) of the present disclosure may be particularly efficacious (due to, for example, limitations of current therapies) are described in more detail hereafter.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic). Exemplary leukemias that may be treated with a compound or method provided herein include, for example, acute non-lymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a USP7 inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, administration includes contact (e.g., in vitro or ex vivo) of a compound to the cell, as well as contact of a compound to a fluid, where the fluid is in contact with the cell.

"Co-administer" means that a composition described herein is administered at the same time, just prior to, or just after the administration of one or more additional therapies. The compounds of the disclosure can be administered alone or can be coadministered to the patient. Co-administration is meant to include simultaneous or sequential administration of the compounds individually or in combination (more than one compound). The compositions of the present disclosure can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, a USP7 associated disease modulator is a compound that reduces the severity of one or more symptoms of a disease associated with USP7 (e.g. cancer, inflammatory disease, autoimmune disease, or infectious disease). A USP7 modulator is a compound that increases or decreases the activity or function or level of activity or level of function of USP7. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an activator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule. In embodiments, the terms "modulate," "modulation" and the like refer to the ability of a molecule (e.g., an activator or an inhibitor) to increase or decrease the function or activity of USP7, either directly or indirectly, relative to the absence of the molecule.

The term "associated" or "associated with" in the context of a substance or substance activity or function associated with a disease (e.g., a protein associated disease, a cancer associated with USP7 activity, USP7 associated cancer, USP7 associated disease (e.g., cancer, inflammatory disease, autoimmune disease, or infectious disease)) means that the disease (e.g., cancer, inflammatory disease, autoimmune disease, or infectious disease) is caused by (in whole or in part), or a symptom of the disease is caused by (in whole or in part) the substance or substance activity or function. For example, a cancer associated with USP7 activity or function may be a cancer that results (entirely or partially) from aberrant USP7 function (e.g. enzyme activity, protein-protein interaction, signaling pathway) or a cancer wherein a particular symptom of the disease is caused (entirely or partially) by aberrant USP7 activity or function. As used herein, what is described as being associated with a disease, if a causative agent, could be a target for treatment of the disease. For example, a cancer associated with USP7 activity or function or a USP7 associated disease (e.g., cancer, inflammatory disease, autoimmune disease, or infectious disease), may be treated with a compound described herein (e.g., USP7 modulator or USP7 inhibitor), in the instance where increased USP7 activity or function (e.g. signaling pathway activity) causes the disease (e.g., cancer, inflammatory disease, autoimmune disease, or infectious disease). For example, an inflammatory disease associated with USP7 activity or function or an USP7 associated inflammatory disease, may be treated with an USP7 modulator or USP7 inhibitor, in the instance where increased USP7 activity or function (e.g. signaling pathway activity) causes the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g., proteins, nucleic acids, small molecules, ions, lipids) that conveys a change in one component to one or more other components, which in turn may convey a change to additional components, which is optionally propogated to other signaling pathway components. For example, binding of a USP7 with a compound as described herein may reduce the level of a product of the USP7 catalyzed reaction or the level of a downstream derivative of the product or binding may reduce the interactions between the USP7 or a reaction product and downstream effectors or signaling pathway components (e.g., USP7, p53, or Foxp3 pathways), resulting in changes in cell growth, proliferation, or survival.

The phrase "in a sufficient amount to affect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition (percentage in a weight per weight basis).

The terms "specifically binds" and "selectively binds," when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least 10-times greater, at least 20-times greater, or at least 100-times greater than the affinity with any other antibody, or binding composition derived therefrom. In embodiments, the antibody will have an affinity that is greater than about $10^9$ liters/mol, as determined by, e.g., Scatchard analysis (Munsen, et al. (1980) Analyt. Biochem. 107:220-239).

The terms "nucleic acid," "nucleic acid molecule," "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, DNA, RNA, messenger RNA (mRNA), complementary DNA (cDNA), recombinant polynucleotides, vectors, probes, primers and the like.

As used herein, the terms "variants" and "homologs" are used interchangeably to refer to amino acid or nucleic acid sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring amino acid and nucleic acid sequences encoded thereby and their isoforms, as well as splice variants of a protein or gene. The terms also encompass nucleic acid sequences that vary in one or more bases from a naturally-occurring nucleic acid sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced; for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

II. Compounds

In an aspect, provided is a compound of structural formula (I) or pharmaceutically acceptable salt thereof:

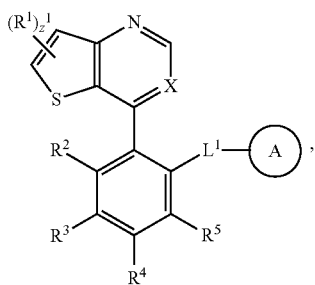

(I)

wherein: $z^1$ is 0 to 2; X is N or CH; $L^1$ is an substituted or unsubstituted alkylene or a bond; ring A is substituted or unsubstituted cycloalkyl, substituted or unsubstituted heterocycloalkyl, substituted or unsubstituted aryl, or substituted or unsubstituted heteroaryl; $R^1$ is (e.g. independently) halogen, —$CR^{1A}R^{1B}$, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —$S(O)_{n1}R^{1A}$, —$S(O)_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCH_2R^{1A}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein if $z^1$ is 2, then the two $R^1$ substituents optionally join together to form a substituted or unsubstituted cycloalkyl, substituted or unsubstituted heterocycloalkyl, substituted or unsubstituted aryl, or substituted or unsubstituted heteroaryl; $R^2$ is hydrogen, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —$S(O)_{n2}R^{2A}$, —$S(O)_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^2BC(O)R^{2D}$, —$NR^2BC(O)OR^{2D}$, —$NR^{2B}OR^{3D}$, —$OCH_2R^{2A}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —$S(O)_{n3}R^{3A}$, —$S(O)_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^3BC(O)R^{3D}$, —$NR^3BC(O)OR^{3D}$, —$NR^{3B}OR^{3D}$, —$OCH_2R^{3A}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —$S(O)_{n4}R^{4A}$, —$S(O)_{v4}NR^{4B}R^{4C}$, —$NHNR^{4B}R^{4C}$, —$ONR^{4B}R^{4C}$, —$NHC(O)NHNR^{4B}R^{4C}$, —$NHC(O)NR^{4B}R^{4C}$, —$N(O)_{m4}$, —$NR^{4B}R^{4C}$, —$C(O)R^{4D}$, —$C(O)OR^{4D}$, —$C(O)NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCH_2R^{4A}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is hydrogen, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —$S(O)_{n5}R^{5A}$, —$S(O)_{v5}NR^{5B}R^{5C}$, —$NHNR^{5B}R^{5C}$, —$ONR^{5B}R^{5C}$, —$NHC(O)NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCH_2R^{5A}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, and $R^{5D}$ are (e.g. independently) hydrogen, halogen, —$N_3$, —$CF_3$, —$CCl_3$, —$CBr_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHSO_2H$, —$NHC(O)H$, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n1, n2, n3, n4, n5 are independently an integer from 0 to 4; v1, v2, v3, v4, v5 are independently 1 or 2; and m1, m2, m3, m4, and m5 are independently 1 or 2.

In embodiments, the compound has structural formula (Ia):

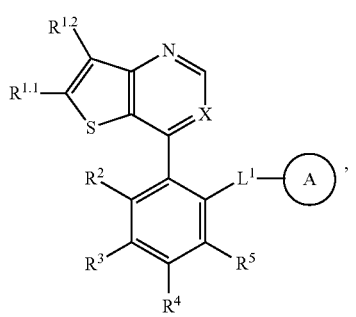

(Ia)

wherein: $R^{1.1}$ is independently —$CR^{1A}R^{1B}$, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —$S(O)_{n1.1}R^{1A}$, —$S(O)_{v1.1}NR^{1B}R^{1C}$, —$NHNR^{1B}R^{1C}$, —ONR$^{1B}$R$^{1C}$, —NHC(O)NHNR$^{1B}$R$^{1C}$, —NHC(O)NR$^{1B}$R$^{1C}$, —N(O)$_{m1.1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1.2}$ is independently hydrogen, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —S(O)$_{n1.2}$R$^{2A}$, —S(O)$_{v1.2}$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m1.2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n1.1 and n1.2 are independently an integer from 0 to 4; v1.1 and v1.2 are independently 1 or 2; and m1.1 and m1.2 are independently 1 or 2.

In embodiments, the compound has the structural formula (Ib):

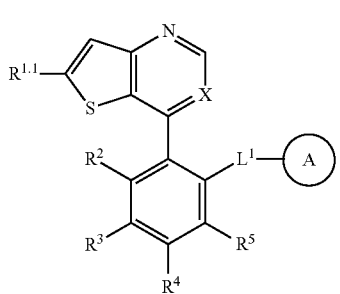

(Ib)

wherein ring A, X, L$^1$, R$^{1.1}$, R$^2$, R$^3$, R$^4$, and R$^5$ are as described herein, including embodiments. In embodiments, R$^{1.1}$ and R$^{1.2}$ are embodiments of R$^1$.

In embodiments, L$^1$ is substituted or unsubstituted alkylene. In embodiments, L$^1$ is a substituted C$_1$-C$_4$ alkylene. In embodiments, L$^1$ is an unsubstituted C$_1$-C$_4$ alkylene or a bond. In embodiments, L$^1$ is unsubstituted methylene. In embodiments, L$^1$ is a bond.

In embodiments, R$^1$ is (e.g. independently)

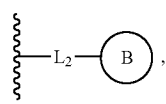

wherein L$^2$ is substituted or unsubstituted alkylene, substituted heteroalkylene, or a bond; and ring B is a substituted or unsubstituted cycloalkyl, substituted or unsubstituted heterocycloalkyl, substituted or unsubstituted aryl, and substituted or unsubstituted heteroaryl.

In embodiments, L$^2$ is an unsubstituted C$^1$-C$^4$ alkylene or a bond. In embodiments, L$^2$ is unsubstituted methylene. In embodiments, L$^2$ is a bond.

In embodiments, ring B is

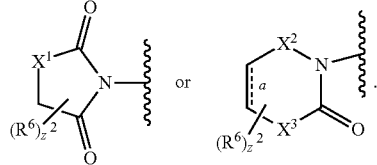

Symbol "a" is a single bond or double bond. X$^1$ is CH$_2$, CHR$^6$, C(R$^6$)$_2$, NH, NR$^6$, S, or O. X$^2$ is CH$_2$, CHR$^6$, C(R$^6$)$_2$, NH, NR$^6$, or C=O. X$^3$ is CH$_2$, CHR$^6$, C(R$^6$)$_2$, NH, or NR$^6$. z$^2$ is independently an integer from 0 to 2. R$^6$ is (e.g. independently) halogen, oxo, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —SO$_{n6}$R$^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{6A}$R$^{6B}$, R$^{6C}$, and R$^{6D}$ are independently hydrogen, halogen, —N$_3$, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{6B}$ and R$^{6C}$ substituents can optionally join together to form a substituted or unsubstituted heterocycloalkyl or substituted or unsubstituted heteroaryl. The symbol n6 is an integer from 0 to 4. The symbol v6 is independently 1 or 2. The symbol m6 is independently 1 or 2. In embodiments, wherein z$^2$ is 2, two R$^6$ substituents optionally join together to form a substituted or unsubstituted cycloalkyl, substituted or unsubstituted heterocycloalkyl, substituted or unsubstituted aryl, or substituted or unsubstituted heteroaryl.

In embodiments, wherein z$^2$ is 2, two R$^6$ substituents optionally join together to form a substituted or unsubstituted cyclopropyl, substituted or unsubstituted cyclobutyl, substituted or unsubstituted cyclopentyl, or substituted or unsubstituted cyclohexyl.

In embodiments, ring B is

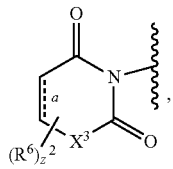

wherein "a", $R^6$, $X^3$ and $z^2$ are as described herein, including embodiments.

In embodiments, ring B is

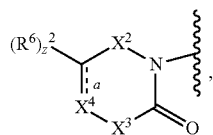

wherein "a", $R^6$, $X^2$, $X^3$ and $z^2$ are as described herein, including embodiments. $X^4$ is a bond, CH, $C(R^{11})$, N, $CH_2$, $CHR^{11}$, $C(R^{11})_2$, O, S, NH or $NR^{10}$. A person having an ordinary skill in the art will recognize that when "a" is a double bond, then $X^4$ is CH, $C(R^{11})$, or N and when "a" is a single bond, then $X^4$ is $CH_2$, $CHR^{11}$, $C(R^{11})_2$, O, S, NH or $NR^{10}$. In embodiments, $X^4$ is CH, $C(R^{11})$, N, $CH_2$, $CHR^{11}$, $C(R^{11})_2$, O, S, NH or $NR^{10}$. In embodiments, $R^{10}$ is hydrogen or substituted or unsubstituted alkyl. In embodiments, $R^{11}$ is hydrogen or substituted or unsubstituted alkyl.

In embodiments, ring B is

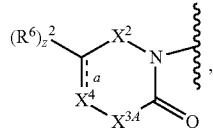

wherein "a", $R^6$, $X^2$, $X^4$, and $z^2$ are as described herein, including embodiments. $X^{3A}$ is $CH_2$, $CHR^{11}$, $C(R^{11})_2$, NH, $NR^{11}$, CH, $CR^{11}$, or N. A person having ordinary skill in the art will recognize that when $X^4$ is a single bond, a 5-membered ring is formed, with a direct bond between $X^{3A}$ and the carbon bearing the $R^6$ substituent. In embodiments, when "a" is a single bond and $X^4$ is a bond, then "a" and $X^4$ collectively form a single bond between $X^{3A}$ and the carbon bearing the $R^6$ substituent, and $X^{3A}$ is a value of $X^3$, including embodiments (e.g., $CH_2$, $CHR^{11}$, $C(R^{11})_2$, NH, or $NR^{11}$). In embodiments, when "a" is a double bond and $X^4$ is a bond, then "a" and $X^4$ collectively form a double bond between $X^{3A}$ and the carbon bearing the $R^6$ substituent, and $X^{3A}$ is CH, $CR^{11}$, or N. A person having an ordinary skill in the art will recognize that when $X^4$ is not a bond and "a" is a double bond, then $X^4$ is CH, $C(R^{11})$, or N and when "a" is a single bond, then $X^4$ is $CH_2$, $CHR^{11}$, $C(R^{11})_2$, O, S, NH or $NR^{11}$. In embodiments, $X^4$ is CH, $C(R^{11})$, N, $CH_2$, $CHR^{11}$, $C(R^{11})_2$, O, S, or $NR^{11}$. In embodiments, when $X^4$ is $NR^{11}$, $R^{11}$ is hydrogen or substituted or unsubstituted alkyl.

In embodiments, ring B is

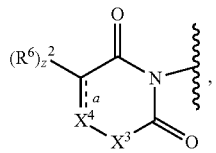

wherein "a", $R^6$, $X^3$, $X^4$, and $z^2$ are as described herein, including embodiments.

In embodiments, the compound has the structural formula (IIa) or (IIb):

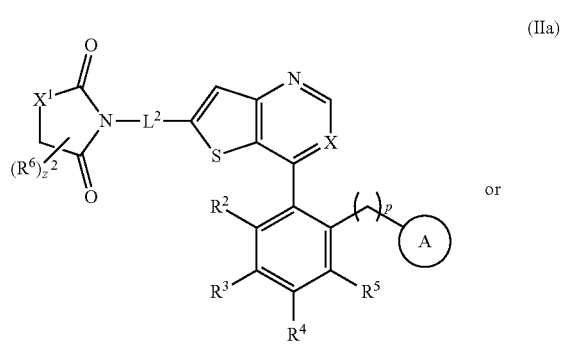

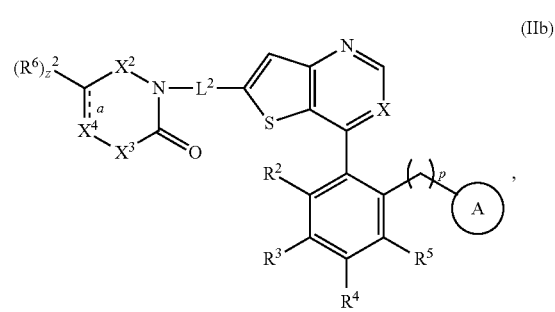

wherein: p is an integer from 0 to 2; $L^2$ is a substituted or unsubstituted methylene; Ring A, X, $X^1$, $X^2$, $X^3$, $X^4$, $R^2$, $R^3$, $R^4$, $R^5$, $R^6$, "a", and $z^2$ are as described herein, including embodiments. In embodiments, $X^{3A}$ is as described herein, including embodiments.

In other embodiments, the compound has the structural formula (IIc) or (IId):

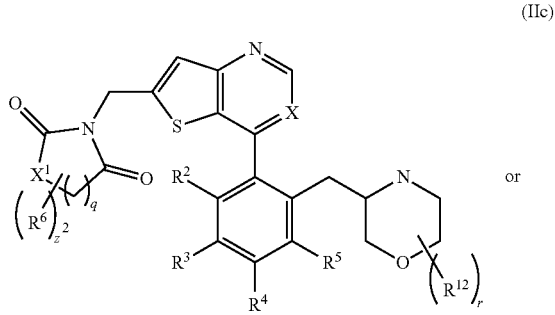

(IId)

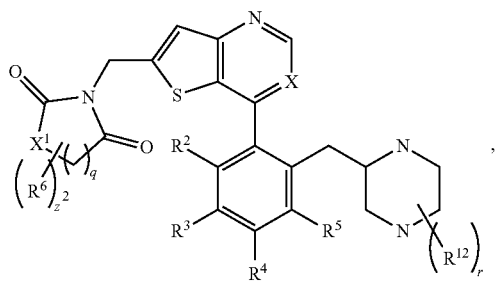

wherein q is 1 or 2; r is 1 or 2, and wherein X, $X^1$, $R^2$, $R^3$, $R^4$, $R^5$, $R^6$, and $z^2$ are as described herein, including embodiments.

$R^{12}$ is (e.g. independently) halogen, oxo, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —$SO_{n12}R^{12A}$, —$SO_{v12}NR^{12B}R^{12C}$, —$NHNR^{12B}R^{12C}$, —$ONR^{12B}R^{12C}$, —$NHC(O)NHNR^{12B}R^{12C}$, —$NHC(O)NR^{12B}R^{12C}$, —$N(O)_{m12}$, —$NR^{12B}R^{2C}$, —$C(O)R^{12D}$, —$C(O)OR^{12D}$, —$C(O)NR^{12B}R^{12C}$, —$OR^{12A}$, —$NR^{12B}SO_2R^{12A}$, —$NR^{12B}C(O)R^{12D}$, —$NR^{12B}C(O)OR^{12D}$, —$NR^{12B}OR^{12D}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12A}$, $R^{12B}$, $R^{12C}$, and $R^{12D}$ are independently hydrogen, halogen, —$N_3$, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{12B}$ and $R^{12C}$ substituents can optionally join together to form a substituted or unsubstituted heterocycloalkyl or substituted or unsubstituted heteroaryl. The symbol n12 is an integer from 0 to 4. The symbol v12 is independently 1 or 2. The symbol m12 is independently 1 or 2. In embodiments, wherein $z^2$ is 2, two $R^{12}$ substituents optionally join together to form a substituted or unsubstituted cycloalkyl, substituted or unsubstituted heterocycloalkyl, substituted or unsubstituted aryl, or substituted or unsubstituted heteroaryl.

In other embodiments, the compound has the structural formula (IIe) or (IIf):

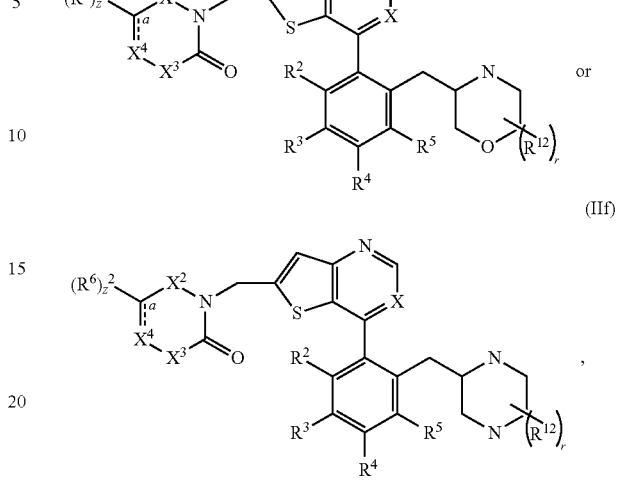

wherein r is 1 or 2 and wherein X, $X^2$, $X^3$, $X^4$, $R^2$, $R^3$, $R^4$, $R^5$, $R^6$, $R^{12}$, and $z^2$ are as described herein, including embodiments.

In embodiments, ring A is substituted or unsubstituted cycloalkyl, substituted or unsubstituted heterocycloalkyl, substituted or unsubstituted aryl, or substituted or unsubstituted heteroaryl.

In embodiments, ring A is substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, ring A is $R^7$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, ring A is a $R^7$-substituted (e.g. with a substituent group, a size-limited substituent group or a lower substituent group) or unsubstituted spirocyclic cycloalkyl (e.g., $C_4$-$C_{10}$ cycloalkyl, $C_4$-$C_9$ cycloalkyl, or $C_5$-$C_9$ cycloalkyl). In embodiments, ring A is a $R^7$-substituted (e.g. with a substituent group, a size-limited substituent group or a lower substituent group) or unsubstituted bridged cycloalkyl (e.g., $C_4$-$C_{10}$ cycloalkyl, $C_4$-$C_9$ cycloalkyl, or $C_5$-$C_9$ cycloalkyl).

In embodiments, ring A is $R^7$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, ring A is a $R^7$-substituted or unsubstituted spirocyclic heterocycloalkyl (e.g., 4 to 10 membered heterocycloalkyl, 4 to 9 membered heterocycloalkyl, or 5 to 9 membered heterocycloalkyl). In embodiments, ring A is a $R^7$-substituted or unsubstituted bridged heterocycloalkyl (e.g., 4 to 10 membered heterocycloalkyl, 4 to 9 membered heterocycloalkyl, or 5 to 9 membered heterocycloalkyl).

In embodiments, ring A is $R^7$-substituted or unsubstituted aryl (e.g., $C_6$-$C_{10}$ aryl, $C_{10}$ aryl, or phenyl). In embodiments, ring A is $R^7$-substituted or unsubstituted heteroaryl (e.g., 5 to 10 membered heteroaryl, 5 to 9 membered heteroaryl, or 5 to 6 membered heteroaryl).

In embodiments, ring A is $R^7$-substituted or unsubstituted cyclopentyl. In embodiments, ring A is $R^7$-substituted or unsubstituted cyclohexyl. In embodiments, ring A is $R^7$-substituted or unsubstituted azetidinyl. In embodiments, ring A is $R^7$-substituted or unsubstituted pyrrolidinyl. In embodiments, ring A is $R^7$-substituted or unsubstituted piperidinyl. In embodiments, ring A is unsubstituted piperazinyl. In embodiments, ring A is unsubstituted morpholinyl. In embodiments, ring A is unsubstituted azepanyl. In embodiments, ring A is unsubstituted oxoazepanyl.

$R^7$ is independently oxo, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —$CN$, —$N_3$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^8$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^8$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^8$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^8$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^8$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^8$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). Two adjacent $R^7$ substituents may optionally combine to form substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, two adjacent $R^7$ substituents combine to form $R^8$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^8$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl), $R^8$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^8$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^7$ is (e.g. independently) —$NH_2$. In embodiments, $R^7$ is (e.g. independently) unsubstituted methyl. In embodiments, $R^7$ is (e.g. independently) unsubstituted ethyl. In embodiments, $R^7$ is (e.g. independently) unsubstituted isopropyl. In embodiments, $R^7$ is (e.g. independently) unsubstituted cyclopropyl. In embodiments, $R^7$ is (e.g. independently) —F. In embodiments, $R^7$ is (e.g. independently) —$CF_3$. In embodiments, $R^7$ is (e.g. independently) —$NHC(O)$. In embodiments, $R^7$ is (e.g. independently) —OH. In embodiments, $R^7$ is (e.g. independently) —$CHF_2$. In embodiments, $R^7$ is (e.g. independently) —$CH_2F$. In embodiments, $R^7$ is (e.g. independently) —O—$CH_3$. In embodiments, $R^7$ is (e.g. independently) —O—$CH_2CH_3$. In embodiments, $R^7$ is (e.g. independently) —$CH_2CH_2CH_2OH$. In embodiments, $R^7$ is (e.g. independently) —$CH_2OH$. In embodiments, $R^7$ is (e.g. independently) unsubstituted azetidinyl. In embodiments, $R^7$ is (e.g. independently) unsubstituted oxetanyl.

In embodiments, $R^7$ is (e.g. independently) $R^8$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl). In embodiments, $R^7$ is $R^8$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^7$ is $R^8$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, $R^7$ is $R^8$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^7$ is $R^8$-substituted (e.g. with a substituent group, a size-limited substituent group or a lower substituent group) or unsubstituted aryl (e.g., $C_6$-$C_{10}$ aryl, C10 aryl, or phenyl). In embodiments, $R^7$ is $R^8$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

$R^8$ is independently oxo, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^9$-substituted or unsubstituted alkyl (e.g., $C_1$-$C_8$ alkyl, $C_1$-$C_6$ alkyl, or $C_1$-$C_4$ alkyl), $R^9$-substituted or unsubstituted heteroalkyl (e.g., 2 to 8 membered heteroalkyl, 2 to 6 membered heteroalkyl, or 2 to 4 membered heteroalkyl), $R^9$-substituted or unsubstituted cycloalkyl (e.g., $C_3$-$C_8$ cycloalkyl, $C_3$-$C_6$ cycloalkyl, or $C_5$-$C_6$ cycloalkyl), $R^9$-substituted or unsubstituted heterocycloalkyl (e.g., 3 to 8 membered heterocycloalkyl, 3 to 6 membered heterocycloalkyl, or 5 to 6 membered heterocycloalkyl), $R^9$-substituted or unsubstituted aryl (e.g., $C_6$-$C_{10}$ aryl, C10 aryl, or phenyl), or $R^9$-substituted or unsubstituted heteroaryl (e.g., 5 to 10 membered heteroaryl, 5 to 9 membered heteroaryl, or 5 to 6 membered heteroaryl).

In embodiments, $R^8$ is (e.g. independently) $R^9$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl). In embodiments, $R^8$ is $R^9$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^8$ is $R^9$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, $R^8$ is $R^9$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^8$ is $R^9$-substituted (e.g. with a substituent group, a size-limited substituent group or a lower substituent group) or unsubstituted aryl (e.g., $C_6$-$C_{10}$ aryl, $C_{10}$ aryl, or phenyl). In embodiments, $R^8$ is $R^9$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). Two adjacent $R^8$ substituents may optionally combine to form substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). In embodiments, two adjacent $R^8$ substituents combine to form $R^9$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^9$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^9$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^9$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

$R^9$ is independently oxo, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$—$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCCl_3$, —$OCF_3$, —$OCBr_3$, —$OCI_3$, —$OCHCl_2$, —$OCHBr_2$, —$OCHI_2$, —$OCHF_2$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, C10 aryl, or phenyl), or unsubstituted heteroaryl (e.g., 5 to 10 membered heteroaryl, 5 to 9 membered heteroaryl, or 5 to 6 membered heteroaryl).

In embodiments, ring A is $R^7$-substituted or unsubstituted $C_3$-$C_6$ cycloalkyl or $R^7$-substituted or unsubstituted 3 to 7 membered heterocycloalkyl.

In embodiments, ring A is

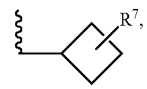

wherein $R^7$ as described herein. In embodiments, ring A is

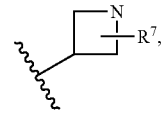

wherein $R^7$ as described herein. In embodiments, ring A

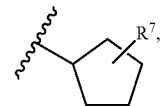

wherein $R^7$ as described herein. In embodiments, ring A is

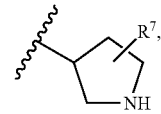

wherein $R^7$ as described herein. In embodiments, ring A is

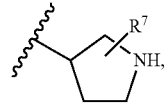

wherein R⁷ as described herein. In embodiments, ring A is

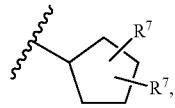

wherein each R⁷ is (e.g. independently) as described herein. In embodiments, ring A is

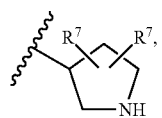

wherein each R⁷ is (e.g. independently) as described herein. In embodiments, ring A is

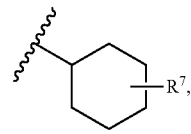

wherein R⁷ as described herein. In embodiments, ring A is

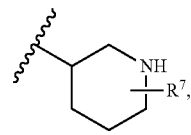

wherein R⁷ as described herein. In embodiments, ring A is

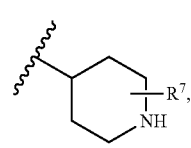

wherein R⁷ as described herein. In embodiments, ring A is

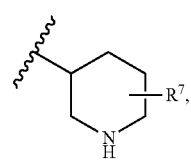

wherein R as described herein. In embodiments, ring A is

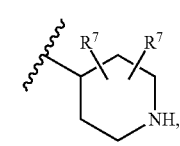

wherein R⁷ as (e.g. independently) as described herein. In embodiments, ring A is

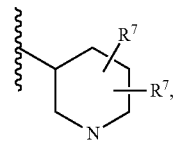

wherein each R⁷ is (e.g. independently) as described herein. In embodiments, ring A is

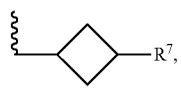

wherein R⁷ as described herein. In embodiments, ring A is

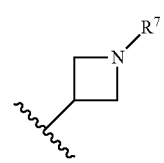

wherein R⁷ as described herein. In embodiments, ring A is

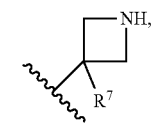

wherein R⁷ as described herein. In embodiments, ring A is

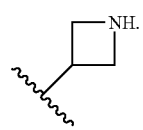

In embodiments, ring A is

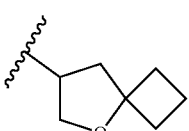

In embodiments, ring A is

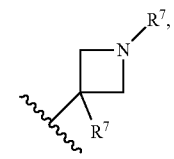

wherein each R⁷ is (e.g. independently) as described herein. In embodiments, ring A is

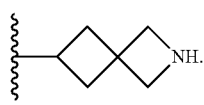 [SMILES: *C1CC2(CNC2)C1]

In embodiments, ring A is

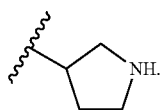

In embodiments, ring A is

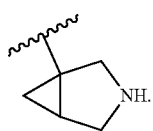 [SMILES: *C12CNCC1C2]

In embodiments, ring A is

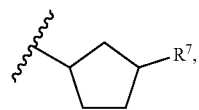

wherein $R^7$ as described herein. In embodiments, ring A is

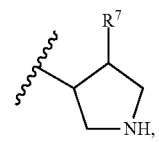

wherein $R^7$ as described herein. In embodiments, ring A is

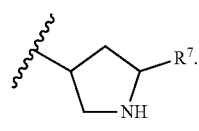

In embodiments, ring A is

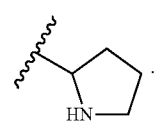

In embodiments, ring A is

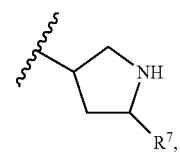

wherein $R^7$ as described herein. In embodiments, ring A is

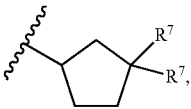

wherein $R^7$ as described herein. In embodiments, ring A is

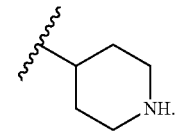

wherein each $R^7$ is (e.g. independently) as described herein. In embodiments, ring A is In embodiments, ring A is

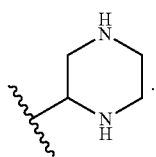

In embodiments, ring A is

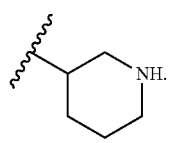 [SMILES: *C1CCCNC1]

In embodiments, ring A is

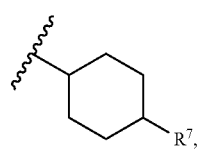

wherein R⁷ as described herein. In embodiments, ring A is

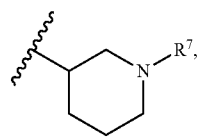

wherein R⁷ as described herein. In embodiments, ring A is

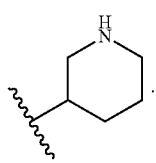 [SMILES: *C1CCCNC1]

In embodiments, ring A is

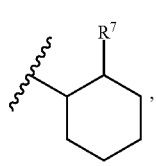

wherein R⁷ as described herein. In embodiments, ring A is

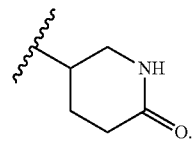 [SMILES: *C1CCC(=O)NC1]

In embodiments, ring A is

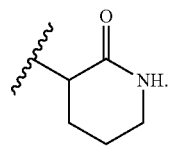 [SMILES: *C1CCCNC1=O]

In embodiments, ring A is

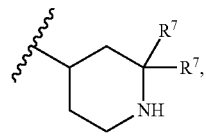

wherein each R⁷ is (e.g. independently) as described herein. In embodiments, ring A is

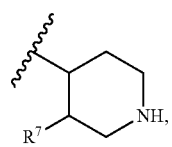

wherein R⁷ as described herein. In embodiments, ring A is

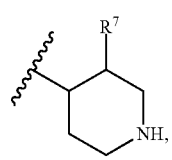

wherein R⁷ as described herein. In embodiments, ring A is

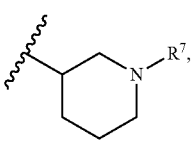

wherein R⁷ as described herein. In embodiments, ring A is

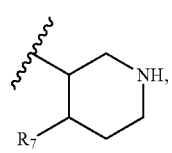

wherein R⁷ as described herein. In embodiments, ring A is

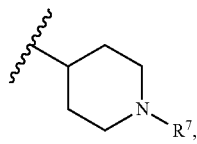

wherein R⁷ as described herein. In embodiments, ring A is

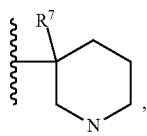

wherein R⁷ as described herein. In embodiments, ring A is

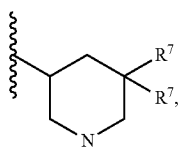

wherein each R⁷ is (e.g. independently) as described herein. In embodiments, ring A is

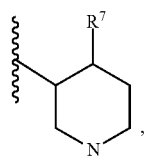

wherein R⁷ as described herein. In embodiments, ring A is

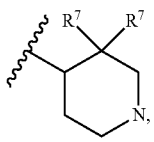

wherein each R⁷ is (e.g. independently) as described herein. In embodiments, ring A is

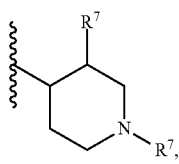

wherein each R⁷ is (e.g. independently) as described herein.

In embodiments, ring A is

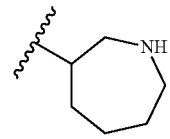

In embodiments, ring A is

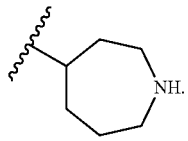

In embodiments, ring A

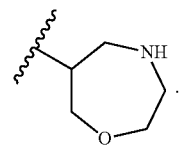 [SMILES: *C1CNCCOC1]

In embodiments, R⁷ is independently halogen, —CN, —NH₂, —OH, —N₃, azido, N,N-dimethylcarbamoyl, methylamino, dimethylamino, methylcarbonyl, methylaminocarbonyl, substituted or unsubstituted C1-C4 alkyl, and substituted or unsubstituted 3 to 6 membered heterocycloalkyl.

In embodiments, R⁷ is halogen. In embodiments, R⁷ is —F.

In embodiments, R⁷ is —CN. In embodiments, R⁷ is —NH₂. In embodiments, R⁷ is —OH. In embodiments, R⁷ is —N₃. In embodiments, R⁷ is azido. In embodiments, R⁷ is N,N-dimethylcarbamoyl. In embodiments, R⁷ is methylamino. In embodiments, R⁷ is dimethylamino. In embodiments, R⁷ is methylcarbonyl. In embodiments, R⁷ is methylaminocarbonyl.

In embodiments, R⁷ is substituted or unsubstituted $C_1$-$C_4$ alkyl. In embodiments, R⁷ is methyl. In embodiments, R⁷ is ethyl. In embodiments, R⁷ is isopropyl. In embodiments, R⁷ is fluoromethyl. In embodiments, R⁷ is difluoromethyl. In embodiments, R⁷ is trifluoromethyl. In embodiments, R⁷ is difluoroethyl. In embodiments, R⁷ is trifluoroethyl. In embodiments, R⁷ is methoxy. In embodiments, R⁷ is ethoxy. In embodiments, R⁷ is hydroxymethyl.

In embodiments, R⁷ is substituted or unsubstituted 3 to 6 membered heterocycloalkyl. In embodiments, R⁷ is azetidinyl. In embodiments, R⁷ is oxetanyl. In embodiments, R⁷ is morpholinyl. In embodiments, R⁷ is substituted or unsubstituted pyrrolidinyl.

In embodiments, R¹ is independently hydrogen, halogen, —CF₃, —CCl₃, —CBr₃, —CI₃, —CHF₂, —CHCl₂, —CHBr₂, —CHI₂, —CH₂F, —CH₂Cl, —CH₂Br, —CH₂I, —CN, —N₃, —S(O)$_{n1}$R$^{1A}$, —S(O)$_{v1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO₂R$^{1A}$, —NR$^{1B}$C(O)R$^{1D}$, —NR$^{1B}$C(O)OR$^{1D}$, —NR$^{1B}$OR$^{1D}$, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^1$ is independently halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —$S(O)_{n1}R^{1A}$, —$S(O)_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). In embodiments, two $R^1$ substituents optionally join together to form a substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl(e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^1$ is independently halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —$S(O)_{n1}R^{1A}$, —$S(O)_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, two $R^1$ substituents optionally join together to form a substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 $C_1$-$C_8$ alkyl, $C_1$-$C_6$ alkyl, or $C_1$-$C_4$ alkyl membered heterocycloalkyl, or 5 to 6 membered heterocycloalkyl), substituted (e.g. with a substituent group, a size-limited substituent group or a lower substituent group) or unsubstituted aryl(e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^1$ is independently halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$SO_{n1}H$, —$SO_{v1}NH_2$, —$NHNH_2$, —$ONH_2$, —$NHC(O)NHNH_2$, —$NHC(O)NH_2$, —$N(O)_{m1}$, —$NH_2$, —$C(O)H$, —$C(O)OH$, —$C(O)NH_2$, —OH, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{35}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{35}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{35}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{35}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{35}$-substituted (e.g.

with a substituent group, a size-limited substituent group or a lower substituent group) or unsubstituted aryl (e.g., $C_6$-$C_{10}$ aryl, $C_{10}$ aryl, or phenyl), or $R^{35}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^1$ is independently $R^{35}$-substituted (e.g. with a substituent group, a size-limited substituent group or a lower substituent group) or unsubstituted alkyl (e.g., $C_1$-$C_5$ alkyl, $C_1$-$C_6$ alkyl, or $C_1$-$C_4$ alkyl), $R^{35}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{35}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{35}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{35}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{35}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^1$ is (e.g. independently) hydroxyl-substituted methyl. In embodiments, $R^1$ is (e.g. independently) hydroxyl-substituted ethyl. In embodiments, $R^1$ is (e.g. independently) hydroxyl-substituted propyl. In embodiments, $R^1$ is (e.g. independently) methyl substituted with —NH—$SO_2CH_3$. In embodiments, $R^1$ is (e.g. independently) ethyl substituted with —NH—$SO_2CH_3$. In embodiments, $R^1$ is (e.g. independently) methyl substituted with —NH—C(O)$CH_3$. In embodiments, $R^1$ is (e.g. independently) ethyl substituted with —NH—(CO)$CH_3$.

$R^{35}$ is independently oxo, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, or —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2F$, —$OCH_2Cl$, —$OCH_2Br$, —$OCH_2I$, $R^{36}$-substituted or unsubstituted alkyl (e.g., $C_1$-$C_8$ alkyl, $C_1$-$C_6$ alkyl, or $C_1$-$C_4$ alkyl), $R^{36}$-substituted or unsubstituted heteroalkyl (e.g., 2 to 8 membered heteroalkyl, 2 to 6 membered heteroalkyl, or 2 to 4 membered heteroalkyl), $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36}$-substituted or unsubstituted aryl (e.g., $C_6$-$C_{10}$ aryl, $C_{10}$ aryl, or phenyl), or $R^{36}$-substituted or unsubstituted heteroaryl (e.g., 5 to 10 membered heteroaryl, 5 to 9 membered heteroaryl, or 5 to 6 membered heteroaryl). Two adjacent $R^{35}$ substituents may optionally join together to form a $R^{36}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{36}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{36}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{36}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). In embodiments, $R^{35}$ is independently —$CH_2Cl$, —$CH_2Br$, —$CH_2F$, —$CH_2I$, —$CHCl_2$, —$CHBr_2$, —$CHF_2$, or —$CHI_2$.

In embodiments, $R^{35}$ is $R^{36}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl). In embodiments, $R^{35}$ is $R^{36}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^{35}$ is $R^{36}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{35}$ is $R^{36}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^{35}$ is $R^{36}$-substituted (e.g. with a substituent group, a size-limited substituent group or a lower substituent group) or unsubstituted aryl (e.g., $C_6$-$C_{10}$ aryl, $C_{10}$ aryl, or phenyl). In embodiments, $R^{35}$ is $R^{36}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{35}$ is

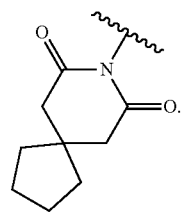 [SMILES: *N1C(=O)CC2(CCCC2)CC1=O]

$R^{36}$ is independently oxo, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, or —$CHI_2$—CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2F$, —$OCH_2Cl$, —$OCH_2Br$, —$OCH_2I$, $R^{37}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{37}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{37}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{37}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{37}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{37}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). Two adjacent $R^{36}$ substituents may optionally join together to form a substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{36}$ is $R^{37}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl). In embodiments, $R^{36}$ is $R^{37}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^{36}$ is $R^{37}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{36}$ is $R^{37}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^{36}$ is $R^{37}$-substituted (e.g. with a substituent group, a size-limited substituent group or a lower substituent group) or unsubstituted aryl (e.g., $C_6$-$C_{10}$ aryl, $C_{10}$ aryl, or phenyl). In embodiments, $R^{36}$ is $R^{37}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

$R^{37}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$F, —OCH$_2$Cl, —OCH$_2$Br, —OCH$_2$I, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). Two adjacent $R^{37}$ substituents may optionally join together to form an unsubstituted cycloalkyl (e.g., $C_3$-$C_8$ cycloalkyl, $C_3$-$C_6$ cycloalkyl, or $C_5$-$C_6$ cycloalkyl), an unsubstituted heterocycloalkyl (e.g., 3 to 8 membered heterocycloalkyl, 3 to 6 membered heterocycloalkyl, or 5 to 6 membered heterocycloalkyl), an unsubstituted aryl (e.g., $C_6$-$C_{10}$ aryl, $C_{10}$ aryl, or phenyl), or an unsubstituted heteroaryl (e.g., 5 to 10 membered heteroaryl, 5 to 9 membered heteroaryl, or 5 to 6 membered heteroaryl).

In embodiments, $R^1$ is (e.g. independently) a substituted alkyl, substituted or unsubstituted heterocycloalky, or substituted or unsubstituted heteroaryl.

In embodiments, $R^1$ is (e.g. independently) a substituted $C_1$-$C_5$ alkyl. In embodiments, $R^1$ is (e.g. independently) a substituted $C_1$-$C_6$ alkyl. In embodiments, $R^1$ is (e.g. independently) a substituted $C_1$-$C_4$ alkyl. In embodiments, $R^1$ is (e.g. independently) hydroxyl-substituted methyl, hydroxyl-substituted ethyl, hydroxyl-substituted propyl, or hydroxyl-substituted isopropyl. In embodiments, $R^1$ is (e.g. independently) methyl substituted with —NH—SO$_2$NH$_3$ or ethyl substituted with —NH—SO$_2$NH$_3$. In embodiments, $R^1$ is methyl substituted with —NH—C(O)CH$_3$ or ethyl substituted with —NH—C(O)CH$_3$. In embodiments, $R^1$ is (e.g. independently) methyl substituted with —NH—SO$_2$CH$_3$ or ethyl substituted with —NH—SO$_2$CH$_3$.

In embodiments, $R^1$ is (e.g. independently) a substituted or unsubstituted heterocycloalkyl, or substituted or unsubstituted heteroaryl.

In embodiments, $R^1$ is (e.g. independently) a substituted or unsubstituted monovalent succinimide moiety, substituted or unsubstituted monovalent hydantoin moiety, substituted or unsubstituted monovalent oxohydantoin moiety, substituted or unsubstituted monovalent thiohydantoin moiety, substituted or unsubstituted monovalent pyrrolidone moiety, substituted or unsubstituted monovalent imidazoledione moiety, substituted or unsubstituted monovalent piperidone moiety, substituted or unsubstituted monovalent pyrimidone moiety, substituted or unsubstituted monovalent pyridinone moiety, substituted or unsubstituted monovalent pyrrolidone moiety, substituted or unsubstituted monovalent isoindoledione moiety, substituted or unsubstituted monovalent phthalimide moiety, substituted or unsubstituted monovalent oxazolidone moiety, 3-azabicyclo[3.1.0]hexanone moiety, and substituted or unsubstituted monovalent cyclopentanepiperidinone moiety. In embodiments, $R^1$ is independently an unsubstituted monovalent succinimide moiety, unsubstituted monovalent hydantoin moiety, unsubstituted monovalent oxohydantoin moiety, unsubstituted monovalent thiohydantoin moiety, unsubstituted monovalent pyrrolidone moiety, unsubstituted monovalent imidazoledione moiety, unsubstituted monovalent piperidone moiety, unsubstituted monovalent pyrimidone moiety, unsubstituted monovalent pyridinone moiety, unsubstituted monovalent pyrrolidone moiety, unsubstituted monovalent isoindoledione moiety, unsubstituted monovalent phthalimide moiety, unsubstituted monovalent oxazolidone moiety, 3-azabicyclo

[3.1.0]hexanone moiety, and unsubstituted monovalent cyclopentanepiperidinone moiety.

In embodiments, $R^1$ is (e.g. independently)

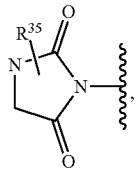

wherein $R^{35}$ is as described herein. In embodiments, $R^1$ is (e.g. independently)

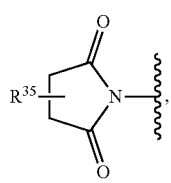

wherein $R^{35}$ is as described herein. In embodiments, $R^1$ is (e.g. independently)

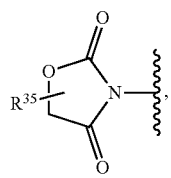

wherein $R^{35}$ is as described herein. In embodiments, $R^1$ is (e.g. independently)

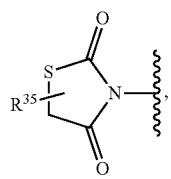

wherein $R^{35}$ is as described herein. In embodiments, $R^1$ is

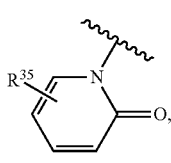

wherein $R^{35}$ is as described herein. In embodiments, $R^1$ is (e.g. independently)

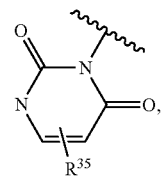

wherein $R^{35}$ is as described herein. In embodiments, $R^1$ is (e.g. independently)

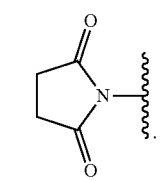

wherein $R^{35}$ is is as described herein. In embodiments, $R^1$ is (e.g. independently)

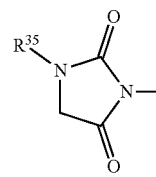

wherein $R^{35}$ is is as described herein.

In embodiments, $R^1$ is (e.g. independently)

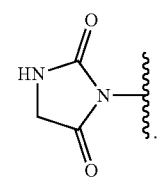 [SMILES: *N1C(=O)CNC1=O]

In embodiments, $R^1$ is (e.g. independently)

In embodiments, R¹ is (e.g. independently)

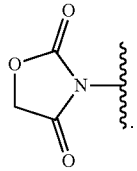 [SMILES: *N1C(=O)COC1=O]

In embodiments, R¹ is (e.g. independently)

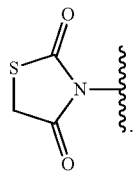

In embodiments, R¹ is (e.g. independently)

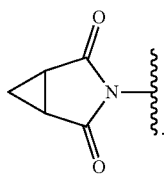 [SMILES: *N1C(=O)C2CC2C1=O]

In embodiments, R¹ is (e.g. independently)

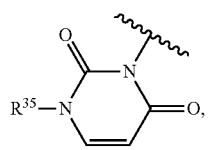

wherein R³⁵ is as described herein. In embodiments, R¹ is (e.g. independently)

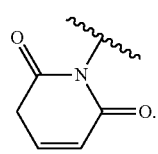 [SMILES: *N1C(=O)C=CCC1=O]

In embodiments, R¹ is (e.g. independently)

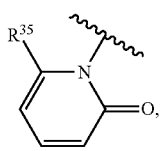

wherein R³⁵ is as described herein. In embodiments, R¹ is (e.g. independently)

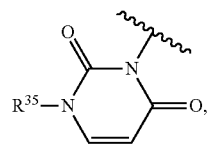

wherein R³⁵ is as described herein. In embodiments, R¹ is (e.g. independently)

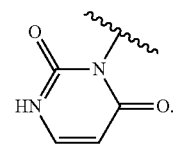

In embodiments, R¹ is (e.g. independently)y

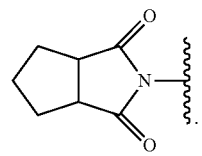 [SMILES: *N1C(=O)C2CCCC2C1=O]

In embodiments, R¹ is (e.g. independently)

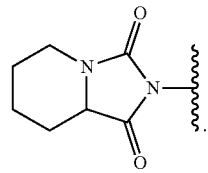 [SMILES: *N1C(=O)C2CCCCN2C1=O]

In embodiments, R¹ is (e.g. independently)

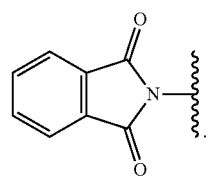 [SMILES: *N1C(=O)c2ccccc2C1=O]

In embodiments, R¹ is (e.g. independently)

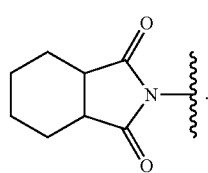 [SMILES: *N1C(=O)C2CCCCC2C1=O]

In embodiments, $R^1$ is (e.g. independently)

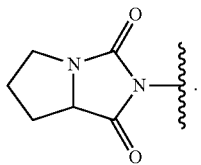 [SMILES: *N1C(=O)C2CCCN2C1=O]

In embodiments, $R^1$ is (e.g. independently)

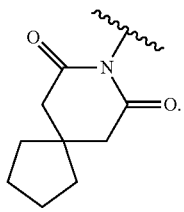 [SMILES: *N1C(=O)CC2(CCCC2)CC1=O]

In embodiments, $R^{35}$ is independently halogen, substituted or unsubstituted $C_1$-$C_4$ alkyl, or substituted or unsubstituted 3 to 6 membered heterocycloalkyl.

In embodiments, $R^{35}$ is halogen. In embodiments, $R^{35}$ is —F.

In embodiments, $R^{35}$ is substituted or unsubstituted $C_1$-$C_4$ alkyl. In embodiments, $R^{35}$ is methyl. In embodiments, $R^{35}$ is ethyl. In embodiments, $R^{35}$ is isopropyl. In embodiments, $R^{35}$ is trifluoromethyl. In embodiments, $R^{35}$ is trifluoroethyl. In embodiments, $R^{35}$ is trifluoropropyl. In embodiments, $R^{35}$ is methoxy.

In embodiments, $R^{35}$ is substituted (e.g. with a substituent group, a size-limited substituent group or a lower substituent group) or unsubstituted 3 to 6 membered heterocycloalkyl. In embodiments, $R^{35}$ is substituted (e.g. with a substituent group, a size-limited substituent group or a lower substituent group) or unsubstituted oxetanyl.

In embodiments, $R^{1A}$ is (e.g. independently) hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, or —CHI$_2$ —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$F, —OCH$_2$Cl, —OCH$_2$Br, —OCH$_2$I, $R^{35}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{35}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{35}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{35}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{35}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{35}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{1A}$ is (e.g. independently) $R^{35}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl). In embodiments, $R^{1A}$ is (e.g. independently) $R^{35}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^{1A}$ is $R^{35}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is $R^{35}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is $R^{35}$-substituted (e.g. with a substituent group, a size-limited substituent group or a lower substituent group) or unsubstituted aryl (e.g., $C_6$-$C_{10}$ aryl, $C_{10}$ aryl, or phenyl). In embodiments, $R^{1A}$ is $R^{35}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{1B}$ is (e.g. independently) hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, or —CHI$_2$ —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$F, —OCH$_2$Cl, —OCH$_2$Br, —OCH$_2$I, $R^{35}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{35}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{35}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{35}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{35}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{35}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). In embodiments, $R^{1B}$ and $R^{1C}$ substituents bonded to the same nitrogen atom may optionally be joined to form a $R^{35}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl) or $R^{35}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{1B}$ is (e.g. independently) $R^{35}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl). In embodiments, $R^{1B}$ is (e.g. independently) $R^{35}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^{1B}$ is $R^{35}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1B}$ is $R^{35}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1B}$ is $R^{35}$-substituted (e.g. with a substituent group, a size-limited substituent group or a lower substituent group) or unsubstituted aryl (e.g., $C_6$-$C_{10}$ aryl, $C_{10}$ aryl, or phenyl). In embodiments, $R^{1B}$ is $R^{35}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{1C}$ is (e.g. independently) hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, or —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$F, —OCH$_2$Cl, —OCH$_2$Br, —OCH$_2$I, $R^{35}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{35}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{35}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{35}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{35}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{35}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). In embodiments, $R^{1B}$ and $R^{1C}$ substituents bonded to the same nitrogen atom may optionally be joined to form a $R^{35}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl) or $R^{35}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{1C}$ is (e.g. independently) $R^{35}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl). In embodiments, $R^{1C}$ is (e.g. independently) $R^{35}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^{1C}$ is $R^{35}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1C}$ is $R^{35}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1C}$ is $R^{35}$-substituted (e.g. with a substituent group, a size-limited substituent group or a lower substituent group) or unsubstituted aryl (e.g., $C_6$-$C_{10}$ aryl, $C_{10}$ aryl, or phenyl). In embodiments, $R^{1C}$ is $R^{35}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{1D}$ is (e.g. independently) hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, or —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$F, —OCH$_2$Cl, —OCH$_2$Br, —OCH$_2$I, $R^{35}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{35}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{35}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{35}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{35}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{35}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{1D}$ is (e.g. independently) $R^{35}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl). In embodiments, $R^{1D}$ is (e.g. independently) $R^{35}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^{1D}$ is $R^{35}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1D}$ is $R^{35}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1D}$ is $R^{35}$-substituted (e.g. with a substituent group, a size-limited substituent group or a lower substituent group) or unsubstituted aryl (e.g., $C_6$-$C_{10}$ aryl, $C_{10}$ aryl, or phenyl). In embodiments, $R^{1D}$ is $R^{35}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

$R^{1.1}$ and $R^{1.2}$ are embodiments of $R^1$. In embodiments, $R^{1.1}$ and $R^{1.2}$ are defined as $R^1$, including embodiments thereof.

In embodiments, $R^2$ is (e.g. independently) hydrogen, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$S(O)_{n2}H$, —$S(O)_{v2}NH_2$, —$NHNH_2$, —$ONH_2$, —$NHC(O)NHNH_2$, —$NHC(O)NH_2$, —$N(O)_{m2}$, —$NH_2$, —$C(O)H$, —$C(O)OH$, —$C(O)NH_2$, —OH, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^2$ is a substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl). In embodiments, $R^2$ is a substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^2$ is a substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is a substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^2$ is a substituted (e.g. with a substituent group, a size-limited substituent group or a lower substituent group) or unsubstituted aryl (e.g., $C_6$-$C_{10}$ aryl, $C_{10}$ aryl, or phenyl). In embodiments, $R^2$ is a substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^2$ is hydrogen.

In embodiments, $R^3$ is hydrogen, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$S(O)_{n3}H$, —$S(O)_{v3}NH_2$, —$NHNH_2$, —$ONH_2$, —$NHC(O)NHNH_2$, —$NHC(O)NH_2$, —$N(O)_{m3}$, —$NH_2$, —$C(O)H$, —$C(O)OH$, —$C(O)NH_2$, —OH, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^3$ is a substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl). In embodiments, $R^3$ is a substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^3$ is a substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is a substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is a substituted (e.g. with a substituent group, a size-limited substituent group or a lower substituent group) or unsubstituted aryl (e.g., $C_6$-$C_{10}$ aryl, $C_{10}$ aryl, or phenyl). In embodiments, $R^3$ is a substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, R$^3$ is substituted (e.g. with a substituent group, a size-limited substituent group or a lower substituent group) or unsubstituted alkyl (e.g., C$_1$-C$_5$ alkyl, C$_1$-C$_6$ alkyl, or C$_1$-C$_4$ alkyl), halogen, or CN. In embodiments, R$^3$ is substituted (e.g. with a substituent group, a size-limited substituent group or a lower substituent group) or unsubstituted C$_1$-C$_4$ alkyl. In embodiments, R$^3$ is substituted (e.g. with a substituent group, a size-limited substituent group or a lower substituent group) C$_1$-C$_4$ alkyl. In embodiments, R$^3$ is unsubstituted C$_1$-C$_4$ alkyl. In embodiments, R$^3$ is methyl, ethyl, or isopropyl. In embodiments, R$^3$ is halogen. In embodiments, R$^3$ is —F, —Cl, —Br, or —I. In embodiments, R$^3$ is —Cl. In embodiments, R$^3$ is —CN.

In embodiments, R$^4$ is hydrogen, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —S(O)$_{n4}$H, —S(O)$_{v4}$NH$_2$, —NHNH$_2$, —ONH$_2$, —NHC(O)NHNH$_2$, —NHC(O)NH$_2$, —N(O)$_{m4}$, —NH$_2$, —C(O)H, —C(O)OH, —C(O)NH$_2$, —OH, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted (e.g. with a substituent group, a size-limited substituent group or a lower substituent group) or unsubstituted alkyl (e.g., C$_1$-C$_8$ alkyl, C$_1$-C$_6$ alkyl, or C$_1$-C$_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., C$_3$-C$_8$ cycloalkyl, C$_3$-C$_6$ cycloalkyl, or C$_5$-C$_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., C$_6$-C$_{10}$ aryl, C$_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, R$^4$ is a substituted (e.g. with a substituent group, a size-limited substituent group or a lower substituent group) or unsubstituted alkyl (e.g., C$_1$-C$_8$ alkyl, C$_1$-C$_6$ alkyl, or C$_1$-C$_4$ alkyl). In embodiments, R$^4$ is a substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, R$^4$ is a substituted (e.g. with a substituent group, a size-limited substituent group or a lower substituent group) or unsubstituted cycloalkyl (e.g., C$_3$-C$_8$ cycloalkyl, C$_3$-C$_6$ cycloalkyl, or C$_5$-C$_6$ cycloalkyl). In embodiments, R$^4$ is a substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, R$^4$ is a substituted (e.g. with a substituent group, a size-limited substituent group or a lower substituent group) or unsubstituted aryl (e.g., C$_6$-C$_{10}$ aryl, C$_{10}$ aryl, or phenyl). In embodiments, R$^4$ is a substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, R$^4$ is hydrogen or halogen. In embodiments, R$^4$ is hydrogen. In embodiments, R$^4$ is halogen. In embodiments, R$^4$ is —F, —Cl, —Br, or —I. In embodiments, R$^4$ is —Cl.

In embodiments, R$^5$ is hydrogen, halogen, oxo, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —S(O)$_{n5}$R$^{5A}$, —S(O)$_{v5}$NR$^{5B}$R$^{5C}$, —NHNR$^{5B}$R$^{5C}$, —ONR$^{5B}$R$^{5C}$, —NHC(O)NHNR$^{5B}$R$^{5C}$, —NHC(O)NR$^{5B}$R$^{5C}$, —N(O)$_{m5}$, —NR$^{5B}$R$^{5C}$, —C(O)R$^{5D}$, —C(O)OR$^{5D}$, —C(O)NR$^{5B}$R$^{5C}$, —OR$^{5A}$, —NR$^{5B}$SO$_2$R$^{5A}$, —NR$^{5B}$C(O)R$^{5D}$, —NR$^{5B}$C(O)OR$^{5D}$, —NR$^{5B}$OR$^{5D}$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted (e.g. with a substituent group, a size-limited substituent group or a lower substituent group) or unsubstituted alkyl (e.g., C$_1$-C$_8$ alkyl, C$_1$-C$_6$ alkyl, or C$_1$-C$_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., C$_3$-C$_8$ cycloalkyl, C$_3$-C$_6$ cycloalkyl, or C$_5$-C$_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., C$_6$-C$_{10}$ aryl, C$_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^5$ is a substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl). In embodiments, $R^5$ is a substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^5$ is a substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, $R^5$ is a substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is a substituted (e.g. with a substituent group, a size-limited substituent group or a lower substituent group) or unsubstituted aryl (e.g., $C_6$-$C_{10}$ aryl, $C_{10}$ aryl, or phenyl). In embodiments, $R^5$ is a substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^5$ is substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), unsubstituted cycloalkyl (e.g., $C_3$-$C_8$ cycloalkyl, $C_3$-$C_6$ cycloalkyl, or $C_5$-$C_6$ cycloalkyl), halogen or CN. In embodiments, $R^5$ is substituted (e.g. with a substituent group, a size-limited substituent group or a lower substituent group) $C_1$-$C_8$ alkyl. In embodiments, $R^5$ is unsubstituted $C_1$-$C_8$ alkyl. In embodiments, $R^5$ is unsubstituted $C_1$-$C_6$ alkyl. In embodiments, $R^5$ is unsubstituted $C_1$-$C_4$ alkyl. In embodiments, $R^5$ is methyl or ethyl. In embodiments, $R^5$ is unsubstituted $C_3$-$C_8$ cycloalkyl. In embodiments, $R^5$ is unsubstituted $C_3$-$C_6$ cycloalkyl. In embodiments, $R^5$ is cyclopropyl. In embodiments, $R^5$ is halogen. In embodiments, $R^5$ is —F, —Cl, —Br, or —I. In embodiments, $R^5$ is —Cl. In embodiments, $R^5$ is CN.

In embodiments, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, and $R^{5D}$ are independently hydrogen, halogen, —$N_3$, —$CF_3$, —$CCl_3$, —$CBr_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl); $R^{6B}$ and $R^{6C}$ substituents bonded to the same nitrogen atom may optionally be joined to form a substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl) or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^6$ is (e.g. independently) hydrogen, halogen, oxo, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$S(O)_{n6}R^{6A}$, —$S(O)_{v6}NR^{6B}R^{6C}$, —$NHNR^{6B}R^{6C}$, —$ONR^{6B}R^{6C}$, —NHC(O)$NHNR^{6B}R^{6C}$, —NHC(O)$NR^{6B}R^{6C}$, —$N(O)_{m6}$, —$NR^{6B}R^{6C}$, —C(O)$R^{6D}$, —C(O)$OR^{6D}$, —C(O)$NR^{6B}R^{6C}$, —$OR^{6A}$, —$NR^{6B}SO_2R^{6A}$, —$NR^{5B}C(O)R^{6D}$, —$NR^{6B}C(O)OR^{6D}$, —$NR^{6B}OR^{6D}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^6$ is (e.g. independently) halogen, oxo, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$S(O)_{n6}R^{6A}$, —$S(O)_{v6}NR^{6B}R^{6C}$, —$NHNR^{6B}R^{6C}$, —$ONR^{6B}R^{6C}$, —NHC(O)$NHNR^{6B}R^{6C}$, —NHC(O)$NR^{6B}R^{6C}$, —$N(O)_{m6}$, —$NR^{6B}R^{6C}$, —C(O)$R^{6D}$, —C(O)$OR^{6D}$, —C(O)$NR^{6B}R^{6C}$, —$OR^{6A}$, —$NR^{6B}SO_2R^{6A}$, —$NR^{5B}C(O)R^{6D}$, —$NR^{6B}C(O)OR^{6D}$, —$NR^{6B}OR^{6D}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group)

or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^6$ is (e.g. independently) halogen, oxo, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$S(O)_{n6}R^{6A}$, —$S(O)_{v6}NR^{6B}R^{6C}$, —$NHNR^{6B}R^{6C}$, —$ONR^{6B}R^{6C}$, —$NHC(O)NHNR^{6B}R^{6C}$, —$NHC(O)NR^{6B}R^{6C}$, —$N(O)_{m6}$, $NR^{6B}R^{6C}$, —$C(O)R^{6D}$, —$C(O)OR^{6D}$, —$C(O)NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^6$ is $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

$R^{38}$ is independently oxo, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, or —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2F$, —$OCH_2Cl$, —$OCH_2Br$, —$OCH_2I$, $R^{39}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{39}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{39}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{39}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{39}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{39}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{38}$ is $R^{39}$-substituted (e.g. with a substituent group, a size-limited substituent group or a lower substituent group) or unsubstituted alkyl (e.g., $C_1$-$C_5$ alkyl, $C_1$-$C_6$ alkyl, or $C_1$-$C_4$ alkyl). In embodiments, $R^{38}$ is $R^{39}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^{38}$ is $R^{39}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{38}$ is $R^{39}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^{38}$ is $R^{39}$-substituted (e.g. with a substituent group, a size-limited substituent group or a lower substituent group) or unsubstituted aryl (e.g., $C_6$-$C_{10}$ aryl, $C_{10}$ aryl, or phenyl). In embodiments, $R^{38}$ is $R^{39}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). Two adjacent $R^{38}$ substituents may optionally join together to form a $R^{39}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{39}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{39}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{39}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

$R^{39}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, or —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$F, —OCH$_2$Cl, —OCH$_2$Br, —OCH$_2$I, $R^{40}$-substituted (e.g. with a substituent group, a size-limited substituent group or a lower substituent group) or unsubstituted alkyl (e.g., C$_1$-C$_8$ alkyl, C$_1$-C$_6$ alkyl, or C$_1$-C$_4$ alkyl), $R^{40}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{40}$-substituted (e.g. with a substituent group, a size-limited substituent group or a lower substituent group) or unsubstituted cycloalkyl (e.g., C$_3$-C$_8$ cycloalkyl, C$_3$-C$_6$ cycloalkyl, or C$_5$-C$_6$ cycloalkyl), $R^{40}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{40}$-substituted (e.g. with a substituent group, a size-limited substituent group or a lower substituent group) or unsubstituted aryl (e.g., C$_6$-C$_{10}$ aryl, C$_{10}$ aryl, or phenyl), or $R^{40}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{39}$ is $R^{40}$-substituted (e.g. with a substituent group, a size-limited substituent group or a lower substituent group) or unsubstituted alkyl (e.g., C$_1$-C$_8$ alkyl, C$_1$-C$_6$ alkyl, or C$_1$-C$_4$ alkyl). In embodiments, $R^{39}$ is $R^{40}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl). In embodiments, $R^{39}$ is $R^{40}$-substituted (e.g. with a substituent group, a size-limited substituent group or a lower substituent group) or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{39}$ is $R^{40}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl). In embodiments, $R^{39}$ is $R^{40}$-substituted (e.g. with a substituent group, a size-limited substituent group or a lower substituent group) or unsubstituted aryl (e.g., C$_6$-C$_{10}$ aryl, C$_{10}$ aryl, or phenyl). In embodiments, $R^{39}$ is or $R^{40}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

$R^{40}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$F, —OCH$_2$Cl, —OCH$_2$Br, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{40}$ is independently unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^6$ is (e.g. independently) hydrogen or halogen. In embodiments, $R^6$ is (e.g. independently) hydrogen. In embodiments, $R^6$ is (e.g. independently) halogen. In embodiments, $R^6$ is (e.g. independently) —F, —Cl, —Br, or —I. In embodiments, $R^6$ is (e.g. independently) —F, —Cl, or —Br.

In embodiments, $R^6$ is (e.g. independently) a substituted or unsubstituted C$_1$-C$_8$ alkyl. In embodiments, $R^6$ is (e.g. independently) substituted C$_1$-C$_8$ alkyl. In embodiments, $R^6$ is (e.g. independently) unsubstituted C$_1$-C$_8$ alkyl. In embodiments, $R^6$ is (e.g. independently) unsubstituted C$_1$-C$_6$ alkyl. In embodiments, $R^6$ is (e.g. independently) unsubstituted C$_1$-C$_4$ alkyl. In embodiments, $R^6$ is (e.g. independently) methyl or ethyl. In embodiments, $R^6$ is (e.g. independently) substituted C$_1$-C$_8$ alkyl. In embodiments, $R^6$ is (e.g. independently) substituted C$_1$-C$_6$ alkyl. In embodiments, $R^6$ is (e.g. independently) substituted C$_1$-C$_4$ alkyl. In embodiments, $R^6$ is (e.g. independently) CF$_3$.

In embodiments, $R^6$ is (e.g. independently) unsubstituted C$_3$-C$_8$ cycloalkyl, unsubstituted 3 to 7 membered heterocycloalkyl, or unsubstituted C$_5$-C$_6$ aryl. In embodiments, $R^6$ is (e.g. independently) unsubstituted C$_3$-C$_8$ cycloalkyl. In embodiments, $R^6$ is (e.g. independently) unsubstituted cyclopropyl, cyclopentyl, or cyclohexyl. In embodiments, $R^6$ is (e.g. independently) unsubstituted 3 to 7 membered heterocycloalkyl. In embodiments, $R^6$ is (e.g. independently) unsubstituted piperidinyl, pyrrolidinyl, or oxetanyl. In embodiments, $R^6$ is (e.g. independently) unsubstituted C$_5$-C$_6$ aryl. In embodiments, $R^6$ is (e.g. independently) unsubstituted phenyl.

In embodiments, $R^{6A}$, $R^{6B}$, $R^{6C}$ and $R^{6D}$ are independently hydrogen, halogen, —N$_3$, —CF$_3$, —CCl$_3$, —CBr$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted (e.g. with a substituent group, a size-limited substituent group or a lower substituent group) or unsubstituted alkyl (e.g., C$_1$-C$_8$ alkyl, C$_1$-C$_6$ alkyl, or C$_1$-C$_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., C$_3$-C$_8$ cycloalkyl, C$_3$-C$_6$ cycloalkyl, or C$_5$-C$_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., C$_6$-C$_{10}$ aryl, C$_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl); R$^{6B}$ and R$^{6C}$ substituents bonded to the same nitrogen atom may optionally be joined to form a substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl) or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, R$^{6A}$ is (e.g. independently) hydrogen, halogen, —N$_3$, —CF$_3$, —CCl$_3$, —CBr$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{38}$-substituted (e.g. with a substituent group, a size-limited substituent group or a lower substituent group) or unsubstituted alkyl (e.g., C$_1$-C$_8$ alkyl, C$_1$-C$_6$ alkyl, or C$_1$-C$_4$ alkyl), R$^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), R$^{38}$-substituted (e.g. with a substituent group, a size-limited substituent group or a lower substituent group) or unsubstituted cycloalkyl (e.g., C$_3$-C$_8$ cycloalkyl, C$_3$-C$_6$ cycloalkyl, or C$_5$-C$_6$ cycloalkyl), R$^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), R$^{38}$-substituted (e.g. with a substituent group, a size-limited substituent group or a lower substituent group) or unsubstituted aryl (e.g., C$_6$-C$_{10}$ aryl, C$_{10}$ aryl, or phenyl), or R$^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, R$^{6A}$ is R$^{38}$-substituted (e.g. with a substituent group, a size-limited substituent group or a lower substituent group) or unsubstituted alkyl (e.g., C$_1$-C$_8$ alkyl, C$_1$-C$_6$ alkyl, or C$_1$-C$_4$ alkyl), R$^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), R$^{38}$-substituted (e.g. with a substituent group, a size-limited substituent group or a lower substituent group) or unsubstituted cycloalkyl (e.g., C$_3$-C$_8$ cycloalkyl, C$_3$-C$_6$ cycloalkyl, or C$_5$-C$_6$ cycloalkyl), R$^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), R$^{38}$-substituted (e.g. with a substituent group, a size-limited substituent group or a lower substituent group) or unsubstituted aryl (e.g., C$_6$-C$_{10}$ aryl, C$_{10}$ aryl, or phenyl), or R$^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, R$^{6B}$ is (e.g. independently) hydrogen, halogen, —N$_3$, —CF$_3$, —CCl$_3$, —CBr$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{38}$-substituted (e.g. with a substituent group, a size-limited substituent group or a lower substituent group) or unsubstituted alkyl (e.g., C$_1$-C$_8$ alkyl, C$_1$-C$_6$ alkyl, or C$_1$-C$_4$ alkyl), R$^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), R$^{38}$-substituted (e.g. with a substituent group, a size-limited substituent group or a lower substituent group) or unsubstituted cycloalkyl (e.g., C$_3$-C$_8$ cycloalkyl, C$_3$-C$_6$ cycloalkyl, or C$_5$-C$_6$ cycloalkyl), R$^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), R$^{38}$-substituted (e.g. with a substituent group, a size-limited substituent group or a lower substituent group) or unsubstituted aryl (e.g., C$_6$-C$_{10}$ aryl, C$_{10}$ aryl, or phenyl), or R$^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). In embodiments, R$^{6B}$ and R$^{6C}$ substituents bonded to the same nitrogen atom may optionally be joined to form a R$^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl) or R$^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, R$^{6B}$ is R$^{38}$-substituted (e.g. with a substituent group, a size-limited substituent group or a lower substituent group) or unsubstituted alkyl (e.g., C$_1$-C$_8$ alkyl, C$_1$-C$_6$ alkyl, or C$_1$-C$_4$ alkyl), R$^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{6C}$ is (e.g. independently) hydrogen, halogen, —$N_3$, —$CF_3$, —$CCl_3$, —$CBr_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). In embodiments, $R^{6B}$ and $R^{6C}$ substituents bonded to the same nitrogen atom may optionally be joined to form a $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl) or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{6C}$ is $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{6D}$ is (e.g. independently) hydrogen, halogen, —$N_3$, —$CF_3$, —$CCl_3$, —$CBr_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{6D}$ is $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group)

or unsubstituted heteroaryl (e.g., 5 to 10 membered heteroaryl, 5 to 9 membered heteroaryl, or 5 to 6 membered heteroaryl).

In embodiments, $R^{12}$ is (e.g. independently) hydrogen, halogen, oxo, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$S(O)_{n12}R^{6A}$, —$S(O)_{v12}NR^{12B}R^{12C}$, —$NHNR^{12B}R^{12C}$, —$ONR^{12B}R^{12C}$, —NHC(O)$NHNR^{12B}R^{12C}$, —$NHC(O)NR^{12B}R^{12C}$, —$N(O)_{m12}$, —$NR^{12B}R^{12C}$, —$C(O)R^{12D}$, —$C(O)OR^{12D}$, —C(O)$NR^{12B}R^{12C}$, —$OR^{12A}$, —$NR^{12B}SO_2R^{12A}$, —$NR^{12}BC(O)R^{12D}$, —$NR^{12}BC(O)OR^{12D}$, —$NR^{12B}OR^{12D}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{12}$ is (e.g. independently) halogen, oxo, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$S(O)_{n12}R^{6A}$, —$S(O)_{v12}NR^{12B}R^{12C}$, —$NHNR^{12B}R^{12C}$, —$ONR^{12B}R^{12C}$, —NHC(O)$NHNR^{12B}R^{12C}$, —$NHC(O)NR^{12B}R^{12C}$, —$N(O)_{m12}$, —$NR^{12B}R^{12C}$, —$C(O)R^{12D}$, —$C(O)OR^{12D}$, —C(O)$NR^{12B}R^{12C}$, —$OR^{12A}$, —$NR^{12B}SO_2R^{12A}$, —$NR^{12B}C(O)R^{12D}$, —$NR^{12B}C(O)OR^{12D}$, —$NR^{12B}OR^{12D}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{12}$ is (e.g. independently) halogen, oxo, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$S(O)_{n12}R^{6A}$, —$S(O)_{v12}NR^{12B}R^{12C}$, —$NHNR^{12B}R^{12C}$, —$ONR^{12B}R^{12C}$, —NHC(O)$NHNR^{12B}R^{12C}$, —$NHC(O)NR^{12B}R^{2C}$, —$N(O)_{m12}$, —$NR^{12B}R^{2C}$, —$C(O)R^{12D}$, —$C(O)OR^{12D}$, —C(O)$NR^{12B}R^{12C}$, —$OR^{12A}$, —$NR^{12B}SO_2R^{12A}$, —$NR^{12B}C(O)R^{12D}$, —$NR^{12B}C(O)OR^{12D}$, —$NR^{12B}OR^{12D}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{12}$ is $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{12}$ is hydrogen, substituted or unsubstituted alkyl, substituted or unsubstituted cycloalkyl, —CO—$CF_3$, spiro cycloalkyl, or spiro heterocycloalkyl, including embodiments.

In embodiments, $R^{12A}$ is (e.g. independently) hydrogen, halogen, —$N_3$, —$CF_3$, —$CCl_3$, —$CBr_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHSO_2H$, —$NHC(O)H$, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{12A}$ is $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{12B}$ is (e.g. independently) hydrogen, halogen, —$N_3$, —$CF_3$, —$CCl_3$, —$CBr_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). In embodiments, $R^{12B}$ and $R^{12C}$ substituents bonded to the same nitrogen atom may optionally be joined to form a $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl) or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{12B}$ is $R^{38}$-substituted (e.g. with a substituent group, a size-limited substituent group or a lower substituent group) or unsubstituted alkyl (e.g., $C_1$-$C_5$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{12C}$ is (e.g. independently) hydrogen, halogen, —$N_3$, —$CF_3$, —$CCl_3$, —$CBr_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl). In embodiments, $R^{12B}$ and $R^{12C}$ substituents bonded to the same nitrogen atom may optionally be joined to form a $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl) or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{12C}$ is $R^{38}$-substituted (e.g. with a substituent group, a size-limited substituent group or a lower substituent group) or unsubstituted alkyl (e.g., $C_1$-$C_5$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{12D}$ is (e.g. independently) hydrogen, halogen, —$N_3$, —$CF_3$, —$CCl_3$, —$CBr_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{12D}$ is $R^{38}$-substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), $R^{38}$-substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), $R^{38}$-substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted (e.g. with a substituent group, a size-limited substituent group or a lower substituent group) or unsubstituted aryl (e.g., $C_6$-$C_{10}$ aryl, $C_{10}$ aryl, or phenyl), or $R^{38}$-substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, r is 1. In embodiments, r is 2.
In embodiments, q is 1. In embodiments, q is 2.
In embodiments, $z^1$ is 0. In embodiments, $z^1$ is 1. In embodiments, $z^1$ is 2. In embodiments, $z^2$ is 0. In embodiments, $z^2$ is 1. In embodiments, $z^2$ is 2.

In embodiments, n1 is 0. In embodiments, n1 is 1. In embodiments, n1 is 2. In embodiments, n1 is 3. In embodiments, n1 is 4. In embodiments, n2 is 0. In embodiments, n2 is 1. In embodiments, n2 is 2. In embodiments, n2 is 3. In embodiments, n2 is 4. In embodiments, n3 is 0. In embodiments, n3 is 1. In embodiments, n3 is 2. In embodiments, n3 is 3. In embodiments, n3 is 4. In embodiments, n4 is 0. In embodiments, n4 is 1. In embodiments, n4 is 2. In embodiments, n4 is 3. In embodiments, n4 is 4. In embodiments, n5 is 0. In embodiments, n5 is 1. In embodiments, n5 is 2. In embodiments, n5 is 3. In embodiments, n5 is 4. In embodiments, n6 is 0. In embodiments, n6 is 1. In embodiments, n6 is 2. In embodiments, n6 is 3. In embodiments, n6 is 4. In embodiments, n12 is 1. In embodiments, n12 is 2. In embodiments, n12 is 3. In embodiments, n12 is 4. In embodiments, n1.1 is 0. In embodiments, n1.1 is 1. In embodiments, n1.1 is 2. In embodiments, n1.1 is 3. In embodiments, n1.1 is 4. In embodiments, n1.2 is 0. In embodiments, n1.2 is 1. In embodiments, n1.2 is 2. In embodiments, n1.2 is 3. In embodiments, n1.2 is 4.

In embodiments, v1 is 1. In embodiments, v1 is 2. In embodiments, v2 is 1. In embodiments, v2 is 2. In embodiments, v3 is 1. In embodiments, v3 is 2. In embodiments, v4 is 1. In embodiments, v4 is 2. In embodiments, v5 is 1. In embodiments, v5 is 2. In embodiments, v6 is 1. In embodiments, v6 is 2. In embodiments, v12 is 1. In embodiments, v12 is 2. In embodiments, v1.1 is 1. In embodiments, v1.1 is 2. In embodiments, v1.2 is 1. In embodiments, v1.2 is 2.

In embodiments, m1 is 1. In embodiments, m1 is 2. In embodiments, m2 is 1. In embodiments, m2 is 2. In embodiments, m3 is 1. In embodiments, m3 is 2. In embodiments, m4 is 1. In embodiments, m4 is 2. In embodiments, m5 is 1. In embodiments, m5 is 2. In embodiments, m6 is 1. In embodiments, m6 is 2. In embodiments, m12 is 1. In embodiments, m12 is 2. In embodiments, m1.1 is 1. In embodiments, m1.1 is 2. In embodiments, m1.2 is 1. In embodiments, m1.2 is 2.

In embodiments p is 0. In embodiments, p is 1. In embodiments, p is 2.

In embodiments, X is N. In embodiments, X is CH.

In embodiments, $X^1$ is $CH_2$, $CHR^{11}$, $C(R^{11})_2$, NH, $NR^6$, S, or O. In embodiments, $X^1$ is $CH_2$. In embodiments, $X^1$ is $CHR^{11}$. In embodiments, $X^1$ is $C(R^{11})_2$. In embodiments, $X^1$ is NH. In embodiments, $X^1$ is $NR^{11}$. In embodiments, $X^1$ is S. In embodiments, $X^1$ is O.

In embodiments, $X^2$ is $CH_2$, $CHR^{11}$, $C(R^{11})_2$, NH, $NR^{11}$, or C=O. In embodiments, $X^2$ is $CH_2$. In embodiments, $X^2$ is $CHR^{11}$. In embodiments, $X^2$ is $C(R^{11})_2$. In embodiments, $X^2$ is NH. In embodiments, $X^2$ is $NR^{11}$. In embodiments, $X^2$ is C=O.

In embodiments, $X^3$ is $CH_2$, $CHR^{11}$, $C(R^{11})_2$, NH or $NR^{11}$. In embodiments, $X^3$ is $CH_2$. In embodiments, $X^3$ is $CHR^{11}$. In embodiments, $X^3$ is $C(R^{11})_2$. In embodiments, $X^3$ is NH. In embodiments, $X^3$ is $NR^{11}$.

In embodiments, $X^{3.4}$ is $CH_2$, $CHR^{11}$, $C(R^{11})_2$, NH, $NR^{11}$, CH, $CR^{11}$, or N. In embodiments, $X^{3.4}$ is $CH_2$. In embodiments, $X^{3.4}$ is $CHR^{11}$. In embodiments, $X^{3.4}$ is $C(R^{11})_2$. In embodiments, $X^{3.4}$ is NH. In embodiments, $X^{3.4}$ is $NR^{11}$. In embodiments, $X^{3.4}$ is CH. In embodiments, $X^{3.4}$ is $CR^{11}$. In embodiments, $X^{3.4}$ is N.

In embodiments, $X^4$ is a single bond, a double bond, CH, $CR^{11}$, N, $CH_2$, $CHR^{11}$, $C(R^{11})_2$, O, S, NH or $NR^{10}$. In embodiments, $X^4$ is a single bond. In embodiments, $X^4$ is a double bond. In embodiments, $X^4$ is CH. In embodiments, $X^4$ is $CR^{11}$. In embodiments, $X^4$ is N. In embodiments, $X^4$ is $CH_2$. In embodiments, $X^4$ is $CHR^{11}$. In embodiments, $X^4$ is $C(R^{11})_2$. In embodiments, $X^4$ is O. In embodiments, $X^4$ is S. In embodiments, $X^4$ is NH. In embodiments, $X^4$ is $NR^{10}$. In embodiments, $R^{10}$ is hydrogen or substituted or unsubstituted alkyl.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In embodiments, the compound is one of those synthesized in the Examples herein, or a pharmaceutically acceptable salt thereof. In embodiments, the compound has the formula as described elsewhere herein, for example within a table, claim or Example.

In another embodiment, the compound is 3-((7-(5-chloro-2-(((2S,6S)-2,6-dimethylpiperazin-1-yl)methyl)-3-methylphenyl)thieno[3,2-b]pyridin-2-yl)methyl)-3-azabicyclo[3.1.0]hexane-2,4-dione having the chemical structure:

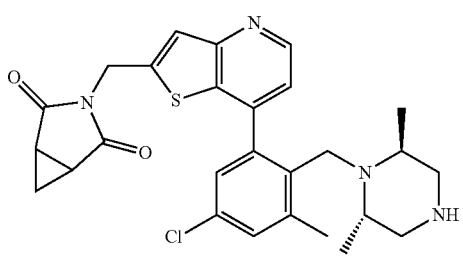 [SMILES: Cc1cc(Cl)cc(-c2ccnc3cc(CN4C(=O)C5CC5C4=O)sc23)c1CN1[C@@H](C)CNC[C@@H]1C]

or a pharmaceutically acceptable salt thereof.

In another embodiment, the compound is 3-((4-(5-chloro-2-(((2S,6S)-2,6-dimethylpiperazin-1-yl)methyl)-3-methylphenyl)thieno[3,2-d]pyrimidin-6-yl)methyl)-3-azabicyclo[3.1.0]hexane-2,4-dione having the chemical structure:

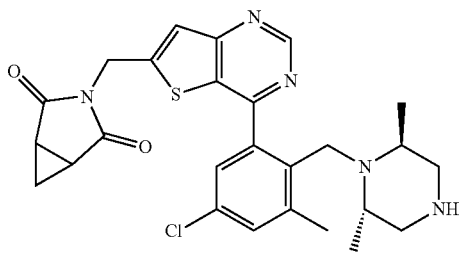 [SMILES: Cc1cc(Cl)cc(-c2ncnc3cc(CN4C(=O)C5CC5C4=O)sc23)c1CN1[C@@H](C)CNC[C@@H]1C]

or a pharmaceutically acceptable salt thereof.

In another embodiment, the compound is 3-((7-(5-chloro-3-methyl-2-(((R)-morpholin-2-yl)methyl)phenyl)thieno[3,2-b]pyridin-2-yl)methyl)-6,6-dimethyl-3-azabicyclo[3.1.0]hexane-2,4-dione having the chemical structure:

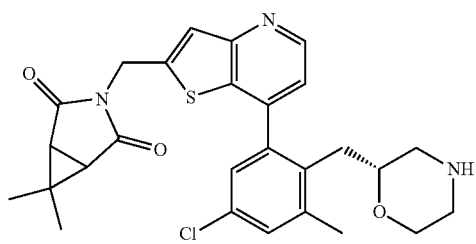 [SMILES: Cc1cc(Cl)cc(-c2ccnc3cc(CN4C(=O)C5C(C4=O)C5(C)C)sc23)c1C[C@@H]1CNCCO1]

or a pharmaceutically acceptable salt thereof.

In another embodiment, the compound is 3-((4-(5-chloro-2-(((R)-6,6-dimethylmorpholin-2-yl)methyl)-3-methylphenyl)thieno[3,2-d]pyrimidin-6-yl)methyl)-3-azabicyclo[3.1.0]hexane-2,4-dione having the chemical structure:

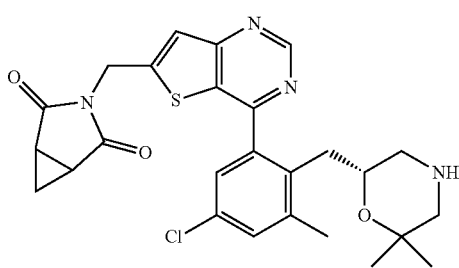 [SMILES: Cc1cc(Cl)cc(-c2ncnc3cc(CN4C(=O)C5CC5C4=O)sc23)c1C[C@@H]1CNCC(C)(C)O1]

or a pharmaceutically acceptable salt thereof.

In another embodiment, the compound is (R)-3-((4-(5-chloro-2-((6,6-dimethylmorpholin-2-yl)methyl)-3-methylphenyl)thieno[3,2-d]pyrimidin-6-yl)methyl)-1-methylpyrimidine-2,4(1H,3H)-dione having the chemical structure:

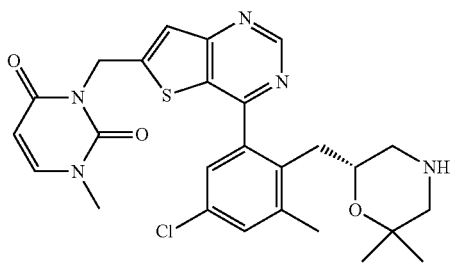

or a pharmaceutically acceptable salt thereof.

In another embodiment, the compound is (R)-3-((4-(5-chloro-2-((6,6-dimethylmorpholin-2-yl)methyl)-3-methylphenyl)thieno[3,2-d]pyrimidin-6-yl)methyl)-1-(2,2,2-trifluoroethyl)dihydropyrimidine-2,4(1H,3H)-dione having the chemical structure:

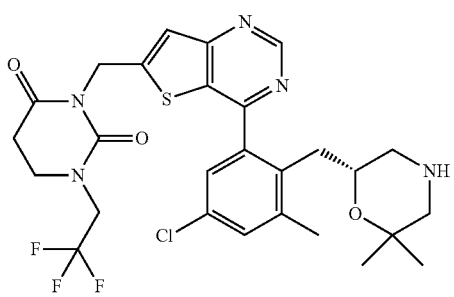

or a pharmaceutically acceptable salt thereof.

In another embodiment, the compound is (R)-3-((4-(5-chloro-2-((6,6-dimethylmorpholin-2-yl)methyl)-3-methylphenyl)thieno[3,2-d]pyrimidin-6-yl)methyl)-1-(2,2-difluoroethyl)dihydropyrimidine-2,4(1H,3H)-dione having the chemical structure:

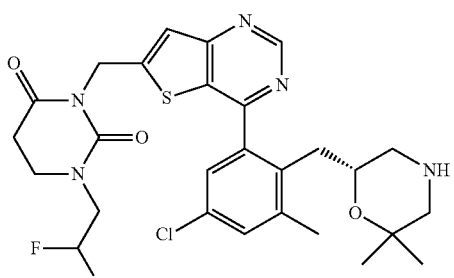

or a pharmaceutically acceptable salt thereof.

In another embodiment, the compound is 3-((4-(3,5-dichloro-2-((6,6-dimethylmorpholin-2-yl)methyl)phenyl)thieno[3,2-d]pyrimidin-6-yl)methyl)-1-methylpyrimidine-2,4(1H,3H)-dione having the chemical structure:

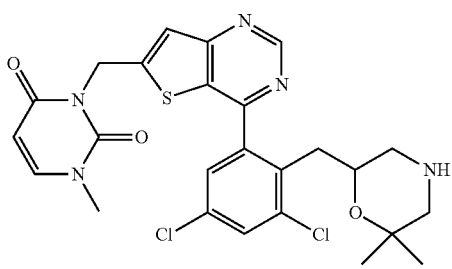 [SMILES: Cn1ccc(=O)n(Cc2cc3ncnc(-c4cc(Cl)cc(Cl)c4CC4CNCC(C)(C)O4)c3s2)c1=O]

or a pharmaceutically acceptable salt thereof.

In another embodiment, the compound is 3-[[4-[5-chloro-2-[[(2R)-6,6-dimethylmorpholin-2-yl]methyl]-3-methyl-phenyl]thieno[3,2-d]pyrimidin-6-yl] methyl]-1-(2-fluoro-ethyl)hexahydropyrimidine-2,4-dione having the chemical structure:

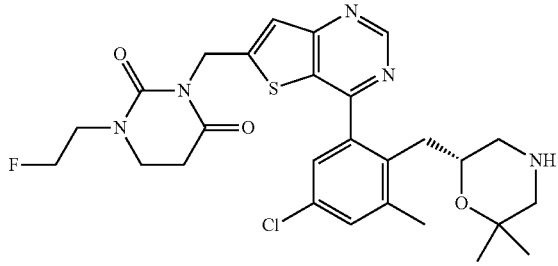 [SMILES: Cc1cc(Cl)cc(-c2ncnc3cc(CN4C(=O)CCN(CCF)C4=O)sc23)c1C[C@@H]1CNCC(C)(C)O1]

or a pharmaceutically acceptable salt thereof.

In another embodiment, the compound is 3-[[4-[5-chloro-2-[[(2S,6S)-2,6-dimethylpiperazin-1-yl]methyl]-3-methyl-phenyl]thieno[3,2-d]pyrimidin-6-yl]methyl]-1-(2-fluoro-ethyl)hexahydropyrimidine-2,4-dione having the chemical structure:

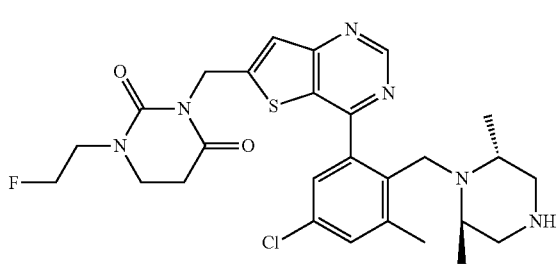 [SMILES: Cc1cc(Cl)cc(-c2ncnc3cc(CN4C(=O)CCN(CCF)C4=O)sc23)c1CN1[C@H](C)CNC[C@H]1C]

or a pharmaceutically acceptable salt thereof.

In another embodiment, the compound is 3-[[4-[5-chloro-2-[[(2S,6S)-2,6-dimethylpiperazin-1-yl]methyl]-3-methyl-phenyl]thieno[3,2-d]pyrimidin-6-yl]methyl]-1-(2,2-difluoroethyl)hexahydropyrimidine-2,4-dione having the chemical structure:

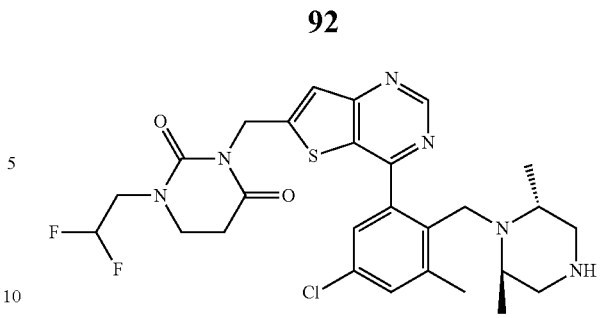

or a pharmaceutically acceptable salt thereof.

In another embodiment, the compound is 3-[[4-[5-chloro-2-[[(2S,6S)-2,6-dimethylpiperazin-1-yl]methyl]-3-methyl-phenyl]thieno[3,2-d]pyrimidin-6-yl]methyl]-1-(2,2,2-trifluoroethyl)hexahydropyrimidine-2,4-dione having the chemical structure:

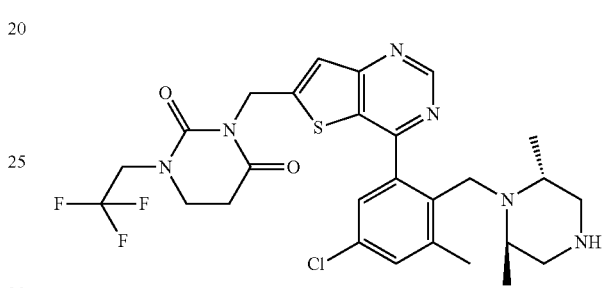

or a pharmaceutically acceptable salt thereof.

In another embodiment, the compound is 3-((7-(5-chloro-2-(((R)-6,6-dimethylmorpholin-2-yl)methyl)-3-methylphenyl)thieno[3,2-b]pyridin-2-yl)methyl)-3-azabicyclo[3.1.0]hexane-2,4-dione having the chemical structure:

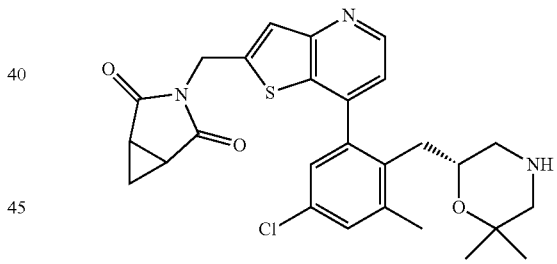

or a pharmaceutically acceptable salt thereof.

In another embodiment, the compound is (R)-1-((4-(5-chloro-2-((6,6-dimethylmorpholin-2-yl)methyl)-3-methylphenyl)thieno[3,2-d]pyrimidin-6-yl)methyl)pyrrolidine-2,5-dione having the chemical structure:

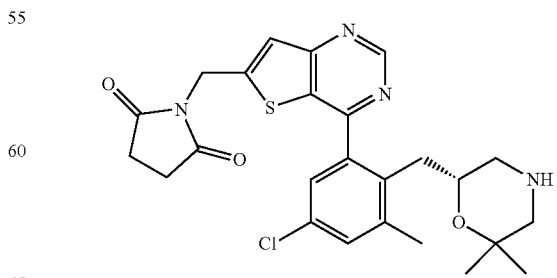

or a pharmaceutically acceptable salt thereof.

In another embodiment, the compound is (R)-3-((4-(5-chloro-2-((6,6-dimethylmorpholin-2-yl)methyl)-3-methylphenyl)thieno[3,2-d]pyrimidin-6-yl)methyl)-1-methyldihydropyrimidine-2,4(1H,3H)-dione having the chemical structure:

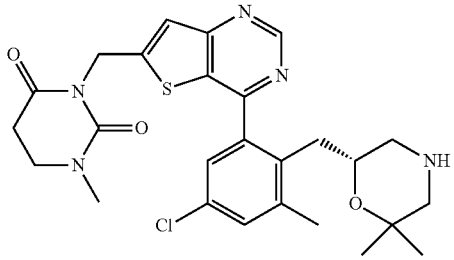 [SMILES: Cc1cc(Cl)cc(-c2ncnc3cc(CN4C(=O)CCN(C)C4=O)sc23)c1C[C@@H]1CNCC(C)(C)O1]

or a pharmaceutically acceptable salt thereof.

In another embodiment, the compound is 3-((7-(5-chloro-2-(((R)-6,6-dimethylmorpholin-2-yl)methyl)-3-methylphenyl)thieno[3,2-b]pyridin-2-yl)methyl)-3-azabicyclo[3.1.0]hexane-2,4-dione having the chemical structure:

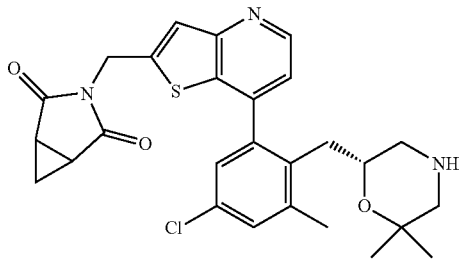 [SMILES: Cc1cc(Cl)cc(-c2ccnc3cc(CN4C(=O)C5CC5C4=O)sc23)c1C[C@@H]1CNCC(C)(C)O1]

or a pharmaceutically acceptable salt thereof.

(R)-1-((4-(5-chloro-2-((6,6-dimethylmorpholin-2-yl)methyl)-3-methylphenyl)thieno[3,2-d]pyrimidin-6-yl)methyl)pyrrolidine-2,5-dione having the chemical structure:

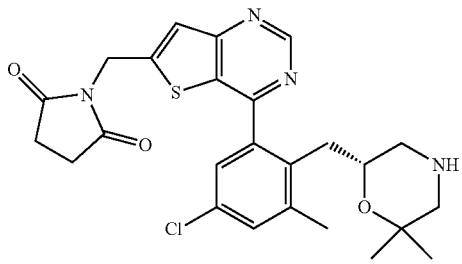

or a pharmaceutically acceptable salt thereof.

(R)-3-((4-(5-chloro-2-((6,6-dimethylmorpholin-2-yl)methyl)-3-methylphenyl)thieno[3,2-d]pyrimidin-6-yl)methyl)-1-methyldihydropyrimidine-2,4(1H,3H)-dione having the chemical structure:

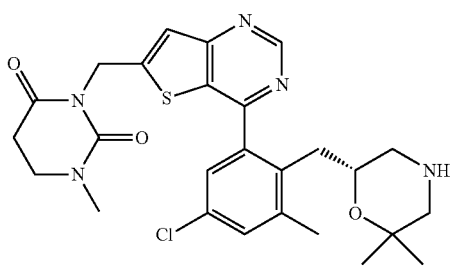 [SMILES: Cc1cc(Cl)cc(-c2ncnc3cc(CN4C(=O)CCN(C)C4=O)sc23)c1C[C@@H]1CNCC(C)(C)O1]

or a pharmaceutically acceptable salt thereof.

III. Pharmaceutical Compositions

In an aspect, there is provided a pharmaceutical composition, including a compound as described herein, including embodiments (e.g., structural Formulae (I), (Ia), (Ib), (IIa), (IIb), (IIc), (IId), (IIe) and (IIf)), and a pharmaceutically acceptable excipient.

The compounds as described herein of the present disclosure may be in the form of compositions suitable for administration to a subject. In general, such compositions are "pharmaceutical compositions" comprising a compound (e.g., compounds described herein) and one or more pharmaceutically acceptable or physiologically acceptable excipients (e.g., acceptable diluents or carriers). In certain embodiments, the compounds are present in a therapeutically effective amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein.

The pharmaceutical compositions containing the active ingredient (e.g., an inhibitor of USP7 function, or a compound described herein) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture thereof. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a compound described herein contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer; N-(2-Hydroxyethyl)piperazine-N'-(2-ethanesulfonic acid) (HEPES); 2-(N-Morpholino)ethanesulfonic acid (MES); 2-(N-Morpholino)ethanesulfonic acid sodium salt (MES); 3-(N-Morpholino)propanesulfonic acid (MOPS); and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver a USP7 inhibitor, including implants (e.g., implantable pumps) and catheter systems, slow injection pumps and devices, all of which are well known to the skilled artisan.

Depot injections, which are generally administered subcutaneously or intramuscularly, may also be utilized to release a compound disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, N.J.) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin).

The present disclosure contemplates the administration of the compounds described herein in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The compounds described herein contemplated by the present disclosure may be in the form of any other suitable pharmaceutical composition (e.g., sprays for nasal or inhalation use) currently known or developed in the future.

IV. Methods of Use

In another aspect, there is provided a method of inhibiting ubiquitin-specific-processing protease 7 (USP7), the method including contacting USP7 with a compound as described herein, including embodiments (e.g., structural Formulae (I), (Ia), (Ib), (IIa), (IIb), (IIc), (IId), (IIe), or (IIf)), or a pharmaceutically acceptable salt thereof.

In an aspect, there is provided a method of treating or preventing a USP7-mediated disease or disorder, including administering to a patient in need thereof a therapeutically effective amount of a compound or pharmaceutical composition as described herein, including embodiments (e.g., structural Formulae (I), (Ia), (Ib), (IIa), (IIb), (IIc), (IId), (IIe), or (IIf)) or a pharmaceutically acceptable salt thereof.

In embodiments, USP7-mediated disease or disorder is an immune disorder, a cardiovascular disease, a viral infection, inflammatory disease (e.g., inflammation), a metabolism/endocrine disorder or a neurological disorder. In embodiments, USP7-mediated disease or disorder is an immune disorder. In embodiments, USP7-mediated disease or disorder is a cardiovascular disease. In embodiments, USP7-mediated disease or disorder is a viral infection. In embodiments, USP7-mediated disease or disorder is inflammatory disease (e.g., inflammation). In embodiments, USP7-mediated disease or disorder is a metabolism/endocrine disorder. In embodiments, USP7-mediated disease or disorder is a neurological disorder.

In embodiments, the USP7-mediated disease or disorder is cancer. In certain embodiments, the cancer includes, but is not limited to, breast cancer, ovarian cancer, cervical cancer, prostate cancer, cancer of the testes, genitourinary tract cancer, cancer of the esophagus, cancer of the larynx, glioblastoma, neuroblastoma, stomach cancer, skin cancer, keratoacanthoma, lung cancer, epidermoid carcinoma, large cell carcinoma, non-small cell lung carcinoma (NSCLC), small cell carcinoma, lung adenocarcinoma, bone cancer, colon cancer, adenoma, pancreatic cancer, adenocarcinoma, thyroid cancer, follicular carcinoma, undifferentiated carcinoma, papillary carcinoma, seminoma, melanoma, sarcoma, bladder carcinoma, liver carcinoma and biliary passages, kidney carcinoma, lymphoma, cancer of the pharynx, cancer of the lip, cancer of the tongue, cancer of the mouth, cancer of the small intestine, colorectal cancer, cancer of the large intestine, rectal cancer, brain cancer Hodgkin's, leukemia, cancer of the bronchus, cancer of the thyroid, liver cancer, intrahepatic bile duct cancer, gastric cancer, glioma/glioblastoma, endometrial cancer, melanoma, kidney cancer, renal cancer, pelvic cancer, urinary bladder cancer, multiple myeloma, acute myelogenous leukemia, chronic myelogenous leukemia, lymphocytic leukemia, chronic lymphoid leukemia (CLL), myeloid leukemia, cancer of the oral cavity and pharynx, non-Hodgkin lymphoma, melanoma or villous colon adenoma.

In embodiments, a method of treating a USP7-mediated cancer by administering to a patient in need thereof a therapeutically effective amount of a compound or pharmaceutical composition as described herein, including embodiments (e.g., structural Formulae (I), (Ia), (Ib), (IIa), (IIb), (IIc), or (IId)), or a pharmaceutically acceptable salt thereof, further includes administering to the patient a chemotherapeutic agent in combination with the compound as described herein.

In embodiments, the disease or disorder is inflammatory bowel disease. In embodiments, the disease or disorder is rheumatoid arthritis. In embodiments, the disease or disorder is psoriasis. In embodiments, the disease or disorder includes allergy-related disorders (e.g., hypersensitivity and anaphylactic responses); gastrointestinal disorders (e.g., Crohn's disease, ulcerative colitis, ileitis and enteritis); psoriasis and inflammatory dermatoses (e.g., dermatitis, eczema, atopic dermatitis, allergic contact dermatitis, dermatomyositis, urticaria and pruritus); vasculitis; scleroderma; asthma, COPD, and respiratory allergic diseases (e.g., allergic rhinitis and hypersensitivity lung diseases); autoimmune diseases, including arthritis (e.g., rheumatoid and psoriatic), multiple sclerosis, systemic lupus erythematosus, type I diabetes and glomerulonephritis; graft rejection (e.g., allograft rejection); transplant rejection (e.g., solid organ); cancers, such as leukemias, lymphomas and metastatic cancers, particularly solid tumors (e.g., gastric cancers); and other diseases in which inhibition of undesired inflammatory and/or immune responses is desired, such as atherosclerosis, neurodegenerative diseases (e.g., Alzheimer's disease), encephalitis, meningitis, hepatitis, nephritis, sepsis, sarcoidosis, allergic conjunctivitis, otitis, and sinusitis. In particular embodiments, the USP7-mediated disease, disorder or condition is asthma, COPD, rhinitis, idiopathic pulmonary fibrosis, psoriasis and contact dermatitis. In embodiments the disease or disorder is pulmonary fibrosis, hepatic inflammation, asthma, atopic dermatitis, cancer (e.g., thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma), or granuloma development.

It is frequently beneficial to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity. Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

In embodiments, compounds of the present disclosure are effective in the treatment and prevention of IBD (e.g., Crohn's disease and ulcerative colitis, both of which are chronic idiopathic diseases that can affect any part of the gastrointestinal tract, and are associated with many untoward effects, and patients with prolonged ulcerative colitis are at an increased risk of developing colon cancer). Current IBD treatments are aimed at controlling inflammatory symptoms, and while certain agents (e.g., corticosteroids, aminosalicylates and standard immunosuppressive agents (e.g., cyclosporine, azathioprine, and methotrexate)) have met with limited success, long-term therapy may cause liver damage (e.g., fibrosis or cirrhosis) and bone marrow suppression, and patients often become refractory to such treatments.

The compounds of the present disclosure can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The compounds described herein can also be used to stimulate the immune system of patients suffering from iatrogenically-induced immune suppression, including those who have undergone bone marrow transplants, chemotherapy, or radiotherapy.

Oncology-related Disorders. In accordance with the present disclosure, a compound (e.g., a compound described herein) or pharmaceutical salt thereof can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The disclosure contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In some embodiments, the tumor or cancer is colon cancer, ovarian cancer, breast cancer, melanoma, lung cancer, glioblastoma, or leukemia. In particular embodiments, the cancer is gastric cancer. The use of the term(s) cancer-related diseases, disorders and conditions is meant to refer broadly to conditions that are associated, directly or indirectly, with cancer, and includes, e.g., angiogenesis and precancerous conditions such as dysplasia. In embodiments, the cancer is thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma.

In embodiments, a cancer be metastatic or at risk of becoming metastatic, or may occur in a diffuse tissue, including cancers of the blood or bone marrow (e.g., leukemia). In some further embodiments, the compounds of the disclosure can be used to overcome T-cell tolerance.

In some embodiments, the present disclosure provides methods for treating a proliferative condition, cancer, tumor, or precancerous condition with a compound described herein and at least one additional therapeutic or diagnostic agent, examples of which are set forth elsewhere herein.

The present disclosure provides methods for treating and/or preventing a proliferative condition, cancer, tumor, or precancerous disease, disorder or condition with a compound described herein.

The compounds disclosed herein have been found to inhibit the enhancer of zeste homolog 2 (EZH2), a histone-lysine N-methyltransferase enzyme encoded by EZH2 gene, that participates in histone methylation and, ultimately, transcriptional repression. EZH2 catalyzes the addition of methyl groups to histone H3 at lysine 27, by using the cofactor S-adenosyl-L-methionine. Methylation activity of EZH2 facilitates heterochromatin formation thereby silences gene function. Remodeling of chromosomal heterochromatin by EZH2 is also required during cell mitosis. EZH2 is the functional enzymatic component of the Polycomb Repressive Complex 2 (PRC2), which is responsible for healthy embryonic development through the epigenetic maintenance of genes responsible for regulating development and differentiation.

As EZH2 inhibitors, the compounds disclosed herein can be advantageously co-administered with a histone deacetylase (HDAC) inhibitor (HDAC is an enzyme that removes the acetyl group from histone proteins on DNA, making the DNA less accessible to transcription factors.), particularly in the treatment of EZH2-deregulated lymphomas.

As EZH2 inhibitors, the compounds disclosed herein can be co-administered with a proteasome inhibitor such as bortezomib, particularly in the treatment of multiple myeloma.

As EZH2 inhibitors, the compounds disclosed herein can be co-administered with a BET inhibitor, particularly in the treatment of diffuse intrinsic pontine gliomas (DIPG).

As EZH2 inhibitors, the compounds disclosed herein can be co-administered with a cisplatin or a B-cell lymphoma 2 (Bcl-2) inhibitor, particularly in the treatment of melanomas.

In embodiments drawn to methods of treating cancer, the administration of a therapeutically effective amount of a compound described herein results in a cancer survival rate greater than the cancer survival rate observed by not administering a therapeutically effective amount of the compound. In further embodiments drawn to methods of treating cancer, the administration of a therapeutically effective amount of a compound described herein results in a reduction of tumor size or a slowing of tumor growth greater than reduction of tumor size or tumor growth observed following lack of administration of a therapeutically effective amount of the compound.

CNS-related and Neurological Disorders. Inhibition of USP7 activity may also represent an important strategy for the treatment or prevention of neurological, neuropsychiatric, neurodegenerative or other diseases, disorders and conditions having some association with the central nervous system, including disorders associated with impairment of cognitive function and/or motor function. Many of these diseases, disorders and conditions include an immune and/or inflammatory component. In embodiments, the disease or disorder is Parkinson's disease, extra pyramidal syndrome (EPS), dystonia, akathisia, tardive dyskinesia, restless leg syndrome, epilepsy, periodic limb movement in sleep, attention deficit disorders, depression, anxiety, dementia, Alzheimer's disease, Huntington's disease, multiple sclerosis, cerebral ischemia, hemorrhagic stroke, subarachnoid hemorrhage, or traumatic brain injury.

Other Disorders. Embodiments of the present disclosure contemplate the administration of the compounds described herein to a subject for the treatment or prevention of any other disorder that may benefit from at least some level of USP7 modulation. Such diseases, disorders and conditions may include, for example, asthma, chronic obstructive pulmonary disease (COPD) including chronic bronchitis and emphysema, idiopathic pulmonary fibrosis, atopic or contact dermatitis, urticaria, allergic rhinitis, nasal polyps, allergic conjunctivitis, thrombosis, reperfusion injury of the myocardium and brain, chronic glomerulonephritis, sepsis, adult respiratory distress syndrome, and pain. Additional diseases, disorders and conditions include allergic bronchopulmonary aspergillosis, allergic fungal sinusitis, severe asthma with fungal sensitization and diseases involving a pathogenic role for fungi including invasion or colonization (such as invasive aspergillosis, aspergilloma or candidiasis).

In embodiments, the disease or disorder includes cardiovascular (e.g., cardiac ischemia), metabolic (e.g., development of insulititis diabetes), hepatic (e.g., hepatic fibrosis, NASH, and NAFLD), ophthalmologic (e.g., diabetic retinopathy), or renal (e.g., renal failure) disorders.

The present disclosure contemplates the administration of the compounds described herein, and compositions (e.g., pharmaceutical salts, pharmaceutical composition) thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the compounds disclosed herein over a defined period of time. In embodiments, the administration is oral administration.

Metabolic and Cardiovascular Diseases. The present disclosure provides methods for treating and/or preventing certain cardiovascular- and/or metabolic-related diseases, disorders and conditions, as well as disorders associated therewith, with a compound described herein.

The compounds of the present disclosure may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the compounds of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In embodiments, the compounds contemplated by the present disclosure may be administered (e.g., orally) at dosage levels of about 0.01 mg/kg to about 50 mg/kg, or about 1 mg/kg to about 25 mg/kg, of subject body weight per day, one, two, three, four or more times a day, to obtain the desired therapeutic effect. For administration of an oral agent, the compositions can be provided in the form of tablets, capsules and the like containing from 0.05 to 1000 milligrams of the active ingredient, particularly 0.05, 0.1, 0.25, 0.5, 0.75, 1.0, 1.25, 1.5, 1.75, 2.0, 2.5, 5.0, 7.5, 10.0, 15.0, 20.0, 25.0, 50.0, 75.0, 100.0, 125.0, 150.0, 175.0, 200.0, 250.0, 300.0, 400.0, 500.0, 600.0, 750.0, 800.0, 900.0, and 1000.0 milligrams of the active ingredient. A pharmaceutically acceptable carrier(s), diluent(s) and/or excipient(s) may be present in an amount of from about 0.1 g to about 2.0 g.

In embodiments, the dosage of the desired compound is contained in a "unit dosage form". The phrase "unit dosage form" refers to physically discrete units, each unit including a predetermined amount of a compound (e.g., a compound described herein), sufficient to produce the desired effect. It will be appreciated that the parameters of a unit dosage form will depend on the particular agent and the effect to be achieved.

V. Combination Therapy

The compounds described herein can be used in combination with one another, with other active agents known to be useful in treating cancer.

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer.

The compounds described herein can be used in combination with anti-cancer agents. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+ estrogen+progesterone; leuprorelin; levamisole; liarozole; linear polyamine analogue; lipophilic disaccharide peptide;

lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin Ii (including recombinant interleukin II, or rIL.sub.2), interferon alfa-2a; interferon alfa-2b; interferon alfa-n1; interferon alfa-n3; interferon beta-1a; interferon gamma-b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751

(Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

Additionally, the compounds described herein can be co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

The compounds disclosed herein may be co-administered with an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin); (ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride; (iii) an agent which inhibits cancer cell invasion (for example a metalloproteinase inhibitor like marimastat or an inhibitor of urokinase plasminogen activator receptor function); (iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazoli-n-4-amine (gefitinib, AZD 1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazoli-n-4-amine (CI 1033)), an inhibitor of the platelet-derived growth factor family, or an inhibitor of the hepatocyte growth factor family; (v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin .alpha.v.beta.3 function or an angiostatin); (vi) a vascular damaging agent such as combretastatin A4, or a compound disclosed in WO 99/02166, WO 00/40529, WO 00/41669, WO 01/92224, WO 02/04434 or WO 02/08213; (vii) an agent used in antisense therapy, for example one directed to one of the targets listed above, such as ISIS 2503, an anti-ras antisense; (viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In embodiments, the compounds disclosed herein can be co-administered with an antibody, such as a monoclonal antibody targeting B-Lymphocytes (such as CD20 (rituximab), MRA-aIL16R and T-Lymphocytes, CTLA4-Ig, HuMax 11-15) or antibody modulating Ig function such as anti-IgE (for example omalizumab).

In embodiments, treatment of cancer includes administration of an effective amount of at least two of the following: a USP7 inhibitor (e.g., compound described herein), an inhibitor of the PD-L1/PD-1 pathway, an inhibitor of CTLA-4, an agonistic antibody of CD137 (4-1BB). In some embodiments, the method may include the use of two or more combinations.

In embodiments, treatment of cancer includes an effective amount of at least two or more of the following: a USP7 inhibitor (e.g., compound described herein) and any combination of agent that may be an immune modulator such as, but not limited to, those listed in Table 1, or described herein (e.g., an anti-cancer agent). These immune modulators can be depleting antibodies, neutralizing antibodies, blocking antibodies, agonistic antibodies, small molecule modulators (inhibitors or stimulators) or small molecule analogs.

TABLE 1

| Target or Therapy | Examples of Agents | Regulatory Mechanism |
| --- | --- | --- |
| TIM-3 | TSR-022, MGB453 | Checkpoint-receptor |
| LAG-3 | BMS-986016, IMP321 | Checkpoint-receptor |

TABLE 1-continued

| Target or Therapy | Examples of Agents | Regulatory Mechanism |
| --- | --- | --- |
| B7-H3 | MGA271, MGD-009 | Checkpoint-receptor |
| TIGIT | RG-6058 | Checkpoint-receptor |
| BTLA | | Checkpoint-receptor |
| CD28 | AMG 557 | Checkpoint-receptor |
| CD40 | SEA-CD40, dacetuzumab, CP-870,893, Chi Lob 7/4, lucatumumab | Checkpoint-receptor |
| CD80 | galiximab | Checkpoint-receptor |
| GITR | INCAGN1876, TRX518 | Checkpoint-receptor |
| ICOS | MEDI-570 | Checkpoint-receptor |
| OX40 (CD134) | MEDI-6469, INCAGN1949, huMab OX40L | Checkpoint-receptor |
| NKG2A | monalizumab | Checkpoint-receptor |
| TGF-beta | Galunisertib, luspatercept, YH-14618, dalantercept, BG-00011, trabedersen, isth-0036, ace-083 | Cytokines |
| IL2 | NKTR-214, recombinant IL2, aldesleukin | Cytokines |
| IL12 | EGEN-001, NHS-IL12 | Cytokines |
| IL7 | Recombinant IL-7 | Cytokines |
| IL15 | NIZ-985, ALT-803 | Cytokines |
| IL21 | Recombinant IL-21, anti-CD20.IL21 | Cytokines |
| IL13 | Tralokinumab, dupilumab | |
| CSF1R | cabiralizumab | Cytokine |
| PI3K delta | INCB50465, idealisib, TGR-1202, AMG319 | Kinase |
| PI3K gamma | IPI-549 | Kinase |
| DNMT (DNA methyl transferase inhibitor) | Azacytidine, decitabine, guadecitabine | Epigenetic Regulator |
| HDAC (histone deacetylase) | Vorinostat, Panobinostat, belinostat, entinostat, mocetinostat, givinostat, chidamide, quisinostat, abexinostat, chr-3996, ar-42 | Epigenetic Regulator |
| Brd4 | INCN54329, INCB57643, birabresib, apabetalone, alvocidib, PLX-51107, FT-1101, RG-6146, AZD-8186, CPI-0610, JQ1 | Transcription regulator |
| HMT (histone methyl transferases) | | Epigenetic Regulator |
| LSD1 | INCB59872, IMG-7289, RG-6016, CC-90011, GSK-2879552, ORY-2001, 4SC-202, ORY-3001 | Epigenetic Regulator |
| TNFa | Recombinant TNFa, MEDI-1873, FPA-154, LKZ-145 | Cytokine |
| IL1 | Recombinant IL1 | Cytokine |
| IFNa | Recombinant interferon alpha-n1, Recombinant interferon alpha-2b, Recombinant interferon alpha-n3 | Cytokine |
| IFNb | Recombinant IFN beta-1a | Cytokine |
| IFNg | actimmune | Cytokine |
| STING | Cyclic di-nucleotides | Signaling Molecule |
| TLR | Poly I:C, IMO-2055, TMX-101, imiquimod, CpG, MGN1703, glucopyranosyl lipid A, CBLB502, BCG, HILTONOL, AMPLIGEN, MOTOLIMOD, DUK-CPG-001, AS15 | Pathogen Recognition Receptor |
| IL10 | Recombinant IL-10 | Cytokine |
| CCR2 | CCX140, CCX872, BMS-813160, CENICRIVIROC, CNTX-6970. PF-4136309, plozalizumab, INCB-9471, PF-04634817 | Chemokine |
| CCR5 | Maraviroc, PRO-140, BMS-813160, NIFEVIROC, OHR-118 | Chemokine |

TABLE 1-continued

| Target or Therapy | Examples of Agents | Regulatory Mechanism |
|---|---|---|
| CXCR4 | Ulocuplumab, plerixafor, x4p-001, usl-311, ly-2510924, APH-0812, BL-8040, BURIXAFOR, BALIXAFORTIDE, PTX-9908, GMI-1359, F-50067 | Chemokine |
| LFA1 | | Adhesion Molecule |
| MICA/B | IPH-4301 | Immune Receptor Ligand |
| VISTA | CA-170 | Checkpoint-Ligand |
| Adenosine | ISTRADEFYLLINE, TOZADENANT, PBF-509, PBF-999, CPI-444 | Nucleoside |
| CD39 | OREG-103. Anti-CD39 antibodies, | Ecto-enzyme |
| CD73 | Oleclumab, PBF-1662, anti-CD73 antibodies | Ecto-Enzyme |
| PD1 | Pembrolizumab, nivolumab, INCSHR1210, CT-011, AMP224 | Checkpoint-receptor |
| PD-L1 | Atezolizumab, avelumab | Checkpoint-Ligand |
| PD-L2 | | Checkpoint-Ligand |
| CTLA4 | Tremelimumab | Checkpoint-receptor |
| CD137 | Urelumab, utomilumab, BMS-663513, PF-05082566 | |
| AXL | BGB-324, BPI-9016M, S-49076 | Kinase |
| MERTK | BGB-324, BPI-9016M, S-49076 | Kinase |
| TYRO | BGB-324, BPI-9016M, S-49076 | |
| BTK | ibrutinib | Kinase |
| ITK | ibrutinib | Kinase |
| LCK | | Kinase |
| TET2 | | Enzyme |
| Arginase | Cb-1158 | Endo/ecto enzyme |
| GCN2 | | Kinase |
| B7-H4 | MDX-1140, AMP-110 | Checkpoint-receptor |
| HIF1alpha | PT2385 | Transcription Factor |
| LIGHT (TNFSF14) | | TNF Superfamily |
| FLT3 | CDX-301, FLX925, quizartinib, gilteritinib, PKC412, midostaurin, crenolanib | Kinase |
| CD158 | Lirlumab, IPH-2101 | |
| CD47 | Anti-CD47, TTI-621, NI-1701, SRF-231, Effi-DEM, RCT-1938 | |
| IDO | Epacadostat, F287, BMS983205, GDC-0919, indoximod | |
| RORgamma | | |

VI. Kits

In another aspect, provided herein is a kit including a compound described herein or pharmaceutical compositions thereof. The kits are generally in the form of a physical structure housing various components, as described below, and may be utilized, for example, in practicing the methods described above.

A kit may include one or more of the compounds disclosed herein (e.g., provided in a sterile container), which may be in the form of a pharmaceutical composition suitable for administration to a subject. In embodiments, the compound has the structure of Formulae (I), (Ia), (Ib), (IIa), (IIb), (IIc), or (IId)), or a pharmaceutically acceptable salt thereof. The compounds described herein can be provided in a form that is ready for use (e.g., a tablet or capsule) or in a form requiring, for example, reconstitution or dilution (e.g., a powder) prior to administration. When the compound is in a form that needs to be reconstituted or diluted by a user, the kit may also include diluents (e.g., sterile water), buffers, pharmaceutically acceptable excipients, and the like, packaged with, or separately from, the compound. Each component of the kit may be enclosed within an individual container, and all of the various containers may be within a single package. A kit of the present disclosure may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Identification of USP7 Inhibitors

In embodiments, compounds described herein possess at least one property or characteristic that is of therapeutic relevance. Candidate inhibitors may be identified by using, for example, an art-accepted assay or model. The Example section described assay(s) that were used to determine the usp7 inhibitory activity of the compounds described herein, as well as assays that could be used to evaluate one or more characteristics of the compounds; the skilled artisan is aware of other procedures, assay formats, and the like that can be employed to generate data and information useful to assess the USP7 inhibitors described herein.

After identification, candidate inhibitors can be further evaluated by using techniques that provide data regarding characteristics of the inhibitors (e.g., pharmacokinetic parameters). Comparisons of the candidate inhibitors to a reference standard (which may the "best-of-class" of current inhibitors) are indicative of the potential viability of such candidates. USP7 inhibitors that can serve as reference or benchmark compounds include those shown to demonstrate desired activity and characteristics useful for analyzing candidate inhibitors which will be apparent to the skilled artisan.

Example A: Chemical Syntheses

Definition of abbreviations used: DCM=dichloromethane; DCE=dichloroethane; THF=tetrahydrofuran;

EtOAc=ethyl acetate; DMF=dimethylformamide; Na₂CO₃=sodium carbonate; MgSO₄=magnesium sulfate; Na₂SO₄=sodium sulfate; HCl=hydrochloric acid; TFA=trifluoroacetic acid; NH₄Cl=ammonium chloride; Boc₂O=Boc anhydride; MTBE=methyl t-butyl ether; DEAD=diethylazodicarboxylate; DIAD=diisopropylazodicarboxylate; NaOH=sodium hydroxide; NIS=N-iodosuccinimide; PBr₃=phosphorus tribromide; HPLC=high pressure liquid chromatography; rt=room temperature.

General Synthetic Schemes

General synthesis of morpholines via morpholinone addition

To a solution of compound 2 in a polar solvent such as THF is added a strong reducing agent such as borane-THF complex. The mixture is heated to between 50 and 100° C. for 2-24 h, cooled and quenched with an aqueous solution. The phases are separated and the organic phase concentrated to a residue which is purified by silica gel chromatography to give compounds of the general structure 3.

Compounds of general structure 4 may be made via Suzuki coupling. To a solution of borylated pyridine, where Z is a leaving group such as halogen, mesylate, triflate or toluenesulfonate. In particular embodiments Z is Br, and 3, a palladium source such as PdCl₂(PPh₃)₂ in a combination of organic solvents such as toluene/ethanol (1:1), and an aque-

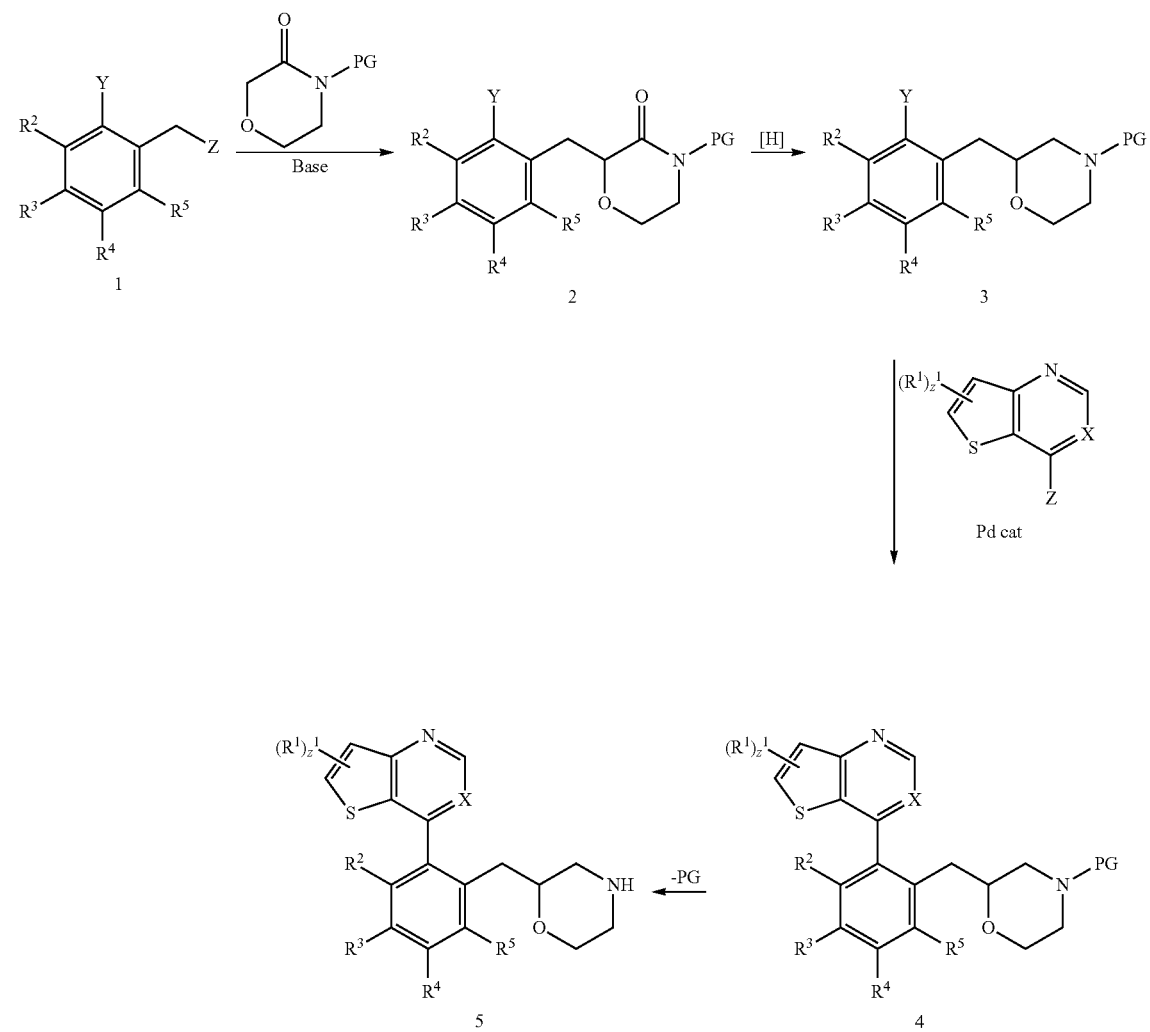

General Synthesis of Morpholines Via Epoxide Opening

To a solution of morpholinone in a polar solvent such as THF at low temperature is added a base such as lithium diisopropylamide followed by compound 1, where Y is a leaving group such as a halogen, mesylate, triflate or toluenesulfonate. In particular embodiments, Y is Br or I. The mixture is stirred overnight and partitioned between aqueous solution and an organic solvent such as EtOAc. The phases are separated and the organic phase concentrated to a residue which is purified by silica gel chromatography to give compounds of the general structure 2.

ous basic solution such as aq. sodium carbonate is stirred vigorously at 100° C. (2-24 h). The mixture is stirred overnight and partitioned between aqueous solution and an organic solvent such as EtOAc. The phases are separated and the organic phase concentrated to a residue which is purified by silica gel chromatography to give compounds of the general structure 4.

Compounds of general structure 4 where PG=t-butyloxycarbonyl (Boc) are exposed to a strong acid such as TFA or HCl, followed by concentration and purification via HPLC to afford compounds of general structure 5.

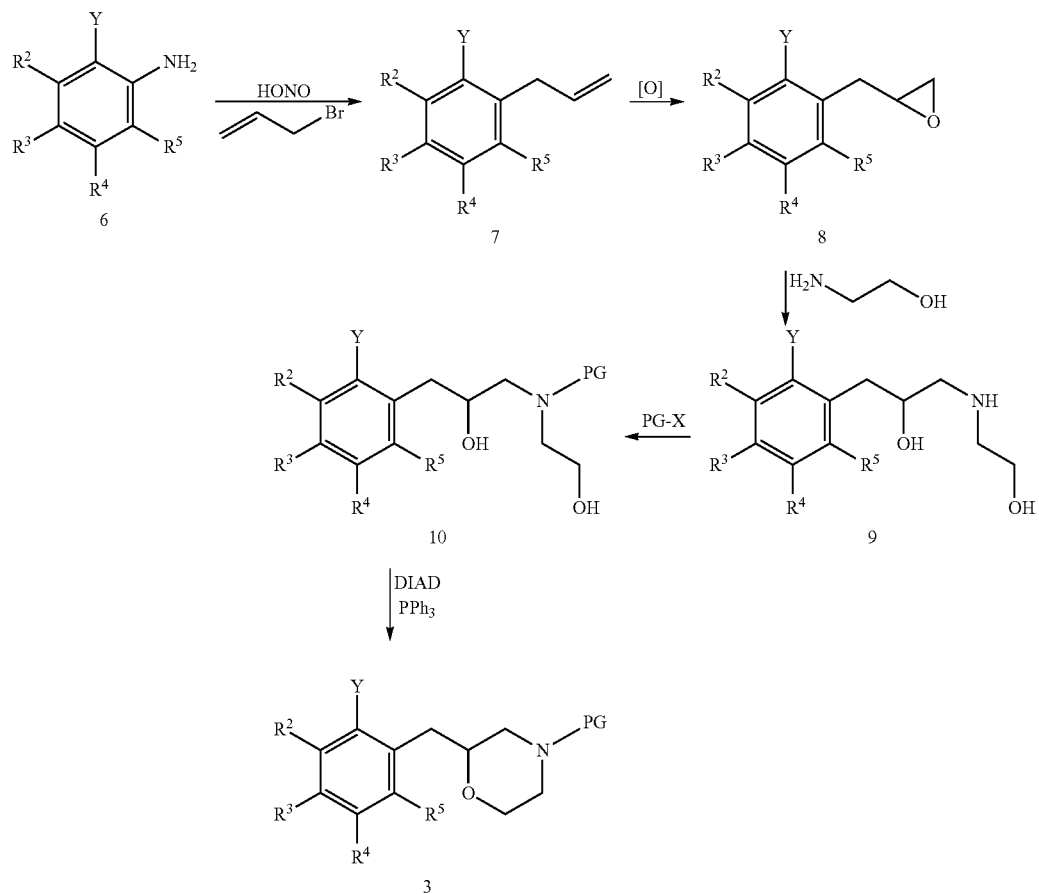

Compounds of general structure 3 may alternately be prepared from anilines of type 6 following nitroso formation with a reagent such as t-butyl nitrite and coupling with allyl bromide. Epoxidation in a polar solvent such as DCM with an oxidant such as m-chloroperbenzoic acid affords compounds of general structure 8. Epoxide opening occurs on exposure to ethanolamine, which is subsequently protected with $Boc_2O$ in DCM to give compounds of type 10. To a solution of compounds of general formula 10 in a polar solvent such as THF is added DEAD or DIAD and the mixture stirred overnight (rt or 50° C.). The solvent is removed and the crude residue purified by silica gel chromatography using a mixture of organic solvents for example a mixture of EtOAc and hexanes to give compounds of the general formula 3.

Piperazine Thienopyridine

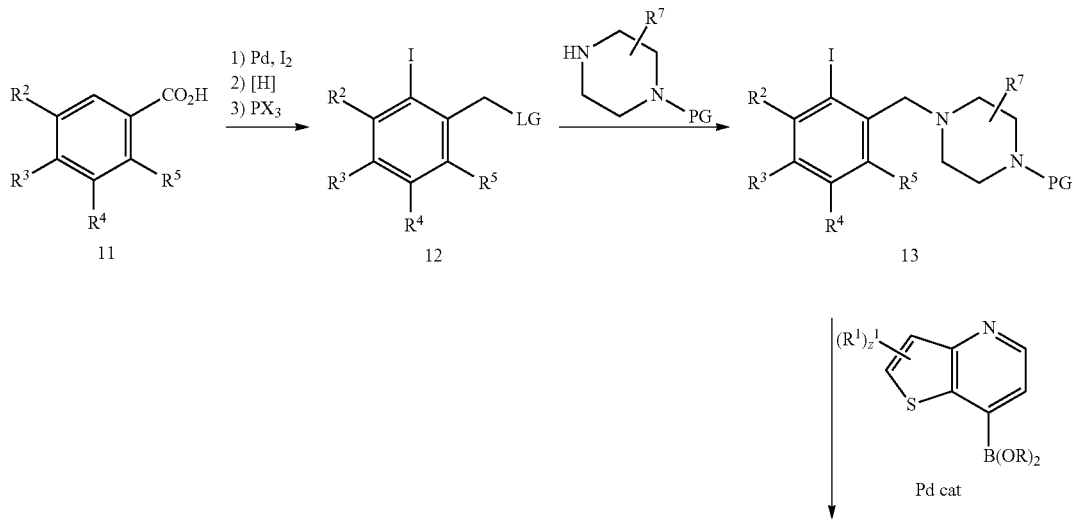

-continued

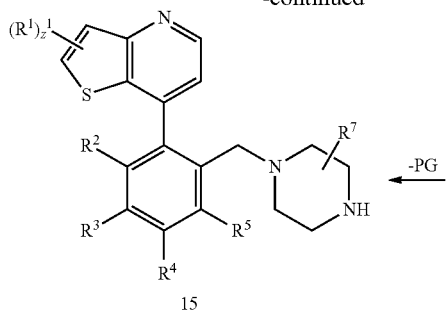

15

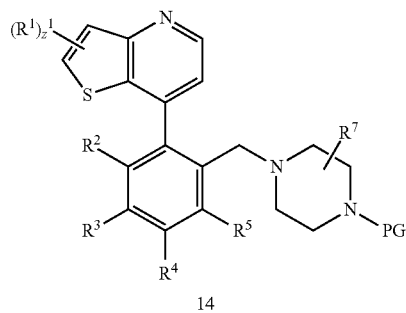

14

Benzoic acids of type 11 are halogenated by treatment with a reagent such as NIS in a polar solvent such as DMF and a palladium source such as palladium acetate at elevated temperature for 12-24 h. The mixture is stirred overnight and partitioned between aqueous solution and an organic solvent such as EtOAc. The phases are separated and the organic phase concentrated to a residue which is purified by silica gel chromatography to give the crude aryl halide which is treated with a strong reducing agent such as borane dimethylsulfide in a polar solvent such at THF. The mixture is heated to between 50 and 100° C. for 2-24 h, cooled and quenched with an aqueous solution. The phases are separated and the organic phase concentrated to a residue which is purified by silica gel chromatography to give compounds of the general structure 12 where LG=OH.

Benzyl alcohols of type 12 are halogenated in a polar solvent such as DCM by phosphorus tribromide (0° C. to rt).

The mixture is stirred overnight and partitioned between aqueous solution and an organic solvent such as EtOAc. The phases are separated and the organic phase concentrated to a residue. Meanwhile a substituted piperazine is treated with a strong base such as sodium hydride in a polar solvent such as DMF. The mixture is stirred for a short time at which the crude bromide 12 (LG=Br) is added. The mixture is stirred for 10-200 minutes and partitioned between aqueous solution and an organic solvent such as EtOAc. The phases are separated and the organic phase concentrated and purified by silica gel chromatography to give general structures 13. Suzuki coupling and Boc deprotection as described previously lead to formation of compounds of general structure 15.

Piperazine Thienopyrimidine

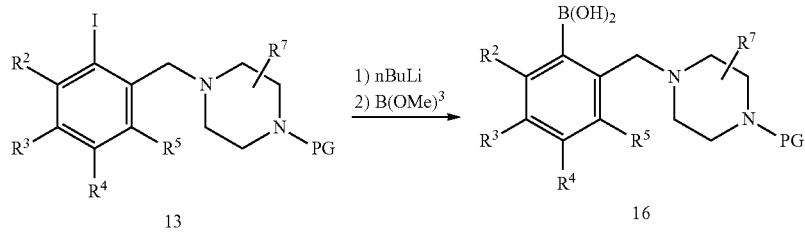

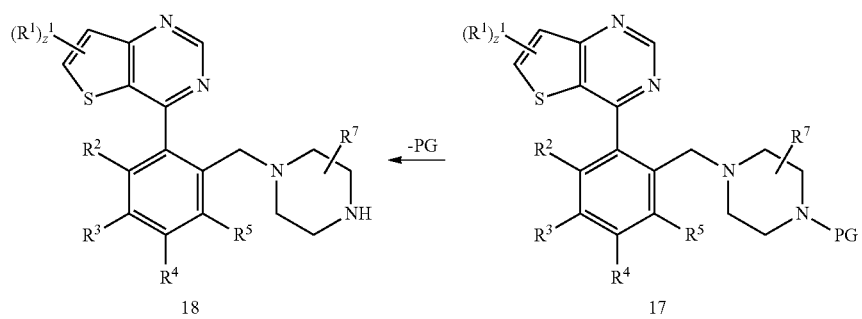

In a certain instance, compounds of general structure 18 may be made via Suzuki coupling. A solution of halobenzene of general structure 13, bis(pinacolato)diboron, a palladium source such as PdCl₂(dppf), and potassium acetate in an organic solvent such as dioxane is heated to 100° C. with stirring (2-4 h). The reaction mixture is cooled and partitioned between aqueous solution and an organic solvent such as EtOAc. The phases are separated and the organic phase concentrated to afford compounds of type 16 which is used directly in the next step.

To compounds of general structure 16 and chloropyrimidines, a palladium source such as PdCl₂(dppf) in a combination of organic solvents such as toluene/ethanol (1:1) and an aqueous basic solution such as aq. Na₂CO₃ is stirred vigorously at 100° C. (2-16 h). The reaction mixture is cooled and partitioned between aqueous solution and an organic solvent such as EtOAc. The phases are separated and the organic phase concentrated to a residue which is purified by silica gel chromatography to furnish compounds of general structure 18 after Boc deprotection.

General Procedure A

Preparation of Morpholine Coupling Partner Via Epoxide Opening

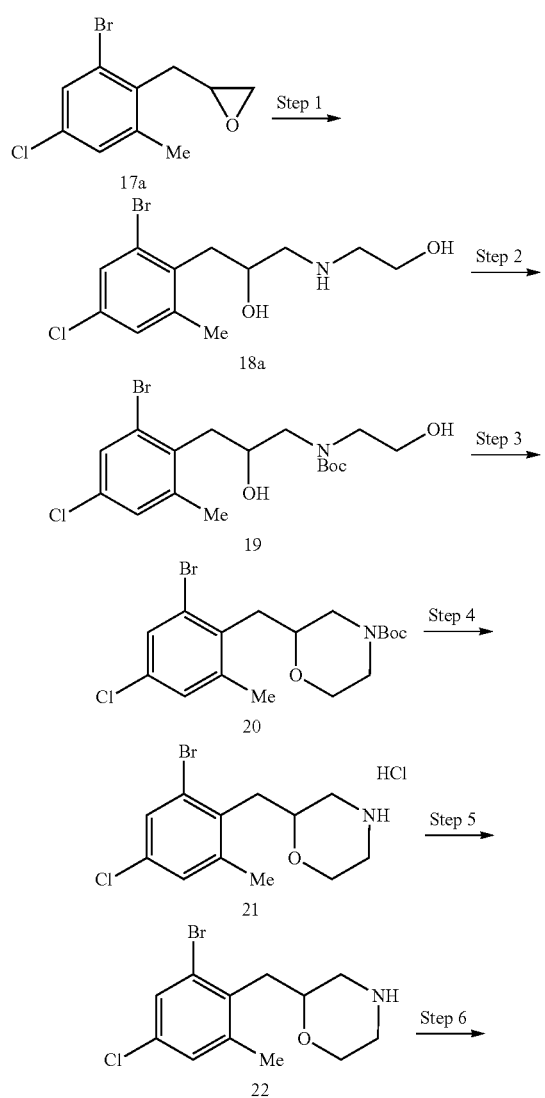

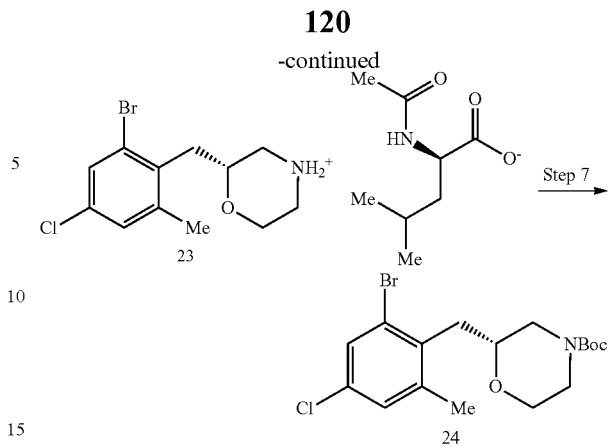

Step 1: Ethanolamine (30 mL) was added to 2-(2-bromo-4-chloro-6-methylbenzyl)oxirane (13 g, 49.7 mmol) in THF (30 mL). The mixture was stirred at 60° C. for 16 h and poured into 1 L of water and stirred for 1 h. The white solid was filtered and rinsed with water (400 mL) to provide 1-(2-bromo-4-chloro-6-methylphenyl)-3-((2-hydroxyethyl)amino)propan-2-ol.

Step 2: 1-(2-bromo-4-chloro-6-methylphenyl)-3-((2-hydroxyethyl)amino)propan-2-ol was suspended in 200 mL of THF and Boc₂O (16.3 g, 74 mmol) was added portionwise. Stirred at rt 1 h at which time imidazole (3.4 g, 49.7 mmol) was added and the solvent removed on the rotavap for 15 min at 40° C. The mixture was diluted in 50% EA/hexanes (400 mL) and rinsed 2 times with 1 M HCl (300 mL), brine (100 ml), dried over Na₂SO₄, and concentrated to afford tert-butyl (3-(2-bromo-4-chloro-6-methylphenyl)-2-hydroxypropyl)(2-hydroxyethyl)carbamate as a white solid (~19 g, 90%).

Step 3: tert-Butyl (3-(2-bromo-4-chloro-6-methylphenyl)-2-hydroxypropyl)(2-hydroxyethyl)carbamate (19 g, 44.8 mmol) was suspended in 250 mL of MTBE and warmed to 50° C. for 20 min to solubilize. The mixture was cooled to 0° C., at which time triphenylphosphine was added in one portion. When triphenylphosphine was all dissolved, DIAD was added dropwise over 15 min at 0° C. The reaction was stirred over night at rt and a solid precipitated over time. LCMS shows full conversion after 16 h. 1 L of hexane was added and the solid was filtered. The solution was concentrated and a thick gum was obtained. 500 mL of hexanes was added and the white solid was triturated. The solid was filtered and the solvent removed to afford tert-butyl 2-(2-bromo-4-chloro-6-methylbenzyl)morpholine-4-carboxylate as a light yellow solid (19 g, 105%).

Step 4: tert-Butyl 2-(2-bromo-4-chloro-6-methylbenzyl)morpholine-4-carboxylate (~19 g, 46 mmol) was dissolved in DCM (200 mL). 4 N HCl in dioxane (30 mL) was added and the reaction stirred at rt for 16 h. A white solid slowly formed over time. 200 mL of ether was added, and the reaction stirred for 15 min. Solid was filtered, rinsed with ether (50 mL) to give 2-(2-bromo-4-chloro-6-methylbenzyl)morpholine hydrochloride (9.1 g, 59% from epoxide).

Step 5: 2-(2-bromo-4-chloro-6-methylbenzyl)morpholine hydrochloride was dissolved in DCM and rinsed with 1 M NaOH. The organic phase was collected, dried with Na₂SO₄, and concentrated to provide 2-(2-bromo-4-chloro-6-methylbenzyl)morpholine as a colorless gum.

Step 6: 2-(2-Bromo-4-chloro-6-methylbenzyl)morpholine was dissolved in DCE (100 mg amine per 1 mL DCE). N-Ac-D-Leu (unnatural enantiomer, 0.5 eq) was added and the DCE solution stirred until the solution became homogeneous. Heptane (equal volume to DCE) was then added to the warm mixture and the solution was swirled until homogeneous. The solution was allowed to stand, cooling to room temperature. The mixture is allowed to stand overnight and the solid collected by filtration. The solid is returned to the original flask and dissolved in hot DCE (85-90° C., 100 mg amine per 1 mL DCE). The recrystallization procedure is repeated three more times to afford (R)-2-(2-bromo-4-chloro-6-methylbenzyl)morpholine Ac-D-Leu salt with >99% ee.

Step 7: To (R)-2-(2-bromo-4-chloro-6-methylbenzyl)morpholine Ac-D-Leu salt (5.55 g, 11.62 mmol) and triethylamine (4.84 mL, 34.9 mmol) in DCM (50 mL) was added Boc₂O (3.8 g, 17.4 mmol) followed by imidazole (1.19 g, 17.4 mmol). Stirred for 30 min, diluted with 1M HCl, and stirred vigorously. The phases were separated and the organic layer washed with water, 1M NaOH, dried, filtered, toluene added, concentrated to give (R)-2-(2-bromo-4-chloro-6-methylbenzyl)morpholine.

General Procedure B

Preparation of morpholine coupling partner via morpholinone addition

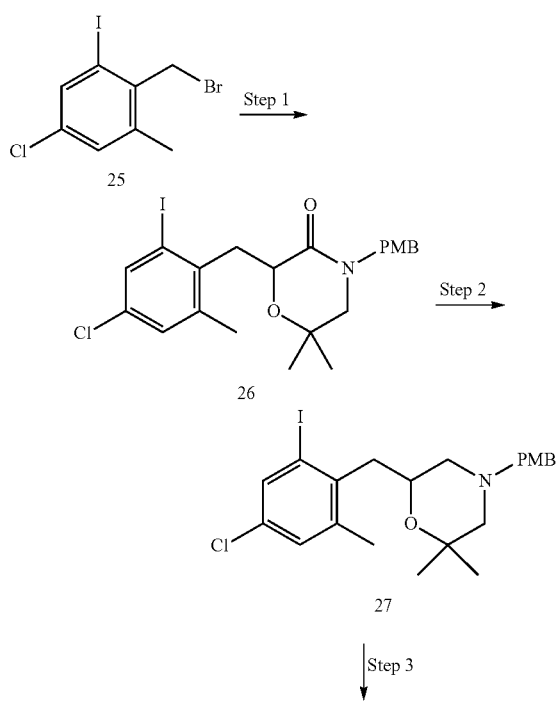

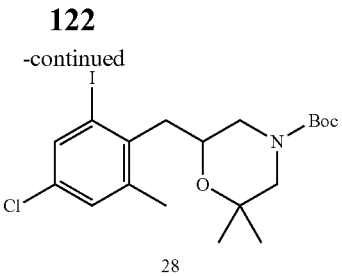

Step 1: To diisopropylamine (0.36 mL, 2.54 mmol) in THF (12 mL) at 0° C. was added n-butyllithium (1.01 mL, 2.54 mmol) dropwise and the solution was stirred at 0° C. for 45 min. The mixture was cooled to −78° C. at which time 4-[(4-methoxyphenyl)methyl]-6,6-dimethyl-morpholin-3-one (0.58 g, 2.31 mmol) in THF (5 mL) was added dropwise. Stirred at −78° C. for 1 h at which time 2-(bromomethyl)-5-chloro-1-iodo-3-methyl-benzene (1.2 g, 3.46 mmol) in THF (5 mL) was added dropwise. The mixture was allowed to warm to rt and stirred 16 h. Quenched with sat. aq. NH4Cl, extracted twice with EtOAc, dried over Na₂SO₄ and concentrated. Silica gel chromatography afforded 0.73 g (79%) of 2-(4-chloro-2-iodo-6-methylbenzyl)-4-(4-methoxybenzyl)-6,6-dimethylmorpholin-3-one.

Step 2: To 2-[(4-chloro-2-iodo-6-methyl-phenyl)methyl]-4-[(4-methoxyphenyl)methyl]-6,6-dimethyl-morpholin-3-one (0.93 g, 1.81 mmol) in THF (3 mL) was added borane tetrahydrofuran (2.0 M in THF, 2.72 mL, 5.44 mmol) dropwise. The mixture was stirred at 70° C. overnight, then cooled to 0° C. and quenched carefully with 1:1 THF/H₂O. Sat. aq. Rochelle's salt was added and the mixture vigorously stirred at rt. The mixture was extracted with EtOAc and purified by silica gel chromatography to furnish 0.80 g (88%) of 6-(4-chloro-2-iodo-6-methylbenzyl)-4-(4-methoxybenzyl)-2,2-dimethylmorpholine.

Step 3: To a solution of 6-[(4-chloro-2-iodo-6-methyl-phenyl)methyl]-4-[(4-methoxyphenyl)methyl]-2,2-dimethylmorpholine (0.29 g, 0.59 mmol) in DCE (5 mL) was added chloroethyl chloroformate (0.19 mL, 1.76 mmol). The mixture was stirred overnight and concentrated. Methanol (5 mL) was added and the mixture heated to 70° C. for 3 h. Cooled, concentrated, and purified by silica gel chromatography to afford 0.21 g (84%) which was protected with Boc as described in General procedure A to give tert-butyl 6-(4-chloro-2-iodo-6-methylbenzyl)-2,2-dimethylmorpholine-4-carboxylate.

General Procedure C

Formation of diamine coupling partner

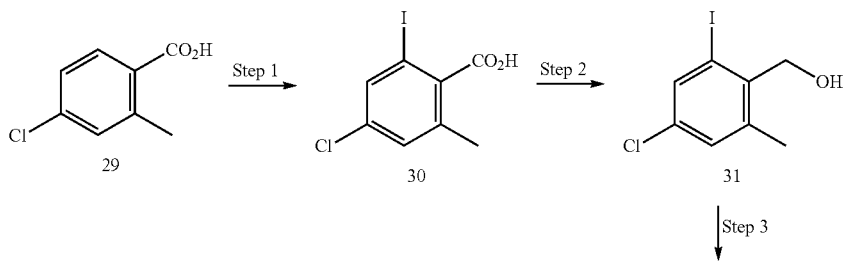

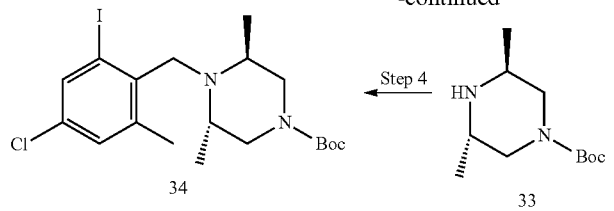 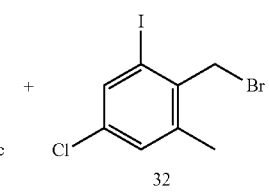

Step 1: 4-Chloro-2-methylbenzoic acid (100 g, 586 mmol) and NIS (158 g, 703 mmol) were dissolved in DMF (1 L, 0.6M) at which time Pd(OAc)₂ (13.2 g, 58.6 mmol) was added. The mixture was heated to 120° C. for 16 h, cooled, concentrated. The mixture was partitioned between EtOAc and water, and the organic phase washed with brine, dried over Na₂SO₄, and concentrated. The crude mixture was purified by silica gel chromatography to yield 4-chloro-2-iodo-6-methylbenzoic acid (51 g, 30%).

Step 2: To 4-chloro-2-iodo-6-methylbenzoic acid (51 g, 172 mmol) in THF (325 mL) at 0° C. was added borane DMS (34.4 mL, 344 mmol). The mixture was heated to 50° C. and stirred for 20 h. Upon completion, the mixture was cooled to 0° C. then quenched carefully with MeOH. The mixture was concentrated, and water was added to precipitate the product. The solid was purified by silica gel chromatography to furnish (4-chloro-2-iodo-6-methylphenyl)methanol (35.3 g, 73%).

Step 3: To (4-chloro-2-iodo-6-methylphenyl)methanol (35.3 g, 125 mmol) in DCM (410 mL) at 0° C. was added PBr₃ (23.6 mL, 250 mmol). The mixture was allowed to warm to room temperature and stirred 3 h. The mixture was cooled to 0° C. then quenched with sat. NaHCO₃. The layers were separated, and the aqueous layer extracted with DCM (3×200 mL). The combined organic layers were washed with brine, dried over Na₂SO₄, and concentrated to afford 2-(bromomethyl)-5-chloro-1-iodo-3-methylbenzene (38 g, 88%).

Step 4. To tert-butyl (3S,5S)-3,5-dimethylpiperazine-1-carboxylate (2.0 g, 9.33 mmol) in DMF (23 mL) was added sodium hydride (0.75 g, 18.7 mmol). The mixture was stirred for 5 min at which time 2-(bromomethyl)-5-chloro-1-iodo-3-methylbenzene (3.87 g, 11.2 mmol) was added. The mixture was stirred for 35 min and partitioned between sat. NH₄Cl (2 mL), H2O (3 mL), and 50% EtOAc/Hexane (15 mL). The organic layer was separated, concentrated and purified by silica gel chromotography to afford tert-butyl (3S,5S)-4-(4-chloro-2-iodo-6-methylbenzyl)-3,5-dimethylpiperazine-1-carboxylate as a colorless oil (3.6 g, 81%).

General Procedure D

Reductive amination of benzaldehyde

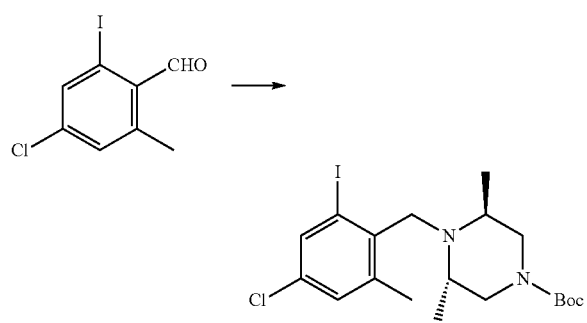

To a mixture of tert-butyl (3S,5S)-4-(4-chloro-2-iodo-6-methylbenzyl)-3,5-dimethylpiperazine-1-carboxylate (0.55 g, 2.57 mmol), 4-chloro-2-iodo-6-methyl-benzaldehyde (1.08 g, 3.85 mmol) in DCE (5 mL) and DMF (5 mL) was added sodium triacetoxyborohydride (0.82 g, 3.85 mmol) and the mixture heated to 70° C. for 3 d. Partitioned between EtOAc and sat. Na₂CO₃, dried, concentrated and purified by silica gel chromatography to afford tert-butyl (3S,5S)-4-(4-chloro-2-iodo-6-methylbenzyl)-3,5-dimethylpiperazine-1-carboxylate (0.50 g, 41%).

General Procedure E

Suzuki Coupling to Thienopyridine Boronate

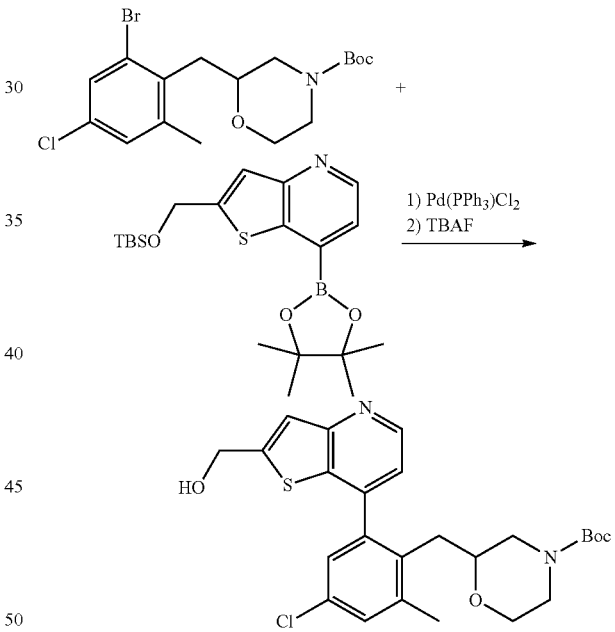

To tert-butyl-dimethyl-[[7-(4,4,5,5-tetramethyl-1,3,2-dioxaborolan-2-yl)thieno[3,2-b]pyridin-2-yl]methoxy]silane (0.39 g, 0.96 mmol) and 1 M sodium carbonate (2.2 mL, 2.2 mmol) in toluene (2.5 mL) and ethanol (2.5 mL) was added tert-butyl 2-[(2-bromo-4-chloro-6-methyl-phenyl)methyl]morpholine-4-carboxylate (0.30 g, 0.74 mmol) and bis(triphenylphosphine)palladium (II) chloride (52 mg, 0.07 mmol). Heated to 80° C. for 35 min. Partitioned between EtOAc and water, the organic phase was separated, dried, and concentrated. The crude material was purified by silica gel chromatography to provide 0.2 g of TBS protected material. The product was then dissolved in THF (8 mL), at which time tetrabutylammonium fluoride (0.89 mL, 0.89 mmol) was added and stirred at rt for 1 h. Concentration and silica gel chromatography furnished the desired product.

General Procedure F

Suzuki Coupling to Thienopyrimidine Chloride

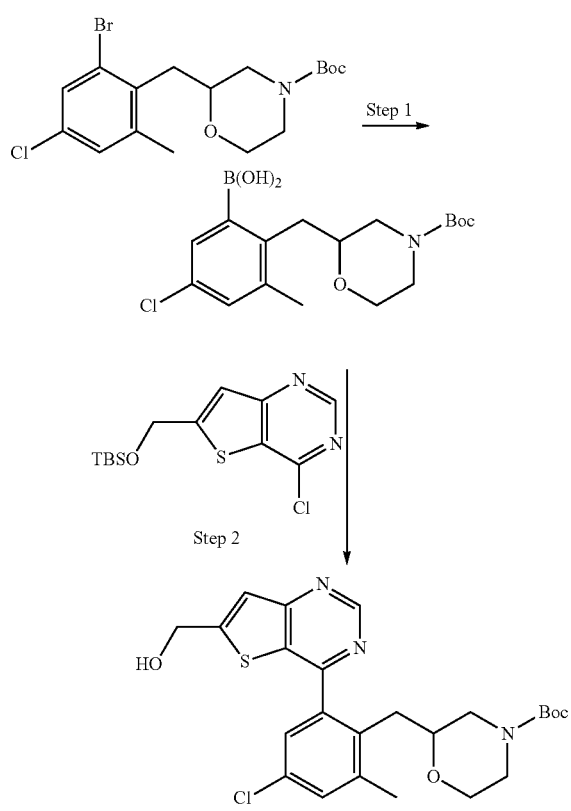

General Procedure G

Incorporation of the Sidechain Motif Via Displacement

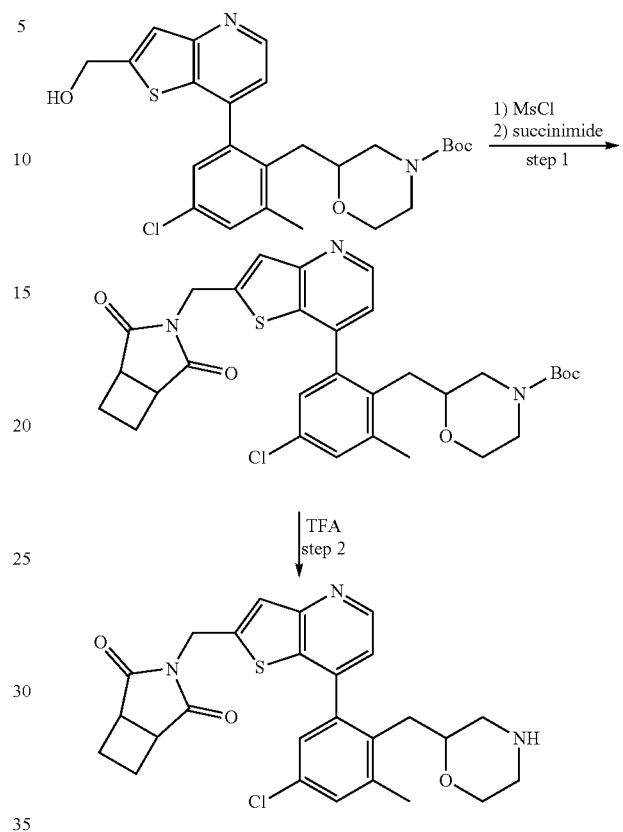

Step 1: A solution of tert-butyl 2-[(2-bromo-4-chloro-6-methyl-phenyl)methyl]morpholine-4-carboxylate (122. mg, 0.3000 mmol) in THF (1.508 mL) was cooled to −78° C. at which time n-butyllithium (0.13 mL, 0.33 mmol) was added dropwise. After stirring for 20 min, trimethyl borate (0.07 mL, 0.60 mmol) was added. The solution was allowed to slowly warm to rt, then stirred for 1 h. The reaction was quenched with 1 N HCl, then extracted with DCM and dried over MgSO$_4$.

Step 2: To tert-Butyl-[(4-chlorothieno[3,2-d]pyrimidin-6-yl)methoxy]-dimethyl-silane (0.11 g, 0.36 mmol) and 1,1'-bis(diphenylphosphino)ferrocene-palladium(II) dichloride (22 mg, 0.03 mmol) in toluene (1.2 mL) and ethanol (1.2 mL) was added 1 M sodium carbonate (1.2 mL, 1.19 mmol) and [2-[(4-tert-butoxycarbonylmorpholin-2-yl)methyl]-5-chloro-3-methyl-phenyl]boronic acid (0.11 g, 0.30 mmol). The mixture was heated to 80° C. for 35 min, then partitioned between iluted with EtOAc and water, the phases were separated, and the organic layer dried and concentrated. The crude material was purified by silica gel chromatography to give 0.11 g of TBS protected product. This was then dissolved in THF (3 mL), at which time tetrabutylammonium fluoride (0.36 mL, 0.36 mmol) was added and stirred at room temp for 1 hour. Concentration and purification by silica gel chromatography afforded 61 mg (41%) of the title compound.

Step 1: To a solution of tert-butyl 2-[[4-chloro-2-[2-(hydroxymethyl)thieno[3,2-b]pyridin-7-yl]-6-methyl-phenyl]methyl]morpholine-4-carboxylate (0.15 g, 0.30 mmol) in DCM (3 mL) was added N,N-diisopropylethylamine (0.15 mL, 0.89 mmol) followed by methanesulfonyl chloride (0.03 mL, 0.44 mmol). The mixture was stirred at rt for 2 h, diluted with DCM, and washed with 1 N HCl, sat aq. NaHCO$_3$, dried and concentrated. To 25 mg of the crude mesylate in acetonitrile (1 mL) was added cesium carbonate (48 mg, 0.15 mmol) and 3-azabicyclo[3.2.0]heptane-2,4-dione (19 mg, 0.15 mmol). The mixture was heated to 60° C. for 3 h, water (1 mL) was added followed by a few drops of TFA. Reverse phase HPLC afforded 22 mg of the desired product.

Step 2: To 22 mg of tert-butyl 2-(4-chloro-2-(2-((2,4-dioxo-3-azabicyclo[3.2.0]heptan-3-yl)methyl)thieno[3,2-b]pyridin-7-yl)-6-methylbenzyl)morpholine-4-carboxylate in DCM (1 mL) was added trifluoroacetic acid (0.08 mL, 0.99 mmol) and the mixture stirred at rt overnight. Concentrated to yield 31 mg of the title compound as the TFA salt.

General Procedure H

Incorporation of the sidechain motif via Mitsunobu

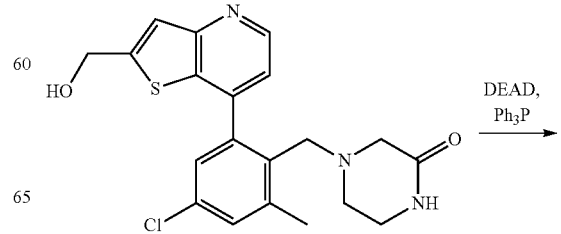

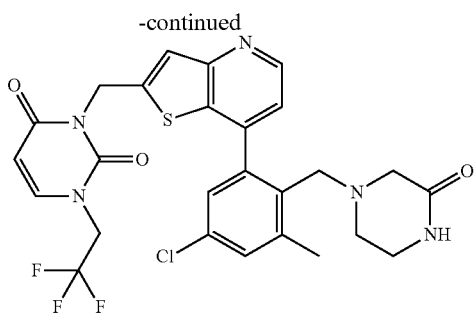

To 4-[[4-chloro-2-[2-(hydroxymethyl)thieno[3,2-b]pyridin-7-yl]-6-methyl-phenyl]methyl]piperazin-2-one (33 mg, 0.08 mmol) and 1-(2,2,2-trifluoroethyl)pyrimidine-2,4-dione (56 mg, 0.29 mmol) in THF (1 mL) was added triphenylphosphine (86 mg, 0.33 mmol) and DEAD (0.12 mL, 0.25 mmol). The mixture was stirred at 60° C. and then concentrated. Purification by reverse phase HPLC furnished 35 mg (53%) of the title compound. [M+H] 578.0

Example 1

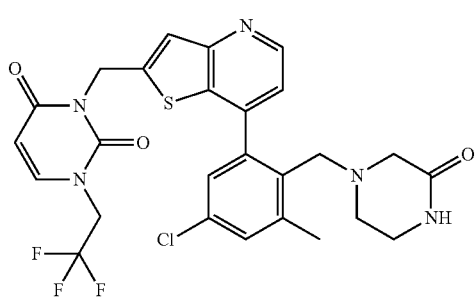 [SMILES: Cc1cc(Cl)cc(-c2ccnc3cc(Cn4c(=O)ccn(CC(F)(F)F)c4=O)sc23)c1CN1CCNC(=O)C1]

3-((7-(5-chloro-3-methyl-2-((3-oxopiperazin-1-yl)methyl)phenyl)thieno[3,2-b]pyridin-2-yl)methyl)-1-(2,2,2-trifluoroethyl)pyrimidine-2,4(1H,3H)-dione. The title compound was prepared by General Procedures D, E, and H. $^1$H NMR (400 MHz, Methanol-d4) δ 8.80 (bs, 1H), 7.68-7.46 (m, 6H), 7.24 (s, 1H), 5.83 (dd, J=21.2, 8.0 Hz, 2H), 5.42 (s, 2H), 4.62-4.53 (m, 4H), 2.86-2.67 (m, 4H), 2.53 (s, 3H). [M+H] 579.0

Example 2

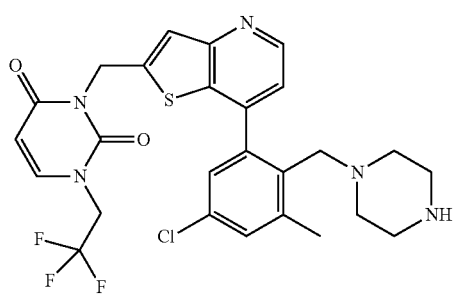 [SMILES: Cc1cc(Cl)cc(-c2ccnc3cc(Cn4c(=O)ccn(CC(F)(F)F)c4=O)sc23)c1CN1CCNCC1]

3-((7-(5-chloro-3-methyl-2-(piperazin-1-ylmethyl)phenyl)thieno[3,2-b]pyridin-2-yl)methyl)-1-(2,2,2-trifluoroethyl)pyrimidine-2,4(1H,3H)-dione. The title compound was prepared by General Procedures D, E, and H. $^1$H NMR (400 MHz, Methanol-d4) δ 9.00 (s, 1H), 8.01 (s, 1H), 7.89 (s, 1H), 7.68-7.58 (m, 2H), 7.43 (s, 1H), 5.89 (d, J=7.6 Hz, 1H), 5.50 (s, 2H), 4.66-4.59 (m, 2H), 3.22 (bs, 4H), 2.99 (bs, 4H), 2.66 (s, 3H). [M+H] 564.0

Example 3

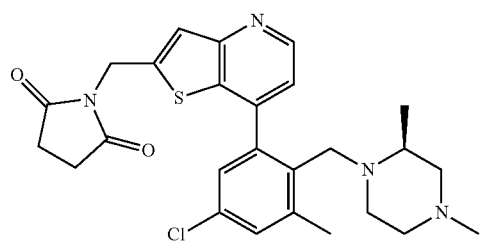 [SMILES: Cc1cc(Cl)cc(-c2ccnc3cc(CN4C(=O)CCC4=O)sc23)c1CN1CCN(C)C[C@@H]1C]

(S)-1-((7-(5-chloro-2-((2,4-dimethylpiperazin-1-yl)methyl)-3-methylphenyl)thieno[3,2-b]pyridin-2-yl)methyl)pyrrolidine-2,5-dione. The title compound was prepared by General Procedures D, E, and H. $^1$H NMR (400 MHz, Methanol-d4) δ 8.96 (d, J=4.8 Hz, 1H), 7.90 (s, 1H), 7.81 (m, 1H), 7.54 (m, 1H), 7.33 (m, 1H), 5.10 (s, 2H), 4.82 (s, 2H), 4.16 (m. 1H), 3.33 (s, 3H), 3.14 (m, 2H), 2.74 (m, 4H). 2.57 (s, 6H), 1.22 (m, 2H), 0.62 (m, 2H). [M+H] 497.0

Example 4

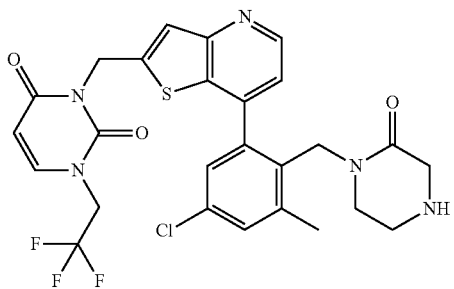 [SMILES: Cc1cc(Cl)cc(-c2ccnc3cc(Cn4c(=O)ccn(CC(F)(F)F)c4=O)sc23)c1CN1CCNCC1=O]

3-((7-(5-chloro-3-methyl-2-((2-oxopiperazin-1-yl)methyl)phenyl)thieno[3,2-b]pyridin-2-yl)methyl)-1-(2,2,2-trifluoroethyl)pyrimidine-2,4(1H,3H)-dione. The title compound was prepared by General Procedure C and E using 3-((7-(4,4,5,5-tetramethyl-1,3,2-dioxaborolan-2-yl)thieno[3,2-b]pyridin-2-yl)methyl)-1-(2,2,2-trifluoroethyl)pyrimidine-2,4(1H,3H)-dione. $^1$H NMR (400 MHz, Methanol-d4) δ 9.05 (bs, 1H), 7.66-7.49 (m, 5H), 7.25 (s, 1H), 5.89 (d, J=8.0 Hz, 1H), 5.42 (d, J=8.4 Hz, 2H), 4.65-4.33 (m, 3H), 3.60-3.39 (m, 2H), 3.26-3.07 (m, 4H), 2.44 (s, 3H). [M+H] 578.0

Example 5

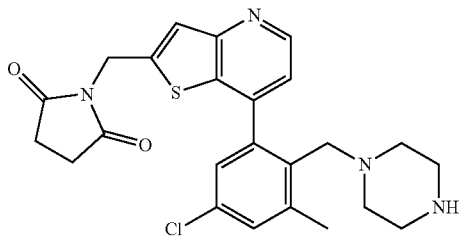 [SMILES: Cc1cc(Cl)cc(-c2ccnc3cc(CN4C(=O)CCC4=O)sc23)c1CN1CCNCC1]

1-((7-(5-chloro-3-methyl-2-(piperazin-1-ylmethyl)phenyl)thieno[3,2-b]pyridin-2-yl)methyl)pyrrolidine-2,5-dione. The title compound was prepared by General Procedures D, E, and H. $^1$H NMR (400 MHz, Methanol-d4) δ 8.99 (bs, 1H), 7.97 (s, 1H), 7.85 (s, 1H), 7.59 (s, 1H), 7.39 (s, 1H), 5.08 (s, 2H), 4.15 (bs, 1H), 3.71 (bs, 1H), 3.02 (bs, 4H), 2.78 (s, 4H), 2.68 (bs, 4H), 2.60 (s, 3H). [M+H] 469.0

Example 6

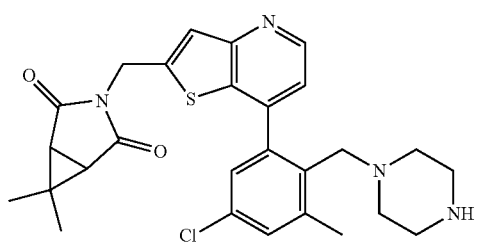 [SMILES: Cc1cc(Cl)cc(-c2ccnc3cc(CN4C(=O)C5C(C4=O)C5(C)C)sc23)c1CN1CCNCC1]

3-((7-(5-chloro-3-methyl-2-(piperazin-1-ylmethyl)phenyl)thieno[3,2-b]pyridin-2-yl)methyl)-6,6-dimethyl-3-azabicyclo[3.1.0]hexane-2,4-dione. The title compound was prepared by General Procedures D, E, and H. $^1$H NMR (400 MHz, Methanol-d4) δ 9.05 (bs, 1H), 8.01 (s, 1H), 7.85 (s, 1H), 7.59 (s, 1H), 7.37 (s, 1H), 4.98 (s, 2H), 4.00 (bs, 1H), 3.69 (bs, 1H), 3.05 (bs, 4H), 2.60 (s, 3H), 2.54 (s, 2H), 1.26 (s, 3H), 1.16 (s, 3H). [M+H] 509.0.

Example 7

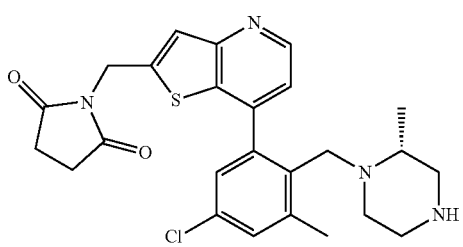 [SMILES: Cc1cc(Cl)cc(-c2ccnc3cc(CN4C(=O)CCC4=O)sc23)c1CN1CCNC[C@H]1C]

(R)-1-((7-(5-chloro-3-methyl-2-((2-methylpiperazin-1-yl)methyl)phenyl)thieno[3,2-b]pyridin-2-yl)methyl)pyrrolidine-2,5-dione. The title compound was prepared by General Procedures D, E, and H. $^1$H NMR (400 MHz, Methanol-d4) δ 8.87 (bs, 1H), 7.70 (s, 1H), 7.66 (s, 1H), 7.47 (s, 1H), 7.27 (s, 1H), 5.03 (s, 2H), 4.29-4.08 (m, 4H), 3.11-2.91 (m, 2H), 2.77 (s, 4H), 2.64-2.56 (m, 1H), 2.52 (s, 3H), 2.45-1.99 (m, 3H), 1.27 (d, J=7.2 Hz, 3). [M+H] 483.0

Example 8

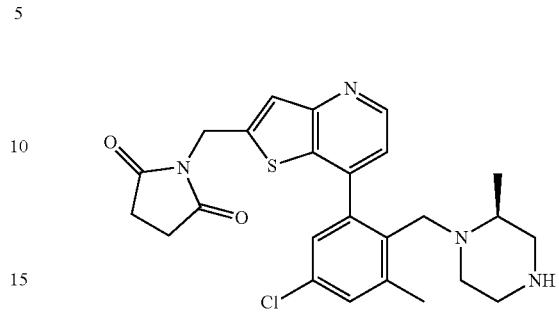

(S)-1-((7-(5-chloro-3-methyl-2-((2-methylpiperazin-1-yl)methyl)phenyl)thieno[3,2-b]pyridin-2-yl)methyl)pyrrolidine-2,5-dione. The title compound was prepared by General Procedures D, E, and H. $^1$H NMR (400 MHz, Methanol-d4) δ 8.87 (bs, 1H), 7.70 (s, 1H), 7.66 (s, 1H), 7.47 (s, 1H), 7.27 (s, 1H), 5.03 (s, 2H), 4.29-4.08 (m, 4H), 3.11-2.91 (m, 2H), 2.77 (s, 4H), 2.64-2.56 (m, 1H), 2.52 (s, 3H), 2.45-1.99 (m, 3H), 1.27 (d, J=7.2 Hz, 3H). [M+H] 483.0

Example 9

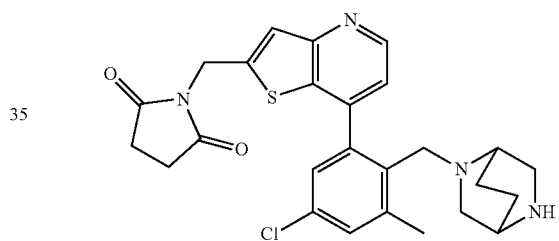

1-((7-(2-((2,5-diazabicyclo[2.2.2]octan-2-yl)methyl)-5-chloro-3-methylphenyl)thieno[3,2-b]pyridin-2-yl)methyl)pyrrolidine-2,5-dione. The title compound was prepared by General Procedures D, E, and H. $^1$H NMR (400 MHz, CD$_3$OD) δ 8.83 (dd, J=5.7, 3.1 Hz, 1H), 7.71 (d, J=7.5 Hz, 1H), 7.66 (d, J=5.5 Hz, 1H), 7.46 (d, J=2.2 Hz, 1H), 7.26 (d, J=2.1 Hz, 1H), 5.02 (s, 2H), 4.91-4.85 (m, 2H), 3.82-3.54 (m, 2H), 3.18-2.89 (m, 2H), 2.80-2.70 (m, 4H), 2.65-2.42 (m, 2H), 2.52 (s, 3H), 1.52-1.24 (m, 4H). [M+H] 495.1

Example 10

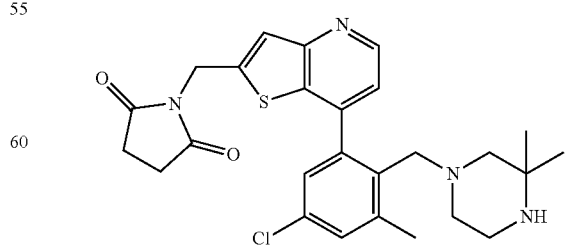

1-((7-(5-chloro-2-((3,3-dimethylpiperazin-1-yl)methyl)-3-methylphenyl)thieno[3,2-b]pyridin-2-yl)methyl)pyrrolidine-2,5-dione. The title compound was prepared by General Procedures D, E, and H. ¹H NMR (400 MHz, Methanol-d4) δ 8.67 (d, J=4.9 Hz, 1H), 7.51 (t, J=1.0 Hz, 1H), 7.45-7.39 (m, 1H), 7.34 (d, J=4.9 Hz, 1H), 7.20 (d, J=2.3 Hz, 1H), 4.95 (s, 2H), 3.61 (d, J=13.1 Hz, 1H), 3.34 (d, J=12.6 Hz, 1H), 3.08-2.75 (m, 6H), 2.52 (s, 3H), 2.12-2.01 (m, 4H), 1.13 (s, 3H), 0.86 (s, 3H). [M+H] 497.0

Example 11

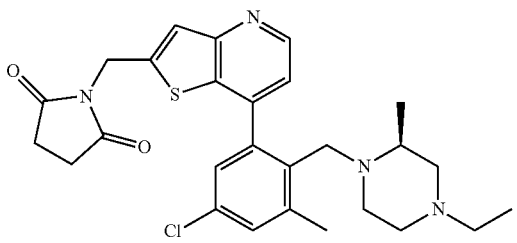 [SMILES: CCN1CCN(Cc2c(C)cc(Cl)cc2-c2ccnc3cc(CN4C(=O)CCC4=O)sc23)[C@@H](C)C1]

(S)-1-((7-(5-chloro-2-((4-ethyl-2-methylpiperazin-1-yl)methyl)-3-methylphenyl)thieno[3,2-b]pyridin-2-yl)methyl)pyrrolidine-2,5-dione. The title compound was prepared by General Procedures D, E, and H. ¹H NMR (400 MHz, Methanol-d4) δ 8.62 (d, J=4.8 Hz, 1H), 7.50 (s, 1H), 7.36 (d, J=2.3 Hz, 1H), 7.25 (t, J=4.6 Hz, 1H), 7.21-7.10 (m, 1H), 4.95 (s, 2H), 4.93 (s, 2H), 4.03-3.90 (m. 1H), 3.33 (s, 3H), 3.04 (m, 2H), 2.74 (m, 4H). 2.50 (s, 3H), 2.05 (m, 2H), 1.30 (m, 2H), 1.01 (m, 2H), 0.59 (m, 3H). [M+H] 511.0

Example 12

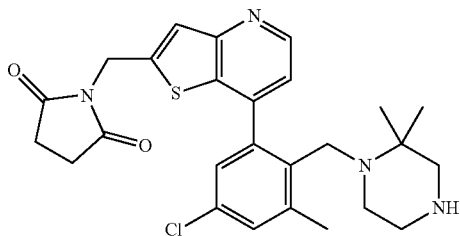 [SMILES: Cc1cc(Cl)cc(-c2ccnc3cc(CN4C(=O)CCC4=O)sc23)c1CN1CCNCC1(C)C]

1-((7-(5-chloro-2-((2,2-dimethylpiperazin-1-yl)methyl)-3-methylphenyl)thieno[3,2-b]pyridin-2-yl)methyl)pyrrolidine-2,5-dione. The title compound was prepared by General Procedures D and E using 1-((7-(4,4,5,5-tetramethyl-1,3,2-dioxaborolan-2-yl)thieno[3,2-b]pyridin-2-yl)methyl)pyrrolidine-2,5-dione. ¹H NMR (400 MHz, Methanol-d4) δ 8.85 (d, J=5.5 Hz, 1H), 7.72 (d, J=1.0 Hz, 1H), 7.68 (d, J=5.5 Hz, 1H), 7.47 (dd, J=2.3, 0.7 Hz, 1H), 7.23 (dd, J=2.3, 0.6 Hz, 1H), 5.04 (d, J=1.0 Hz, 2H), 3.74 (d, J=13.2 Hz, 1H), 3.48 (d, J=13.2 Hz, 1H), 3.42-3.32 (m, 2H), 3.01-2.77 (m, 4H), 2.50 (d, J=0.6 Hz, 3H), 2.45-2.22 (m, 4H), 0.81 (s, 3H), 0.61 (s, 3H). [M+H] 497.2

Example 13

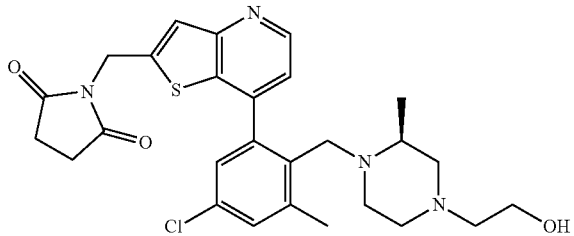 [SMILES: Cc1cc(Cl)cc(-c2ccnc3cc(CN4C(=O)CCC4=O)sc23)c1CN1CCN(CCO)C[C@@H]1C]

(S)-1-((7-(5-chloro-2-((4-(2-hydroxyethyl)-2-methylpiperazin-1-yl)methyl)-3-methylphenyl)thieno[3,2-b]pyridin-2-yl)methyl)pyrrolidine-2,5-dione. The title compound was prepared by General Procedures D, E, and H. ¹H NMR (400 MHz, Methanol-d4) δ 8.62 (d, J=4.8 Hz, 1H), 7.50 (s, 1H), 7.36 (d, J=2.3 Hz, 1H), 7.25 (t, J=4.6 Hz, 1H), 7.21-7.10 (m, 1H), 4.95 (s, 2H), 4.82 (s, 2H), 4.03-3.90 (m. 1H), 3.59 (m, 2H), 3.33 (s, 3H), 2.74 (m, 4H). 2.50 (s, 3H), 2.43 (m, 2H), 1.95 (m, 4H), 1.29 (m, 1H), 0.59 (m, 2H). [M+H] 527.0

Example 14

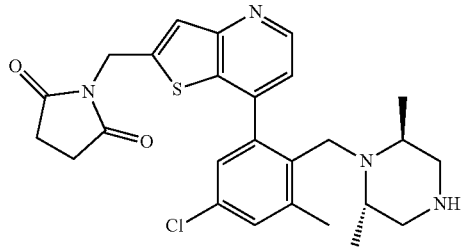 [SMILES: Cc1cc(Cl)cc(-c2ccnc3cc(CN4C(=O)CCC4=O)sc23)c1CN1[C@@H](C)CNC[C@@H]1C]

1-((7-(5-chloro-2-(((2S,6S)-2,6-dimethylpiperazin-1-yl)methyl)-3-methylphenyl)thieno[3,2-b]pyridin-2-yl)methyl)pyrrolidine-2,5-dione. The title compound was prepared by General Procedures D, E, and G. ¹H NMR (400 MHz, Methanol-d4) δ 9.00 (s, 1H), 8.02 (s, 1H), 7.93 (s, 1H), 7.55 (s, 1H), 7.38 (s, 1H), 5.07 (s, 2H), 4.33-3.95 (m, 2H), 3.15-2.54 (m, 4H), 2.79 (s, 3H), 2.68 (d, J=11.0 Hz, 4H), 0.93 (bs, 3H), 0.84 (bs, 3H). [M+H] 497.1

Example 15

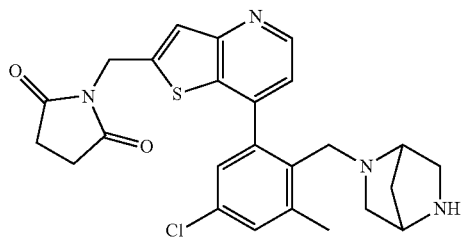 [SMILES: Cc1cc(Cl)cc(-c2ccnc3cc(CN4C(=O)CCC4=O)sc23)c1CN1CC2CC1CN2]

1-((7-(2-((2,5-diazabicyclo[2.2.1]heptan-2-yl)methyl)-5-chloro-3-methylphenyl)thieno[3,2-b]pyridin-2-yl)methyl)pyrrolidine-2,5-dione. The title compound was prepared by General Procedures D and E using 1-((7-(4,4,5,5-tetramethyl-1,3,2-dioxaborolan-2-yl)thieno[3,2-b]pyridin-2-yl)

methyl)pyrrolidine-2,5-dione. ¹H NMR (400 MHz, Methanol-d4) δ 8.73 (t, J=5.0 Hz, 1H), 7.58 (s, 1H), 7.50-7.34 (m, 2H), 7.20 (s, 1H), 5.00-4.95 (m, 2H), 3.75 (dd, J=28.8, 13.6 Hz, 1H), 3.64-3.44 (m, 1H), 3.20-3.01 (m, 1H), 2.97-2.81 (m, 1H), 2.79-2.55 (m, 4H), 2.53 (s, 3H), 2.45-2.40 (m, 4H), 1.48 (s, 2H). [M+H] 481.1

Example 16

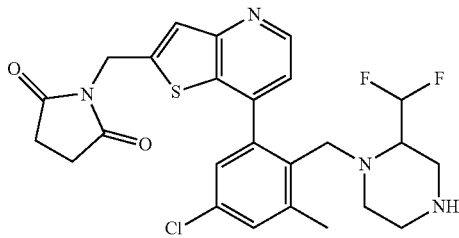 [SMILES: Cc1cc(Cl)cc(-c2ccnc3cc(CN4C(=O)CCC4=O)sc23)c1CN1CCNCC1C(F)F]

1-((7-(5-chloro-2-((2-(difluoromethyl)piperazin-1-yl)methyl)-3-methylphenyl)thieno[3,2-b]pyridin-2-yl)methyl)pyrrolidine-2,5-dione. The title compound was prepared by General Procedures C and E using 1-((7-(4,4,5,5-tetramethyl-1,3,2-dioxaborolan-2-yl)thieno[3,2-b]pyridin-2-yl)methyl)pyrrolidine-2,5-dione. [M+H] 519.1

Example 17

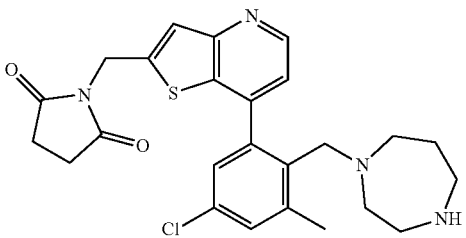 [SMILES: Cc1cc(Cl)cc(-c2ccnc3cc(CN4C(=O)CCC4=O)sc23)c1CN1CCCNCC1]

1-((7-(2-((1,4-diazepan-1-yl)methyl)-5-chloro-3-methylphenyl)thieno[3,2-b]pyridin-2-yl)methyl)pyrrolidine-2,5-dione. The title compound was prepared by General Procedure D using 4-chloro-2-(2-((2,5-dioxopyrrolidin-1-yl)methyl)thieno[3,2-b]pyridin-7-yl)-6-methylbenzaldehyde. ¹H NMR (400 MHz, Methanol-d4) δ 8.89 (d, J=5.5 Hz, 1H), 7.79-7.72 (m, 2H), 7.56 (d, J=2.2 Hz, 1H), 7.36 (d, J=2.2 Hz, 1H), 5.03-4.98 (m, 2H), 4.21 (d, J=14.0 Hz, 1H), 3.95 (d, J=14.0 Hz, 1H), 3.43-3.37 (m, 2H), 3.21-2.97 (m, 4H), 2.89-2.75 (m, 2H), 2.57 (s, 3H), 2.12-1.95 (m, 4H), 1.86-1.78 (m, 2H). [M+H] 483.1

Example 18

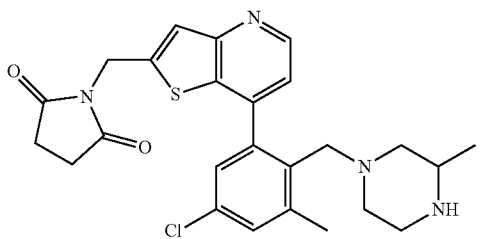 [SMILES: Cc1cc(Cl)cc(-c2ccnc3cc(CN4C(=O)CCC4=O)sc23)c1CN1CCNC(C)C1]

1-((7-(5-chloro-3-methyl-2-((3-methylpiperazin-1-yl)methyl)phenyl)thieno[3,2-b]pyridin-2-yl)methyl)pyrrolidine-2,5-dione. The title compound was prepared by General Procedure D using 4-chloro-2-(2-((2,5-dioxopyrrolidin-1-yl)methyl)thieno[3,2-b]pyridin-7-yl)-6-methylbenzaldehyde. ¹H NMR (400 MHz, Methanol-d4) δ 8.78 (d, J=5.3 Hz, 1H), 7.73-7.62 (m, 1H), 7.57 (dd, J=10.4, 5.3 Hz, 1H), 7.51-7.39 (m, 1H), 7.25 (s, 1H), 5.01 (d, J=3.1 Hz, 2H), 3.62 (dd, J=18.2, 13.5 Hz, 1H), 3.38 (dd, J=13.5, 4.9 Hz, 1H), 3.08 (d, J=12.5 Hz, 1H), 2.84-2.78 (m, 2H), 2.76 (s, 4H), 2.51 (d, J=2.9 Hz, 3H), 2.49-1.97 (m, 4H), 1.07 (dd, J=6.7, 3.4 Hz, 3H). [M+H] 483.1

Example 19

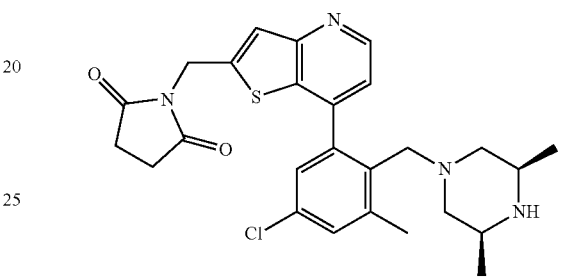

1-((7-(5-chloro-2-(((3 S,5R)-3,5-dimethylpiperazin-1-yl)methyl)-3-methylphenyl)thieno[3,2-b]pyridin-2-yl)methyl)pyrrolidine-2,5-dione. The title compound was prepared by General Procedure D using 4-chloro-2-(2-((2,5-dioxopyrrolidin-1-yl)methyl)thieno[3,2-b]pyridin-7-yl)-6-methylbenzaldehyde. ¹H NMR (400 MHz, Methanol-d4) δ 8.80 (d, J=5.4 Hz, 1H), 7.67 (d, J=1.0 Hz, 1H), 7.59 (d, J=5.3 Hz, 1H), 7.46 (d, J=2.3 Hz, 1H), 7.26 (d, J=2.3 Hz, 1H), 5.01 (d, J=1.0 Hz, 2H), 3.61 (d, J=13.5 Hz, 1H), 3.42 (d, J=13.5 Hz, 1H), 2.83-2.78 (m, 1H), 2.76 (s, 4H), 2.70-2.54 (m, 2H), 2.50 (s, 3H), 2.49-2.45 (m, 1H), 1.73 (dt, J=31.3, 11.7 Hz, 2H), 1.21-1.10 (d, J=6.6 Hz, 3H), 1.06 (d, J=6.6 Hz, 3H). [M+H] 497.2

Example 20

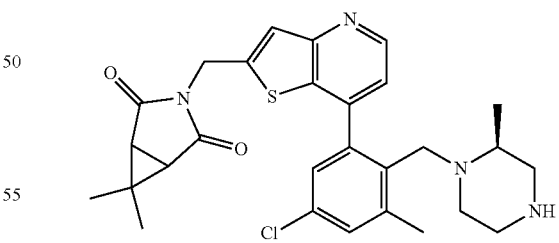

3-((7-(5-chloro-3-methyl-2-(((S)-2-methylpiperazin-1-yl)methyl)phenyl)thieno[3,2-b]pyridin-2-yl)methyl)-6,6-dimethyl-3-azabicyclo[3.1.0]hexane-2,4-dione. The title compound was prepared by General Procedures D, E, and H. ¹H NMR (400 MHz, Methanol-d4) δ 8.65 (d, J=4.9 Hz, 1H), 7.50 (s, 1H), 7.40 (s, 1H), 7.29 (d, J=4.9 Hz, 1H), 7.18-7.09 (m, 1H), 4.92 (s, 2H), 4.82 (s, 2H), 4.06-3.84 (m, 1H), 3.34 (s, 3H), 2.94-2.84 (m, 2H), 2.50 (m, 5H), 2.15 (m, 1H), 1.24 (m, 6H), 1.10 (m, 2H), 0.60 (m, 2H). [M+H] 523.0

Example 21

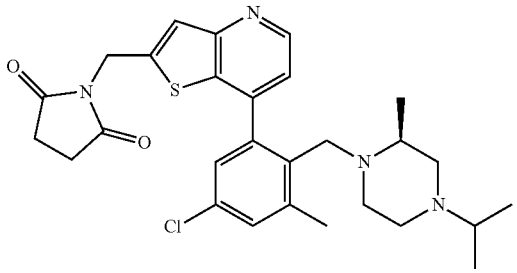 [SMILES: Cc1cc(Cl)cc(-c2ccnc3cc(CN4C(=O)CCC4=O)sc23)c1CN1CCN(C(C)C)C[C@@H]1C]

(S)-1-((7-(5-chloro-2-((4-isopropyl-2-methylpiperazin-1-yl)methyl)-3-methylphenyl)thieno[3,2-b]pyridin-2-yl)methyl)pyrrolidine-2,5-dione. The title compound was prepared by General Procedures D, E, and H. $^1$H NMR (400 MHz, Methanol-d4) δ 8.95 (m, 1H), 7.88 (m, 1H), 7.80 (s, 1H), 7.55 (m, 1H), 7.31 (m, 1H), 5.08 (s, 2H), 4.82 (s, 2H), 3.65 (m, 1H), 3.33 (s, 3H), 2.74 (m, 4H), 2.57 (m, 3H), 1.22 (m, 6H), 1.19 (m, 1H), 0.78 (m, 6H). [M+H] 525.0

Example 22

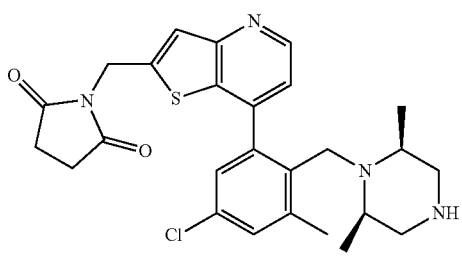 [SMILES: Cc1cc(Cl)cc(-c2ccnc3cc(CN4C(=O)CCC4=O)sc23)c1CN1[C@H](C)CNC[C@@H]1C]

1-((7-(5-chloro-2-(((2R,6S)-2,6-dimethylpiperazin-1-yl)methyl)-3-methylphenyl)thieno[3,2-b]pyridin-2-yl)methyl)pyrrolidine-2,5-dione. The title compound was prepared by General Procedures D and E using 1-((7-(4,4,5,5-tetramethyl-1,3,2-dioxaborolan-2-yl)thieno[3,2-b]pyridin-2-yl)methyl)pyrrolidine-2,5-dione. $^1$H NMR (400 MHz, Methanol-d4) δ 8.75 (dd, J=5.2, 3.2 Hz, 1H), 7.62 (d, J=3.5 Hz, 1H), 7.50 (t, J=6.0 Hz, 1H), 7.41 (d, J=2.3 Hz, 1H), 7.20 (d, J=1.4 Hz, 1H), 5.00 (dd, J=2.7, 1.3 Hz, 2H), 3.82 (d, J=14.9 Hz, 1H), 3.72 (d, J=14.9 Hz, 1H), 2.76 (s, 4H), 2.69-2.40 (m, 6H), 2.55 (s, 3H), 0.86 (d, J=6.6 Hz, 3H), 0.67 (d, J=6.7 Hz, 3H). [M+H] 497.2

Example 23

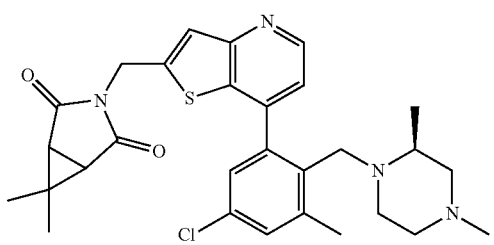

3-((7-(5-chloro-2-(((S)-2,4-dimethylpiperazin-1-yl)methyl)-3-methylphenyl)thieno[3,2-b]pyridin-2-yl)methyl)-6,6-dimethyl-3-azabicyclo[3.1.0]hexane-2,4-dione. The title compound was prepared by General Procedures D, E, and H. $^1$H NMR (400 MHz, Methanol-d4) δ 8.62 (d, J=4.9 Hz, 1H), 7.50 (s, 1H), 7.37 (s, 1H), 7.25 (d, J=4.9 Hz, 1H), 7.13-7.10 (m, 1H), 4.92 (s, 2H), 4.82 (s, 2H), 4.03-3.82 (m, 1H), 3.34 (s, 3H), 2.50 (s, 3H), 2.48 (m, 2H), 2.35 (m, 2H), 2.08 (s, 3H), 1.24 (m, 6H), 1.10 (m, 2H), 0.56 (m, 2H). [M+H] 538.0

Example 24

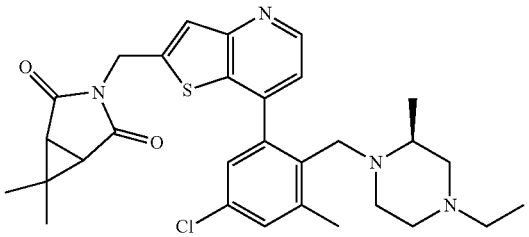 [SMILES: CCN1CCN(Cc2c(C)cc(Cl)cc2-c2ccnc3cc(CN4C(=O)C5C(C4=O)C5(C)C)sc23)[C@@H](C)C1]

3-((7-(5-chloro-2-(((S)-4-ethyl-2-methylpiperazin-1-yl)methyl)-3-methylphenyl)thieno[3,2-b]pyridin-2-yl)methyl)-6,6-dimethyl-3-azabicyclo[3.1.0]hexane-2,4-dione. The title compound was prepared by General Procedures D, E, and H. $^1$H NMR (400 MHz, Methanol-d4) δ 8.62 (d, J=4.9 Hz, 1H), 7.51 (s, 1H), 7.35 (s, 1H), 7.26 (d, J=4.9 Hz, 1H), 7.12-7.08 (m, 1H), 4.92 (s, 2H), 4.82 (s, 2H), 3.92-3.61 (m, 1H), 3.34 (s, 3H), 2.50 (s, 3H), 2.48 (m, 2H), 2.37-2.03 (m, 4H), 1.25 (m, 6H), 1.09 (s, 3H), 0.98 (m, 2H), 0.55 (m, 2H). [M+H] 552.0

Example 25

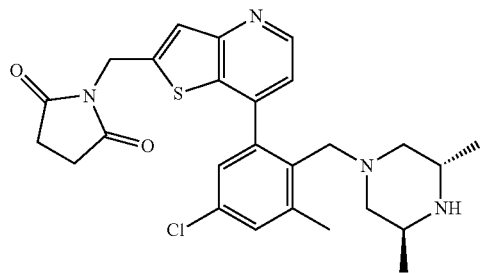 [SMILES: Cc1cc(Cl)cc(-c2ccnc3cc(CN4C(=O)CCC4=O)sc23)c1CN1C[C@H](C)N[C@@H](C)C1]

1-((7-(5-chloro-2-(((3 S,5 S)-3,5-dimethylpiperazin-1-yl)methyl)-3-methylphenyl)thieno[3,2-b]pyridin-2-yl)methyl)pyrrolidine-2,5-dione. The title compound was prepared by General Procedure D using 4-chloro-2-(2-((2,5-dioxopyrrolidin-1-yl)methyl)thieno[3,2-b]pyridin-7-yl)-6-methylbenzaldehyde. $^1$H NMR (400 MHz, Methanol-d4, HCl salt) δ 8.73 (d, J=5.1 Hz, 1H), 7.58 (d, J=5.4 Hz, 1H), 7.55-7.30 (m, 2H), 7.23 (s, 1H), 4.98 (d, J=9.2 Hz, 2H), 3.71-3.35 (m, 2H), 3.20 (s, 2H), 2.92-2.65 (m, 4H), 2.65-2.47 (m, 3H), 2.39 (d, J=12.3 Hz, 2H), 2.02 (s, 2H), 1.14 (d, J=6.6 Hz, 3H), 0.88 (d, J=6.6 Hz, 4H). [M+H] 497.0

Example 26

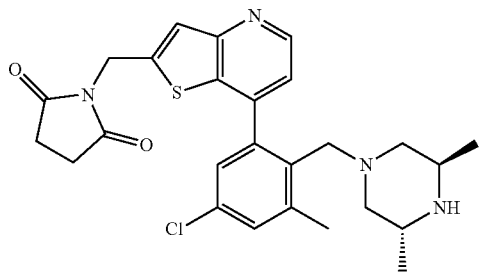 [SMILES: Cc1cc(Cl)cc(-c2ccnc3cc(CN4C(=O)CCC4=O)sc23)c1CN1C[C@@H](C)N[C@H](C)C1]

1-((7-(5-chloro-2-(((3R,5R)-3,5-dimethylpiperazin-1-yl)methyl)-3-methylphenyl)thieno[3,2-b]pyridin-2-yl)methyl)pyrrolidine-2,5-dione. The title compound was prepared by General Procedure D using 4-chloro-2-(2-((2,5-dioxopyrrolidin-1-yl)methyl)thieno[3,2-b]pyridin-7-yl)-6-methylbenzaldehyde. $^1$H NMR (400 MHz, Methanol-d4, HCl salt) δ 8.72 (d, J=5.1 Hz, 1H), 7.57 (d, J=6.1 Hz, 1H), 7.55-7.35 (m, 2H), 7.23 (d, J=2.6 Hz, 1H), 4.98 (d, J=8.8 Hz, 2H), 3.79-3.35 (m, 3H), 3.16 (d, J=30.8 Hz, 2H), 2.81-2.67 (m, 4H), 2.62-2.43 (m, 3H), 2.47-2.23 (m, 2H), 2.14-1.78 (m, 2H), 1.14 (d, J=6.7 Hz, 3H), 0.88 (d, J=6.7 Hz, 3H). [M+H]497.0

Example 27

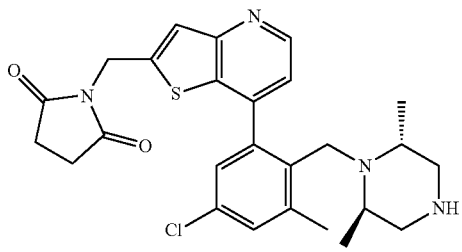 [SMILES: Cc1cc(Cl)cc(-c2ccnc3cc(CN4C(=O)CCC4=O)sc23)c1CN1[C@H](C)CNC[C@H]1C]

1-((7-(5-chloro-2-(((2R,6R)-2,6-dimethylpiperazin-1-yl)methyl)-3-methylphenyl)thieno[3,2-b]pyridin-2-yl)methyl)pyrrolidine-2,5-dione. The title compound was prepared by General Procedures D and E using 1-((7-(4,4,5,5-tetramethyl-1,3,2-dioxaborolan-2-yl)thieno[3,2-b]pyridin-2-yl)methyl)pyrrolidine-2,5-dione. $^1$H NMR (400 MHz, Methanol-d4) δ 8.63 (s, 1H), 7.52 (s, 1H), 7.40-7.36 (m, 1H), 7.30 (dd, J=25.6, 4.8 Hz, 1H), 7.18 (s, 1H), 4.96 (s, 2H), 4.05 (d, J=14.0 Hz, 1H), 3.92 (s, 1H), 3.63 (d, J=14.3 Hz, 2H), 3.54-3.44 (m, 4H), 2.76 (s, 4H), 2.55 (s, 3H), 0.78 (d, J=6.7 Hz, 3H), 0.67 (d, J=6.6 Hz, 3H). [M+H] 497.2

Example 28

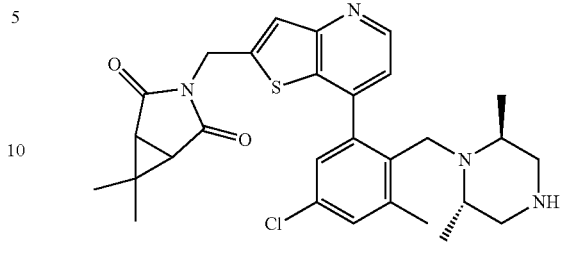

3-((7-(5-chloro-2-(((2S,6S)-2,6-dimethylpiperazin-1-yl)methyl)-3-methylphenyl)thieno[3,2-b]pyridin-2-yl)methyl)-6,6-dimethyl-3-azabicyclo[3.1.0]hexane-2,4-dione. The title compound was prepared by General Procedures D and E using 6,6-dimethyl-3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.75 (t, J=4.6 Hz, 1H), 7.61 (d, J=0.7 Hz, 1H), 7.48 (dd, J=25.5, 5.1 Hz, 1H), 7.44-7.40 (m, 1H), 7.22 (dd, J=13.4, 2.3 Hz, 1H), 4.88 (s, 2H), 4.01 (dd, J=48.7, 14.3 Hz, 1H), 3.55 (dd, J=84.7, 14.3 Hz, 1H), 2.77-2.59 (m, 4H), 2.56 (d, J=6.5 Hz, 3H), 2.51 (d, J=0.8 Hz, 2H), 2.46 (dd, J=12.6, 6.3 Hz, 2H), 1.25 (d, J=0.8 Hz, 3H), 1.12 (d, J=5.0 Hz, 3H), 0.79 (d, J=6.6 Hz, 3H), 0.68 (d, J=6.6 Hz, 3H). [M+H] 537.2

Example 29

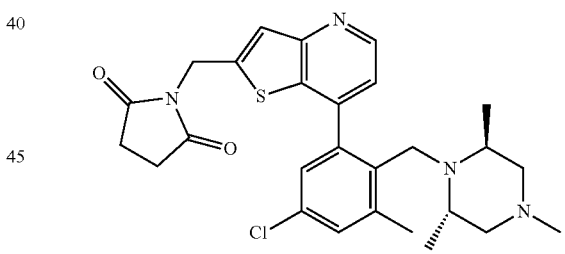

1-((7-(5-chloro-3-methyl-2-(((2S,6S)-2,4,6-trimethylpiperazin-1-yl)methyl)phenyl)thieno[3,2-b]pyridin-2-yl)methyl)pyrrolidine-2,5-dione. The title compound was prepared by General Procedures D, E, and H. $^1$H NMR (400 MHz, Methanol-d4) δ 7.65 (s, 1H), 7.57 (s, 1H), 7.52 (s, 1H), 7.42 (dd, J=7.9, 2.2 Hz, 1H), 7.24 (dd, J=11.0, 2.3 Hz, 1H), 5.02 (s, 2H), 4.08 (d, J=14.0 Hz, 1H), 3.94 (d, J=14.6 Hz, 1H), 3.65 (d, J=14.6 Hz, 1H), 3.03 (dd, J=19.1, 12.2 Hz, 2H), 2.85 (s, 1H), 2.80-2.74 (s, 3H), 2.67 (d, J=9.5 Hz, 3H), 2.56 (d, J=7.4 Hz, 3H), 2.35 (d, J=12.0 Hz, 1H), 2.21-1.99 (m, 3H), 1.93 (t, J=11.6 Hz, 1H), 0.88 (d, J=7.0 Hz, 3H), 0.76-0.62 (m, 3H). [M+H] 511.0

Example 30

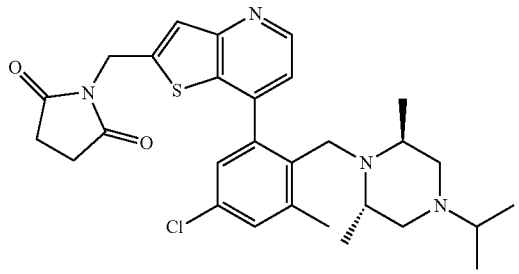 [SMILES: Cc1cc(Cl)cc(-c2ccnc3cc(CN4C(=O)CCC4=O)sc23)c1CN1[C@@H](C)CN(C(C)C)C[C@@H]1C]

1-((7-(5-chloro-2-(((2S,6S)-4-isopropyl-2,6-dimethylpiperazin-1-yl)methyl)-3-methylphenyl)thieno[3,2-b]pyridin-2-yl)methyl)pyrrolidine-2,5-dione. The title compound was prepared by General Procedures D, E, and H. $^1$H NMR (400 MHz, Methanol-d4) δ 7.61 (s, 1H), 7.40 (d, J=11.2 Hz, 1H), 7.23 (s, 1H), 7.13 (s, 1H), 6.97 (s, 1H), 5.00 (s, 2H), 4.08 (d, J=14.1 Hz, 1H), 3.92 (d, J=14.5 Hz, 1H), 3.68 (d, J=14.3 Hz, 1H), 3.52 (d, J=14.1 Hz, 1H), 3.04 (s, 2H), 2.92 (d, J=11.4 Hz, 2H), 2.78 (s, 3H), 2.66 (s, 1H), 2.54 (d, J=10.0 Hz, 1H), 2.27 (s, 1H), 2.06 (d, J=10.7 Hz, 2H), 1.92 (t, J=12.2 Hz, 3H), 1.27-1.11 (m, 3H), 0.93 (d, J=6.9 Hz, 3H), 0.81-0.68 (m, 3H), 0.50 (s, 1H). [M+H] 539.0

Example 31

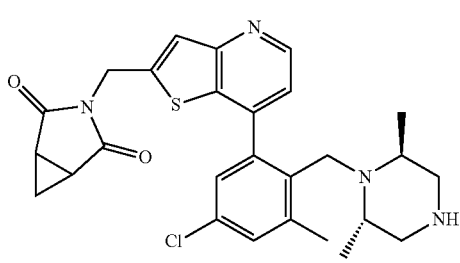 [SMILES: Cc1cc(Cl)cc(-c2ccnc3cc(CN4C(=O)C5CC5C4=O)sc23)c1CN1[C@@H](C)CNC[C@@H]1C]

3-((7-(5-chloro-2-(((2S,6S)-2,6-dimethylpiperazin-1-yl)methyl)-3-methylphenyl)thieno[3,2-b]pyridin-2-yl)methyl)-3-azabicyclo[3.1.0]hexane-2,4-dione. The title compound was prepared by General Procedures D, E, and H. $^1$H NMR (400 MHz, Methanol-d4) δ 8.91 (s, 1H), 7.84 (s, 1H), 7.74 (s, 1H), 7.45 (d, J=7.3 Hz, 1H), 7.28 (s, 1H), 4.87 (s, 2H), 4.17-4.06 (m, 1H), 4.02-3.89 (m, 1H), 3.80-3.61 (m, 1H), 3.59-3.53 (m, 1H), 2.74 (d, J=18.0 Hz, 2H), 2.54 (d, J=9.0 Hz, 5H), 2.00 (s, 2H), 1.56 (d, J=7.9 Hz, 2H), 1.45-1.42 (m, 1H), 1.39 (t, J=7.0 Hz, 1H), 0.80 (s, 3H), 0.69 (s, 3H). [M+H] 509.0

Example 32

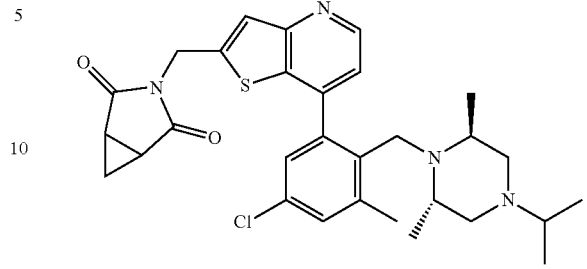

3-((7-(5-chloro-2-(((2S,6S)-4-isopropyl-2,6-dimethylpiperazin-1-yl)methyl)-3-methylphenyl)thieno[3,2-b]pyridin-2-yl)methyl)-3-azabicyclo[3.1.0]hexane-2,4-dione. The title compound was prepared by General Procedures D, E, and H. $^1$H NMR (400 MHz, Methanol-d4) δ 8.92 (m, 1H), 7.88-7.81 (m, 1H), 7.74 (s, 1H), 7.52-7.49 (m, 1H), 7.33 (m, 1H), 5.48 (s, 2H), 4.92 (s, 2H), 4.15-3.98 (m, 1H), 3.72-3.51 (m, 1H), 3.33 (s, 3H), 2.99 (m, 3H), 2.72 (m, 1H), 2.62 (m, 2H), 2.58 (d, J=4.8 Hz, 2H), 1.98 (m, 3H), 1.23 (s, 3H), 1.18 (s, 3H), 0.96 (m, 1H), 0.85 (m, 1H), 0.77 (m, 1H), 0.70 (m, 1H). [M+H] 551.0

Example 33

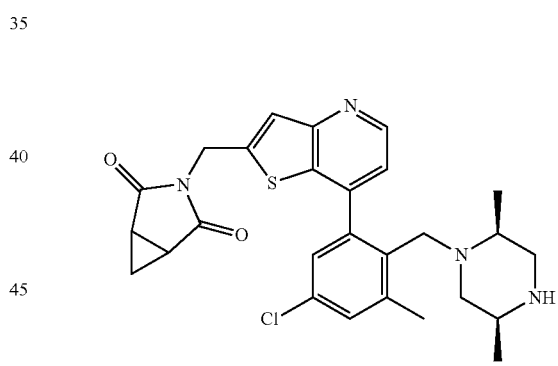

3-((7-(5-chloro-2-(((2S,5 S)-2,5-dimethylpiperazin-1-yl)methyl)-3-methylphenyl)thieno[3,2-b]pyridin-2-yl)methyl)-3-azabicyclo[3.1.0]hexane-2,4-dione. The title compound was prepared by General Procedures D and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. 1H NMR (400 MHz, Methanol-d4) δ 8.86-8.75 (m, 1H), 7.71-7.52 (m, 2H), 7.45 (s, 1H), 7.32-7.20 (m, 1H), 4.88-4.82 (m, 2H), 3.82 (d, J=23.4 Hz, 1H), 3.72-3.50 (m, 1H), 2.96-2.56 (m, 5H), 2.52 (d, J=13.5 Hz, 3H), 2.47-2.13 (m, 3H), 1.62 (tt, J=8.5, 4.6 Hz, 1H), 1.46 (dd, J=10.0, 4.2 Hz, 1H), 1.11 (dd, J=20.2, 6.6 Hz, 3H), 0.87 (dd, J=35.1, 6.7 Hz, 3H). [M+H] 509.1

Example 34

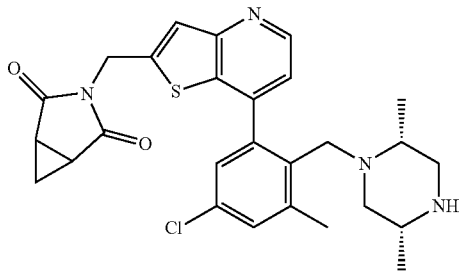 [SMILES: Cc1cc(Cl)cc(-c2ccnc3cc(CN4C(=O)C5CC5C4=O)sc23)c1CN1C[C@@H](C)NC[C@H]1C]

3-((7-(5-chloro-2-(((2R,5R)-2,5-dimethylpiperazin-1-yl)methyl)-3-methylphenyl)thieno[3,2-b]pyridin-2-yl)methyl)-3-azabicyclo[3.1.0]hexane-2,4-dione. The title compound was prepared by General Procedures D and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.83 (d, J=5.4 Hz, 1H), 7.66 (q, J=9.0, 7.0 Hz, 2H), 7.47 (s, 1H), 7.38-7.20 (m, 1H), 4.91-4.74 (m, 2H), 3.89-3.49 (m, 2H), 2.99-2.56 (m, 4H), 2.52 (d, J=13.2 Hz, 3H), 2.45-2.25 (m, 4H), 1.63 (d, J=4.9 Hz, 1H), 1.48 (d, J=7.9 Hz, 1H), 1.11 (dd, J=19.6, 6.6 Hz, 3H), 0.88 (dd, J=31.2, 6.7 Hz, 3H). [M+H] 509.1

Example 35

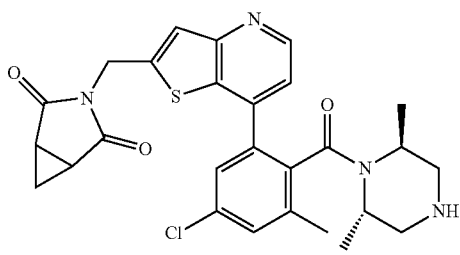 [SMILES: Cc1cc(Cl)cc(-c2ccnc3cc(CN4C(=O)C5CC5C4=O)sc23)c1C(=O)N1[C@@H](C)CNC[C@@H]1C]

3-((7-(5-chloro-2-((2S,6S)-2,6-dimethylpiperazine-1-carbonyl)-3-methylphenyl)thieno[3,2-b]pyridin-2-yl)methyl)-3-azabicyclo[3.1.0]hexane-2,4-dione. The title compound was prepared by General Procedures D, E, and H. [M+H] 523.0

Example 36

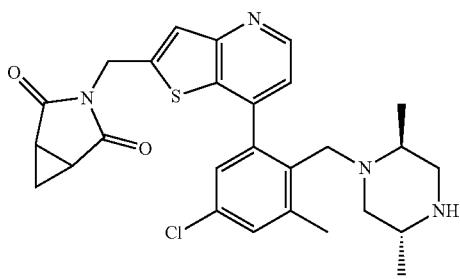 [SMILES: Cc1cc(Cl)cc(-c2ccnc3cc(CN4C(=O)C5CC5C4=O)sc23)c1CN1C[C@@H](C)NC[C@@H]1C]

3-((7-(5-chloro-2-(((2S,5R)-2,5-dimethylpiperazin-1-yl)methyl)-3-methylphenyl)thieno[3,2-b]pyridin-2-yl)methyl)-3-azabicyclo[3.1.0]hexane-2,4-dione. The title compound was prepared by General Procedures D and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.73 (t, J=4.9 Hz, 1H), 7.54 (d, J=4.4 Hz, 1H), 7.50-7.34 (m, 2H), 7.24 (dd, J=19.5, 2.3 Hz, 1H), 4.87-4.77 (m, 2H), 4.18-3.99 (m, 1H), 3.21-2.92 (m, 2H), 2.92-2.70 (m, 1H), 2.64-2.42 (m, 5H), 2.27-2.15 (m, 1H), 1.88 (dt, J=54.6, 11.9 Hz, 1H), 1.69-1.56 (m, 1H), 1.54-1.37 (m, 1H), 1.14 (d, J=6.6 Hz, 3H), 1.02 (d, J=6.5 Hz, 1H), 0.81 (d, J=6.3 Hz, 1H), 0.56 (d, J=6.2 Hz, 3H). [M+H] 509.2

Example 37

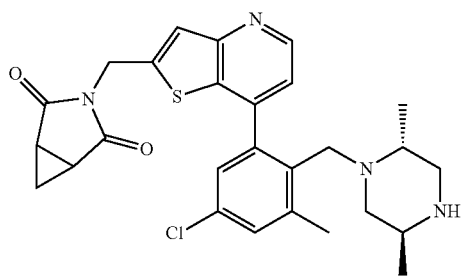 [SMILES: Cc1cc(Cl)cc(-c2ccnc3cc(CN4C(=O)C5CC5C4=O)sc23)c1CN1C[C@H](C)NC[C@H]1C]

3-((7-(5-chloro-2-(((2R,5 S)-2,5-dimethylpiperazin-1-yl)methyl)-3-methylphenyl)thieno[3,2-b]pyridin-2-yl)methyl)-3-azabicyclo[3.1.0]hexane-2,4-dione. The title compound was prepared by General Procedures D and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.73 (t, J=5.5 Hz, 1H), 7.54 (d, J=3.8 Hz, 1H), 7.52-7.37 (m, 2H), 7.24 (dd, J=19.0, 2.3 Hz, 1H), 4.86-4.81 (m, 2H), 4.18-4.02 (m, 1H), 3.20-2.93 (m, 2H), 2.81 (d, J=48.3 Hz, 1H), 2.65-2.42 (m, 5H), 2.21 (s, 1H), 1.87 (dt, J=54.6, 11.9 Hz, 1H), 1.64 (td, J=7.7, 4.5 Hz, 1H), 1.54-1.39 (m, 1H), 1.14 (d, J=6.6 Hz, 3H), 1.02 (d, J=6.5 Hz, 1H), 0.80 (d, J=6.2 Hz, 1H), 0.56 (d, J=6.2 Hz, 3H). [M+H] 509.2

Example 38

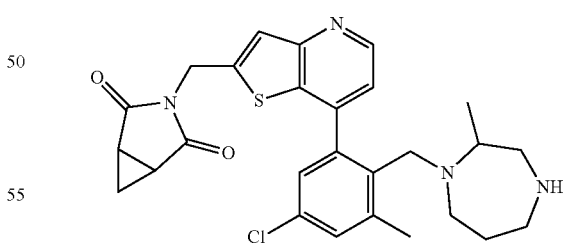

3-((7-(5-chloro-3-methyl-2-((2-methyl-1,4-diazepan-1-yl)methyl)phenyl)thieno[3,2-b]pyridin-2-yl)methyl)-3-azabicyclo[3.1.0]hexane-2,4-dione. The title compound was prepared by General Procedures D and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.78 (s, 1H), 7.58 (s, 1H), 7.48 (d, J=2.2 Hz, 2H), 7.27 (dd, J=13.0, 2.2 Hz, 1H), 4.84 (s, 2H), 3.95-3.73 (m, 1H), 3.61 (d, J=13.7 Hz, 1H), 3.00

(dd, J=30.4, 11.7 Hz, 5H), 2.69-2.49 (m, 6H), 1.68-1.50 (m, 2H), 1.45-1.37 (m, 2H), 1.33-1.24 (m, 2H), 0.84 (dd, J=16.1, 5.9 Hz, 3H). [M+H] 509.0

Example 39

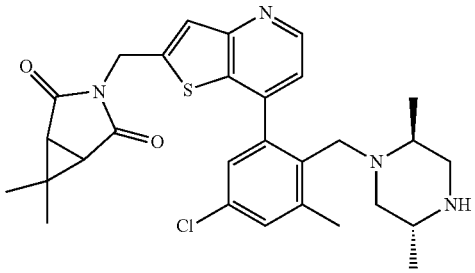 [SMILES: Cc1cc(Cl)cc(-c2ccnc3cc(CN4C(=O)C5C(C4=O)C5(C)C)sc23)c1CN1C[C@@H](C)NC[C@@H]1C]

3-((7-(5-chloro-2-(((2S,5R)-2,5-dimethylpiperazin-1-yl)methyl)-3-methylphenyl)thieno[3,2-b]pyridin-2-yl)methyl)-6,6-dimethyl-3-azabicyclo[3.1.0]hexane-2,4-dione. The title compound was prepared by General Procedures D and E using 6,6-dimethyl-3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. ¹H NMR (400 MHz, Methanol-d4) δ 8.96-8.83 (m, 1H), 7.83-7.67 (m, 2H), 7.52 (s, 1H), 7.33-7.21 (m, 1H), 4.96 (s, 2H), 4.23-4.01 (m, 1H), 3.26-2.87 (m, 2H), 2.83-2.22 (m, 1H), 2.62-2.47 (m, 6H), 2.07-1.74 (m, 1H), 1.70-1.35 (m, 1H), 1.31-1.24 (m, 4H), 1.22-1.13 (m, 6H), 1.12-1.02 (m, 1H), 0.77-0.68 (m, 1H), 0.67-0.58 (m, 1H). [M+H] 537.1

Example 40

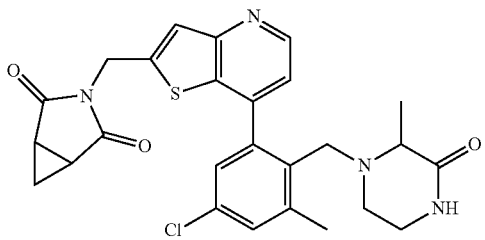 [SMILES: Cc1cc(Cl)cc(-c2ccnc3cc(CN4C(=O)C5CC5C4=O)sc23)c1CN1CCNC(=O)C1C]

3-((7-(5-chloro-3-methyl-2-((2-methyl-3-oxopiperazin-1-yl)methyl)phenyl)thieno[3,2-b]pyridin-2-yl)methyl)-3-azabicyclo[3.1.0]hexane-2,4-dione. The title compound was prepared by General Procedures D, E, and H. ¹H NMR (400 MHz, Methanol-d4) δ 8.83 (d, J=5.4 Hz, 1H), 7.72-7.65 (m, 2H), 7.50 (d, J=3.1 Hz, 1H), 7.30 (d, J=8.6 Hz, 1H), 4.87 (s, 2H), 4.02 (d, J=13.6 Hz, 1H), 3.83 (d, J=13.9 Hz, 1H), 3.66 (d, J=13.9 Hz, 1H), 3.44 (d, J=13.6 Hz, 1H), 2.96-2.65 (m, 4H), 2.63-2.57 (m, 3H), 2.23 (dp, J=10.9, 5.6, 4.9 Hz, 1H), 1.73-1.49 (m, 1H), 1.44 (q, J=3.8 Hz, 2H), 0.91 (dd, J=15.9, 6.8 Hz, 3H). [M+H] 509.0

Example 41

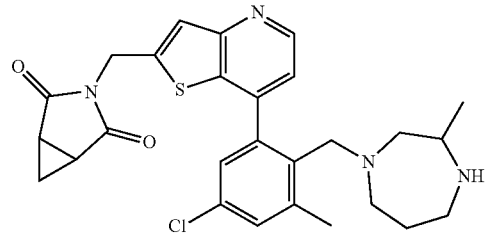 [SMILES: Cc1cc(Cl)cc(-c2ccnc3cc(CN4C(=O)C5CC5C4=O)sc23)c1CN1CCCNC(C)C1]

3-((7-(5-chloro-3-methyl-2-((3-methyl-1,4-diazepan-1-yl)methyl)phenyl)thieno[3,2-b]pyridin-2-yl)methyl)-3-azabicyclo[3.1.0]hexane-2,4-dione. The title compound was prepared by General Procedures D, E, and H. ¹H NMR (400 MHz, Methanol-d4) δ 8.84 (s, 1H), 7.64 (d, J=5.4 Hz, 2H), 7.50 (s, 1H), 7.31 (s, 1H), 4.86 (s, 2H), 4.09 (dd, J=15.3, 3.1 Hz, 1H), 3.88-3.72 (m, 2H), 3.64 (d, J=13.0 Hz, 1H), 3.48 (ddd, J=29.5, 14.1, 6.8 Hz, 3H), 3.23-3.04 (m, 2H), 2.90 (d, J=24.2 Hz, 2H), 2.57 (d, J=9.8 Hz, 3H), 2.15 (d, J=5.0 Hz, 1H), 1.94 (s, 1H), 1.77 (s, 1H), 1.62 (dt, J=13.1, 6.1 Hz, 3H), 1.47 (q, J=4.0 Hz, 1H), 1.03 (t, J=8.2 Hz, 1H). [M+H] 509.0

Example 42

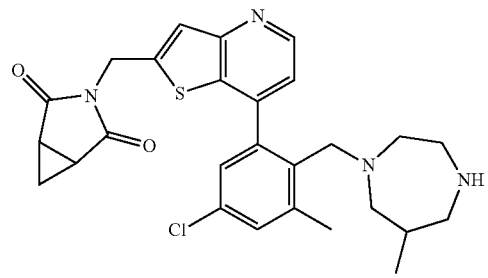 [SMILES: Cc1cc(Cl)cc(-c2ccnc3cc(CN4C(=O)C5CC5C4=O)sc23)c1CN1CCNCC(C)C1]

3-((7-(5-chloro-3-methyl-2-((6-methyl-1,4-diazepan-1-yl)methyl)phenyl)thieno[3,2-b]pyridin-2-yl)methyl)-3-azabicyclo[3.1.0]hexane-2,4-dione. The title compound was prepared by General Procedures D, E, and H. ¹H NMR (400 MHz, Methanol-d4) δ 8.86 (d, J=5.6 Hz, 1H), 7.68 (d, J=8.2 Hz, 2H), 7.51 (s, 1H), 7.33 (s, 1H), 4.87 (s, 4H), 3.90 (d, J=11.5 Hz, 1H), 3.73 (d, J=11.8 Hz, 1H), 3.18-2.83 (m, 3H), 2.78-2.63 (m, 1H), 2.57 (d, J=12.3 Hz, 7H), 2.14 (t, J=20.3 Hz, 1H), 1.63 (q, J=8.4 Hz, 1H), 1.47 (d, J=6.0 Hz, 1H), 1.31 (d, J=1.9 Hz, 3H), 1.24 (d, J=6.7 Hz, 4H), 0.75 (d, J=6.7 Hz, 3H). [M+H] 509.0

Example 43

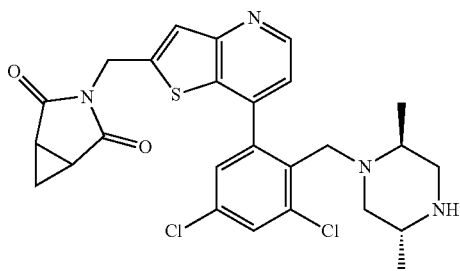

3-((7-(3,5-dichloro-2-(((2S,5R)-2,5-dimethylpiperazin-1-yl)methyl)phenyl)thieno[3,2-b]pyridin-2-yl)methyl)-3-azabicyclo[3.1.0]hexane-2,4-dione. The title compound was prepared by General Procedures D, E, and G. 1H NMR (400 MHz, Methanol-d4) δ 8.62 (m, 1H), 7.65 (m, 1H), 7.47-7.45 (m, 1H), 7.34 (m, 1H), 7.28 (m, 1H), 5.50 (s, 2H), 4.80 (s, 2H), 4.63 (m, 1H), 4.61 (m, 1H), 3.35 (s, 6H), 2.56 (m, 2H), 2.28 (m, 2H), 1.56 (m, 2H), 0.87 (m, 2H), 0.35 (m, 1H). [M+H]529.0

Example 44

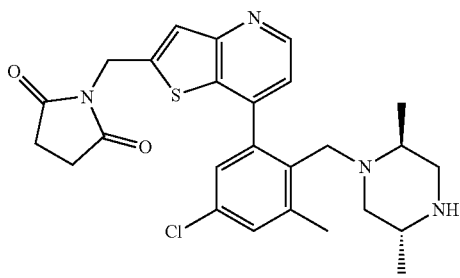 [SMILES: Cc1cc(Cl)cc(-c2ccnc3cc(CN4C(=O)CCC4=O)sc23)c1CN1C[C@@H](C)NC[C@@H]1C]

1-((7-(5-chloro-2-(((2S,5R)-2,5-dimethylpiperazin-1-yl)methyl)-3-methylphenyl)thieno[3,2-b]pyridin-2-yl)methyl)pyrrolidine-2,5-dione. The title compound was prepared by General Procedures D, E, and G. $^1$H NMR (400 MHz, Methanol-d4) δ 8.96 (s, 1H), 7.92-7.85 (m, 1H), 7.82 (s, 1H), 7.55 (s, 1H), 7.40-7.30 (m, 1H), 5.12-5.05 (m, 2H), 4.31-4.15 (m, 1H), 3.24-3.09 (m, 1H), 3.09-2.94 (m, 1H), 2.84-2.73 (m, 5H), 2.67-2.29 (m, 4H), 2.16-1.66 (m, 1H), 1.21-1.02 (m, 3H), 0.93-0.74 (m, 1H), 0.74-0.58 (m, 2H). [M+H] 497.0

Example 45

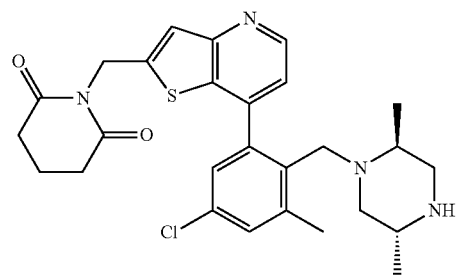 [SMILES: Cc1cc(Cl)cc(-c2ccnc3cc(CN4C(=O)CCCC4=O)sc23)c1CN1C[C@@H](C)NC[C@@H]1C]

1-((7-(5-chloro-2-(((2S,5R)-2,5-dimethylpiperazin-1-yl)methyl)-3-methylphenyl)thieno[3,2-b]pyridin-2-yl)methyl)piperidine-2,6-dione. The title compound was prepared by General Procedures D, E, and G. $^1$H NMR (400 MHz, Methanol-d4) δ 9.00-8.92 (m, 1H), 7.95-7.84 (m, 1H), 7.79 (d, J=10.2 Hz, 1H), 7.57 (d, J=7.7 Hz, 1H), 7.44-7.28 (m, 1H), 5.41-5.23 (m, 2H), 4.41-4.17 (m, 1H), 3.24-2.98 (m, 2H), 2.88-2.63 (m, 9H), 2.63-2.48 (m, 3H), 2.23-1.81 (m, 3H), 1.21-1.03 (m, 3H), 0.89 (s, 1H), 0.74 (s, 1H). [M+H] 511.1

Example 46

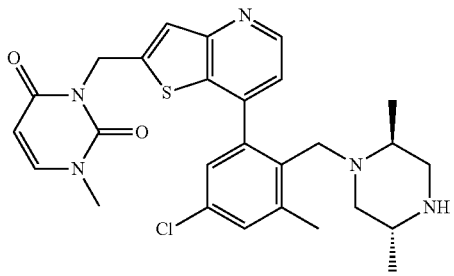 [SMILES: Cc1cc(Cl)cc(-c2ccnc3cc(Cn4c(=O)ccn(C)c4=O)sc23)c1CN1C[C@@H](C)NC[C@@H]1C]

3-((7-(5-chloro-2-(((2S,5R)-2,5-dimethylpiperazin-1-yl)methyl)-3-methylphenyl)thieno[3,2-b]pyridin-2-yl)methyl)-1-methylpyrimidine-2,4(1H,3H)-dione. The title compound was prepared by General Procedures D, E, and G. 1H NMR (400 MHz, Methanol-d4) δ 8.93 (s, 1H), 7.88-7.78 (m, 2H), 7.68-7.57 (m, 1H), 7.53 (s, 1H), 7.38-7.27 (m, 1H), 5.84-5.70 (m, 1H), 5.55-5.43 (m, 2H), 4.23-4.09 (m, 1H), 3.47-3.36 (m, 3H), 3.28-2.89 (m, 4H), 2.74-2.42 (m, 4H), 2.33 (s, 1H), 2.13-1.51 (m, 2H), 1.19-0.96 (m, 3H), 0.79 (s, 1H), 0.63 (s, 1H). [M+H] 524.1

Example 47

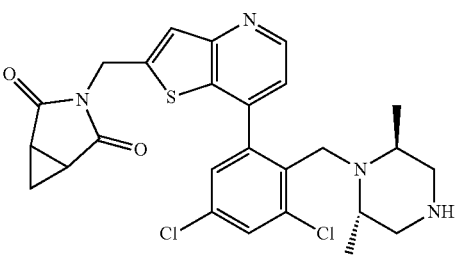 [SMILES: C[C@H]1CNC[C@H](C)N1Cc1c(Cl)cc(Cl)cc1-c1ccnc2cc(CN3C(=O)C4CC4C3=O)sc12]

3-((7-(3,5-dichloro-2-(((2S,6S)-2,6-dimethylpiperazin-1-yl)methyl)phenyl)thieno[3,2-b]pyridin-2-yl)methyl)-3-azabicyclo[3.1.0]hexane-2,4-dione. The title compound was prepared by General Procedures D, E, and G. $^1$H NMR (400 MHz, Methanol-d4) δ 8.97 (d, J=5.8 Hz, 1H), 7.93 (dd, J=16.8, 5.8 Hz, 1H) 7.80 (m, 1H), 7.78 (m, 1H), 7.50 (dd, J=11.5, 2.2 Hz, 1H), 4.94 (s, 2H), 4.14 (m, 1H), 3.89 (m, 1H), 2.72 (m, 2H), 2.62 (m, 3H), 2.42 (m, 3H), 1.64 (m, 1H), 1.51 (m, 1H), 0.77 (m, 6H). [M+H] 529.0

Example 48

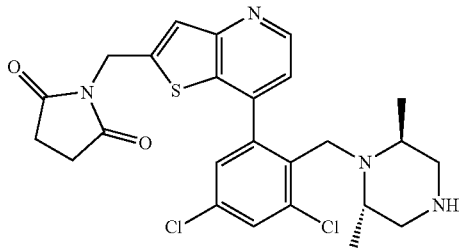

1-((7-(3,5-dichloro-2-(((2S,6S)-2,6-dimethylpiperazin-1-yl)methyl)phenyl)thieno[3,2-b]pyridin-2-yl)methyl)pyrrolidine-2,5-dione. The title compound was prepared by General Procedures D, E, and G. $^1$H NMR (400 MHz, Methanol-d4) δ 8.98 (d, J=5.8 Hz, 1H), 7.93 (dd, J=16.8, 5.8 Hz, 1H) 7.84 (m, 1H), 7.79 (m, 1H), 7.50 (dd, J=11.5, 2.2 Hz, 1H), 5.10 (s, 2H), 4.15 (m, 1H), 3.89 (m, 1H), 2.78 (s, 4H), 2.73 (m, 2H), 2.55 (m, 1H), 2.39 (m, 2H), 2.33 (m, 1H), 0.77 (m, 6H). [M+H] 517.0

Example 49

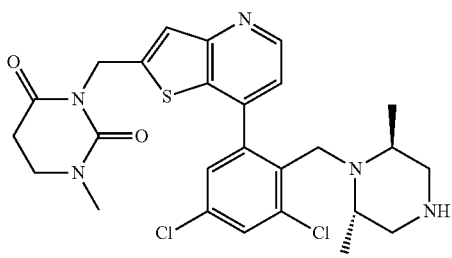 [SMILES: C[C@H]1CNC[C@H](C)N1Cc1c(Cl)cc(Cl)cc1-c1ccnc2cc(CN3C(=O)CCN(C)C3=O)sc12]

3-((7-(3,5-dichloro-2-(((2S,6S)-2,6-dimethylpiperazin-1-yl)methyl)phenyl)thieno[3,2-b]pyridin-2-yl)methyl)-1-methyldihydropyrimidine-2,4(1H,3H)-dione. The title compound was prepared by General Procedures D, E, and G. $^1$H NMR (400 MHz, Methanol-d4) δ 8.96 (d, J=5.8 Hz, 1H), 7.93 (dd, J=16.8, 5.8 Hz, 1H) 7.81 (m, 1H), 7.79 (m, 1H), 7.50 (dd, J=11.5, 2.2 Hz, 1H), 5.33 (m, 2H), 4.14 (m, 1H), 3.89 (m, 1H), 3.46 (m, 2H), 3.03 (s, 3H), 2.80 (m, 2H), 2.72 (m, 2H), 2.57 (m, 1H), 2.41 (m, 2H), 2.32 (m, 1H), 0.76 (m, 6H). [M+H] 546.0

Example 50

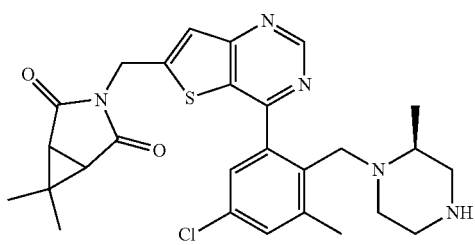

3-((4-(5-chloro-3-methyl-2-(((S)-2-methylpiperazin-1-yl)methyl)phenyl)thieno[3,2-d]pyrimidin-6-yl)methyl)-6,6-dimethyl-3-azabicyclo[3.1.0]hexane-2,4-dione. The title compound was prepared by General Procedures D and F using 6,6-dimethyl-3-((7-(4,4,5,5-tetramethyl-1,3,2-dioxaborolan-2-yl)thieno[3,2-b]pyridin-2-yl)methyl)-3-azabicyclo [3.1.0]hexane-2,4-dione. $^1$H NMR (400 MHz, Methanol-d4, HCl salt) δ 9.15 (s, 1H), 7.56 (s, 1H), 7.46 (d, J=2.2 Hz, 1H), 7.32 (d, J=2.2 Hz, 1H), 5.48 (s, 1H), 4.91 (s, 2H), 4.13 (d, J=13.3 Hz, 1H), 2.79 (d, J=12.9 Hz, 1H), 2.68 (d, J=12.3 Hz, 1H), 2.52 (s, 2H), 2.51-2.41 (m, 5H), 2.41-2.31 (m, 1H), 2.26-2.20 (m, 1H), 2.04-1.76 (m, 2H), 1.28 (s, 1H), 1.25 (s, 3H), 1.15 (s, 3H), 0.61 (d, J=6.3 Hz, 3H). [M+H] 524.0

Example 51

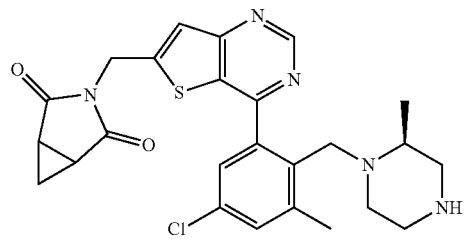 [SMILES: Cc1cc(Cl)cc(-c2ncnc3cc(CN4C(=O)C5CC5C4=O)sc23)c1CN1CCNC[C@@H]1C]

3-((4-(5-chloro-3-methyl-2-(((S)-2-methylpiperazin-1-yl)methyl)phenyl)thieno[3,2-d]pyrimidin-6-yl)methyl)-3-azabicyclo[3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4, HCl salt) δ 9.17 (s, 1H), 7.53 (s, 1H), 7.49 (d, J=2.2 Hz, 1H), 7.40 (d, J=2.3 Hz, 1H), 4.20 (d, J=13.5 Hz, 1H), 3.38 (d, J=13.5 Hz, 1H), 2.95 (d, J=12.8 Hz, 1H), 2.85 (d, J=12.5 Hz, 1H), 2.64-2.55 (m, 3H), 2.55-2.37 (m, 4H), 2.22-2.02 (m, 2H), 1.70-1.59 (m, 1H), 1.53-1.40 (m, 1H), 0.70 (d, J=6.4 Hz, 3H). [M+H] 496.0

Example 52

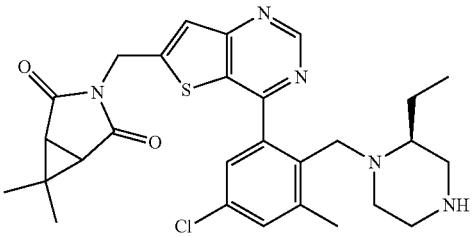 [SMILES: CC[C@H]1CNCCN1Cc1c(C)cc(Cl)cc1-c1ncnc2cc(CN3C(=O)C4C(C3=O)C4(C)C)sc12]

3-((4-(5-chloro-2-(((S)-2-ethylpiperazin-1-yl)methyl)-3-methylphenyl)thieno[3,2-d]pyrimidin-6-yl)methyl)-6,6-dimethyl-3-azabicyclo[3.1.0]hexane-2,4-dione. The title compound was prepared by General Procedures D and F using 6,6-dimethyl-3-((7-(4,4,5,5-tetramethyl-1,3,2-dioxaborolan-2-yl)thieno[3,2-b]pyridin-2-yl)methyl)-3-azabicyclo [3.1.0]hexane-2,4-dione. $^1$H NMR (400 MHz, Methanol-d4, HCl salt) δ 9.19 (s, 1H), 7.58 (d, J=1.0 Hz, 1H), 7.50 (d, J=2.2 Hz, 1H), 7.41 (d, J=2.2 Hz, 1H), 4.20 (d, J=13.5 Hz, 1H), 3.54 (d, J=13.5 Hz, 1H), 2.89 (d, J=12.0 Hz, 1H), 2.66 (td, J=10.5, 8.9, 5.0 Hz, 2H), 2.53 (s, 2H), 2.51 (s, 3H), 2.47-2.22 (m, 3H), 1.62-1.45 (m, 1H), 1.25 (s, 3H), 1.15 (s, 3H), 1.01-0.83 (m, 1H), 0.74 (t, J=7.4 Hz, 3H). [M+H] 538.0

Example 53

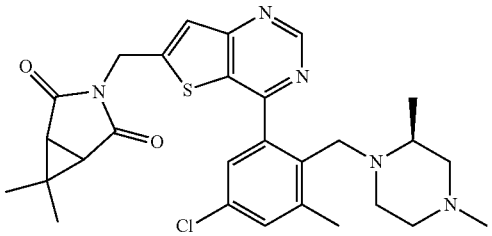

3-((4-(5-chloro-2-(((S)-2,4-dimethylpiperazin-1-yl)methyl)-3-methylphenyl)thieno[3,2-d]pyrimidin-6-yl)methyl)-6,6-dimethyl-3-azabicyclo[3.1.0]hexane-2,4-dione. The title compound was prepared by General Procedures D and F using 6,6-dimethyl-3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4, HCl salt) δ 9.17 (s, 1H), 7.56 (s, 1H), 7.48 (d, J=2.3 Hz, 1H), 7.35 (d, J=2.3 Hz, 1H), 4.93 (d, J=4.4 Hz, 2H), 4.35-4.11 (m, 1H), 2.71 (s, 3H), 2.64-2.46 (m, 6H), 2.42-2.21 (m, 1H), 2.20-1.99 (m, 1H), 1.97-1.74 (m, 1H), 1.26 (s, 3H), 1.17 (s, 3H), 0.78-0.53 (m, 3H). [M+H]=538.1

Example 54

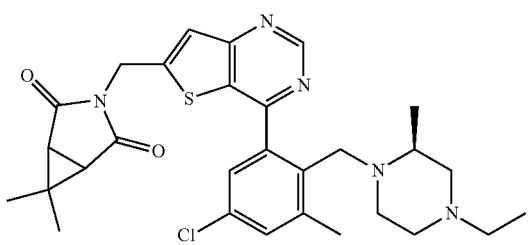 [SMILES: CCN1CCN(Cc2c(C)cc(Cl)cc2-c2ncnc3cc(CN4C(=O)C5C(C4=O)C5(C)C)sc23)[C@@H](C)C1]

3-((4-(5-chloro-2-(((S)-4-ethyl-2-methylpiperazin-1-yl)methyl)-3-methylphenyl)thieno[3,2-d]pyrimidin-6-yl)methyl)-6,6-dimethyl-3-azabicyclo[3.1.0]hexane-2,4-dione. The title compound was prepared by General Procedures D and F using 6,6-dimethyl-3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4, HCl salt) δ 9.17 (s, 1H), 7.56 (s, 1H), 7.48 (d, J=2.3 Hz, 1H), 7.35 (d, J=2.3 Hz, 1H), 4.94-4.91 (m, 2H), 4.31-4.18 (m, 1H), 3.07-2.92 (m, 2H), 2.54 (s, 2H), 2.50 (s, 3H), 2.34-2.13 (m, 2H), 2.10-1.96 (m, 1H), 1.83-1.66 (m, 1H), 1.34-1.11 (m, 10H). [M+H] 552.1

Example 55

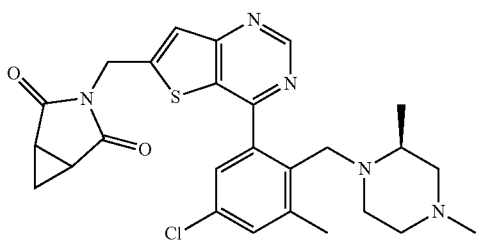 [SMILES: Cc1cc(Cl)cc(-c2ncnc3cc(CN4C(=O)C5CC5C4=O)sc23)c1CN1CCN(C)C[C@@H]1C]

3-((4-(5-chloro-2-(((S)-2,4-dimethylpiperazin-1-yl)methyl)-3-methylphenyl)thieno[3,2-d]pyrimidin-6-yl)methyl)-3-azabicyclo[3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4, HCl salt) δ 9.04 (s, 1H), 7.40 (s, 1H), 7.35 (d, J=2.2 Hz, 1H), 7.25 (s, 1H), 4.11 (s, 1H), 2.59 (s, 3H), 2.56-2.31 (m, 7H), 2.30-2.09 (m, 1H), 2.05-1.87 (m, 1H), 1.83-1.60 (m, 1H), 1.58-1.44 (m, 1H), 1.39 (q, J=4.0 Hz, 1H), 1.31-1.03 (m, 1H), 0.73-0.27 (m, 3H). [M+H] 510.0

Example 56

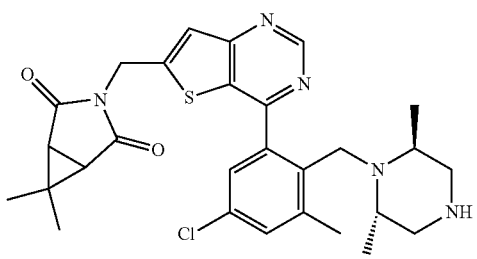 [SMILES: Cc1cc(Cl)cc(-c2ncnc3cc(CN4C(=O)C5C(C4=O)C5(C)C)sc23)c1CN1[C@@H](C)CNC[C@@H]1C]

3-((4-(5-chloro-2-(((2S,6S)-2,6-dimethylpiperazin-1-yl)methyl)-3-methylphenyl)thieno[3,2-d]pyrimidin-6-yl)methyl)-6,6-dimethyl-3-azabicyclo[3.1.0]hexane-2,4-dione. The title compound was prepared by General Procedures D and F using 6,6-dimethyl-3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Chloroform-d) δ 9.27 (s, 1H), 7.68 (s, 1H), 7.55 (s, 1H), 7.44 (s, 1H), 5.02 (s, 2H), 4.25-4.13 (m, 1H), 3.86-3.73 (m, 1H), 2.84-2.78 (m, 3H), 2.62 (s, 3H), 2.38 (s, 6H), 1.36 (s, 3H), 1.25 (s, 3H), 0.84 (d, J=6.9 Hz, 6H). [M+H] 538.0

Example 57

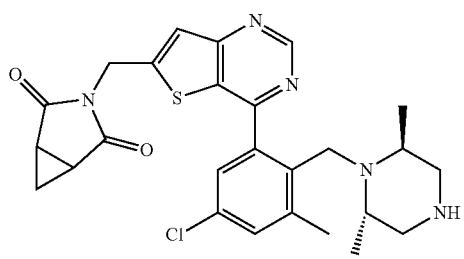 [SMILES: Cc1cc(Cl)cc(-c2ncnc3cc(CN4C(=O)C5CC5C4=O)sc23)c1CN1[C@@H](C)CNC[C@@H]1C]

3-((4-(5-chloro-2-(((2S,6S)-2,6-dimethylpiperazin-1-yl)methyl)-3-methylphenyl)thieno[3,2-d]pyrimidin-6-yl)methyl)-3-azabicyclo[3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 9.17

(s, 1H), 7.54 (d, J=1.1 Hz, 1H), 7.46 (d, J=2.3 Hz, 1H), 7.37 (d, J=2.3 Hz, 1H), 4.88 (d, J=5.8 Hz, 2H), 4.10 (d, J=14.1 Hz, 1H), 3.71 (d, J=14.5 Hz, 1H), 2.73 (dd, J=10.2, 5.6 Hz, 2H), 2.60 (dd, J=8.2, 3.6 Hz, 2H), 2.53 (s, 3H), 2.43 (d, J=12.0 Hz, 2H), 2.34-2.21 (m, 2H), 1.63 (td, J=8.1, 4.6 Hz, 1H), 1.54-1.43 (m, 1H), 0.76 (d, J=6.9 Hz, 6H). [M+H] 511.0

Example 58

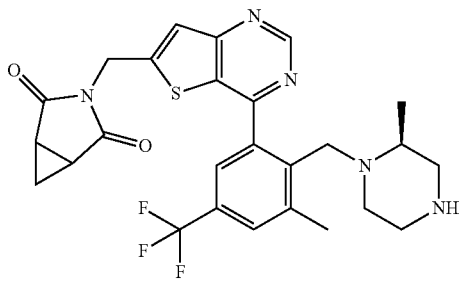 [SMILES: Cc1cc(C(F)(F)F)cc(-c2ncnc3cc(CN4C(=O)C5CC5C4=O)sc23)c1CN1CCNC[C@@H]1C]

3-((4-(3-methyl-2-(((S)-2-methylpiperazin-1-yl)methyl)-5-(trifluoromethyl)phenyl)thieno[3,2-d]pyrimidin-6-yl)methyl)-3-azabicyclo[3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. [M+H] 530.0

Example 59

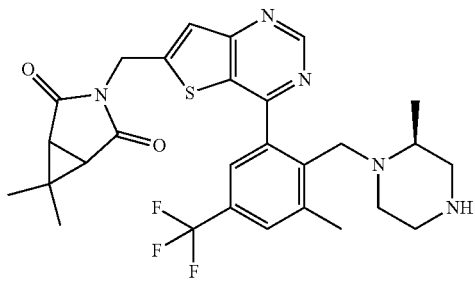 [SMILES: Cc1cc(C(F)(F)F)cc(-c2ncnc3cc(CN4C(=O)C5C(C4=O)C5(C)C)sc23)c1CN1CCNC[C@@H]1C]

6,6-dimethyl-3-((4-(3-methyl-2-(((S)-2-methylpiperazin-1-yl)methyl)-5-(trifluoromethyl)phenyl)thieno[3,2-d]pyrimidin-6-yl)methyl)-3-azabicyclo[3.1.0]hexane-2,4-dione. The title compound was prepared by General Procedures D and F using 6,6-dimethyl-3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 9.19 (s, 1H), 7.75 (s, 1H), 7.62 (s, 1H), 7.59 (s, 1H), 7.46 (s, 1H), 4.93 (s, 2H), 4.25 (d, J=13.6 Hz, 1H), 3.46 (d, J=13.2 Hz, 1H), 2.93-2.79 (m, 2H), 2.54 (s, 2H), 2.51-2.36 (m, 4H), 2.50 (s, 3H), 2.15-1.99 (m, 3H), 1.25 (s, 3H), 1.15 (s, 3H), 0.67 (d, J=6.4 Hz, 3H). [M+H] 558.1

Example 60

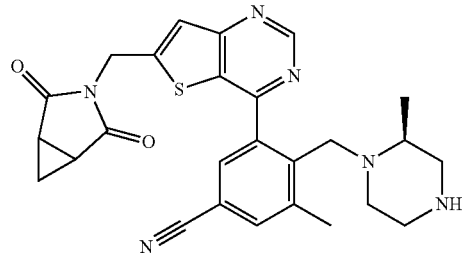 [SMILES: Cc1cc(C#N)cc(-c2ncnc3cc(CN4C(=O)C5CC5C4=O)sc23)c1CN1CCNC[C@@H]1C]

3-(6-((2,4-dioxo-3-azabicyclo[3.1.0]hexan-3-yl)methyl)thieno[3,2-d]pyrimidin-4-yl)-5-methyl-4-(((S)-2-methylpiperazin-1-yl)methyl)benzonitrile. The title compound was prepared by General Procedures D and F using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. [M+H] 487.0

Example 61

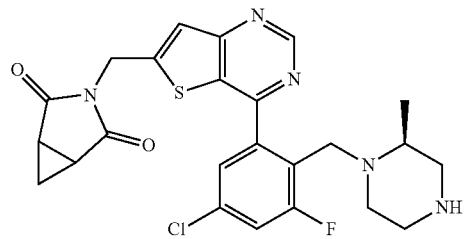 [SMILES: C[C@H]1CNCCN1Cc1c(F)cc(Cl)cc1-c1ncnc2cc(CN3C(=O)C4CC4C3=O)sc12]

3-((4-(5-chloro-3-fluoro-2-(((S)-2-methylpiperazin-1-yl)methyl)phenyl)thieno[3,2-d]pyrimidin-6-yl)methyl)-3-azabicyclo[3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 9.13 (s, 1H), 7.53 (s, 1H), 7.45 (s, 1H), 7.42 (s, 1H), 4.73 (s, 2H), 4.02 (m, 1H), 3.35 (s, 3H), 2.38 (s, 4H), 2.03 (m, 4H), 1.60 (m, 2H), 0.50 (s, 2H). [M+H] 500.0

Example 62

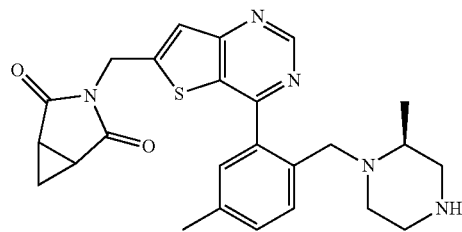 [SMILES: Cc1ccc(CN2CCNC[C@@H]2C)c(-c2ncnc3cc(CN4C(=O)C5CC5C4=O)sc23)c1]

3-((4-(5-methyl-2-(((S)-2-methylpiperazin-1-yl)methyl)phenyl)thieno[3,2-d]pyrimidin-6-yl)methyl)-3-azabicyclo[3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl)

methyl)-3-azabicyclo[3.1.0]hexane-2,4-dione. ¹H NMR (400 MHz, Methanol-d4) δ 9.29 (s, 1H), 7.87 (s, 1H), 7.65 (d, J=8.0 Hz, 1H), 7.57 (s, 1H), 7.54 (d, J=8 Hz, 1H), 4.88 (s, 2H), 4.73 (d, J=12.8 Hz, 1H), 4.08 (d, J=12.8 Hz, 1H), 3.66-3.25 (m, 4H), 2.61 (dd, J=8.0, 3.6 Hz, 2H), 2.51 (s, 3H), 1.64-1.44 (m, 2H), 1.36 (d, J=6.4 Hz, 3H). [M+H] 462.1

Example 63

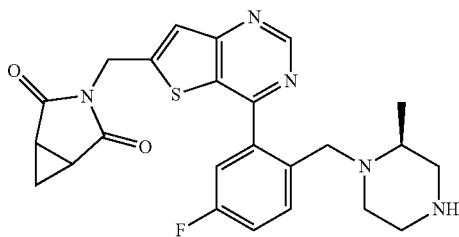 [SMILES: C[C@H]1CNCCN1Cc1ccc(F)cc1-c1ncnc2cc(CN3C(=O)C4CC4C3=O)sc12]

3-((4-(5-fluoro-2-(((S)-2-methylpiperazin-1-yl)methyl) phenyl)thieno[3,2-d]pyrimidin-6-yl)methyl)-3-azabicyclo [3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl) methyl)-3-azabicyclo[3.1.0]hexane-2,4-dione. ¹H NMR (400 MHz, Methanol-d4) δ 9.23 (s, 1H), 7.67-7.64 (m, 1H), 7.56-7.52 (m, 3H), 7.41-7.35 (m, 2H), 4.95 (s, 2H), 4.47 (d, J=13.2 Hz, 2H), 3.56-3.51 (m, 2H), 3.13-2.46 (m, 9H), 1.48-1.33 (m, 2H), 0.94 (d, J=6.8 Hz, 3H). [M+H] 466.0

Example 64

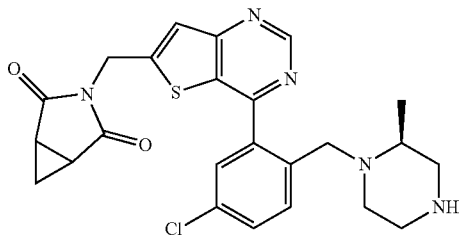 [SMILES: C[C@H]1CNCCN1Cc1ccc(Cl)cc1-c1ncnc2cc(CN3C(=O)C4CC4C3=O)sc12]

3-((4-(5-chloro-2-(((S)-2-methylpiperazin-1-yl)methyl) phenyl)thieno[3,2-d]pyrimidin-6-yl)methyl)-3-azabicyclo [3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl) methyl)-3-azabicyclo[3.1.0]hexane-2,4-dione. ¹H NMR (400 MHz, Methanol-d4) δ 9.22 (s, 1H), 7.75 (s, 1H), 7.63 (s, 2H), 7.57 (s, 2H), 4.88 (s, 2H), 4.45 (d, J=13.0 Hz, 1H), 3.49 (d, J=13.0 Hz, 1H), 3.17-2.43 (m, 9H), 1.66-1.47 (m, 2H), 0.92 (d, J=7.0 Hz, 3H). [M+H] 482.0

Example 65

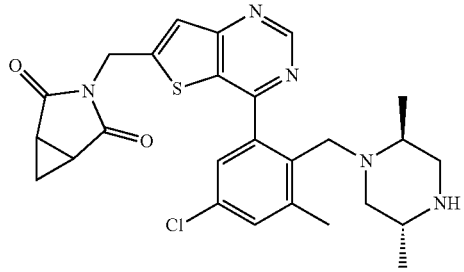 [SMILES: Cc1cc(Cl)cc(-c2ncnc3cc(CN4C(=O)C5CC5C4=O)sc23)c1CN1C[C@@H](C)NC[C@@H]1C]

3-((4-(5-chloro-2-(((2S,5R)-2,5-dimethylpiperazin-1-yl) methyl)-3-methylphenyl)thieno[3,2-d]pyrimidin-6-yl) methyl)-3-azabicyclo[3.1.0]hexane-2,4-dione. The title compound was prepared by General Procedures C and F using 3-((7-(4,4,5,5-tetramethyl-1,3,2-dioxaborolan-2-yl) thieno[3,2-b]pyridin-2-yl)methyl)-3-azabicyclo[3.1.0] hexane-2,4-dione. [M+H] 510.0

Example 66

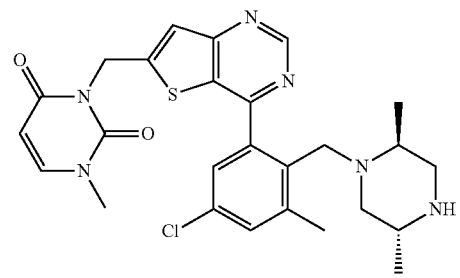 [SMILES: Cc1cc(Cl)cc(-c2ncnc3cc(Cn4c(=O)ccn(C)c4=O)sc23)c1CN1C[C@@H](C)NC[C@@H]1C]

3-((4-(5-chloro-2-(((2S,5R)-2,5-dimethylpiperazin-1-yl) methyl)-3-methylphenyl)thieno[3,2-d]pyrimidin-6-yl) methyl)-1-methylpyrimidine-2,4(1H,3H)-dione. The title compound was prepared by General Procedures C and F using 1-methyl-3-((4-(4,4,5,5-tetramethyl-1,3,2-dioxaborolan-2-yl)thieno[3,2-d]pyrimidin-6-yl)methyl)pyrimidine-2, 4(1H,3H)-dione. [M+H]525.0

Example 67

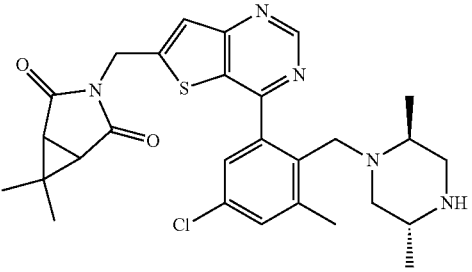 [SMILES: Cc1cc(Cl)cc(-c2ncnc3cc(CN4C(=O)C5C(C4=O)C5(C)C)sc23)c1CN1C[C@@H](C)NC[C@@H]1C]

3-((4-(5-chloro-2-(((2S,5R)-2,5-dimethylpiperazin-1-yl) methyl)-3-methylphenyl)thieno[3,2-d]pyrimidin-6-yl) methyl)-6,6-dimethyl-3-azabicyclo[3.1.0]hexane-2,4-dione. The title compound was prepared by General Procedures C and F using 6,6-dimethyl-3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, DMSO-d6) δ 9.39 (s, 1H), 7.75-7.55 (m, 3H), 4.86 (s, 2H), 4.60-4.37 (m, 1H), 4.06-3.95 (m, 1H), 3.36-3.12 (m, 1H), 2.81-2.53 (m, 8H), 1.97 (s, 2H), 1.18 (s, 3H), 1.17-1.12 (m, 3H), 1.09 (s, 3H), 0.99-0.93 (m, 3H). [M+H] 538.0

Example 68

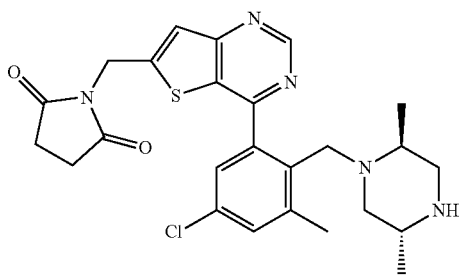 [SMILES: Cc1cc(Cl)cc(-c2ncnc3cc(CN4C(=O)CCC4=O)sc23)c1CN1C[C@@H](C)NC[C@@H]1C]

1-((4-(5-chloro-2-(((2S,5R)-2,5-dimethylpiperazin-1-yl)methyl)-3-methylphenyl)thieno[3,2-d]pyrimidin-6-yl)methyl)pyrrolidine-2,5-dione. The title compound was prepared by General Procedures C and F using 1-((4-(4,4,5,5-tetramethyl-1,3,2-dioxaborolan-2-yl)thieno[3,2-d]pyrimidin-6-yl)methyl)pyrrolidine-2,5-dione. [M+H] 498.0

Example 69

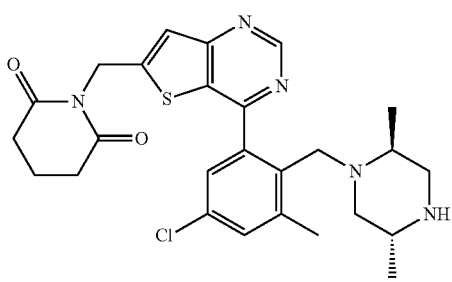 [SMILES: Cc1cc(Cl)cc(-c2ncnc3cc(CN4C(=O)CCCC4=O)sc23)c1CN1C[C@@H](C)NC[C@@H]1C]

1-((4-(5-chloro-2-(((2S,5R)-2,5-dimethylpiperazin-1-yl)methyl)-3-methylphenyl)thieno[3,2-d]pyrimidin-6-yl)methyl)piperidine-2,6-dione. The title compound was prepared by General Procedures C and F using 1-((4-(4,4,5,5-tetramethyl-1,3,2-dioxaborolan-2-yl)thieno[3,2-d]pyrimidin-6-yl)methyl)piperidine-2,6-dione. $^1$H NMR (400 MHz, DMSO-d6) δ 9.23 (s, 1H), 7.63-7.43 (m, 3H), 5.14 (s, 2H), 4.30-3.51 (m, 2H), 3.11-2.95 (m, 1H), 2.74-2.33 (m, 8H), 1.87-1.79 (m, 4H), 0.97-0.66 (m, 8H). [M+H] 512.0

Example 70

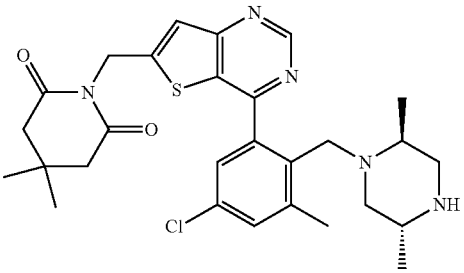 [SMILES: Cc1cc(Cl)cc(-c2ncnc3cc(CN4C(=O)CC(C)(C)CC4=O)sc23)c1CN1C[C@@H](C)NC[C@@H]1C]

1-((4-(5-chloro-2-(((2S,5R)-2,5-dimethylpiperazin-1-yl)methyl)-3-methylphenyl)thieno[3,2-d]pyrimidin-6-yl)methyl)-4,4-dimethylpiperidine-2,6-dione. The title compound was prepared by General Procedures C and F using 4,4-dimethyl-1-((4-(4,4,5,5-tetramethyl-1,3,2-dioxaborolan-2-yl)thieno[3,2-d]pyrimidin-6-yl)methyl)piperidine-2,6-dione. [M+H] 540.1

Example 71

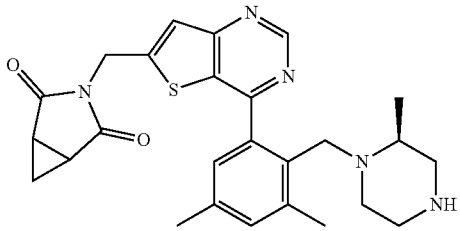 [SMILES: Cc1cc(C)c(CN2CCNC[C@@H]2C)c(-c2ncnc3cc(CN4C(=O)C5CC5C4=O)sc23)c1]

3-((4-(3,5-dimethyl-2-(((S)-2-methylpiperazin-1-yl)methyl)phenyl)thieno[3,2-d]pyrimidin-6-yl)methyl)-3-azabicyclo[3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 9.06 (s, 1H), 7.49 (s, 1H), 7.20 (s, 1H), 7.11 (s, 1H), 4.84 (s, 2H), 4.09 (m, 1H), 3.34 (s, 3H), 2.58 (m, 1H), 2.43 (s, 3H), 2.35 (s, 3H), 2.07 (m, 3H), 1.97 (m, 2H), 1.61 (m, 3H), 1.31 (s, 1H), 1.25 (m, 1H), 0.56 (m, 2H). [M+H] 476.0

Example 72

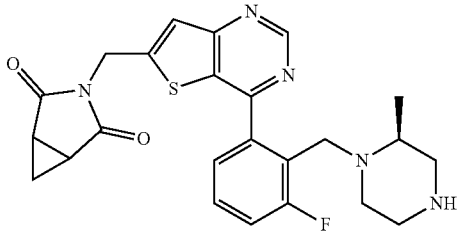 [SMILES: C[C@H]1CNCCN1Cc1c(F)cccc1-c1ncnc2cc(CN3C(=O)C4CC4C3=O)sc12]

3-((4-(3-fluoro-2-(((S)-2-methylpiperazin-1-yl)methyl)phenyl)thieno[3,2-d]pyrimidin-6-yl)methyl)-3-azabicyclo[3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 9.07 (s, 1H), 7.55 (m, 2H), 7.37 (m, 2H), 4.84 (s, 2H), 4.18 (m, 1H), 3.49 (m, 1H), 3.35 (s, 3H), 2.61 (m, 2H), 2.32 (m, 2H), 2.13 (m, 1H), 1.93 (m, 1H), 1.86 (s, 2H), 1.64 (m, 1H), 1.48 (m, 1H), 0.61 (m, 2H). [M+H] 466.0

Example 73

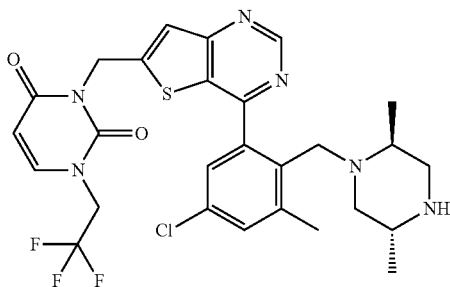 [SMILES: Cc1cc(Cl)cc(-c2ncnc3cc(Cn4c(=O)ccn(CC(F)(F)F)c4=O)sc23)c1CN1C[C@@H](C)NC[C@@H]1C]

3-((4-(5-chloro-2-(((2S,5R)-2,5-dimethylpiperazin-1-yl)methyl)-3-methylphenyl)thieno[3,2-d]pyrimidin-6-yl)methyl)-1-(2,2,2-trifluoroethyl)pyrimidine-2,4(1H,3H)-dione. The title compound was prepared by General Procedures C, F, and H. $^1$H NMR (400 MHz, DMSO-d6) δ 9.44-9.21 (m, 2H), 7.77 (d, J=8.1 Hz, 1H), 7.67 (s, 1H), 7.64-7.51 (m, 1H), 5.91 (d, J=7.9 Hz, 1H), 5.40-5.27 (m, 2H), 4.78-4.64 (m, 2H), 4.20 (s, 3H), 3.20-3.02 (m, 1H), 2.61-2.42 (m, 7H), 1.21-0.80 (m, 6H). [M+H] 593.0

Example 74

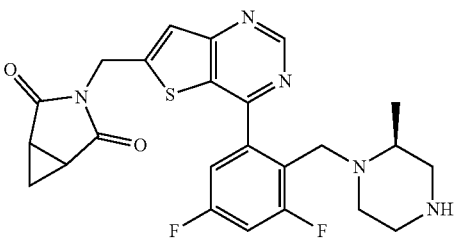 [SMILES: C[C@H]1CNCCN1Cc1c(F)cc(F)cc1-c1ncnc2cc(CN3C(=O)C4CC4C3=O)sc12]

3-((4-(3,5-difluoro-2-(((S)-2-methylpiperazin-1-yl)methyl)phenyl)thieno[3,2-d]pyrimidin-6-yl)methyl)-3-azabicyclo[3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 9.07 (s, 1H), 7.53 (s, 1H), 7.45 (s, 1H), 7.19 (s, 1H), 4.82 (s, 2H), 4.09 (m, 1H), 3.35 (s, 3H), 2.38 (s, 4H), 2.03 (m, 2H), 1.20 (m, 4H), 0.48 (m, 2H). [M+H] 484.0

Example 75

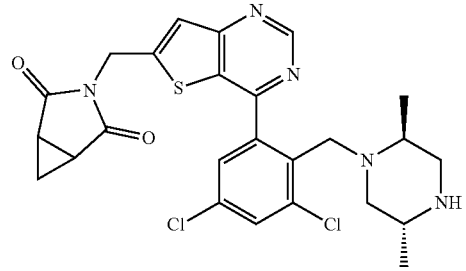 [SMILES: C[C@@H]1CN(Cc2c(Cl)cc(Cl)cc2-c2ncnc3cc(CN4C(=O)C5CC5C4=O)sc23)[C@@H](C)CN1]

3-((4-(3,5-dichloro-2-(((2S,5R)-2,5-dimethylpiperazin-1-yl)methyl)phenyl)thieno[3,2-d]pyrimidin-6-yl)methyl)-3-azabicyclo[3.1.0]hexane-2,4-dione. The title compound was prepared by General Procedures D, F, and G. $^1$H NMR (400 MHz, Methanol-d4) δ 9.22 (s, 1H), 7.80 (s, 1H), 7.64 (s, 1H), 7.54 (s, 1H), 4.84 (s, 2H), 4.32 (m, 1H), 3.72 (m, 1H), 3.58 (m, 1H), 3.33 (s, 6H), 3.13 (m, 2H), 2.61 (m, 2H), 1.28 (s, 2H), 1.12 (s, 2H), 0.64 (s, 2H). [M+H] 530.0

Example 76

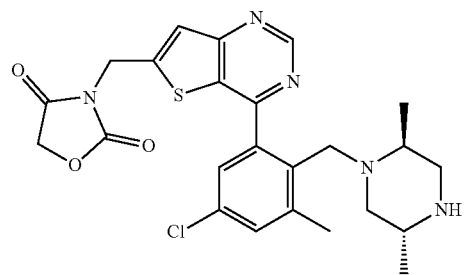 [SMILES: Cc1cc(Cl)cc(-c2ncnc3cc(CN4C(=O)COC4=O)sc23)c1CN1C[C@@H](C)NC[C@@H]1C]

3-((4-(5-chloro-2-(((2S,5R)-2,5-dimethylpiperazin-1-yl)methyl)-3-methylphenyl)thieno[3,2-d]pyrimidin-6-yl)methyl)oxazolidine-2,4-dione. The title compound was prepared by General Procedures D, F, and G. $^1$H NMR (400 MHz, Methanol-d4) δ 9.42 (s, 1H), 7.85 (s, 1H), 7.74 (s, 1H), 7.68 (s, 1H), 5.10 (s, 2H), 4.72 (s, 2H), 4.23 (s, 2H), 3.65 (m, 2H), 3.12 (m, 2H), 3.03 (s, 1H), 2.63 (s, 3H), 1.30 (s, 2H), 1.26 (s, 6H). [M+H] 500.0

Example 77

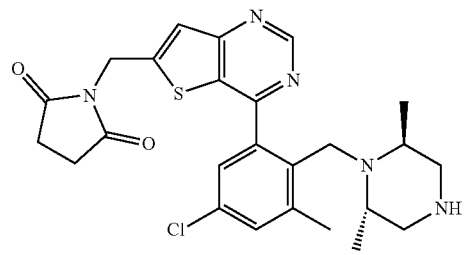 [SMILES: Cc1cc(Cl)cc(-c2ncnc3cc(CN4C(=O)CCC4=O)sc23)c1CN1[C@@H](C)CNC[C@@H]1C]

1-((4-(5-chloro-2-(((2S,6S)-2,6-dimethylpiperazin-1-yl)methyl)-3-methylphenyl)thieno[3,2-d]pyrimidin-6-yl)methyl)pyrrolidine-2,5-dione. The title compound was prepared by General Procedures D, F, and G. $^1$H NMR (400 MHz, Methanol-d4) δ 9.18 (d, J=1.6 Hz, 1H), 7.64-7.54 (m, 1H), 7.47 (s, 2H), 4.96 (d, J=1.3 Hz, 2H), 4.20 (d, J=14.4 Hz, 1H), 3.86 (d, J=14.4 Hz, 1H), 3.02 (s, 2H), 2.72-2.64 (m, 6H), 2.57 (s, 3H), 2.49 (s, 3H), 0.88 (d, J=6.7 Hz, 6H). [M+H] 498.0

Example 78

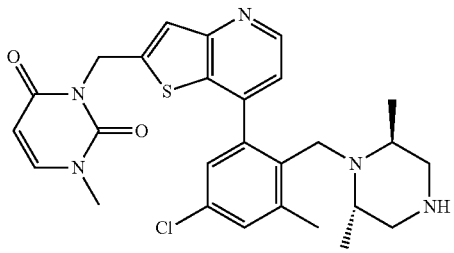 [SMILES: Cc1cc(Cl)cc(-c2ccnc3cc(Cn4c(=O)ccn(C)c4=O)sc23)c1CN1[C@@H](C)CNC[C@@H]1C]

3-((7-(5-chloro-2-(((2S,6S)-2,6-dimethyl piperazin-1-yl)methyl)-3-methylphenyl)thieno[3,2-b]pyridin-2-yl)methyl)-1-methylpyrimidine-2,4(1H,3H)-dione. The title compound was prepared by General Procedures D, F, and G. $^1$H NMR (400 MHz, Methanol-d4) δ 9.19 (d, J=0.6 Hz, 1H), 7.59 (q, J=0.9 Hz, 1H), 7.53 (dd, J=7.9, 0.6 Hz, 1H), 7.48 (s, 3H), 5.69 (dd, J=7.9, 0.7 Hz, 1H), 5.39 (d, J=0.8 Hz, 2H), 4.21 (d, J=14.6 Hz, 1H), 3.88 (d, J=14.5 Hz, 1H), 3.31 (d, J=0.7 Hz, 1H), 3.09 (d, J=30.5 Hz, 3H), 2.72 (d, J=12.8 Hz, 2H), 2.61 (s, 3H), 2.49 (q, J=0.9 Hz, 3H), 0.89 (d, J=6.7 Hz, 6H). [M+H] 525.0

Example 79

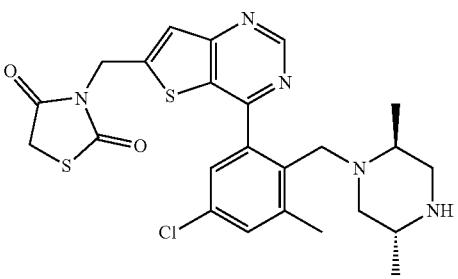 [SMILES: Cc1cc(Cl)cc(-c2ncnc3cc(CN4C(=O)CSC4=O)sc23)c1CN1C[C@@H](C)NC[C@@H]1C]

3-((4-(5-chloro-2-(((2S,5R)-2,5-dimethylpiperazin-1-yl)methyl)-3-methylphenyl)thieno[3,2-d]pyrimidin-6-yl)methyl)thiazolidine-2,4-dione. The title compound was prepared by General Procedures D, F, and G. $^1$H NMR (400 MHz, Methanol-d4) δ 9.29 (s, 1H), 7.65 (s, 1H), 7.59 (s, 1H), 7.46 (s, 1H), 5.15 (s, 2H), 4.18 (m, 1H), 3.67 (m, 1H), 3.12 (m, 2H), 3.03 (s, 1H), 2.57 (s, 3H), 1.27 (s, 6H), 1.17 (m, 2H), 1.00 (m, 2H), 0.89 (m, 2H). [M+H] 516.0

Example 80

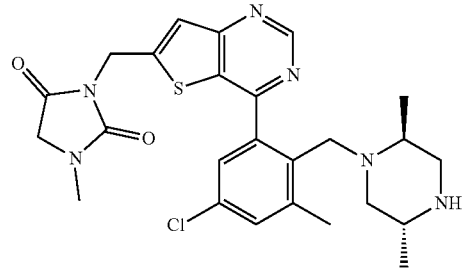 [SMILES: Cc1cc(Cl)cc(-c2ncnc3cc(CN4C(=O)CN(C)C4=O)sc23)c1CN1C[C@@H](C)NC[C@@H]1C]

3-((4-(5-chloro-2-(((2S,5R)-2,5-dimethylpiperazin-1-yl)methyl)-3-methylphenyl)thieno[3,2-d]pyrimidin-6-yl)methyl)-1-methylimidazolidine-2,4-dione. The title compound was prepared by General Procedures D, F, and G. $^1$H NMR (400 MHz, Methanol-d4) δ 9.38 (s, 1H), 7.80 (s, 1H), 7.66 (s, 2H), 5.03 (s, 2H), 4.65 (m, 1H), 4.12 (m, 1H), 4.03 (s, 2H), 3.52 (m, 2H), 3.14 (m, 2H), 2.97 (s, 3H), 2.61 (s, 3H), 1.26 (s, 2H), 1.24 (s, 6H). [M+H] 513.0

Example 81

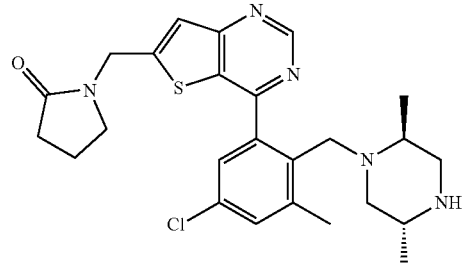

1-((4-(5-chloro-2-(((2S,5R)-2,5-dimethylpiperazin-1-yl)methyl)-3-methylphenyl)thieno[3,2-d]pyrimidin-6-yl)methyl)pyrrolidin-2-one. The title compound was prepared by General Procedures D and F using 1-((4-(4,4,5,5-tetramethyl-1,3,2-dioxaborolan-2-yl)thieno[3,2-d]pyrimidin-6-yl)methyl)pyrrolidin-2-one. $^1$H NMR (400 MHz, Methanol-d4) δ 9.11 (s, 1H), 7.47 (s, 1H), 7.33 (s, 1H), 7.24 (s, 1H), 4.74 (s, 2H), 4.27 (s, 2H), 3.45 (m, 2H), 2.77 (m, 4H), 2.51 (s, 3H), 2.25 (m, 2H), 1.50 (m, 4H), 1.26 (s, 6H). [M+H] 484.0

Example 82

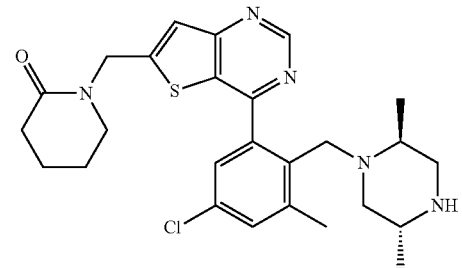

1-((4-(5-chloro-2-(((2S,5R)-2,5-dimethylpiperazin-1-yl)methyl)-3-methylphenyl)thieno[3,2-d]pyrimidin-6-yl)

methyl)piperidin-2-one. The title compound was prepared by General Procedures D and F using 1-((4-(4,4,5,5-tetramethyl-1,3,2-dioxaborolan-2-yl)thieno[3,2-d]pyrimidin-6-yl)methyl)piperidin-2-one. ¹H NMR (400 MHz, Methanol-d4) δ 9.13 (s, 1H), 7.37 (s, 1H), 7.30 (s, 1H), 7.24 (s, 1H), 4.67 (s, 2H), 4.08 (s, 2H), 3.46 (m, 2H), 2.68 (m, 4H), 2.48 (s, 3H), 1.99 (m, 4H), 1.45 (m, 4H), 1.24 (s, 6H). [M+H] 498.0

Example 83

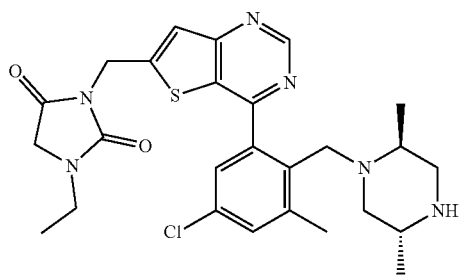 [SMILES: CCN1CC(=O)N(Cc2cc3ncnc(-c4cc(Cl)cc(C)c4CN4C[C@@H](C)NC[C@@H]4C)c3s2)C1=O]

3-((4-(5-chloro-2-(((2S,5R)-2,5-dimethylpiperazin-1-yl)methyl)-3-methylphenyl)thieno[3,2-d]pyrimidin-6-yl)methyl)-1-ethylimidazolidine-2,4-dione. The title compound was prepared by General Procedures D, F, and G. ¹H NMR (400 MHz, Methanol-d4) δ 9.29 (s, 1H), 7.66 (s, 1H), 7.63 (s, 1H), 7.60 (s, 1H), 5.06 (s, 2H), 4.47 (m, 1H), 4.08 (s, 2H), 3.74 (m, 1H), 3.46 (m, 2H), 3.13 (s, 1H), 2.57 (s, 3H), 1.27 (s, 6H), 1.19 (m, 5H), 1.01 (s, 2H), 0.91 (m, 2H). [M+H] 527.0

Example 84

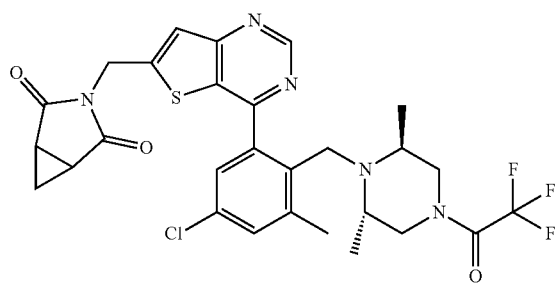 [SMILES: Cc1cc(Cl)cc(-c2ncnc3cc(CN4C(=O)C5CC5C4=O)sc23)c1CN1[C@@H](C)CN(C(=O)C(F)(F)F)C[C@@H]1C]

3-((4-(5-chloro-2-(((2S,6S)-2,6-dimethyl-4-(2,2,2-trifluoroacetyl)piperazin-1-yl)methyl)-3-methylphenyl)thieno[3,2-d]pyrimidin-6-yl)methyl)-3-azabicyclo[3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. ¹H NMR (400 MHz, Methanol-d4) δ 9.14 (s, 1H), 7.55 (s, 1H), 7.43 (s, 1H), 7.33 (s, 1H), 4.91 (s, 2H), 4.06 (bs, 1H), 3.65 (bs, 1H), 2.86-2.49 (m, 7H), 2.51 (s, 3H), 1.62-1.34 (m, 2H), 0.61 (t, J=6.6 Hz, 6H). [M+H] 606.0

Example 85

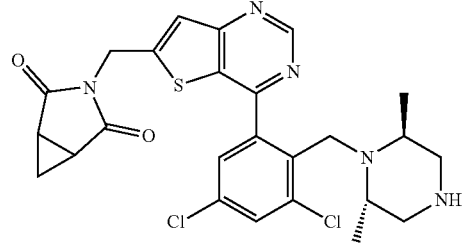

3-((4-(3,5-dichloro-2-(((2S,6S)-2,6-dimethylpiperazin-1-yl)methyl)phenyl)thieno[3,2-d]pyrimidin-6-yl)methyl)-3-azabicyclo[3.1.0]hexane-2,4-dione. The title compound was prepared by General Procedures D and F using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. ¹H NMR (400 MHz, Methanol-d4) δ 9.28 (s, 1H), 7.83 (s, 1H), 7.73 (s, 1H), 7.59 (s, 1H), 4.89 (s, 2H), 4.44 (m, 1H), 4.15 (m, 1H), 3.10 (m, 2H), 2.74 (m, 2H), 2.60 (m, 4H), 1.63 (m, 1H), 1.48 (m, 1H), 0.98 (s, 6H). [M+H] 532.0

Example 86

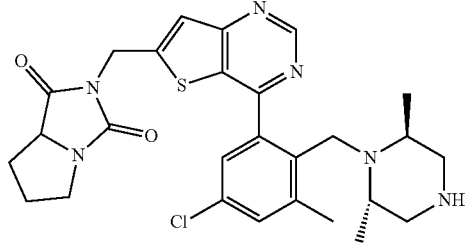 [SMILES: Cc1cc(Cl)cc(-c2ncnc3cc(CN4C(=O)C5CCCN5C4=O)sc23)c1CN1[C@@H](C)CNC[C@@H]1C]

2-((4-(5-chloro-2-(((2S,6S)-2,6-dimethylpiperazin-1-yl)methyl)-3-methylphenyl)thieno[3,2-d]pyrimidin-6-yl)methyl)tetrahydro-1H-pyrrolo[1,2-c]imidazole-1,3(2H)-dione. The title compound was prepared by General Procedures D, F, and G. ¹H NMR (400 MHz, Methanol-d4) δ 9.41 (s, 1H), 7.80 (s, 1H), 7.68 (s, 1H), 7.67 (d, J=2.2 Hz, 1H), 5.05 (s, 2H), 4.53 (d, J=14.0 Hz, 1H), 4.37-4.20 (m, 2H), 3.74-3.53 (m, 3H), 3.29-3.06 (m, 5H), 2.64 (s, 3H), 2.34-2.18 (m, 1H), 2.18-2.01 (m, 2H), 1.77-1.63 (m, 1H), 1.25 (s, 3H), 1.23 (s, 3H). [M+H] 539.2

Example 87

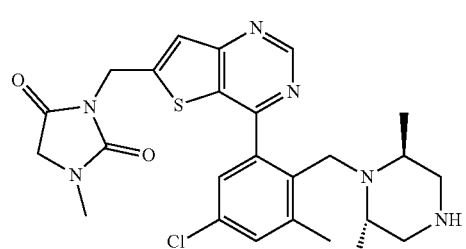

3-((4-(5-chloro-2-(((2S,6S)-2,6-dimethylpiperazin-1-yl)methyl)-3-methylphenyl)thieno[3,2-d]pyrimidin-6-yl)methyl)-1-methylimidazolidine-2,4-dione. The title compound was prepared by General Procedures D, F, and G. $^1$H NMR (400 MHz, Methanol-d4) δ 9.38 (s, 1H), 7.74 (s, 1H), 7.69 (s, 1H), 7.64 (d, J=2.0 Hz, 1H), 5.06 (s, 2H), 4.47 (d, J=13.9 Hz, 1H), 4.20 (d, J=14.0 Hz, 1H), 4.05 (s, 2H), 3.61-3.41 (m, 2H), 3.22-3.01 (m, 4H), 2.98 (s, 3H), 2.63 (s, 3H), 1.18 (s, 3H), 1.17 (s, 3H). [M+H] 513.2

Example 88

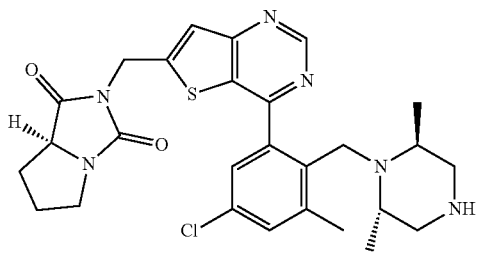 [SMILES: Cc1cc(Cl)cc(-c2ncnc3cc(CN4C(=O)[C@@H]5CCCN5C4=O)sc23)c1CN1[C@@H](C)CNC[C@@H]1C]

(S)-2-((4-(5-chloro-2-(((2S,6S)-2,6-dimethylpiperazin-1-yl)methyl)-3-methylphenyl)thieno[3,2-d]pyrimidin-6-yl)methyl)tetrahydro-1H-pyrrolo[1,2-c]imidazole-1,3(2H)-dione. The title compound was prepared by General Procedures D, F, and G. $^1$H NMR (400 MHz, Methanol-d4) δ 9.29 (s, 1H), 7.64 (s, 1H), 7.62-7.57 (m, 1H), 7.59-7.54 (m, 1H), 5.03 (d, J=2.9 Hz, 2H), 4.38-4.22 (m, 2H), 4.00 (d, J=14.4 Hz, 1H), 3.62 (q, J=8.7 Hz, 1H), 3.27-3.07 (m, 3H), 2.93-2.64 (m, 4H), 2.58 (s, 3H), 2.33-2.17 (m, 1H), 2.17-2.02 (m, 2H), 1.79-1.63 (m, 1H), 1.01 (s, 3H), 1.00 (s, 3H). [M+H] 539.2

Example 89

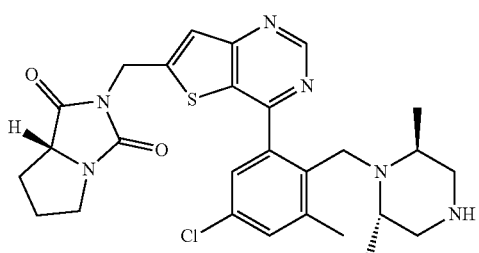

(R)-2-((4-(5-chloro-2-(((2S,6S)-2,6-dimethylpiperazin-1-yl)methyl)-3-methylphenyl)thieno[3,2-d]pyrimidin-6-yl)methyl)tetrahydro-1H-pyrrolo[1,2-c]imidazole-1,3(2H)-dione. The title compound was prepared by General Procedures D, F, and G. $^1$H NMR (400 MHz, Methanol-d4) δ 9.26 (s, 1H), 7.63 (s, 1H), 7.54 (s, 2H), 5.07-5.00 (m, 2H), 4.35-4.20 (m, 2H), 3.92 (d, J=14.5 Hz, 1H), 3.70-3.57 (m, 1H), 3.05 (s, 2H), 2.78-2.59 (m, 2H), 2.57 (s, 3H), 2.29-2.00 (m, 3H), 1.78-1.64 (m, 1H), 0.94 (s, 3H), 0.93 (s, 3H). [M+H] 539.2

Example 90

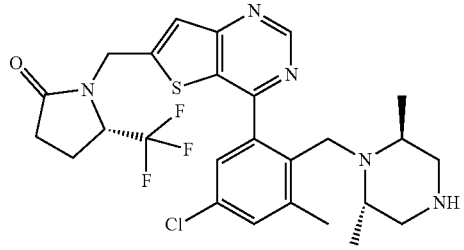 [SMILES: Cc1cc(Cl)cc(-c2ncnc3cc(CN4C(=O)CC[C@H]4C(F)(F)F)sc23)c1CN1[C@@H](C)CNC[C@@H]1C]

(S)-1-((4-(5-chloro-2-(((2S,6S)-2,6-dimethylpiperazin-1-yl)methyl)-3-methylphenyl)thieno[3,2-d]pyrimidin-6-yl)methyl)-5-(trifluoromethyl)pyrrolidin-2-one. The title compound was prepared by General Procedures D, F, and G. 1H NMR (400 MHz, Methanol-d4) δ 9.31 (s, 1H), 7.62 (s, 1H), 7.61 (s, 1H), 7.57 (d, J=2.0 Hz, 1H), 5.09 (d, J=16.5 Hz, 1H), 4.86 (d, J=16.5 Hz, 1H), 4.51-4.27 (m, 2H), 4.03 (d, J=13.8 Hz, 1H), 3.22 (s, 3H), 3.03-2.71 (m, 4H), 2.59 (s, 3H), 2.52-2.30 (m, 2H), 2.23 (t, J=10.5 Hz, 1H), 1.04 (s, 3H), 1.03 (s, 3H). [M+H] 552.2

Example 91

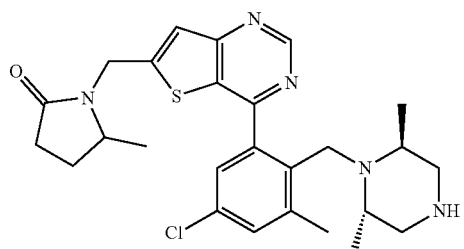

1-((4-(5-chloro-2-(((2S,6S)-2,6-dimethylpiperazin-1-yl)methyl)-3-methylphenyl)thieno[3,2-d]pyrimidin-6-yl)methyl)-5-methylpyrrolidin-2-one. The title compound was prepared by General Procedures D, F, and G. [M+H] 523.2

Example 92

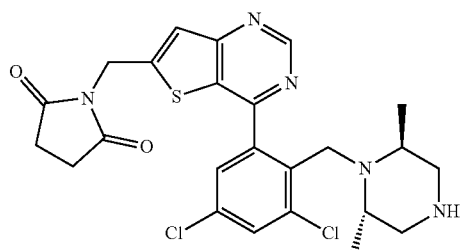

1-((4-(3,5-dichloro-2-(((2S,6S)-2,6-dimethylpiperazin-1-yl)methyl)phenyl)thieno[3,2-d]pyrimidin-6-yl)methyl)pyrrolidine-2,5-dione. The title compound was prepared by General Procedures D, F, and G. $^1$H NMR (400 MHz, Methanol-d4) δ 9.27 (s, 1H), 7.82 (s, 1H), 7.71 (s, 1H), 7.64

(s, 1H), 5.04 (s, 2H), 4.43 (m, 1H), 4.13 (m, 1H), 3.07 (m, 2H), 2.77 (m, 4H), 2.70 (m, 2H), 2.56 (m, 2H), 0.96 (s, 6H). [M+H] 518.0

Example 93

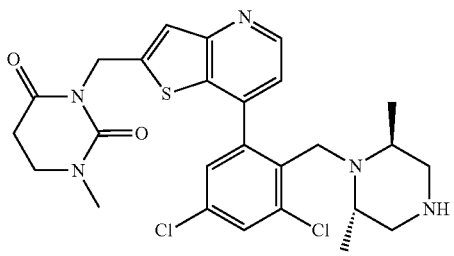 [SMILES: C[C@H]1CNC[C@H](C)N1Cc1c(Cl)cc(Cl)cc1-c1ccnc2cc(CN3C(=O)CCN(C)C3=O)sc12]

3-((7-(3,5-dichloro-2-(((2S,6S)-2,6-dimethylpiperazin-1-yl)methyl)phenyl)thieno[3,2-b]pyridin-2-yl)methyl)-1-methyldihydropyrimidine-2,4(1H,3H)-dione. The title compound was prepared by General Procedures D, F, and G. $^1$H NMR (400 MHz, Methanol-d4) δ 9.27 (s, 1H), 7.83 (s, 1H), 7.73 (s, 1H), 7.61 (s, 1H), 5.27 (s, 2H), 4.44 (m, 1H), 4.14 (m, 1H), 3.45 (m, 2H), 3.11 (m, 2H), 3.00 (s, 3H), 2.76 (m, 4H), 2.60 (m, 2H), 0.97 (s, 6H). [M+H] 547.0

Example 94

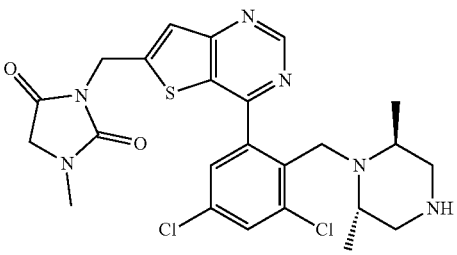 [SMILES: C[C@H]1CNC[C@H](C)N1Cc1c(Cl)cc(Cl)cc1-c1ncnc2cc(CN3C(=O)CN(C)C3=O)sc12]

3-((4-(3,5-dichloro-2-(((2S,6S)-2,6-dimethylpiperazin-1-yl)methyl)phenyl)thieno[3,2-d]pyrimidin-6-yl)methyl)-1-methylimidazolidine-2,4-dione. The title compound was prepared by General Procedures D, F, and G. $^1$H NMR (400 MHz, Chloroform-d) δ 9.21-9.08 (m, 1H), 7.59 (s, 1H), 7.51 (m, 1H), 7.31 (m, 1H), 4.97 (s, 2H), 4.13 (m, 1H), 3.95 (m, 2H), 3.76 (m, 1H), 3.00 (s, 3H), 2.39 (m, 2H), 2.10 (m, 3H), 1.80 (m, 2H), 0.66 (s, 6H). [M+H] 533.0

Example 95

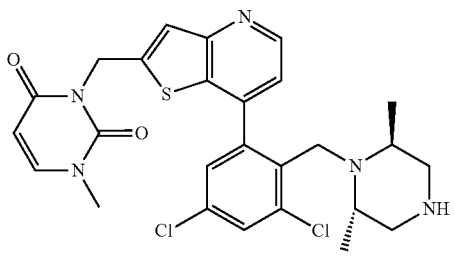

3-((7-(3,5-dichloro-2-(((2S,6S)-2,6-dimethylpiperazin-1-yl)methyl)phenyl)thieno[3,2-b]pyridin-2-yl)methyl)-1-methylpyrimidine-2,4(1H,3H)-dione. The title compound was prepared by General Procedures D, F, and G. $^1$H NMR (400 MHz, Methanol-d4) δ 9.25 (s, 1H), 7.80 (s, 1H), 7.67 (m, 2H), 7.60 (s, 1H), 5.77 (m, 1H), 5.47 (s, 2H), 4.38 (m, 1H), 4.09 (m, 1H), 3.39 (s, 3H), 3.00 (m, 2H), 2.65 (m, 2H), 2.50 (m, 2H), 0.92 (s, 6H). [M+H] 545.0

Example 96

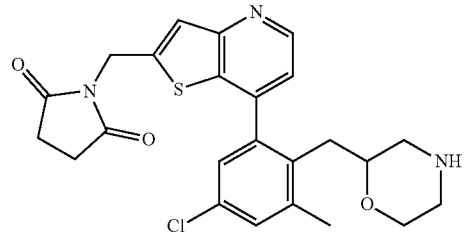 [SMILES: Cc1cc(Cl)cc(-c2ccnc3cc(CN4C(=O)CCC4=O)sc23)c1CC1CNCCO1]

1-((7-(5-chloro-3-methyl-2-(morpholin-2-ylmethyl)phenyl)thieno[3,2-b]pyridin-2-yl)methyl)pyrrolidine-2,5-dione. The title compound was prepared by General Procedures B and E using 1-((4-(4,4,5,5-tetramethyl-1,3,2-dioxaborolan-2-yl)thieno[3,2-d]pyrimidin-6-yl)methyl)pyrrolidine-2,5-dione. $^1$H NMR (400 MHz, Methanol-d4) δ 8.83 (s, 1H), 7.85-7.55 (m, 2H), 7.46 (d, J=2.2 Hz, 1H), 7.20 (dd, J=11.6, 2.3 Hz, 1H), 5.01 (d, J=5.0 Hz, 2H), 3.90 (dd, J=13.0, 3.8 Hz, 1H), 3.59 (d, J=10.4 Hz, 1H), 3.47 (d, J=7.0 Hz, 1H), 3.19-2.52 (m, 10H), 2.47 (s, 3H). [M+H] 470.1

Example 97

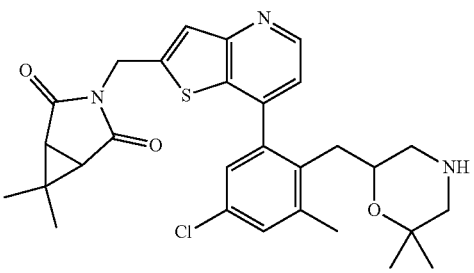 [SMILES: Cc1cc(Cl)cc(-c2ccnc3cc(CN4C(=O)C5C(C4=O)C5(C)C)sc23)c1CC1CNCC(C)(C)O1]

3-((7-(5-chloro-2-((6,6-dimethylmorpholin-2-yl)methyl)-3-methylphenyl)thieno[3,2-b]pyridin-2-yl)methyl)-6,6-dimethyl-3-azabicyclo[3.1.0]hexane-2,4-dione. The title compound was prepared by General Procedures B and E using 6,6-dimethyl-3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.72 (d, J=4.7 Hz, 1H), 7.56 (s, 1H), 7.47-7.35 (m, 2H), 7.18 (dd, J=21.8, 2.3 Hz, 1H), 4.85 (d, J=0.4 Hz, 2H), 3.98 (d, J=13.0, 1H), 3.73 (d, J=17.1 Hz, 1H), 3.10-2.77 (m, 3H), 2.75-2.50 (m, 2H), 2.49 (s, 2H), 2.46 (d, J=2.2 Hz, 3H), 1.24 (s, 3H), 1.19-0.78 (m, 9H). [M+H] 538.2

Example 98

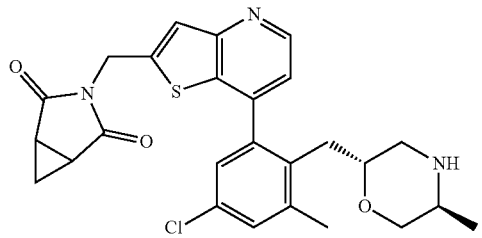 [SMILES: Cc1cc(Cl)cc(-c2ccnc3cc(CN4C(=O)C5CC5C4=O)sc23)c1C[C@@H]1CN[C@@H](C)CO1]

3-((7-(5-chloro-3-methyl-2-((5-methylmorpholin-2-yl)methyl)phenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.73 (d, J=5.1 Hz, 1H), 7.52 (d, J=7.2 Hz, 1H), 7.49-7.36 (m, 2H), 7.18 (dd, J=7.0, 2.2 Hz, 1H), 4.84-4.81 (m, 2H), 3.63-3.44 (m, 2H), 3.19-2.97 (m, 3H), 2.98-2.80 (m, 1H), 2.76-2.61 (m, 2H), 2.58 (dd, J=8.1, 3.6 Hz, 2H), 2.46 (s, 3H), 1.61 (td, J=8.1, 4.6 Hz, 1H), 1.44 (dd, J=4.3, 2.2 Hz, 1H), 1.11 (dd, J=9.1, 6.3 Hz, 3H). [M+H] 496.0

Example 99

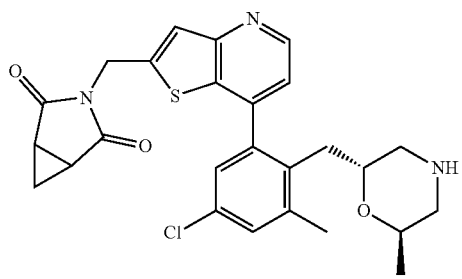 [SMILES: Cc1cc(Cl)cc(-c2ccnc3cc(CN4C(=O)C5CC5C4=O)sc23)c1C[C@@H]1CNC[C@@H](C)O1]

3-((7-(5-chloro-3-methyl-2-(((2R,6R)-6-methylmorpholin-2-yl)methyl)phenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.73 (d, J=5.1 Hz, 1H), 7.53 (d, J=1.4 Hz, 1H), 7.51-7.38 (m, 2H), 7.20 (d, J=25.8 Hz, 1H), 4.81 (d, J=3.0 Hz, 2H), 3.72-3.41 (m, 2H), 3.19-2.85 (m, 3H), 2.66-2.51 (m, 5H), 2.47 (d, J=2.8 Hz, 3H), 1.61 (td, J=8.1, 4.6 Hz, 1H), 1.43 (p, J=4.8 Hz, 1H), 1.14-0.79 (m, 3H). [M+H] 496.0

Example 100

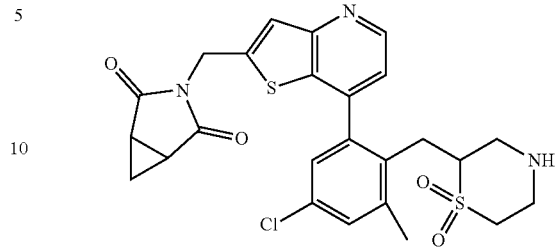

3-((7-(5-chloro-2-((1,1-dioxidothiomorpholin-2-yl)methyl)-3-methylphenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.81 (t, J=2.6 Hz, 1H), 7.61-7.52 (m, 2H), 7.50 (t, J=2.3 Hz, 1H), 7.27 (t, J=3.2 Hz, 1H), 4.84 (s, 2H), 3.70 (dd, J=9.6, 2.8 Hz, 1H), 3.58-3.32 (m, 5H), 3.18 (dd, J=15.2, 5.4 Hz, 1H), 3.05 (t, J=12.9 Hz, 1H), 3.00-2.89 (m, 1H), 2.58 (ddd, J=9.1, 5.7, 3.5 Hz, 2H), 2.52 (d, J=7.2 Hz, 3H), 1.65-1.54 (m, 1H), 1.41 (dq, J=20.6, 4.0 Hz, 1H). [M+H] 530.0

Example 101

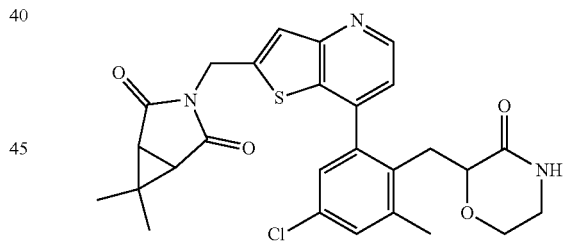

3-((7-(5-chloro-3-methyl-2-((3-oxomorpholin-2-yl)methyl)phenyl)thieno[3,2-b]pyridin-2-yl)methyl)-6,6-dimethyl-3-azabicyclo[3.1.0]hexane-2,4-dione. The title compound was prepared by General Procedures B and E using 6,6-dimethyl-3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione (omitted the lactam reduction step). $^1$H NMR (400 MHz, Methanol-d4) δ 8.84 (s, 1H), 7.66 (d, J=16.2 Hz, 2H), 7.44 (s, 1H), 7.19 (d, J=18.6 Hz, 1H), 4.93 (s, 1H), 3.94 (dd, J=19.2, 10.4 Hz, 1H), 3.66 (d, J=11.9 Hz, 1H), 3.70-2.64 (m, 7H), 2.49 (s, 3H), 1.23 (d, J=5.2 Hz, 3H), 1.08 (d, J=27.3 Hz, 3H). [M+H] 524.0

Example 102

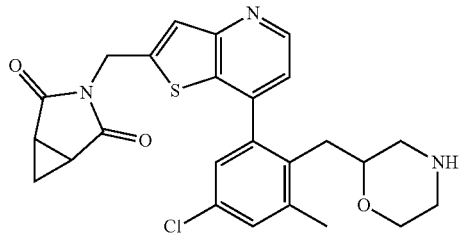 [SMILES: Cc1cc(Cl)cc(-c2ccnc3cc(CN4C(=O)C5CC5C4=O)sc23)c1CC1CNCCO1]

3-((7-(5-chloro-3-methyl-2-(morpholin-2-ylmethyl)phenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.82 (d, J=5.2 Hz, 1H), 7.68-7.53 (m, 2H), 7.47 (s, 1H), 7.22 (dd, J=9.5, 2.2 Hz, 1H), 4.86 (d, J=4.1 Hz, 2H), 3.69-3.42 (m, 3H), 3.16-2.55 (m, 8H), 2.48 (s, 3H), 1.68-1.58 (m, 1H), 1.46 (d, J=4.3 Hz, 1H). [M+H] 482.1

Example 103

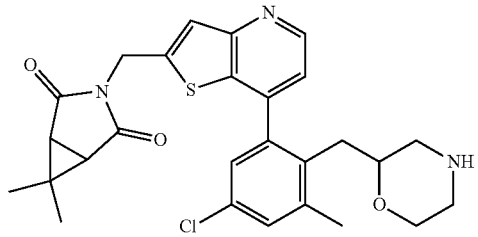

3-((7-(5-chloro-3-methyl-2-(morpholin-2-ylmethyl)phenyl)thieno[3,2-b]pyridin-2-yl)methyl)-6,6-dimethyl-3-azabicyclo[3.1.0]hexane-2,4-dione. The title compound was prepared by General Procedures B and E using 6,6-dimethyl-3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.86 (s, 1H), 7.87-7.58 (m, 2H), 7.47 (d, J=2.0 Hz, 1H), 7.32-7.13 (m, 1H), 4.92 (d, J=3.4 Hz, 2H), 3.96-3.42 (m, 3H), 3.21-2.55 (m, 8H), 2.48 (s, 3H), 1.25 (d, J=1.3 Hz, 3H), 1.13 (d, J=4.5 Hz, 3H). [M+H] 510.2

Example 104

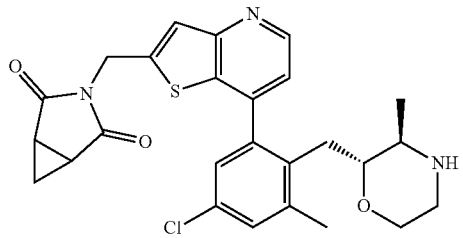 [SMILES: Cc1cc(Cl)cc(-c2ccnc3cc(CN4C(=O)C5CC5C4=O)sc23)c1C[C@H]1OCCN[C@@H]1C]

3-((7-(5-chloro-3-methyl-2-(((2R,3R)-3-methylmorpholin-2-yl)methyl)phenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.77 (d, J=5.2 Hz, 1H), 7.60-7.46 (m, 2H), 7.43 (dd, J=5.3, 2.2 Hz, 1H), 7.20 (dd, J=12.1, 2.5 Hz, 1H), 4.84 (s, 2H), 3.93 (dd, J=13.2, 3.3 Hz, 1H), 3.46-3.31 (m, 1H), 3.17-3.01 (m, 2H), 3.00-2.82 (m, 2H), 2.77 (dd, J=14.5, 10.3 Hz, 1H), 2.65-2.55 (m, 2H), 2.47 (s, 3H), 1.62 (tdd, J=8.2, 4.6, 1.7 Hz, 1H), 1.52 (d, J=6.4 Hz, 1H), 1.45 (ddt, J=6.0, 4.5, 3.6 Hz, 1H), 0.96 (dd, J=12.8, 6.5 Hz, 3H). [M+H] 496.0

Example 105

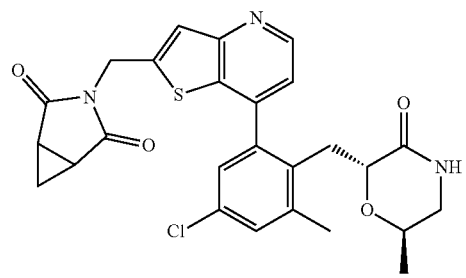 [SMILES: Cc1cc(Cl)cc(-c2ccnc3cc(CN4C(=O)C5CC5C4=O)sc23)c1C[C@H]1O[C@H](C)CNC1=O]

3-((7-(5-chloro-3-methyl-2-(((2R,6R)-6-methyl-3-oxomorpholin-2-yl)methyl)phenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione (omitted the lactam reduction step). $^1$H NMR (400 MHz, Methanol-d4) δ 8.83 (dd, J=12.4, 5.3 Hz, 1H), 7.74-7.60 (m, 2H), 7.46 (s, 1H), 7.24 (d, J=41.8 Hz, 1H), 4.86 (s, 2H), 3.97 (dd, J=28.4, 10.2 Hz, 1H), 3.61 (d, J=28.3 Hz, 1H), 3.42 (d, J=14.7 Hz, 1H), 3.15-2.88 (m, 2H), 2.74 (t, J=11.4 Hz, 1H), 2.58 (d, J=8.7 Hz, 2H), 2.51 (d, J=3.0 Hz, 3H), 1.60 (t, J=5.2 Hz, 1H), 1.44 (d, J=23.1 Hz, 1H), 1.17-0.68 (m, 3H). [M+H] 510.1

Example 106

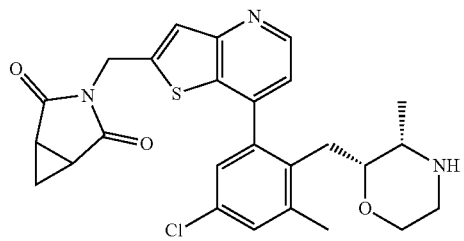 [SMILES: Cc1cc(Cl)cc(-c2ccnc3cc(CN4C(=O)C5CC5C4=O)sc23)c1C[C@H]1OCCN[C@H]1C]

3-((7-(5-chloro-3-methyl-2-(((2R,3 S)-3-methylmorpholin-2-yl)methyl)phenyl)thieno[3,2-b]pyridin-2-yl)methyl)-3-azabicyclo[3.1.0]hexane-2,4-dione. Step 1: tert-Butyl 2-[(4-chloro-2-iodo-6-methyl-phenyl)methyl]-3-oxo-morpholine-4-carboxylate (1.4 g, 3.01 mmol) was dissolved in ether (15 mL), then cooled to −78° C. Then, methylmagnesium bromide (2 mL, 6.01 mmol) was added dropwise. This was stirred for 3 h, then quenched with ammonium chloride and extracted with EtOAc. Purification by column chromatography (10-50% EtOAc/hexane) to yield 700 mg of the ring-opened ketone. The ketone was dissolved in Methanol (10 mL), then conc HCl (1.25 mL, 15.03 mmol) was added. This solution was stirred overnight and concentrated to afford 6-(4-chloro-2-iodo-6-methylbenzyl)-5-methyl-3,6-dihydro-2H-1,4-oxazine. Step 2: 6-[(4-Chloro-2-iodo-6-methyl-phenyl)methyl]-5-methyl-3,6-dihydro-2H-1,4-oxazine (165 mg, 0.45 mmol) was dissolved in THF (4 mL) and cooled to 0° C. Borane dimethylsulfide complex 2 M in THF (0.45 mL, 0.9100 mmol) was added dropwise and the mixture was stirred at rt for 90 m. The reaction was quenched with dropwise addition of 1M HCl and stirred for 10 min. Then, NaHCO$_3$ was added dropwise, then extracted with DCM. Subjected to standard Boc protection procedure (Boc2O (10 equiv), DMAP, Et3N, MeCN) and stirred overnight. Diluted with DCM, washed 1 N HCl, then NaHCO$_3$, then brine. Column (5-15% EtOAc/hexane) to yield separated cis and trans isomers. The title compound was prepared by General Procedure E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.82 (d, J=5.4 Hz, 1H), 7.70-7.53 (m, 2H), 7.46 (d, J=4.9 Hz, 1H), 7.23 (d, J=17.4 Hz, 1H), 4.86 (d, J=7.7 Hz, 2H), 3.94 (d, J=13.2 Hz, 1H), 3.39 (t, J=12.3 Hz, 1H), 3.12 (dd, J=26.9, 12.7 Hz, 2H), 3.03-2.78 (m, 3H), 2.63-2.56 (m, 2H), 2.48 (s, 3H), 1.66-1.52 (m, 1H), 1.46 (s, 1H), 1.29 (s, 1H), 1.04 (d, J=6.6 Hz, 3H). [M+H] 496.0

Example 107

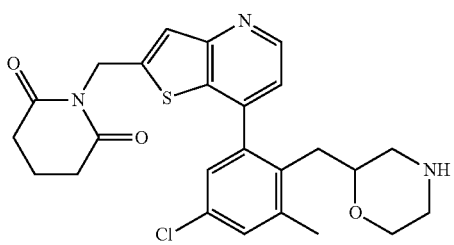

1-((7-(5-chloro-3-methyl-2-(morpholin-2-ylmethyl)phenyl)thieno[3,2-b]pyridin-2-yl)methyl)piperidine-2,6-dione. The title compound was prepared by General Procedures B, E, and G. $^1$H NMR (400 MHz, Methanol-d4) δ 8.96 (s, 1H), 7.88-7.66 (m, 2H), 7.49 (s, 1H), 7.24 (d, J=14.7 Hz, 1H), 5.29 (d, J=5.7 Hz, 2H), 3.90 (d, J=14.0 Hz, 1H), 3.62 (t, J=10.9 Hz, 1H), 3.56-3.39 (m, 1H), 3.15 (t, J=14.2 Hz, 2H), 3.09-2.89 (m, 2H), 2.79 (d, J=14.6 Hz, 1H), 2.71 (dq, J=6.7, 3.4 Hz, 4H), 2.68-2.53 (m, 1H), 2.48 (s, 3H), 1.94 (t, J=6.8 Hz, 2H). [M+H] 484.0

Example 108

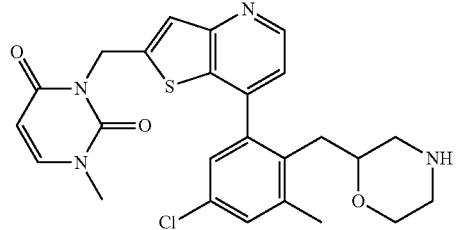 [SMILES: Cc1cc(Cl)cc(-c2ccnc3cc(Cn4c(=O)ccn(C)c4=O)sc23)c1CC1CNCCO1]

3-((7-(5-chloro-3-methyl-2-(morpholin-2-ylmethyl)phenyl)thieno[3,2-b]pyridin-2-yl)methyl)-1-methylpyrimidine-2,4(1H,3H)-dione. The title compound was prepared by General Procedures B, E, and G. $^1$H NMR (400 MHz, Methanol-d4) δ 8.89 (t, J=5.4 Hz, 1H), 7.85-7.69 (m, 2H), 7.59 (dd, J=7.9, 2.6 Hz, 1H), 7.49 (s, 1H), 7.24 (d, J=13.7 Hz, 1H), 5.76 (d, J=7.9 Hz, 1H), 5.46 (s, 2H), 3.89 (d, J=15.4 Hz, 1H), 3.62 (t, J=9.2 Hz, 1H), 3.55-3.41 (m, 1H), 3.38 (s, 3H), 3.22-3.09 (m, 2H), 3.06-2.84 (m, 2H), 2.78 (d, J=7.2 Hz, 1H), 2.71-2.51 (m, 1H), 2.48 (s, 3H). [M+H] 497.0

Example 109

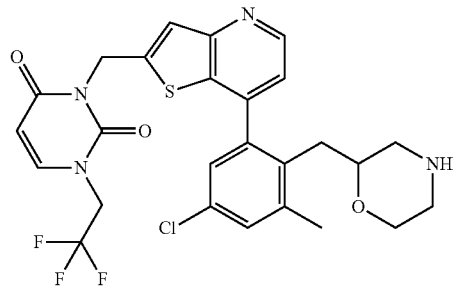

3-((7-(5-chloro-3-methyl-2-(morpholin-2-ylmethyl)phenyl)thieno[3,2-b]pyridin-2-yl)methyl)-1-(2,2,2-trifluoroethyl)pyrimidine-2,4(1H,3H)-dione. The title compound was prepared by General Procedures B, E, and G. $^1$H NMR (400 MHz, Methanol-d4) δ 8.85 (d, J=5.9 Hz, 1H), 7.79-7.61 (m, 3H), 7.48 (s, 1H), 7.23 (d, J=12.6 Hz, 1H), 5.89 (d, J=8.0 Hz, 1H), 5.46 (d, J=5.2 Hz, 2H), 4.62 (q, J=9.7, 9.1 Hz, 2H), 3.60 (t, J=10.0 Hz, 1H), 3.54-3.37 (m, 2H), 3.13 (t, J=12.2 Hz, 1H), 3.07-2.89 (m, 2H), 2.83-2.52 (m, 3H), 2.48 (s, 3H). [M+H] 565.0

Example 110

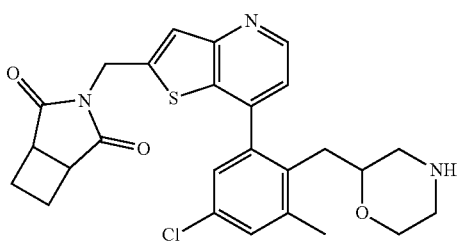 [SMILES: Cc1cc(Cl)cc(-c2ccnc3cc(CN4C(=O)C5CCC5C4=O)sc23)c1CC1CNCCO1]

3-((7-(5-chloro-3-methyl-2-(morpholin-2-ylmethyl)phenyl)thieno[3,2-b]pyridin-2-yl)methyl)-3-azabicyclo[3.2.0]heptane-2,4-dione. The title compound was prepared by General Procedures B, E, and G. $^1$H NMR (400 MHz, Methanol-d4) δ 8.89 (s, 1H), 7.83-7.66 (m, 2H), 7.49 (s, 1H), 7.26 (d, J=13.8 Hz, 1H), 5.11 (d, J=6.6 Hz, 2H), 3.90 (d, J=13.0 Hz, 1H), 3.67-3.41 (m, 2H), 3.38 (s, 2H), 3.22-2.91 (m, 3H), 2.87-2.53 (m, 5H), 2.48 (s, 3H), 2.09 (s, 2H). [M+H]496.0

Example 111

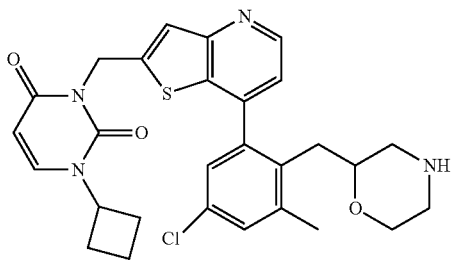 [SMILES: Cc1cc(Cl)cc(-c2ccnc3cc(Cn4c(=O)ccn(C5CCC5)c4=O)sc23)c1CC1CNCCO1]

3-((7-(5-chloro-3-methyl-2-(morpholin-2-ylmethyl)phenyl)thieno[3,2-b]pyridin-2-yl)methyl)-1-cyclobutylpyrimidine-2,4(1H,3H)-dione. The title compound was prepared by General Procedures B, E, and G. $^1$H NMR (400 MHz, Methanol-d4) δ 8.86 (d, J=5.0 Hz, 1H), 7.81-7.63 (m, 3H), 7.49 (s, 1H), 7.23 (d, J=12.5 Hz, 1H), 5.81 (d, J=8.1 Hz, 1H), 5.44 (d, J=5.7 Hz, 2H), 4.79 (p, J=8.7 Hz, 1H), 3.90 (d, J=13.1 Hz, 1H), 3.60 (t, J=10.2 Hz, 1H), 3.45 (dt, J=26.1, 13.0 Hz, 1H), 3.12 (d, J=13.4 Hz, 1H), 3.05-2.53 (m, 5H), 2.48 (s, 3H), 2.40-2.23 (m, 4H), 1.83 (s, 2H). [M+H] 537.0

Example 112

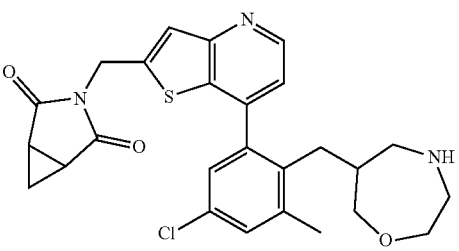 [SMILES: Cc1cc(Cl)cc(-c2ccnc3cc(CN4C(=O)C5CC5C4=O)sc23)c1CC1CNCCOC1]

3-((7-(2-((1,4-oxazepan-6-yl)methyl)-5-chloro-3-methylphenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.80 (s, 1H), 7.58 (s, 1H), 7.56-7.46 (m, 2H), 7.24 (d, J=5.5 Hz, 1H), 4.84 (s, 2H), 3.83-3.50 (m, 3H), 3.28-3.14 (m, 1H), 3.14-3.04 (m, 3H), 2.84-2.72 (m, 2H), 2.58 (t, J=4.3 Hz, 2H), 2.49 (s, 3H), 2.47-2.34 (m, 1H), 2.13 (d, J=37.8 Hz, 1H), 1.62 (s, 1H), 1.43 (d, J=15.1 Hz, 1H). [M+H] 496.0

Example 113

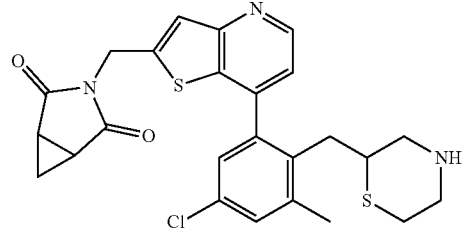

3-((7-(5-chloro-3-methyl-2-(thiomorpholin-2-ylmethyl)phenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. [M+H] 498.0

Example 114

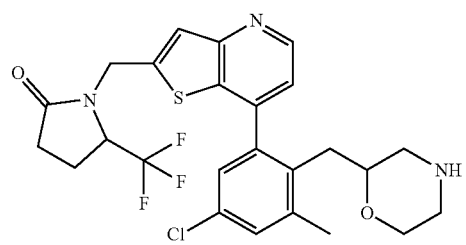 [SMILES: Cc1cc(Cl)cc(-c2ccnc3cc(CN4C(=O)CCC4C(F)(F)F)sc23)c1CC1CNCCO1]

1-((7-(5-chloro-3-methyl-2-(morpholin-2-ylmethyl)phenyl)thieno[3,2-b]pyridin-2-yl)methyl)-5-(trifluoromethyl)pyrrolidin-2-one. The title compound was prepared by General Procedures B and E using 1-((7-(4,4,5,5-tetramethyl-1,3,2-dioxaborolan-2-yl)thieno[3,2-b]pyridin-2-yl)methyl)-5-(trifluoromethyl)pyrrolidin-2-one. $^1$H NMR (400 MHz, Methanol-d4) δ 8.89 (t, J=5.8 Hz, 1H), 7.84-7.68 (m, 2H), 7.49 (s, 1H), 7.31-7.22 (m, 1H), 5.11 (q, J=15.9 Hz, 1H), 4.91 (q, J=18.5, 17.0 Hz, 1H), 4.50-4.37 (m, 1H), 3.66-3.40 (m, 2H), 3.16 (t, J=16.0 Hz, 2H), 3.08-2.90 (m, 2H), 2.90-2.73 (m, 2H), 2.68-2.54 (m, 3H), 2.48 (s, 3H), 2.43 (d, J=12.6 Hz, 2H). [M+H] 524.0

Example 115

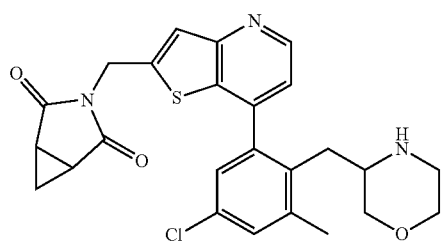 [SMILES: Cc1cc(Cl)cc(-c2ccnc3cc(CN4C(=O)C5CC5C4=O)sc23)c1CC1COCCN1]

3-((7-(5-chloro-3-methyl-2-(morpholin-3-ylmethyl)phenyl)thieno[3,2-b]pyridin-2-yl)methyl)-3-azabicyclo[3.1.0]hexane-2,4-dione. The title compound was prepared by General Procedures B and E using tert-butyl 2-oxomorpholine-4-carboxylate and 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. The lactone is reduced with NaBH$_4$ and the resultant diol cyclized to the morpholine according to General Procedure H. $^1$H NMR (400 MHz, Methanol-d4) δ 8.87 (t, J=5.0 Hz, 1H), 7.69-7.62 (m, 2H), 7.54 (d, J=2.3 Hz, 1H), 7.29 (dd, J=24.8, 2.3 Hz, 1H), 4.85 (d, J=8.8 Hz, 2H), 3.81 (t, J=15.7 Hz, 1H), 3.60-3.48 (m, 2H), 3.24-2.68 (m, 6H), 2.61-2.55 (m, 2H), 2.53 (d, J=4.0 Hz, 3H), 1.64-1.51 (m, 1H), 1.43 (dt, J=13.1, 3.8 Hz, 1H). [M+H] 482.0

Example 116

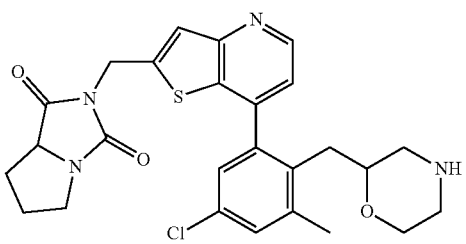 [SMILES: Cc1cc(Cl)cc(-c2ccnc3cc(CN4C(=O)C5CCCN5C4=O)sc23)c1CC1CNCCO1]

2-((7-(5-chloro-3-methyl-2-(morpholin-2-ylmethyl)phenyl)thieno[3,2-b]pyridin-2-yl)methyl)tetrahydro-1H-pyrrolo[1,2-c]imidazole-1,3(2H)-dione. The title compound was prepared by General Procedures B, E, and G. $^1$H NMR (400 MHz, Methanol-d4) δ 8.98 (s, 1H), 7.96-7.74 (m, 2H), 7.51 (s, 1H), 7.28 (d, J=12.1 Hz, 1H), 5.05 (s, 2H), 4.29 (s, 1H), 3.98-3.39 (m, 5H), 3.30-2.55 (m, 6H), 2.49 (s, 3H), 2.29-2.01 (m, 3H), 1.80-1.65 (m, 1H).

Example 117

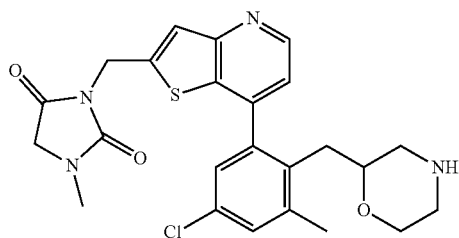 [SMILES: Cc1cc(Cl)cc(-c2ccnc3cc(CN4C(=O)CN(C)C4=O)sc23)c1CC1CNCCO1]

3-((7-(5-chloro-3-methyl-2-(morpholin-2-ylmethyl)phenyl)thieno[3,2-b]pyridin-2-yl)methyl)-1-methylimidazolidine-2,4-dione. The title compound was prepared by General Procedures B, E, and G. $^1$H NMR (400 MHz, Methanol-d4) δ 8.98 (s, 1H), 7.99-7.71 (m, 2H), 7.50 (s, 1H), 7.27 (dd, J=13.3, 2.1 Hz, 1H), 5.49 (s, OH), 5.08 (d, J=7.1 Hz, 2H), 4.05 (d, J=5.6 Hz, 2H), 3.89 (d, J=12.8 Hz, 1H), 3.70 (d, J=18.6 Hz, 1H), 3.60-3.38 (m, 1H), 3.25-3.03 (m, 2H), 2.97 (d, J=2.4 Hz, 3H), 2.84-2.53 (m, 4H), 2.49 (s, 3H).

Example 118

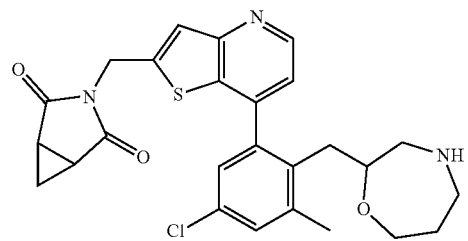 [SMILES: Cc1cc(Cl)cc(-c2ccnc3cc(CN4C(=O)C5CC5C4=O)sc23)c1CC1CNCCCO1]

3-((7-(2-(((1,4-oxazepan-2-yl)methyl)-5-chloro-3-methylphenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.84 (s, 1H), 7.70-7.57 (m, 2H), 7.48 (s, 1H), 7.25 (d, J=30.7 Hz, 1H), 4.87 (d, J=7.8 Hz, 2H), 3.86-3.61 (m, 2H), 3.28-3.16 (m, 3H), 3.09 (t, J=15.1 Hz, 1H), 2.92-2.71 (m, 3H), 2.59 (dd, J=7.9, 4.0 Hz, 2H), 2.49 (s, 3H), 1.99-1.80 (m, 2H), 1.62 (p, 1H), 1.45 (d, J=4.4 Hz, 1H). [M+H] 496.0

Example 119

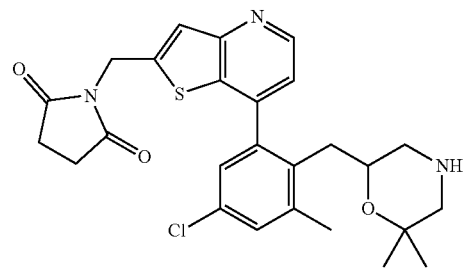 [SMILES: Cc1cc(Cl)cc(-c2ccnc3cc(CN4C(=O)CCC4=O)sc23)c1CC1CNCC(C)(C)O1]

1-((7-(5-chloro-2-((6,6-dimethylmorpholin-2-yl)methyl)-3-methylphenyl)thieno[3,2-b]pyridin-2-yl)methyl)pyrrolidine-2,5-dione. The title compound was prepared by General Procedures B, E, and G. $^1$H NMR (400 MHz, Methanol-d4) δ 8.91 (s, 1H), 7.82-7.69 (m, 2H), 7.49 (d, J=7.1 Hz, 1H), 7.28 (dd, J=36.6, 2.2 Hz, 1H), 5.04 (d, J=7.2 Hz, 2H), 3.81 (t, J=9.1 Hz, 1H), 3.10 (dd, J=26.2, 12.5 Hz, 2H), 2.95 (dd, J=23.9, 13.1 Hz, 1H), 2.76 (s, 4H), 2.72 (d, J=11.2 Hz, 1H), 2.61-2.50 (m, 2H), 2.48 (d, J=4.6 Hz, 3H), 1.21-0.58 (m, 6H). [M+H] 498.0

Example 120

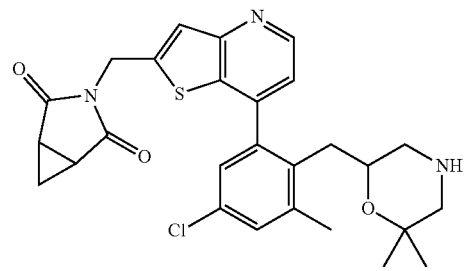 [SMILES: Cc1cc(Cl)cc(-c2ccnc3cc(CN4C(=O)C5CC5C4=O)sc23)c1CC1CNCC(C)(C)O1]

3-((7-(5-chloro-2-((6,6-dimethylmorpholin-2-yl)methyl)-3-methylphenyl)thieno[3,2-b]pyridin-2-yl)methyl)-3-azabicyclo[3.1.0]hexane-2,4-dione. The title compound was prepared by General Procedures B, E, and G. ¹H NMR (400 MHz, Methanol-d4) δ 8.89 (s, 1H), 7.80-7.67 (m, 2H), 7.49 (d, J=8.0 Hz, 1H), 7.28 (d, J=35.6 Hz, 1H), 4.87 (d, J=4.0 Hz, 2H), 3.79 (q, J=10.5, 9.4 Hz, 1H), 3.17-3.02 (m, 2H), 2.95 (dd, J=20.8, 13.3 Hz, 2H), 2.73 (dd, J=13.2, 4.5 Hz, 1H), 2.62-2.50 (m, 3H), 2.48 (d, J=4.6 Hz, 3H), 1.62 (d, J=7.0 Hz, 1H), 1.48 (dd, J=11.4, 4.2 Hz, 1H), 1.23-0.59 (m, 6H). [M+H] 510.0

Example 121

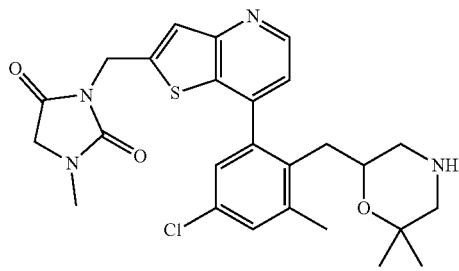 [SMILES: Cc1cc(Cl)cc(-c2ccnc3cc(CN4C(=O)CN(C)C4=O)sc23)c1CC1CNCC(C)(C)O1]

3-((7-(5-chloro-2-((6,6-dimethylmorpholin-2-yl)methyl)-3-methylphenyl)thieno[3,2-b]pyridin-2-yl)methyl)-1-methylimidazolidine-2,4-dione. The title compound was prepared by General Procedures B, E, and G. ¹H NMR (400 MHz, Methanol-d4) δ 8.88 (s, 1H), 7.78-7.64 (m, 2H), 7.48 (d, J=8.6 Hz, 1H), 7.28 (d, J=35.9 Hz, 1H), 5.03 (d, J=5.7 Hz, 2H), 4.02 (s, 2H), 3.79 (q, J=8.5 Hz, 1H), 3.16-3.01 (m, 2H), 2.96 (s, 3H), 2.92 (d, J=14.3 Hz, 1H), 2.72 (dd, J=14.3, 7.6 Hz, 1H), 2.63-2.49 (m, 2H), 2.48 (d, J=4.7 Hz, 3H), 1.21-0.58 (m, 6H). [M+H] 513.0

Example 122

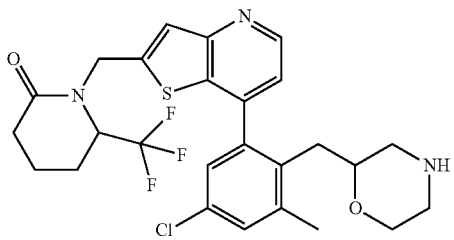 [SMILES: Cc1cc(Cl)cc(-c2ccnc3cc(CN4C(=O)CCCC4C(F)(F)F)sc23)c1CC1CNCCO1]

1-((7-(5-chloro-3-methyl-2-(morpholin-2-ylmethyl)phenyl)thieno[3,2-b]pyridin-2-yl)methyl)-6-(trifluoromethyl)piperidin-2-one. The title compound was prepared by General Procedures B and E using 1-((7-(4,4,5,5-tetramethyl-1,3,2-dioxaborolan-2-yl)thieno[3,2-b]pyridin-2-yl)methyl)-6-(trifluoromethyl)piperidin-2-one. ¹H NMR (400 MHz, Methanol-d4) δ 8.88 (t, J=5.5 Hz, 1H), 7.82-7.66 (m, 2H), 7.49 (s, 1H), 7.31-7.21 (m, 1H), 5.30-4.86 (m, 2H), 4.47 (h, J=6.1 Hz, 1H), 3.90 (ddd, J=13.0, 9.8, 3.6 Hz, 1H), 3.66-3.36 (m, 3H), 3.22-3.01 (m, 2H), 2.93 (dd, J=15.3, 3.5 Hz, 1H), 2.88-2.56 (m, 3H), 2.52 (d, J=8.0 Hz, 2H), 2.48 (s, 3H), 2.25-1.94 (m, 2H), 1.85 (s, 1H). [M+H] 538.0

Example 123

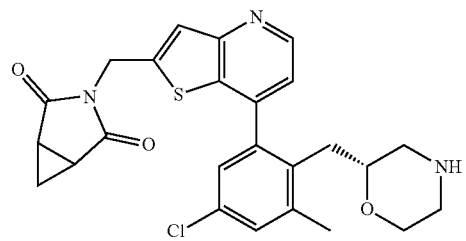 [SMILES: Cc1cc(Cl)cc(-c2ccnc3cc(CN4C(=O)C5CC5C4=O)sc23)c1C[C@@H]1CNCCO1]

3-((7-(5-chloro-3-methyl-2-(((R)-morpholin-2-yl)methyl)phenyl)thieno[3,2-b]pyridin-2-yl)methyl)-3-azabicyclo[3.1.0]hexane-2,4-dione. The title compound was prepared by General Procedures B, E, and G. ¹H NMR (400 MHz, Methanol-d4) δ 8.87 (dd, J=5.8, 2.6 Hz, 1H), 7.81-7.63 (m, 2H), 7.49 (d, J=2.2 Hz, 1H), 7.24 (dd, J=13.2, 2.3 Hz, 1H), 4.88 (d, J=6.5 Hz, 2H), 3.89 (dd, J=13.0, 3.7 Hz, 1H), 3.65-3.38 (m, 2H), 3.21-3.02 (m, 2H), 2.95 (ddd, J=17.8, 13.6, 3.6 Hz, 1H), 2.87-2.62 (m, 3H), 2.59 (dt, J=8.1, 3.3 Hz, 2H), 2.48 (s, 3H), 1.63 (tdd, J=7.9, 4.6, 3.0 Hz, 1H), 1.47 (p, J=3.6 Hz, 1H). [M+H] 482.0

Example 124

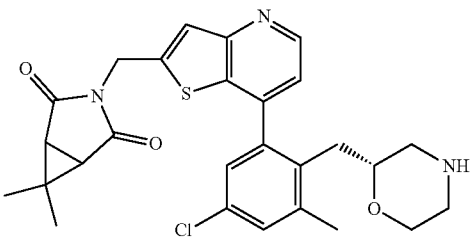

3-((7-(5-chloro-3-methyl-2-(((R)-morpholin-2-yl)methyl)phenyl)thieno[3,2-b]pyridin-2-yl)methyl)-6,6-dimethyl-3-azabicyclo[3.1.0]hexane-2,4-dione. The title compound was prepared by General Procedures B, E, and G. ¹H NMR (400 MHz, Methanol-d4) δ 8.88 (t, J=4.8, 3.8 Hz, 1H), 7.81-7.65 (m, 2H), 7.49 (d, J=2.3 Hz, 1H), 7.22 (dd, J=11.2, 2.3 Hz, 1H), 4.93 (d, J=5.0 Hz, 2H), 3.89 (dd, J=13.0, 3.7 Hz, 1H), 3.67-3.39 (m, 2H), 3.20-3.02 (m, 2H), 3.02-2.89 (m, 1H), 2.88-2.54 (m, 3H), 2.52 (d, J=3.6 Hz, 2H), 2.48 (s, 3H), 1.25 (d, J=2.0 Hz, 3H), 1.13 (d, J=8.5 Hz, 3H). [M+H] 510.0

Example 125

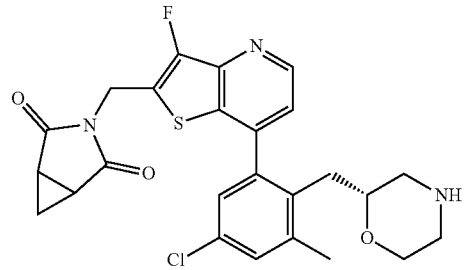 [SMILES: Cc1cc(Cl)cc(-c2ccnc3c(F)c(CN4C(=O)C5CC5C4=O)sc23)c1C[C@@H]1CNCCO1]

3-((7-(5-chloro-3-methyl-2-(((R)-morpholin-2-yl)methyl)phenyl)-3-fluorothieno[3,2-b]pyridin-2-yl)methyl)-3-azabicyclo[3.1.0]hexane-2,4-dione. The title compound was prepared by General Procedures B, E, and G. [M+H] 499.0

Example 126

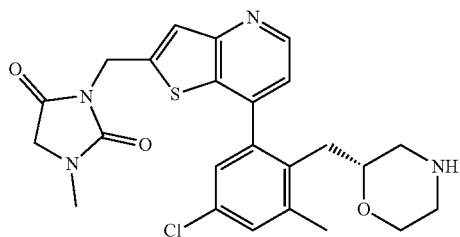 [SMILES: Cc1cc(Cl)cc(-c2ccnc3cc(CN4C(=O)CN(C)C4=O)sc23)c1C[C@@H]1CNCCO1]

(R)-3-((7-(5-chloro-3-methyl-2-(morpholin-2-ylmethyl)phenyl)thieno[3,2-b]pyridin-2-yl)methyl)-1-methylimidazolidine-2,4-dione. The title compound was prepared by General Procedures B, E, and G. $^1$H NMR (400 MHz, Methanol-d4) δ 8.88 (s, 1H), 7.81-7.65 (m, 2H), 7.49 (d, J=2.1 Hz, 1H), 7.24 (dd, J=13.9, 2.3 Hz, 1H), 5.04 (d, J=6.5 Hz, 2H), 4.03 (d, J=3.1 Hz, 2H), 3.89 (dd, J=13.1, 3.7 Hz, 1H), 3.65-3.37 (m, 2H), 3.21-3.01 (m, 2H), 2.96 (s, 3H), 2.92 (dd, J=14.7, 3.2 Hz, 1H), 2.82-2.55 (m, 3H), 2.47 (s, 3H). [M+H] 585.0

Example 127

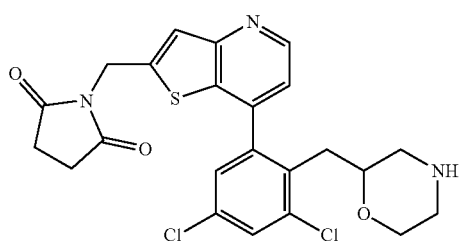 [SMILES: O=C1CCC(=O)N1Cc1cc2nccc(-c3cc(Cl)cc(Cl)c3CC3CNCCO3)c2s1]

1-((7-(3,5-dichloro-2-(morpholin-2-ylmethyl)phenyl)thieno[3,2-b]pyridin-2-yl)methyl)pyrrolidine-2,5-dione. The title compound was prepared by General Procedures B, E, and G. $^1$H NMR (400 MHz, Chloroform-d) δ 8.71 (dd, J=4.8 Hz, 1H), 7.57 (s, 1H), 7.50 (d, J=2.2 Hz, 1H), 7.14-7.12 (m, 1H), 7.05 (m, 1H), 4.92 (s, 2H), 3.63 (m, 1H), 3.49 (m, 1H), 3.33 (m, 1H), 2.75 (s, 4H), 2.67 (m, 2H), 2.54 (m, 2H), 2.21 (m, 1H). [M+H] 490.0

Example 128

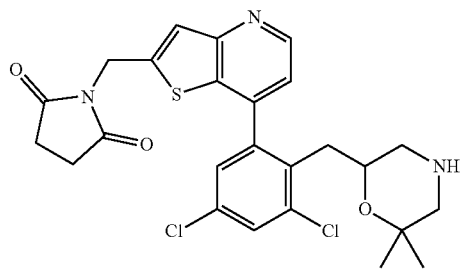 [SMILES: CC1(C)CNCC(Cc2c(Cl)cc(Cl)cc2-c2ccnc3cc(CN4C(=O)CCC4=O)sc23)O1]

1-((7-(3,5-dichloro-2-((6,6-dimethylmorpholin-2-yl)methyl)phenyl)thieno[3,2-b]pyridin-2-yl)methyl)pyrrolidine-2,5-dione. The title compound was prepared by General Procedures B, E, and G. $^1$H NMR (400 MHz, Chloroform-d) δ 8.71 (dd, J=4.8 Hz, 1H), 7.57 (s, 1H), 7.50 (d, J=2.2 Hz, 1H), 7.14-7.12 (m, 1H), 7.05 (m, 1H), 4.92 (s, 2H), 3.83-3.62 (m, 1H), 2.76 (s, 4H), 2.55 (m, 2H), 2.38 (m, 2H), 1.65 (s, 6H), 1.18 (m, 2H). [M+H] 519.0

Example 129

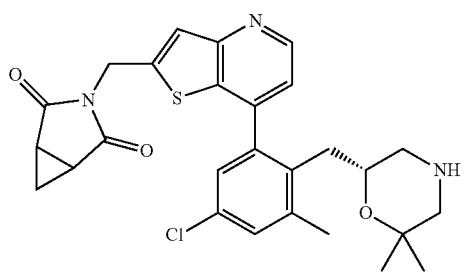 [SMILES: Cc1cc(Cl)cc(-c2ccnc3cc(CN4C(=O)C5CC5C4=O)sc23)c1C[C@@H]1CNCC(C)(C)O1]

3-((7-(5-chloro-2-(((R)-6,6-dimethylmorpholin-2-yl)methyl)-3-methylphenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.85 (d, J=5.4 Hz, 1H), 7.71-7.60 (m, 2H), 7.51-7.45 (m, 1H), 7.33-7.22 (m, 1H), 4.89-4.88 (m, 2H), 3.78 (q, J=10.2 Hz, 1H), 3.15-2.89 (m, 3H), 2.76-2.68 (m, 1H), 2.63-2.50 (m, 4H), 2.50-2.44 (m, 3H), 1.67-1.58 (m, 1H), 1.51-1.44 (m, 1H), 1.20-0.61 (m, 6H). [M+H] 510.0

Example 130

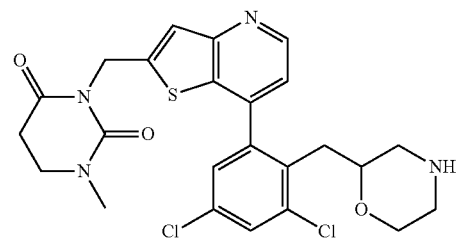

3-((7-(3,5-dichloro-2-(morpholin-2-ylmethyl)phenyl)thieno[3,2-b]pyridin-2-yl)methyl)-1-methyldihydropyrimidine-2,4(1H,3H)-dione. The title compound was prepared by General Procedures B, E, and G. $^1$H NMR (400 MHz, Methanol-d4) δ 8.94 (m, 1H), 7.90 (m, 1H), 7.82 (m, 1H), 7.79 (m, 1H), 7.49-7.46 (m, 1H), 5.32 (m, 2H), 3.89-3.84 (m, 1H), 3.44 (m, 2H), 3.11 (m, 1H), 3.03 (s, 4H), 1.89 (s, 2H), 1.31 (s, 6H). [M+H] 519.0

Example 131

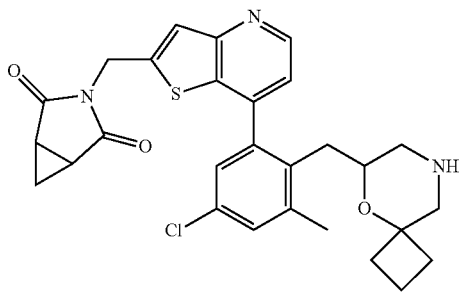

3-((7-(2-((5-oxa-8-azaspiro[3.5]nonan-6-yl)methyl)-5-chloro-3-methylphenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.73 (dt, J=37.5, 8.8 Hz, 1H), 7.53 (s, 1H), 7.50-7.36 (m, 2H), 7.22 (d, J=17.3 Hz, 1H), 4.81 (s, 2H), 3.53 (dt, J=37.5, 8.4 Hz, 1H), 3.35 (dd, J=19.3, 12.8 Hz, 1H), 3.03-2.88 (m, 2H), 2.78-2.59 (m, 3H), 2.57 (ddd, J=8.4, 3.7, 1.0 Hz, 2H), 2.47 (s, 3H), 2.09-1.88 (m, 2H), 1.79-1.52 (m, 5H), 1.44 (p, J=3.9 Hz, 1H). [M+H] 522.0

Example 132

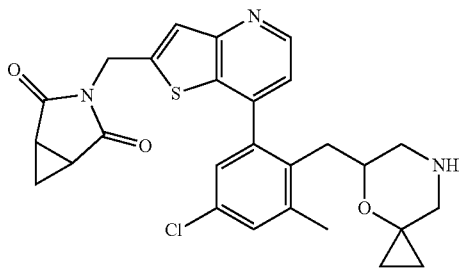 [SMILES: Cc1cc(Cl)cc(-c2ccnc3cc(CN4C(=O)C5CC5C4=O)sc23)c1CC1CNCC2(CC2)O1]

3-((7-(2-((4-oxa-7-azaspiro[2.5]octan-5-yl)methyl)-5-chloro-3-methylphenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.71 (d, J=5.1 Hz, 1H), 7.53 (s, 1H), 7.46-7.32 (m, 2H), 7.18 (dd, J=14.2, 1.9 Hz, 1H), 4.81 (s, 2H), 3.65 (dt, J=41.0, 9.9 Hz, 1H), 3.41 (d, J=12.7 Hz, 1H), 3.11 (dd, J=25.2, 13.0 Hz, 1H), 3.01-2.91 (m, 1H), 2.78-2.61 (m, 3H), 2.58 (dt, J=7.7, 3.7 Hz, 2H), 2.44 (d, J=2.2 Hz, 3H), 1.67-1.56 (m, 1H), 1.46 (t, J=2.8 Hz, 1H), 0.84-0.35 (m, 4H). [M+H]508.0

Example 133

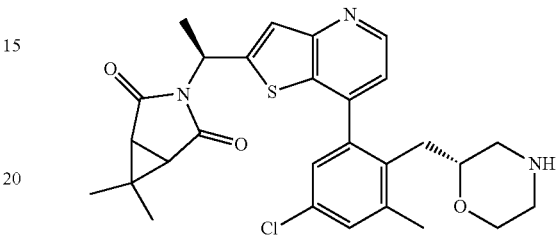

3-((S)-1-(7-(5-chloro-3-methyl-2-(((R)-morpholin-2-yl)methyl)phenyl)thieno[3,2-b]pyridin-2-yl)ethyl)-6,6-dimethyl-3-azabicyclo[3.1.0]hexane-2,4-dione. The title compound was prepared by General Procedures A and E using 6,6-dimethyl-3-((S)-1-(7-(4,4,5,5-tetramethyl-1,3,2-dioxaborolan-2-yl)thieno[3,2-b]pyridin-2-yl)ethyl)-3-azabicyclo[3.1.0]hexane-2,4-dione. $^1$H NMR (400 MHz, Methanol-d4) δ 8.77 (dd, J=5.3, 2.0 Hz, 1H), 7.62-7.42 (m, 3H), 7.18 (dd, J=4.0, 2.3 Hz, 1H), 5.64 (q, J=7.1 Hz, 1H), 3.89 (dd, J=13.0, 3.8 Hz, 1H), 3.72-3.41 (m, 2H), 3.14-3.03 (m, 2H), 3.02-2.77 (m, 2H), 2.72-2.55 (m, 2H), 2.52-2.45 (m, 4H), 2.42 (dd, J=5.2, 0.7 Hz, 1H), 1.83 (d, J=7.1 Hz, 3H), 1.23 (s, 3H), 1.21 (d, J=5.5 Hz, 3H). [M+H] 524.0

Example 134

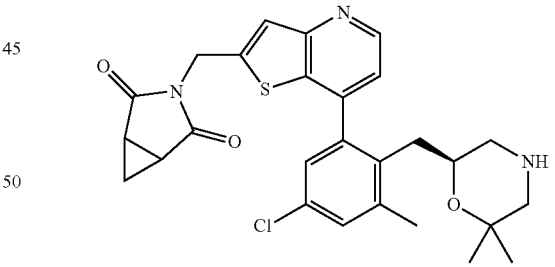

3-((7-(5-chloro-2-(((S)-6,6-dimethylmorpholin-2-yl)methyl)-3-methylphenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. $^1$H NMR (400 MHz, Methanol-d4) δ 8.85 (d, J=5.4 Hz, 1H), 7.71-7.60 (m, 2H), 7.51-7.45 (m, 1H), 7.33-7.22 (m, 1H), 4.89-4.88 (m, 2H), 3.78 (q, J=10.2 Hz, 1H), 3.15-2.89 (m, 3H), 2.76-2.68 (m, 1H), 2.63-2.50 (m, 4H), 2.50-2.44 (m, 3H), 1.67-1.58 (m, 1H), 1.51-1.44 (m, 1H), 1.20-0.61 (m, 6H). 510.0

Example 135

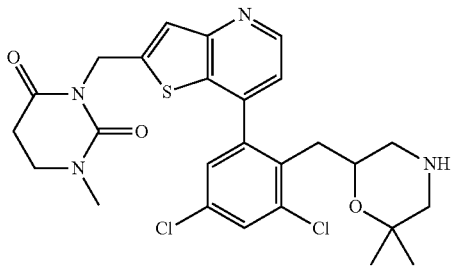 [SMILES: CN1CCC(=O)N(Cc2cc3nccc(-c4cc(Cl)cc(Cl)c4CC4CNCC(C)(C)O4)c3s2)C1=O]

3-((7-(3,5-dichloro-2-((6,6-dimethylmorpholin-2-yl)methyl)phenyl)thieno[3,2-b]pyridin-2-yl)methyl)-1-methyldihydropyrimidine-2,4(1H,3H)-dione. The title compound was prepared by General Procedures B, E, and G. ¹H NMR (400 MHz, Methanol-d4) δ 8.93 (m, 1H), 7.80 (m, 1H), 7.75 (m, 1H), 7.56 (m, 1H), 7.44 (m, 1H), 5.27 (m, 2H), 4.20-3.98 (m, 1H), 3.44 (m, 2H), 3.22-3.11 (m, 2H), 3.00 (s, 3H), 2.76 (m, 2H), 2.54 (m, 2H), 1.89 (s, 2H), 1.31 (s, 6H). [M+H] 547.0

Example 136

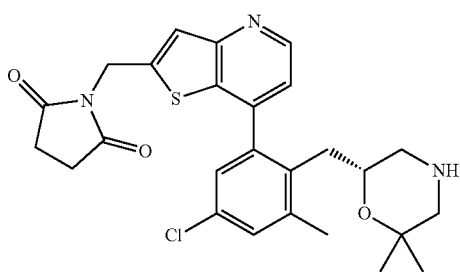 [SMILES: Cc1cc(Cl)cc(-c2ccnc3cc(CN4C(=O)CCC4=O)sc23)c1C[C@@H]1CNCC(C)(C)O1]

(R)-1-((7-(5-chloro-2-((6,6-dimethylmorpholin-2-yl)methyl)-3-methylphenyl)thieno[3,2-b]pyridin-2-yl)methyl)pyrrolidine-2,5-dione. The title compound was prepared by General Procedures B, E, and G. ¹H NMR (400 MHz, Methanol-d4) δ 8.86 (d, J=5.5 Hz, 1H), 7.74-7.61 (m, 2H), 7.54-7.45 (m, 1H), 7.35-7.19 (m, 1H), 5.07-5.00 (m, 2H), 3.85-3.71 (m, 1H), 3.30-2.86 (m, 4H), 2.78-2.66 (m, 4H), 2.64-2.50 (m, 2H), 2.50-2.44 (m, 3H), 1.20-0.58 (m, 6H). [M+H] 498.0

Example 137

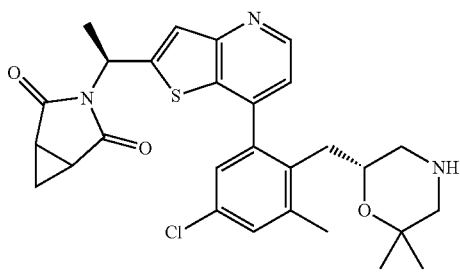 [SMILES: Cc1cc(Cl)cc(-c2ccnc3cc([C@H](C)N4C(=O)C5CC5C4=O)sc23)c1C[C@@H]1CNCC(C)(C)O1]

3-((S)-1-(7-(5-chloro-2-(((R)-6,6-dimethylmorpholin-2-yl)methyl)-3-methylphenyl)thieno[3,2-b]pyridin-2-yl)ethyl)-3-azabicyclo[3.1.0]hexane-2,4-dione. The title compound was prepared by General Procedures A and E using 6,6-dimethyl-3-((S)-1-(7-(4,4,5,5-tetramethyl-1,3,2-dioxaborolan-2-yl)thieno[3,2-b]pyridin-2-yl)ethyl)-3-azabicyclo[3.1.0]hexane-2,4-dione. ¹H NMR (400 MHz, Methanol-d4) δ 8.82 (d, J=5.4 Hz, 1H), 7.67-7.54 (m, 2H), 7.46 (dd, J=9.6, 2.2 Hz, 1H), 7.25 (dd, J=27.5, 2.3 Hz, 1H), 5.52 (qd, J=7.4, 1.0 Hz, 1H), 3.84-3.67 (m, 1H), 3.12-2.89 (m, 3H), 2.77-2.65 (m, 1H), 2.65-2.50 (m, 4H), 2.47 (d, J=3.4 Hz, 3H), 1.81 (dd, J=7.1, 5.8 Hz, 3H), 1.61 (tt, J=8.2, 4.3 Hz, 1H), 1.45 (ddt, J=8.2, 4.6, 3.6 Hz, 1H), 1.20-0.67 (m, 6H). [M+H] 524.0

Example 138

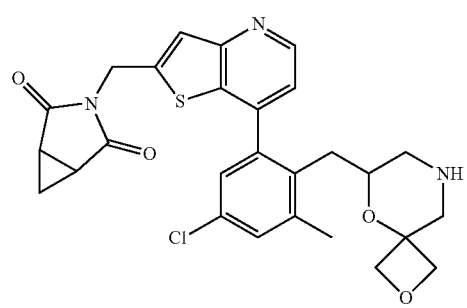 [SMILES: Cc1cc(Cl)cc(-c2ccnc3cc(CN4C(=O)C5CC5C4=O)sc23)c1CC1CNCC2(COC2)O1]

3-((7-(2-((2,5-dioxa-8-azaspiro[3.5]nonan-6-yl)methyl)-5-chloro-3-methylphenyl)thieno[3,2-b]pyridin-2-yl)methyl)-3-azabicyclo[3.1.0]hexane-2,4-dione. The title compound was prepared by General Procedures B and E using 3-((7-(4,4,5,5-tetramethyl-1,3,2-dioxaborolan-2-yl)thieno[3,2-b]pyridin-2-yl)methyl)-3-azabicyclo[3.1.0]hexane-2,4-dione. ¹H NMR (400 MHz, Methanol-d4) δ 8.73 (s, 1H), 7.55 (d, J=14.2 Hz, 1H), 7.52-7.41 (m, 2H), 7.28 (dd, J=29.9, 1.9 Hz, 1H), 4.82 (s, 2H), 4.42 (dd, J=6.7, 3.2 Hz, 1H), 4.19 (dd, J=17.2, 6.9 Hz, 1H), 3.74-3.46 (m, 2H), 3.40 (d, J=7.3 Hz, 1H), 3.14 (d, J=12.2 Hz, 1H), 3.07-2.93 (m, 2H), 2.87-2.72 (m, 2H), 2.67 (t, J=12.0 Hz, 1H), 2.57 (dd, J=8.1, 3.6 Hz, 1H), 2.51 (dd, J=7.7, 3.5 Hz, 1H), 2.47 (d, J=10.9 Hz, 3H), 1.64-1.55 (m, 1H), 1.47 (dt, J=7.9, 3.8 Hz, 1H). [M+H] 524.0

Example 139

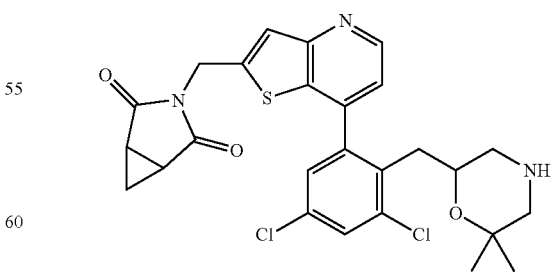

3-((7-(3,5-dichloro-2-((6,6-dimethylmorpholin-2-yl)methyl)phenyl)thieno[3,2-b]pyridin-2-yl)methyl)-3-azabicyclo[3.1.0]hexane-2,4-dione. The title compound was prepared by General Procedures B, E, and G. ¹H NMR (400

MHz, Methanol-d4) δ 8.73 (m, 1H), 7.71 (m, 1H), 7.52 (m, 1H), 7.49-7.45 (m, 1H), 7.40-7.35 (m, 1H), 4.78 (s, 2H), 4.11-3.93 (m, 1H), 3.14-2.95 (m, 4H), 2.71 (m, 1H), 2.55 (m, 4H), 1.60 (m, 1H), 1.45-1.40 (m, 1H), 1.15 (m, 3H), 1.02 (s, 1H), 0.58 (s, 1H). [M+H] 530.0

Example 140

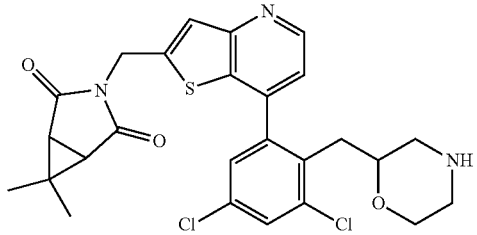 [SMILES: CC1(C)C2C(=O)N(Cc3cc4nccc(-c5cc(Cl)cc(Cl)c5CC5CNCCO5)c4s3)C(=O)C21]

3-((7-(3,5-dichloro-2-(morpholin-2-ylmethyl)phenyl)thieno[3,2-b]pyridin-2-yl)methyl)-6,6-dimethyl-3-azabicyclo[3.1.0]hexane-2,4-dione. The title compound was prepared by General Procedures B, E, and G. $^1$H NMR (400 MHz, Methanol-d4) δ 8.91 (d, J=5.7 Hz, 1H), 7.81 (m, 1H), 7.74 (s, 1H), 7.72 (m, 1H), 7.44-7.42 (m, 1H), 4.94 (s, 2H), 3.91-3.80 (m, 1H), 3.49 (m, 2H), 3.25 (s, 1H), 3.06 (m, 3H), 2.72 (m, 3H), 2.52 (d, J=4.8 Hz, 2H), 1.26 (s, 3H), 1.15 (s, 3H). [M+H] 530.0

Example 141

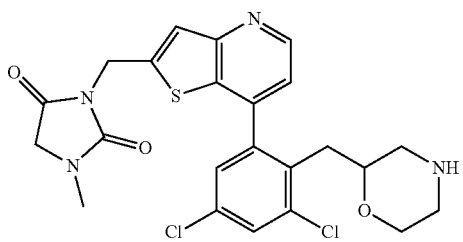 [SMILES: CN1CC(=O)N(Cc2cc3nccc(-c4cc(Cl)cc(Cl)c4CC4CNCCO4)c3s2)C1=O]

3-((7-(3,5-dichloro-2-(morpholin-2-ylmethyl)phenyl)thieno[3,2-b]pyridin-2-yl)methyl)-1-methylimidazolidine-2,4-dione. The title compound was prepared by General Procedures B, E, and G. $^1$H NMR (400 MHz, Methanol-d4) δ 8.91 (d, J=5.4 Hz, 1H), 7.79 (m, 1H), 7.77-7.7 (m, 1H), 7.71-7.70 (m, 1H), 7.45 (dd, J=11.9, 2.2 Hz, 1H), 5.05 (d, J=10.0 Hz, 2H), 4.03 (d, J=7.8 Hz, 2H), 3.91-3.80 (m, 2H), 3.46 (m, 3H), 3.08 (m, 2H), 2.97 (s, 3H), 2.71 (m, 2H), 1.29 (m, 1H). [M+H] 505.0

Example 142

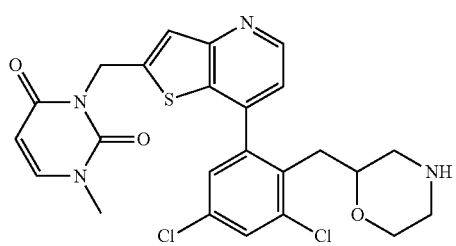 [SMILES: Cn1ccc(=O)n(Cc2cc3nccc(-c4cc(Cl)cc(Cl)c4CC4CNCCO4)c3s2)c1=O]

3-((7-(3,5-dichloro-2-(morpholin-2-ylmethyl)phenyl)thieno[3,2-b]pyridin-2-yl)methyl)-1-methylpyrimidine-2,4(1H,3H)-dione. The title compound was prepared by General Procedures B, E, and G. $^1$H NMR (400 MHz, Chloroform-d) δ 8.70 (m, 1H), 7.66 (m, 1H), 7.50 (s, 1H), 7.21-7.04 (m, 1H), 7.14 (s, 1H), 7.11 (s, 1H), 5.76 (d, J=8.0 Hz, 1H), 5.37 (s, 2H), 3.69 (m, 1H), 3.54 (m, 1H), 3.43 (s, 3H), 2.65 (m, 5H), 2.25 (m, 2H), 1.34 (m, 1H). [M+H] 517.0

Example 143

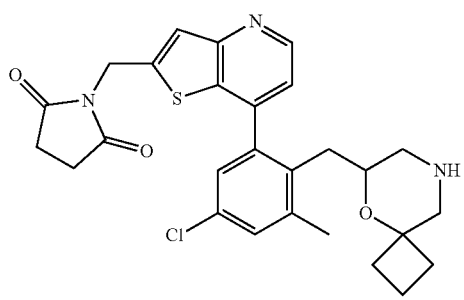 [SMILES: Cc1cc(Cl)cc(-c2ccnc3cc(CN4C(=O)CCC4=O)sc23)c1CC1CNCC2(CCC2)O1]

1-((7-(2-((5-oxa-8-azaspiro[3.5]nonan-6-yl)methyl)-5-chloro-3-methylphenyl)thieno[3,2-b]pyridin-2-yl)methyl)pyrrolidine-2,5-dione. The title compound was prepared by General Procedures B, E, and G. $^1$H NMR (400 MHz, Methanol-d4) δ 8.90 (d, J=5.6 Hz, 1H), 7.84-7.70 (m, 2H), 7.52 (dd, J=4.5, 2.0 Hz, 1H), 7.31 (dd, J=29.1, 2.3 Hz, 1H), 5.04 (d, J=4.2 Hz, 2H), 3.60 (q, J=11.8, 11.0 Hz, 1H), 3.38 (dd, J=26.6, 12.8 Hz, 1H), 3.11-2.90 (m, 2H), 2.76 (d, J=3.1 Hz, 4H), 2.81-2.69 (m, 1H), 2.63 (dd, J=15.1, 10.5 Hz, 2H), 2.49 (d, J=1.9 Hz, 3H), 2.14-2.04 (m, 1H), 1.78-1.54 (m, 4H), 1.45-1.29 (m, 1H). [M+H] 510.0

Example 144

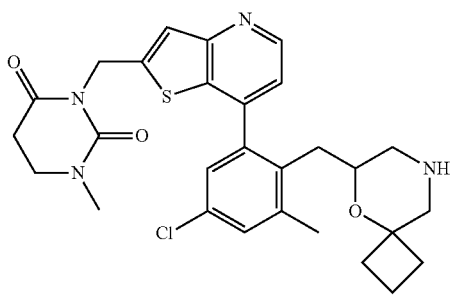 [SMILES: Cc1cc(Cl)cc(-c2ccnc3cc(CN4C(=O)CCN(C)C4=O)sc23)c1CC1CNCC2(CCC2)O1]

3-((7-(2-((5-oxa-8-azaspiro[3.5]nonan-6-yl)methyl)-5-chloro-3-methylphenyl)thieno[3,2-b]pyridin-2-yl)methyl)-1-methyldihydropyrimidine-2,4(1H,3H)-dione. The title compound was prepared by General Procedures B, E, and G. $^1$H NMR (400 MHz, Methanol-d4) δ 8.90 (dd, J=5.5, 1.2 Hz, 1H), 7.86-7.72 (m, 2H), 7.53 (dd, J=6.4, 2.2 Hz, 1H), 7.33 (dd, J=33.4, 2.1 Hz, 1H), 5.27 (d, J=3.0 Hz, 2H), 3.60 (dt, J=19.0, 8.6 Hz, 1H), 3.52-3.36 (m, 2H), 3.11 (d, J=12.6 Hz, 1H), 3.02 (s, 3H), 3.06-2.90 (m, 2H), 2.84-2.69 (m, 3H), 2.62 (dd, J=15.6, 7.9 Hz, 2H), 2.49 (s, 3H), 2.09 (s, 1H), 1.78-1.52 (m, 4H), 1.40-1.26 (m, 1H). [M+H] 539.1

Example 145

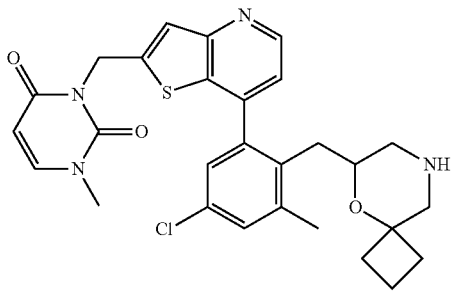 [SMILES: Cc1cc(Cl)cc(-c2ccnc3cc(Cn4c(=O)ccn(C)c4=O)sc23)c1CC1CNCC2(CCC2)O1]

3-((7-(2-((5-oxa-8-azaspiro[3.5]nonan-6-yl)methyl)-5-chloro-3-methylphenyl)thieno[3,2-b]pyridin-2-yl)methyl)-1-methylpyrimidine-2,4(1H,3H)-dione. The title compound was prepared by General Procedures B, E, and G. $^1$H NMR (400 MHz, Methanol-d4) δ 8.91 (d, J=5.7 Hz, 1H), 7.85-7.73 (m, 2H), 7.59 (dd, J=7.9, 1.2 Hz, 1H), 7.52 (dd, J=7.0, 1.9 Hz, 1H), 7.32 (dd, J=36.7, 2.3 Hz, 1H), 5.75 (dd, J=7.8, 4.6 Hz, 1H), 5.47 (d, J=5.4 Hz, 2H), 3.59 (dt, J=27.0, 9.4, 9.0 Hz, 1H), 3.37 (s, 3H), 3.11 (d, J=12.0 Hz, 1H), 3.04-2.89 (m, 2H), 2.84-2.54 (m, 3H), 2.48 (d, J=2.0 Hz, 3H), 2.10-1.86 (m, 1H), 1.77-1.46 (m, 4H), 1.28 (s, 1H). [M+H] 537.2

Example 146

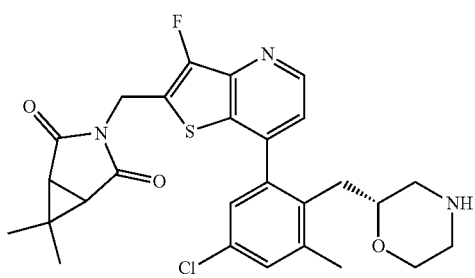 [SMILES: Cc1cc(Cl)cc(-c2ccnc3c(F)c(CN4C(=O)C5C(C4=O)C5(C)C)sc23)c1C[C@@H]1CNCCO1]

3-((7-(5-chloro-3-methyl-2-(((R)-morpholin-2-yl)methyl)phenyl)-3-fluorothieno[3,2-b]pyridin-2-yl)methyl)-6,6-dimethyl-3-azabicyclo[3.1.0]hexane-2,4-dione. The title compound was prepared by General Procedures B, E, and G. $^1$H NMR (400 MHz, Methanol-d4) δ 8.87-8.81 (m, 1H), 7.66-7.55 (m, 1H), 7.46 (s, 1H), 7.19-7.14 (m, 1H), 4.88 (s, 2H), 3.95-3.43 (m, 4H), 3.16-3.03 (m, 2H), 3.03-2.77 (m, 2H), 2.73-2.53 (m, 2H), 2.49 (d, J=9.9 Hz, 4H), 1.31 (s, 3H), 1.24 (s, 3H). [M+H] 528.1

Example 147

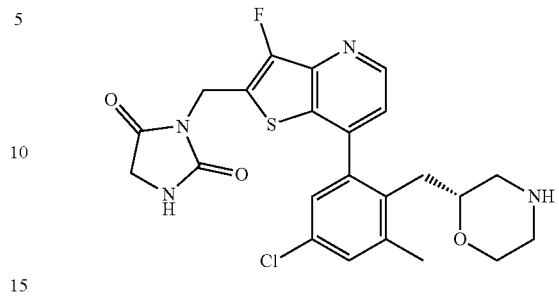

(R)-3-((7-(5-chloro-3-methyl-2-(morpholin-2-ylmethyl)phenyl)-3-fluorothieno[3,2-b]pyridin-2-yl)methyl)imidazolidine-2,4-dione. The title compound was prepared by General Procedures B, E, and G. $^1$H NMR (400 MHz, Methanol-d4) δ 8.89 (d, J=5.2 Hz, 1H), 7.79-7.61 (m, 1H), 7.47 (s, 1H), 7.25-7.14 (m, 1H), 5.02 (s, 2H), 4.01 (s, 2H), 3.96-3.40 (m, 3H), 3.18-3.03 (m, 2H), 3.03-2.54 (m, 4H), 2.40 (s, 3H). [M+H] 489.0

Example 148

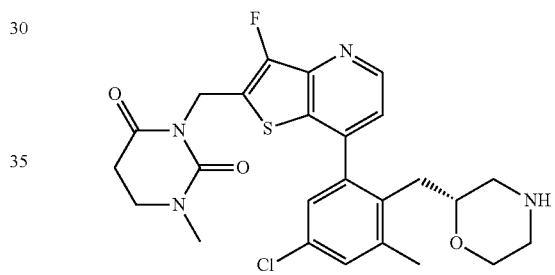

(R)-3-((7-(5-chloro-3-methyl-2-(morpholin-2-ylmethyl)phenyl)-3-fluorothieno[3,2-b]pyridin-2-yl)methyl)-1-methyldihydropyrimidine-2,4(1H,3H)-dione. The title compound was prepared by General Procedures B, E, and G. $^1$H NMR (400 MHz, Methanol-d4) δ 8.84 (d, J=5.2 Hz, 1H), 7.71-7.54 (m, 1H), 7.46 (s, 1H), 7.23-7.13 (m, 1H), 5.38-5.25 (m, 1H), 5.20 (dd, J=15.2, 6.7 Hz, 1H), 4.87 (s, 2H), 3.98-3.37 (m, 4H), 3.17-3.04 (m, 1H), 3.01 (s, 3H), 2.93-2.82 (m, 1H), 2.82-2.73 (m, 2H), 2.73-2.53 (m, 3H), 2.47 (s, 3H). [M+H] 517.0

Example 149

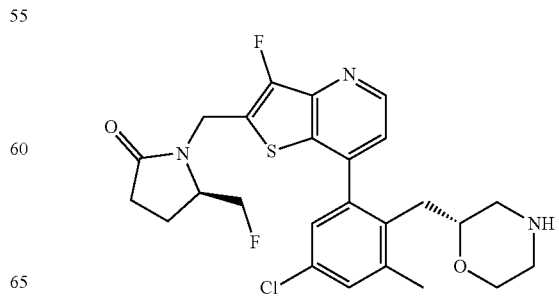

(R)-1-((7-(5-chloro-3-methyl-2-(((R)-morpholin-2-yl)methyl)phenyl)-3-fluorothieno[3,2-b]pyridin-2-yl)methyl)-5-(fluoromethyl)pyrrolidin-2-one. The title compound was prepared by General Procedures B, E, and G (LiHMDS was used instead of cesium carbonate). $^1$H NMR (400 MHz, Methanol-d4) δ 8.85 (t, J=5.3 Hz, 1H), 7.73-7.54 (m, 1H), 7.46 (s, 1H), 7.24-7.14 (m, 1H), 4.99 (dd, J=16.3, 10.5 Hz, 1H), 4.82 (d, J=16.3 Hz, 2H), 4.78-4.57 (m, 1H), 4.57-4.36 (m, 1H), 4.15-3.85 (m, 2H), 3.65-3.55 (m, 1H), 3.55-3.39 (m, 1H), 3.20-3.02 (m, 2H), 3.02-2.75 (m, 2H), 2.75-2.57 (m, 2H), 2.47 (s, 3H), 2.45-2.31 (m, 1H), 2.31-2.14 (m, 1H), 1.97-1.82 (m, 1H). [M+H] 506.0

Example 150

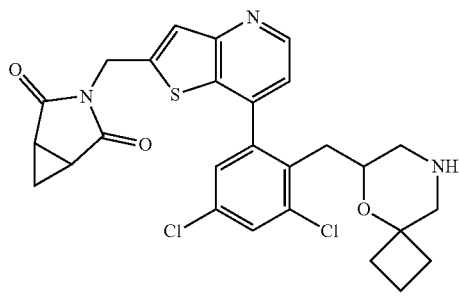 [SMILES: O=C1C2CC2C(=O)N1Cc1cc2nccc(-c3cc(Cl)cc(Cl)c3CC3CNCC4(CCC4)O3)c2s1]

3-((7-(2-((5-oxa-8-azaspiro[3.5]nonan-6-yl)methyl)-3,5-dichlorophenyl)thieno[3,2-b]pyridin-2-yl)methyl)-3-azabicyclo[3.1.0]hexane-2,4-dione. The title compound was prepared by General Procedures B, E, and G. $^1$H NMR (400 MHz, Methanol-d4) δ 8.96 (d, J=5.6 Hz, 1H), 7.90 (d, J=5.8 Hz, 1H), 7.84 (t, J=2.4 Hz, 1H), 7.74 (d, J=5.1 Hz, 1H), 7.59-7.49 (m, 1H), 4.89 (s, 2H), 3.99-3.87 (m, 1H), 3.44 (m, 1H), 3.14 (m, 2H), 2.93-2.73 (m, 1H), 2.60 (m, 3H), 2.13 (m, 1H), 1.87 (s, 1H), 1.59 (m, 4H), 1.31 (s, 4H). [M+H] 542.0

Example 151

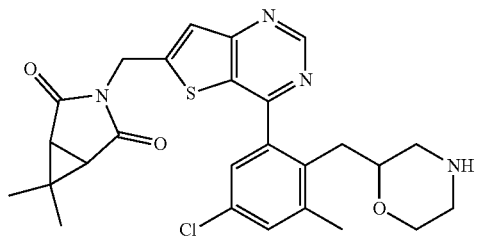 [SMILES: Cc1cc(Cl)cc(-c2ncnc3cc(CN4C(=O)C5C(C4=O)C5(C)C)sc23)c1CC1CNCCO1]

3-((4-(5-chloro-3-methyl-2-(morpholin-2-ylmethyl)phenyl)thieno[3,2-d]pyrimidin-6-yl)methyl)-6,6-dimethyl-3-azabicyclo[3.1.0]hexane-2,4-dione. The title compound was prepared by General Procedures B and F using 3-((4-chlorothieno[3,2-d]pyrimidin-6-yl)methyl)-6,6-dimethyl-3-azabicyclo[3.1.0]hexane-2,4-dione. $^1$H NMR (400 MHz, Methanol-d4) δ 9.27 (s, 1H), 7.65 (d, J=0.9 Hz, 1H), 7.52 (dd, J=2.3, 0.7 Hz, 1H), 7.40 (d, J=2.3 Hz, 1H), 4.95 (d, J=0.9 Hz, 2H), 3.81-3.61 (m, 2H), 3.52-3.42 (m, 1H), 3.17 (d, J=12.6 Hz, 1H), 3.08 (d, J=12.7 Hz, 1H), 2.91 (qd, J=14.7, 8.7 Hz, 3H), 2.70 (t, J=11.9 Hz, 1H), 2.53 (s, 2H), 2.49 (s, 3H), 1.25 (s, 3H), 1.15 (s, 3H). [M+H] 511.1

Example 152

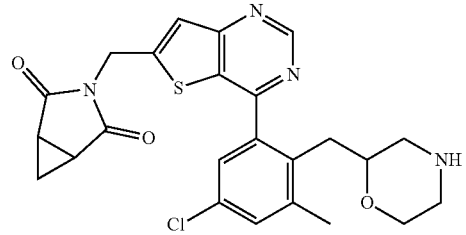

3-((4-(5-chloro-3-methyl-2-(morpholin-2-ylmethyl)phenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. $^1$H NMR (400 MHz, Methanol-d4) δ 9.17 (s, 1H), 7.51 (s, 1H), 7.46 (dd, J=2.2, 0.8 Hz, 1H), 7.37 (d, J=2.3 Hz, 1H), 4.86 (d, J=1.0 Hz, 2H), 3.67 (td, J=12.5, 6.0 Hz, 2H), 3.48-3.38 (m, 1H), 3.16-2.79 (m, 5H), 2.74-2.63 (m, 1H), 2.60 (dd, J=8.2, 3.6 Hz, 2H), 2.47 (d, J=0.7 Hz, 3H), 1.62 (td, J=8.1, 4.6 Hz, 1H), 1.47 (dt, J=4.6, 3.6 Hz, 1H). [M+H] 483.1

Example 153

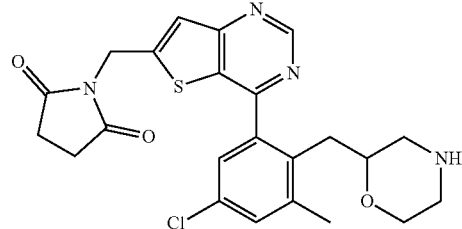 [SMILES: Cc1cc(Cl)cc(-c2ncnc3cc(CN4C(=O)CCC4=O)sc23)c1CC1CNCCO1]

1-((4-(5-chloro-3-methyl-2-(morpholin-2-ylmethyl)phenyl)thieno[3,2-d]pyrimidin-6-yl)methyl)pyrrolidine-2,5-dione. The title compound was prepared by General Procedures B and F using 1-((4-chlorothieno[3,2-d]pyrimidin-6-yl)methyl)pyrrolidine-2,5-dione. $^1$H NMR (400 MHz, Methanol-d4) δ 9.34 (s, 1H), 7.73 (d, J=1.1 Hz, 1H), 7.55 (dd, J=2.2, 0.7 Hz, 1H), 7.45 (d, J=2.3 Hz, 1H), 5.08 (d, J=0.9 Hz, 2H), 3.79-3.68 (m, 1H), 3.64 (dd, J=13.1, 3.6 Hz, 1H), 3.54-3.37 (m, 1H), 3.20 (d, J=12.3 Hz, 1H), 3.08 (d, J=12.7 Hz, 1H), 2.99-2.83 (m, 3H), 2.78 (s, 4H), 2.71 (t, J=11.8 Hz, 1H), 2.49 (s, 3H). [M+H] 471.1

Example 154

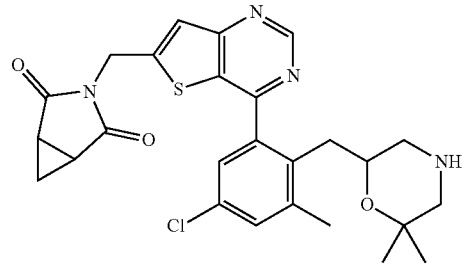 [SMILES: Cc1cc(Cl)cc(-c2ncnc3cc(CN4C(=O)C5CC5C4=O)sc23)c1CC1CNCC(C)(C)O1]

3-((4-(5-chloro-2-((6,6-dimethylmorpholin-2-yl)methyl)-3-methylphenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. ¹H NMR (400 MHz, Methanol-d4) δ 9.22 (s, 1H), 7.55 (s, 1H), 7.48 (d, J=2.0 Hz, 1H), 7.43 (d, J=2.2 Hz, 1H), 4.86 (s, 2H), 3.84 (t, J=9.9 Hz, 1H), 3.18-3.06 (m, 2H), 2.99 (d, J=12.3 Hz, 1H), 2.87 (d, J=14.4 Hz, 1H), 2.69-2.53 (m, 4H), 2.47 (s, 3H), 1.63 (dq, J=8.1, 4.3 Hz, 1H), 1.53-1.43 (m, 1H), 1.05 (s, 3H), 0.70 (s, 3H). [M+H] 511.1

Example 155

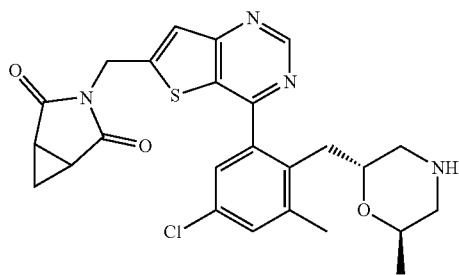 [SMILES: Cc1cc(Cl)cc(-c2ncnc3cc(CN4C(=O)C5CC5C4=O)sc23)c1C[C@@H]1CNC[C@@H](C)O1]

3-((4-(5-chloro-3-methyl-2-(((2R,6R)-6-methylmorpholin-2-yl)methyl)phenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. [M+H] 497.0

Example 156

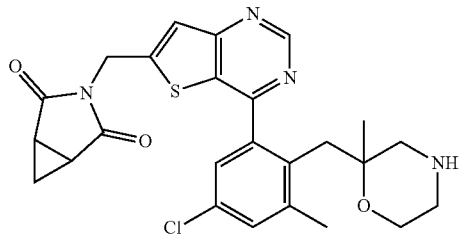 [SMILES: Cc1cc(Cl)cc(-c2ncnc3cc(CN4C(=O)C5CC5C4=O)sc23)c1CC1(C)CNCCO1]

3-((4-(5-chloro-3-methyl-2-((2-methylmorpholin-2-yl)methyl)phenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. ¹H NMR (400 MHz, Methanol-d4) δ 9.12 (s, 1H), 7.49 (dd, J=2.3, 0.7 Hz, 1H), 7.48 (t, J=1.0 Hz, 1H), 7.44 (d, J=2.3 Hz, 1H), 4.86 (t, J=1.0 Hz, 2H), 3.44-3.34 (m, 1H), 3.11 (d, J=12.6 Hz, 1H), 2.90 (d, J=12.6 Hz, 1H), 2.70-2.52 (m, 7H), 2.46 (d, J=0.7 Hz, 3H), 1.63 (td, J=8.1, 4.6 Hz, 1H), 1.47 (dt, J=4.6, 3.6 Hz, 1H), 1.11 (s, 3H). [M+H] 497.2

Example 157

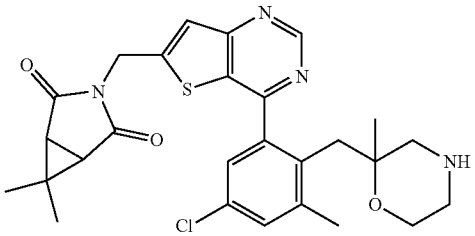 [SMILES: Cc1cc(Cl)cc(-c2ncnc3cc(CN4C(=O)C5C(C4=O)C5(C)C)sc23)c1CC1(C)CNCCO1]

3-((4-(5-chloro-3-methyl-2-((2-methylmorpholin-2-yl)methyl)phenyl)thieno[3,2-d]pyrimidin-6-yl)methyl)-6,6-dimethyl-3-azabicyclo[3.1.0]hexane-2,4-dione. The title compound was prepared by General Procedures B and F using 3-((4-chlorothieno[3,2-d]pyrimidin-6-yl)methyl)-6,6-dimethyl-3-azabicyclo[3.1.0]hexane-2,4-dione. ¹H NMR (400 MHz, Methanol-d4) δ 9.12 (s, 1H), 7.53 (d, J=1.0 Hz, 1H), 7.49 (dd, J=2.3, 0.7 Hz, 1H), 7.41 (d, J=2.3 Hz, 1H), 4.91 (dd, J=1.7, 0.9 Hz, 2H), 3.45-3.35 (m, 1H), 3.10 (d, J=12.6 Hz, 1H), 2.90 (d, J=12.7 Hz, 1H), 2.70 (d, J=13.7 Hz, 1H), 2.68-2.55 (m, 4H), 2.52 (d, J=0.5 Hz, 2H), 2.46 (t, J=0.6 Hz, 3H), 1.25 (s, 3H), 1.14 (s, 3H), 1.10 (s, 3H). [M+H] 525.2

Example 158

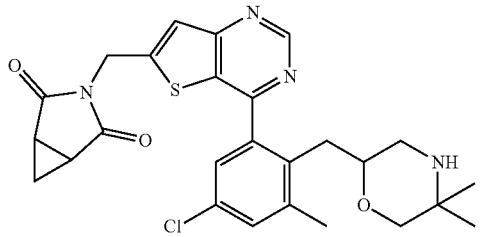 [SMILES: Cc1cc(Cl)cc(-c2ncnc3cc(CN4C(=O)C5CC5C4=O)sc23)c1CC1CNC(C)(C)CO1]

3-((4-(5-chloro-2-((5,5-dimethylmorpholin-2-yl)methyl)-3-methylphenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. ¹H NMR (400 MHz, Methanol-d4) δ 9.15 (d, J=11.0 Hz, 1H), 7.52 (s, 1H), 7.46 (d, J=2.3 Hz, 1H), 7.39 (d, J=2.4 Hz, 1H), 3.32 (s, 2H), 3.97 (s, 1H), 3.77 (s, 1H), 3.67-3.56 (m, 1H), 3.19 (q, J=12.7 Hz, 1H), 3.11-3.00 (m, 1H), 2.94-2.83 (m, 1H), 2.60 (dd, J=8.1, 3.6 Hz, 2H), 2.47 (s, 3H), 1.72-1.59 (m, 1H), 1.55-1.45 (m, 1H), 1.23 (d, J=2.9 Hz, 3H), 1.17 (s, 3H), 1.06 (s, 2H). [M+H] 511.0

Example 159

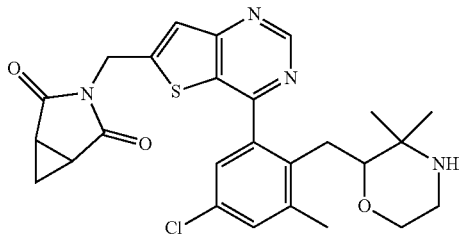 [SMILES: Cc1cc(Cl)cc(-c2ncnc3cc(CN4C(=O)C5CC5C4=O)sc23)c1CC1OCCNC1(C)C]

3-((4-(5-chloro-2-((3,3-dimethylmorpholin-2-yl)methyl)-3-methylphenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. $^1$H NMR (400 MHz, Methanol-d4) δ 9.18 (d, J=1.4 Hz, 1H), 7.45 (d, J=2.3 Hz, 1H), 7.38 (d, J=2.3 Hz, 1H), 7.16 (d, J=2.1 Hz, 1H), 4.87 (d, J=1.3 Hz, 2H), 4.00-3.95 (m, 2H), 3.60-3.50 (m, 2H), 3.17-3.07 (m, 2H), 2.98-2.91 (m, 2H), 2.83 (d, J=2.0 Hz, 1H), 2.67-2.59 (m, 1H), 2.31 (s, 2H), 1.63 (ddd, J=9.4, 7.4, 4.6 Hz, 1H), 1.50 (d, J=7.1 Hz, 6H), 1.20 (s, 1H), 1.05 (s, 1H). [M+H] 511.0

Example 160

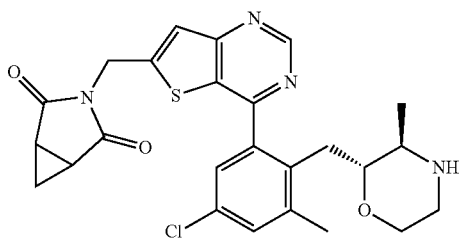 [SMILES: Cc1cc(Cl)cc(-c2ncnc3cc(CN4C(=O)C5CC5C4=O)sc23)c1C[C@H]1OCCN[C@@H]1C]

3-((4-(5-chloro-3-methyl-2-(((2R,3R)-3-methylmorpholin-2-yl)methyl)phenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. $^1$H NMR (400 MHz, Methanol-d4) δ 9.17 (s, 1H), 7.51 (t, J=1.0 Hz, 1H), 7.45 (dd, J=2.3, 0.5 Hz, 1H), 7.37 (dd, J=2.3, 0.3 Hz, 1H), 4.86 (d, J=1.2 Hz, 2H), 3.65 (dd, J=12.8, 3.7 Hz, 1H), 3.30-3.27 (m, 1H), 3.25-3.16 (m, 1H), 3.08 (d, J=13.0 Hz, 2H), 3.02-2.88 (m, 3H), 2.60 (dd, J=8.2, 3.6 Hz, 2H), 2.47 (s, 3H), 1.63 (td, J=8.1, 4.6 Hz, 1H), 1.48 (dt, J=4.6, 3.6 Hz, 1H), 1.00 (d, J=6.6 Hz, 3H). [M+H] 497.1

Example 161

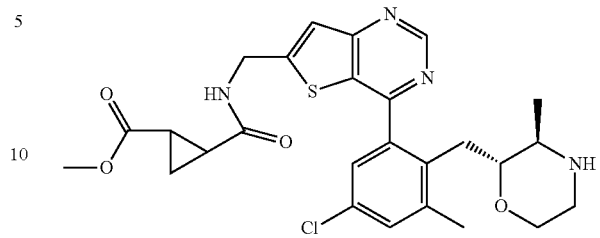

methyl 2-(((4-(5-chloro-3-methyl-2-(((2R,3R)-3-methylmorpholin-2-yl)methyl)phenyl)thieno[3,2-d]pyrimidin-6-yl)methyl)carbamoyl)cyclopropane-1-carboxylate. The compound was formed upon methanolysis of 3-((4-(5-chloro-3-methyl-2-(((2R,3R)-3-methylmorpholin-2-yl)methyl)phenyl)thieno[3,2-d]pyrimidin-6-yl)methyl)-3-azabicyclo[3.1.0]hexane-2,4-dione. $^1$H NMR (400 MHz, Methanol-d4) δ 9.15 (s, 1H), 7.50 (dt, J=2.4, 1.2 Hz, 1H), 7.44 (d, J=2.3 Hz, 1H), 7.36 (t, J=2.2 Hz, 1H), 4.85-4.61 (m, 2H), 3.69 (dd, J=13.1, 3.7 Hz, 1H), 3.48 (d, J=20.5 Hz, 3H), 3.39-3.30 (m, 1H), 3.12-3.03 (m, 3H), 3.03-2.86 (m, 3H), 2.46 (s, 3H), 2.19-2.06 (m, 2H), 1.59-1.50 (m, 1H), 1.28-1.20 (m, 1H), 0.92 (dd, J=10.8, 6.5 Hz, 3H). [M+H] 529.2

Example 162

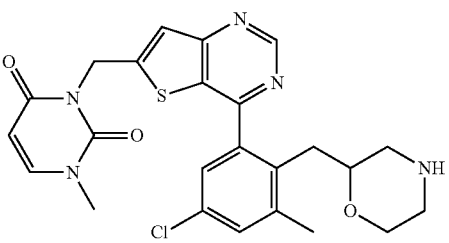 [SMILES: Cc1cc(Cl)cc(-c2ncnc3cc(Cn4c(=O)ccn(C)c4=O)sc23)c1CC1CNCCO1]

3-((4-(5-chloro-3-methyl-2-(morpholin-2-ylmethyl)phenyl)thieno[3,2-d]pyrimidin-6-yl)methyl)-1-methylpyrimidine-2,4(1H,3H)-dione. The title compound was prepared by General Procedures B, F, and H. $^1$H NMR (400 MHz, Methanol-d4) δ 9.17 (s, 1H), 7.62-7.55 (m, 2H), 7.46 (d, J=2.3 Hz, 1H), 7.35 (d, J=2.1 Hz, 1H), 5.76 (d, J=7.8 Hz, 1H), 5.44 (s, 2H), 3.71-3.62 (m, 2H), 3.44 (t, J=12.6 Hz, 1H), 3.38 (s, 3H), 3.08 (dd, J=19.3, 12.8 Hz, 2H), 3.02-2.78 (m, 3H), 2.68 (t, J=11.9 Hz, 1H), 2.47 (s, 3H). [M+H] 498.0

Example 163

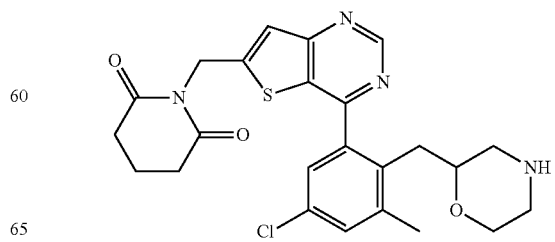

1-((4-(5-chloro-3-methyl-2-(morpholin-2-ylmethyl)phenyl)thieno[3,2-d]pyrimidin-6-yl)methyl)piperidine-2,6-dione. The title compound was prepared by General Procedures B, F, and G. ¹H NMR (400 MHz, Methanol-d4) δ 9.16 (s, 1H), 7.52 (s, 1H), 7.46 (s, 1H), 7.35 (s, 1H), 5.26 (s, 2H), 3.69 (dd, J=19.4, 11.3 Hz, 2H), 3.45 (t, J=12.6 Hz, 1H), 3.09 (dd, J=19.9, 12.7 Hz, 2H), 3.01-2.77 (m, 3H), 2.76-2.64 (m, 5H), 2.47 (s, 3H), 1.95 (p, J=7.0, 6.3 Hz, 2H). [M+H] 485.0

Example 164

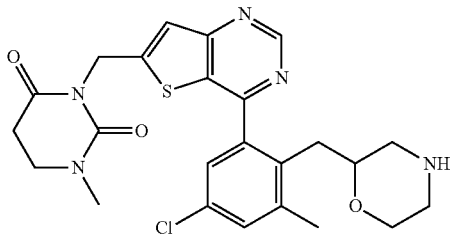 [SMILES: Cc1cc(Cl)cc(-c2ncnc3cc(CN4C(=O)CCN(C)C4=O)sc23)c1CC1CNCCO1]

3-((4-(5-chloro-3-methyl-2-(morpholin-2-ylmethyl)phenyl)thieno[3,2-d]pyrimidin-6-yl)methyl)-1-methyldihydropyrimidine-2,4(1H,3H)-dione. The title compound was prepared by General Procedures B, F, and G. ¹H NMR (400 MHz, Acetonitrile-d3) δ 9.34 (s, 1H), 7.74 (s, 1H), 7.58 (s, 1H), 7.41 (s, 1H), 5.28 (s, 2H), 3.81-3.65 (m, 2H), 3.49 (t, J=13.2 Hz, 1H), 3.41 (t, J=6.8 Hz, 2H), 3.20 (d, J=12.2 Hz, 1H), 3.12 (d, J=13.2 Hz, 1H), 2.98 (s, 3H), 2.91-2.78 (m, 3H), 2.78-2.62 (m, 3H), 2.47 (s, 3H). [M+H] 500.0

Example 165

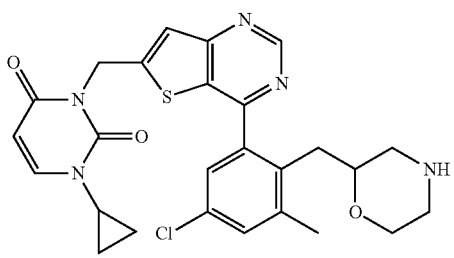 [SMILES: Cc1cc(Cl)cc(-c2ncnc3cc(Cn4c(=O)ccn(C5CC5)c4=O)sc23)c1CC1CNCCO1]

3-((4-(5-chloro-3-methyl-2-(morpholin-2-ylmethyl)phenyl)thieno[3,2-d]pyrimidin-6-yl)methyl)-1-cyclopropylpyrimidine-2,4(1H,3H)-dione. The title compound was prepared by General Procedures B, F, and G. ¹H NMR (400 MHz, Acetonitrile-d3) δ 9.33 (s, 1H), 7.77 (s, 1H), 7.56 (s, 1H), 7.46 (d, J=8.0 Hz, 1H), 7.40 (s, 1H), 5.70 (d, J=8.1 Hz, 1H), 5.42 (s, 2H), 3.80-3.64 (m, 2H), 3.47 (t, J=13.4, 13.0 Hz, 1H), 3.18 (d, J=12.8 Hz, 1H), 3.14-3.02 (m, 2H), 2.92-2.78 (m, 3H), 2.68 (tt, J=12.6, 7.3 Hz, 1H), 2.46 (s, 3H), 0.99 (q, J=6.5, 5.1 Hz, 2H), 0.83 (qt, J=3.8, 2.7, 1.9 Hz, 2H). [M+H] 524.0

Example 166

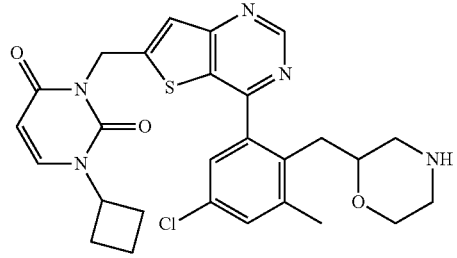 [SMILES: Cc1cc(Cl)cc(-c2ncnc3cc(Cn4c(=O)ccn(C5CCC5)c4=O)sc23)c1CC1CNCCO1]

3-((4-(5-chloro-3-methyl-2-(morpholin-2-ylmethyl)phenyl)thieno[3,2-d]pyrimidin-6-yl)methyl)-1-cyclobutylpyrimidine-2,4(1H,3H)-dione. The title compound was prepared by General Procedures B, F, and G. ¹H NMR (400 MHz, Acetonitrile-d3) δ 9.30 (s, 1H), 7.73 (s, 1H), 7.60 (d, J=8.0 Hz, 1H), 7.54 (s, 1H), 7.38 (s, 1H), 5.77 (d, J=7.9 Hz, 1H), 5.41 (s, 2H), 4.77 (p, J=8.8 Hz, 1H), 3.80-3.63 (m, 2H), 3.46 (t, J=12.7 Hz, 1H), 3.20-3.02 (m, 2H), 2.94-2.77 (m, 3H), 2.68 (q, J=9.6 Hz, 1H), 2.46 (s, 3H), 2.36-2.27 (m, 2H), 2.24 (t, J=10.2 Hz, 2H), 1.85-1.76 (m, 2H). [M+H] 538.0

Example 167

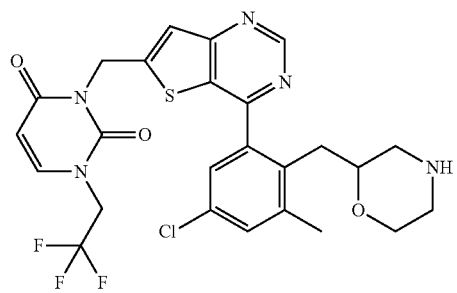 [SMILES: Cc1cc(Cl)cc(-c2ncnc3cc(Cn4c(=O)ccn(CC(F)(F)F)c4=O)sc23)c1CC1CNCCO1]

3-((4-(5-chloro-3-methyl-2-(morpholin-2-ylmethyl)phenyl)thieno[3,2-d]pyrimidin-6-yl)methyl)-1-(2,2,2-trifluoroethyl)pyrimidine-2,4(1H,3H)-dione. The title compound was prepared by General Procedures B, F, and G. [M+H] 566.0

Example 168

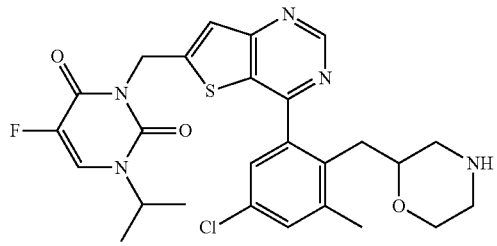 [SMILES: Cc1cc(Cl)cc(-c2ncnc3cc(Cn4c(=O)c(F)cn(C(C)C)c4=O)sc23)c1CC1CNCCO1]

3-((4-(5-chloro-3-methyl-2-(morpholin-2-ylmethyl)phenyl)thieno[3,2-d]pyrimidin-6-yl)methyl)-5-fluoro-1-isopropylpyrimidine-2,4(1H,3H)-dione. The title compound was prepared by General Procedures B, F, and G. ¹H NMR (400

MHz, Acetonitrile-d3) δ 9.32 (s, 1H), 7.77 (s, 1H), 7.71 (d, J=7.3 Hz, 1H), 7.55 (s, 1H), 7.40 (s, 1H), 5.45 (s, 2H), 4.80 (hept, J=6.6 Hz, 1H), 3.76 (q, J=5.3 Hz, 1H), 3.68 (d, J=13.6 Hz, 1H), 3.47 (t, J=12.7 Hz, 1H), 3.16 (d, J=12.7 Hz, 1H), 3.10 (d, J=12.9 Hz, 1H), 2.92-2.80 (m, 3H), 2.74-2.61 (m, 1H), 2.46 (s, 3H), 1.30 (d, J=6.7 Hz, 6H). [M+H] 544.0

Example 169

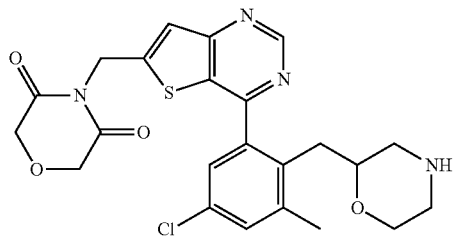 [SMILES: Cc1cc(Cl)cc(-c2ncnc3cc(CN4C(=O)COCC4=O)sc23)c1CC1CNCCO1]

4-((4-(5-chloro-3-methyl-2-(morpholin-2-ylmethyl)phenyl)thieno[3,2-d]pyrimidin-6-yl)methyl)morpholine-3,5-dione. The title compound was prepared by General Procedures B, F, and G. $^1$H NMR (400 MHz, Acetonitrile-d3) δ 9.30 (s, 1H), 7.69 (s, 1H), 7.53 (s, 1H), 7.39 (s, 1H), 5.28 (s, 2H), 4.42 (s, 4H), 3.74 (t, J=9.5 Hz, 1H), 3.66 (d, J=13.1 Hz, 1H), 3.47 (t, J=12.2 Hz, 1H), 3.19-3.06 (m, 2H), 2.94-2.78 (m, 3H), 2.67 (q, J=9.7, 8.8 Hz, 1H), 2.46 (s, 3H). [M+H] 487.0

Example 170

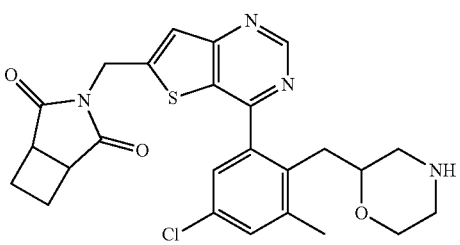 [SMILES: Cc1cc(Cl)cc(-c2ncnc3cc(CN4C(=O)C5CCC5C4=O)sc23)c1CC1CNCCO1]

3-((4-(5-chloro-3-methyl-2-(morpholin-2-ylmethyl)phenyl)thieno[3,2-d]pyrimidin-6-yl)methyl)-3-azabicyclo[3.2.0]heptane-2,4-dione. The title compound was prepared by General Procedures B, F, and G. $^1$H NMR (400 MHz, Acetonitrile-d3) δ 9.30 (s, 1H), 7.69 (s, 1H), 7.53 (s, 1H), 7.41 (s, 1H), 5.05 (s, 2H), 3.75 (t, J=9.2 Hz, 1H), 3.68 (d, J=13.2 Hz, 1H), 3.46 (t, J=12.7 Hz, 1H), 3.34 (d, J=8.4 Hz, 2H), 3.12 (t, J=15.8, 14.8 Hz, 2H), 2.95-2.79 (m, 3H), 2.74-2.59 (m, 3H), 2.46 (s, 3H), 2.15-2.04 (m, 2H). [M+H] 497.0

Example 171

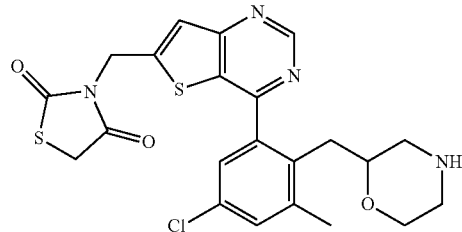 [SMILES: Cc1cc(Cl)cc(-c2ncnc3cc(CN4C(=O)CSC4=O)sc23)c1CC1CNCCO1]

3-((4-(5-chloro-3-methyl-2-(morpholin-2-ylmethyl)phenyl)thieno[3,2-d]pyrimidin-6-yl)methyl)thiazolidine-2,4-dione. The title compound was prepared by General Procedures B, F, and G. $^1$H NMR (400 MHz, Acetonitrile-d3) δ 9.29 (s, 1H), 7.68 (s, 1H), 7.52 (s, 1H), 7.39 (s, 1H), 5.10 (s, 2H), 4.10 (s, 2H), 3.74 (t, J=10.2 Hz, 1H), 3.66 (d, J=12.8 Hz, 1H), 3.46 (t, J=12.7 Hz, 1H), 3.12 (t, J=13.4 Hz, 2H), 2.93-2.78 (m, 3H), 2.67 (q, J=11.5 Hz, 1H), 2.46 (s, 3H). [M+H] 488.9

Example 172

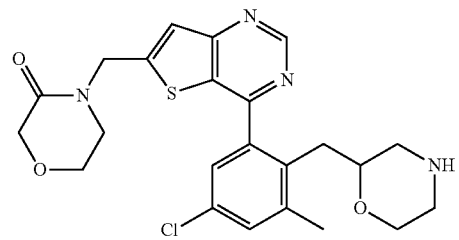 [SMILES: Cc1cc(Cl)cc(-c2ncnc3cc(CN4CCOCC4=O)sc23)c1CC1CNCCO1]

4-((4-(5-chloro-3-methyl-2-(morpholin-2-ylmethyl)phenyl)thieno[3,2-d]pyrimidin-6-yl)methyl)morpholin-3-one. The title compound was prepared by General Procedures B, F, and G. $^1$H NMR (400 MHz, Methanol-d4) δ 9.39 (s, 1H), 7.80 (s, 1H), 7.67 (s, 1H), 7.59 (s, 1H), 5.04 (s, 2H), 4.39 (s, 2H), 4.11 (t, J=5.5 Hz, 2H), 3.89 (q, J=12.5 Hz, 2H), 3.73 (t, J=5.0 Hz, 2H), 3.71-3.60 (m, 1H), 3.36-2.99 (m, 5H), 2.91 (t, J=11.9 Hz, 1H), 2.68 (s, 3H). [M+H]473.0

Example 173

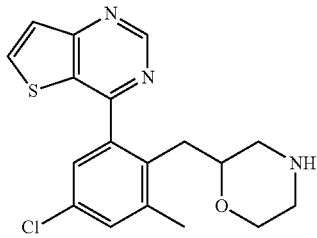 [SMILES: Cc1cc(Cl)cc(-c2ncnc3ccsc23)c1CC1CNCCO1]

2-(4-chloro-2-methyl-6-(thieno[3,2-d]pyrimidin-4-yl)benzyl)morpholine. The title compound was prepared by General Procedures B and F using 4-chlorothieno[3,2-d]pyrimidine. $^1$H NMR (400 MHz, Methanol-d4) δ 9.23 (s, 1H), 8.41 (d, J=5.3 Hz, 1H), 7.67 (d, J=5.8 Hz, 1H), 7.48 (s, 1H), 7.42 (s, 1H), 3.68 (d, J=14.1 Hz, 2H), 3.45 (t, J=12.7 Hz, 1H), 3.16-2.99 (m, 3H), 2.96-2.80 (m, 2H), 2.70 (t, J=11.9 Hz, 1H), 2.49 (s, 3H). [M+H] 360.0

Example 174

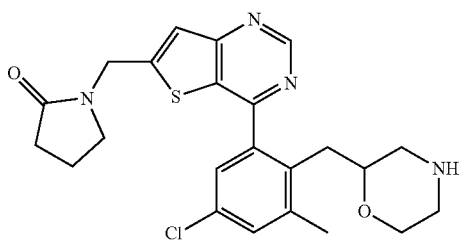 [SMILES: Cc1cc(Cl)cc(-c2ncnc3cc(CN4CCCC4=O)sc23)c1CC1CNCCO1]

1-((4-(5-chloro-3-methyl-2-(morpholin-2-ylmethyl)phenyl)thieno[3,2-d]pyrimidin-6-yl)methyl)pyrrolidin-2-one. The title compound was prepared by General Procedures B and F using 1-((4-chlorothieno[3,2-d]pyrimidin-6-yl)methyl)pyrrolidin-2-one. ¹H NMR (400 MHz, Methanol-d4) δ 8.90 (s, 1H), 7.21 (s, 1H), 7.19 (s, 1H), 7.12 (s, 1H), 4.57 (d, J=16.7 Hz, 1H), 4.40 (d, J=16.7 Hz, 1H), 4.20 (t, J=7.0, 6.6 Hz, 2H), 4.04 (d, J=12.9 Hz, 1H), 3.85 (t, J=10.3 Hz, 1H), 3.64 (t, J=11.9 Hz, 1H), 3.42 (d, J=12.7 Hz, 1H), 3.26-3.09 (m, 2H), 3.09-2.82 (m, 3H), 2.72 (t, J=8.2 Hz, 2H), 2.37 (s, 3H), 2.23 (p, J=7.9 Hz, 2H). [M+H] 457.0

Example 175

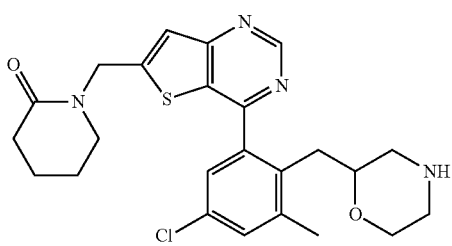

1-((4-(5-chloro-3-methyl-2-(morpholin-2-ylmethyl)phenyl)thieno[3,2-d]pyrimidin-6-yl)methyl)piperidin-2-one. The title compound was prepared by General Procedures B and F using 1-((4-(4,4,5,5-tetramethyl-1,3,2-dioxaborolan-2-yl)thieno[3,2-d]pyrimidin-6-yl)methyl)piperidin-2-one. ¹H NMR (400 MHz, Methanol-d4) δ 8.98 (s, 1H), 7.21-7.12 (m, 3H), 4.57 (d, J=16.8 Hz, 1H), 4.37 (d, J=16.8 Hz, 1H), 4.07-3.96 (m, 3H), 3.87-3.67 (m, 2H), 3.59 (t, J=13.1 Hz, 1H), 3.39 (d, J=12.6 Hz, 1H), 3.28-3.09 (m, 3H), 3.07-2.77 (m, 5H), 2.64 (t, J=6.4 Hz, 2H), 2.36 (s, 3H). [M+H] 471.0

Example 176

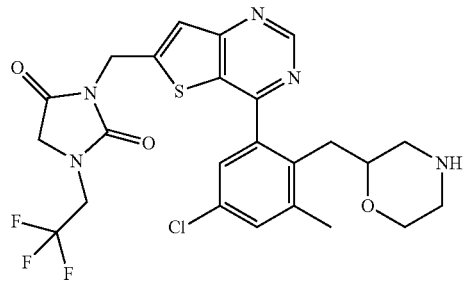 [SMILES: Cc1cc(Cl)cc(-c2ncnc3cc(CN4C(=O)CN(CC(F)(F)F)C4=O)sc23)c1CC1CNCCO1]

3-((4-(5-chloro-3-methyl-2-(morpholin-2-ylmethyl)phenyl)thieno[3,2-d]pyrimidin-6-yl)methyl)-1-(2,2,2-trifluoroethyl)imidazolidine-2,4-dione. The title compound was prepared by General Procedures B and F using 3-((4-chlorothieno[3,2-d]pyrimidin-6-yl)methyl)-1-(2,2,2-trifluoroethyl)imidazolidine-2,4-dione. ¹H NMR (400 MHz, Methanol-d4) δ 9.37 (s, 1H), 7.78 (s, 1H), 7.56 (s, 1H), 7.46 (s, 1H), 5.14 (s, 2H), 4.21 (s, 2H), 4.13 (d, J=9.2 Hz, 2H), 3.80-3.41 (m, 3H), 3.27-3.00 (m, 2H), 3.00-2.60 (m, 4H), 2.49 (s, 3H). [M+H] 554.1

Example 177

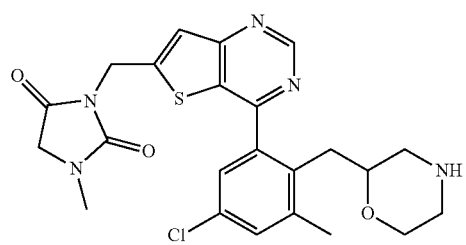

3-((4-(5-chloro-3-methyl-2-(morpholin-2-ylmethyl)phenyl)thieno[3,2-d]pyrimidin-6-yl)methyl)-1-methylimidazolidine-2,4-dione. The title compound was prepared by General Procedures B, F, and G. ¹H NMR (400 MHz, Methanol-d4) δ 9.29 (s, 1H), 7.70 (d, J=1.1 Hz, 1H), 7.53 (d, J=2.3 Hz, 1H), 7.43 (d, J=2.3 Hz, 1H), 5.07 (d, J=0.9 Hz, 2H), 4.05 (s, 2H), 3.75-3.59 (m, 2H), 3.51-3.39 (m, 1H), 3.18 (d, J=12.7 Hz, 1H), 3.07 (d, J=12.7 Hz, 1H), 2.98 (s, 3H), 2.95-2.79 (m, 3H), 2.70 (t, J=11.9 Hz, 1H), 2.49 (s, 3H). [M+H] 486.1

Example 178

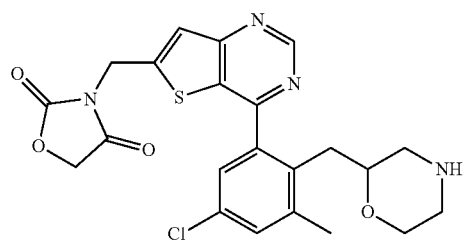

3-((4-(5-chloro-3-methyl-2-(morpholin-2-ylmethyl)phenyl)thieno[3,2-d]pyrimidin-6-yl)methyl)oxazolidine-2,4-dione. The title compound was prepared by General Procedures B, F, and G. $^1$H NMR (400 MHz, Methanol-d4) δ 9.19 (s, 1H), 7.65 (s, 1H), 7.47 (s, 1H), 7.39 (s, 1H), 5.08 (s, 2H), 4.89 (s, 2H), 3.69 (dd, J=15.0, 11.0 Hz, 2H), 3.44 (t, J=12.7 Hz, 1H), 3.17-2.95 (m, 3H), 2.94-2.79 (m, 2H), 2.70 (t, J=11.9 Hz, 1H), 2.48 (s, 3H). [M+H] 473.0

Example 179

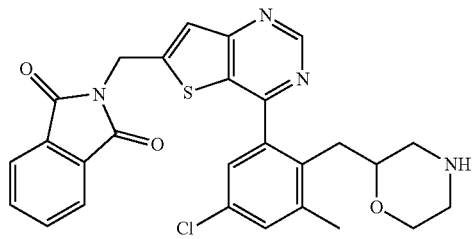 [SMILES: Cc1cc(Cl)cc(-c2ncnc3cc(CN4C(=O)c5ccccc5C4=O)sc23)c1CC1CNCCO1]

2-((4-(5-chloro-3-methyl-2-(morpholin-2-ylmethyl)phenyl)thieno[3,2-d]pyrimidin-6-yl)methyl)isoindoline-1,3-dione. The title compound was prepared by General Procedures B, F, and G. $^1$H NMR (400 MHz, Methanol-d4) δ 9.16 (s, 1H), 7.90 (dp, J=5.4, 3.1, 2.4 Hz, 2H), 7.83 (dq, J=7.2, 2.3 Hz, 2H), 7.60 (s, 1H), 7.43 (s, 1H), 7.34 (s, 1H), 5.22 (s, 2H), 3.67 (t, J=10.1 Hz, 1H), 3.60 (d, J=12.8 Hz, 1H), 3.40 (t, J=12.6 Hz, 1H), 3.11 (d, J=12.8 Hz, 1H), 3.05-2.91 (m, 2H), 2.90-2.79 (m, 2H), 2.67 (t, J=11.9 Hz, 1H), 2.45 (s, 3H). [M+H] 519.0

Example 180

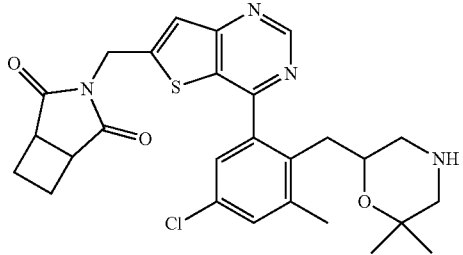 [SMILES: Cc1cc(Cl)cc(-c2ncnc3cc(CN4C(=O)C5CCC5C4=O)sc23)c1CC1CNCC(C)(C)O1]

3-((4-(5-chloro-2-((6,6-dimethylmorpholin-2-yl)methyl)-3-methylphenyl)thieno[3,2-d]pyrimidin-6-yl)methyl)-3-azabicyclo[3.2.0]heptane-2,4-dione. The title compound was prepared by General Procedures B, F, and G. $^1$H NMR (400 MHz, Methanol-d4) δ 9.30 (s, 1H), 7.69 (d, J=1.0 Hz, 1H), 7.54-7.51 (m, 1H), 7.48 (d, J=2.3 Hz, 1H), 5.12 (t, J=1.0 Hz, 2H), 3.86 (dd, J=11.3, 8.7 Hz, 1H), 3.44-3.32 (m, 2H), 3.18-3.06 (m, 2H), 2.99 (d, J=12.7 Hz, 1H), 2.91 (dd, J=14.6, 3.0 Hz, 1H), 2.70 (td, J=6.9, 4.7 Hz, 2H), 2.61 (dd, J=12.7, 9.7 Hz, 2H), 2.48 (s, 3H), 2.18-2.06 (m, 2H), 1.04 (s, 3H), 0.71 (s, 3H). [M+H] 525.2

Example 181

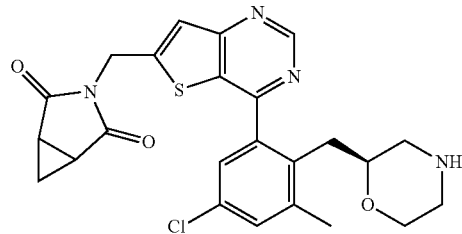 [SMILES: Cc1cc(Cl)cc(-c2ncnc3cc(CN4C(=O)C5CC5C4=O)sc23)c1C[C@H]1CNCCO1]

3-((4-(5-chloro-3-methyl-2-(((S)-morpholin-2-yl)methyl)phenyl)thieno[3,2-d]pyrimidin-6-yl)methyl)-3-azabicyclo[3.1.0]hexane-2,4-dione. The title compound was prepared by General Procedures A and F using 3-((4-chlorothieno[3,2-d]pyrimidin-6-yl)methyl)-3-azabicyclo[3.1.0]hexane-2,4-dione. [M+H] 483.0

Example 182

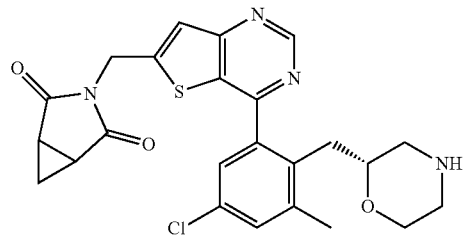 [SMILES: Cc1cc(Cl)cc(-c2ncnc3cc(CN4C(=O)C5CC5C4=O)sc23)c1C[C@@H]1CNCCO1]

3-((4-(5-chloro-3-methyl-2-(((R)-morpholin-2-yl)methyl)phenyl)thieno[3,2-d]pyrimidin-6-yl)methyl)-3-azabicyclo[3.1.0]hexane-2,4-dione. The title compound was prepared by General Procedures A and F using 3-((4-chlorothieno[3,2-d]pyrimidin-6-yl)methyl)-3-azabicyclo[3.1.0]hexane-2,4-dione. $^1$H NMR (400 MHz, Methanol-d4) δ 9.23 (s, 1H), 7.57 (s, 1H), 7.51 (s, 1H), 7.41 (s, 1H), 4.88 (s, 2H), 3.78-3.61 (m, 3H), 3.45 (t, J=12.4 Hz, 1H), 3.15 (d, J=13.0 Hz, 1H), 3.08 (d, J=12.8 Hz, 1H), 3.02-2.82 (m, 3H), 2.71 (t, J=11.9 Hz, 1H), 2.65-2.58 (m, 2H), 2.49 (s, 3H), 1.71-1.59 (m, 1H), 1.49 (s, 1H), 1.24 (t, J=7.2 Hz, 1H). [M+H] 483.0

Example 183

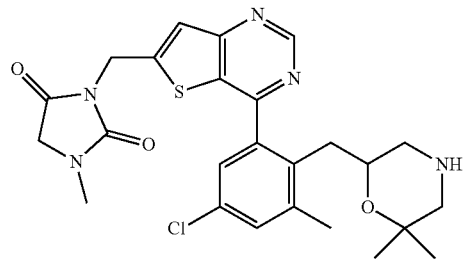 [SMILES: Cc1cc(Cl)cc(-c2ncnc3cc(CN4C(=O)CN(C)C4=O)sc23)c1CC1CNCC(C)(C)O1]

3-((4-(5-chloro-2-((6,6-dimethylmorpholin-2-yl)methyl)-3-methylphenyl)thieno[3,2-d]pyrimidin-6-yl)methyl)-1-methylimidazolidine-2,4-dione. The title compound was prepared by General Procedures B, F and G. $^1$H NMR (400

MHz, Methanol-d4) δ 9.29 (s, 1H), 7.69 (s, 1H), 7.52 (d, J=2.1 Hz, 1H), 7.46 (d, J=2.2 Hz, 1H), 5.05 (s, 2H), 4.04 (s, 2H), 3.83 (t, J=10.3 Hz, 1H), 3.16-3.04 (m, 2H), 2.97 (s, 3H), 2.89 (d, J=14.4 Hz, 1H), 2.67-2.54 (m, 3H), 2.48 (s, 3H), 1.04 (s, 3H), 0.71 (s, 3H). [M+H] 514.2

Example 184

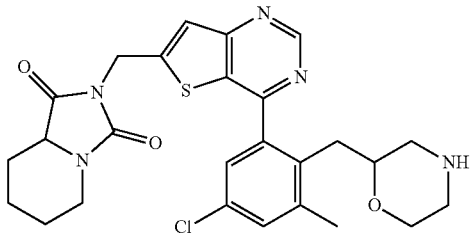 [SMILES: Cc1cc(Cl)cc(-c2ncnc3cc(CN4C(=O)C5CCCCN5C4=O)sc23)c1CC1CNCCO1]

2-((4-(5-chloro-3-methyl-2-(morpholin-2-ylmethyl)phenyl)thieno[3,2-d]pyrimidin-6-yl)methyl)tetrahydroimidazo[1,5-a]pyridine-1,3(2H,5H)-dione. The title compound was prepared by General Procedures B, F and G. $^1$H NMR (400 MHz, Methanol-d4) δ 9.24 (s, 1H), 7.62 (s, 1H), 7.50 (d, J=2.2 Hz, 1H), 7.41 (d, J=2.3 Hz, 1H), 5.05 (s, 2H), 4.14-3.95 (m, 2H), 3.68 (dd, J=24.7, 11.9 Hz, 2H), 3.45 (t, J=12.4 Hz, 1H), 3.15 (d, J=12.6 Hz, 1H), 3.07 (d, J=12.8 Hz, 1H), 3.02-2.80 (m, 4H), 2.70 (t, J=11.8 Hz, 1H), 2.48 (s, 3H), 2.16 (d, J=12.9 Hz, 1H), 2.07-1.89 (m, 1H), 1.75 (d, J=13.4 Hz, 1H), 1.57 (q, J=13.0 Hz, 1H), 1.48-1.16 (m, 2H). [M+H] 528.2

Example 185

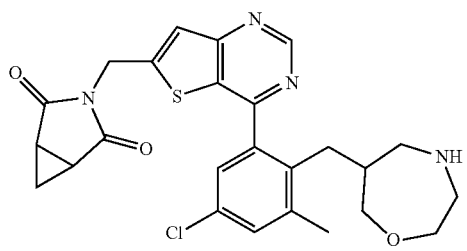 [SMILES: Cc1cc(Cl)cc(-c2ncnc3cc(CN4C(=O)C5CC5C4=O)sc23)c1CC1CNCCOC1]

3-((4-(2-((1,4-oxazepan-6-yl)methyl)-5-chloro-3-methylphenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. $^1$H NMR (400 MHz, Methanol-d4) δ 9.22 (s, 1H), 7.54 (s, 1H), 7.51 (s, 1H), 7.38 (s, 1H), 4.85 (s, 2H), 3.99-3.63 (m, 5H), 3.55 (dd, J=12.4, 9.5 Hz, 2H), 3.27-3.11 (m, 2H), 2.75-2.54 (m, 4H), 2.48 (s, 3H), 1.62 (q, J=7.2, 6.5, 5.5 Hz, 1H), 1.44 (dd, J=5.7, 1.9 Hz, 1H). [M+H] 497.1

Example 186

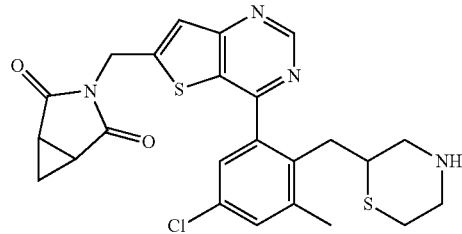 [SMILES: Cc1cc(Cl)cc(-c2ncnc3cc(CN4C(=O)C5CC5C4=O)sc23)c1CC1CNCCS1]

3-((4-(5-chloro-3-methyl-2-(thiomorpholin-2-ylmethyl)phenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. $^1$H NMR (400 MHz, Methanol-d4) δ 9.21 (s, 1H), 7.53 (s, 1H), 7.50 (s, 1H), 7.42 (s, 1H), 4.86 (s, 2H), 3.59-3.36 (m, 3H), 3.22-2.72 (m, 5H), 2.65-2.56 (m, 3H), 2.50 (s, 3H), 1.62 (dd, J=10.2, 5.1 Hz, 1H), 1.45 (d, J=4.2 Hz, 1H). [M+H] 499.0

Example 187

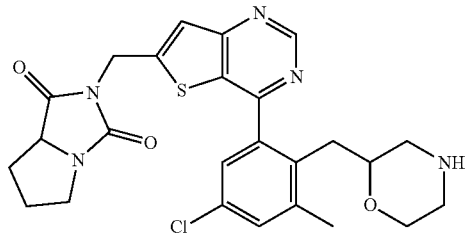 [SMILES: Cc1cc(Cl)cc(-c2ncnc3cc(CN4C(=O)C5CCCN5C4=O)sc23)c1CC1CNCCO1]

2-((4-(5-chloro-3-methyl-2-(morpholin-2-ylmethyl)phenyl)thieno[3,2-d]pyrimidin-6-yl)methyl)tetrahydro-1H-pyrrolo[1,2-c]imidazole-1,3(2H)-dione. The title compound was prepared by General Procedures B, F and G. $^1$H NMR (400 MHz, Methanol-d4) δ 9.18 (s, 1H), 7.55 (s, 1H), 7.46 (d, J=2.2 Hz, 1H), 7.37 (d, J=2.3 Hz, 1H), 5.00 (d, J=3.1 Hz, 2H), 4.28 (dd, J=9.3, 7.4 Hz, 1H), 3.76-3.56 (m, 3H), 3.53-3.38 (m, 1H), 3.28-3.21 (m, 1H), 3.18-2.94 (m, 3H), 2.93-2.80 (m, 2H), 2.69 (t, J=11.8 Hz, 1H), 2.47 (s, 3H), 2.29-2.03 (m, 3H), 1.77-1.61 (m, 1H). [M+H] 512.2

Example 188

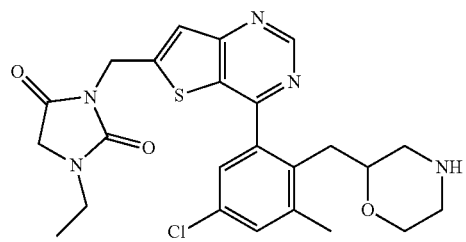 [SMILES: CCN1CC(=O)N(Cc2cc3ncnc(-c4cc(Cl)cc(C)c4CC4CNCCO4)c3s2)C1=O]

3-((4-(5-chloro-3-methyl-2-(morpholin-2-ylmethyl)phenyl)thieno[3,2-d]pyrimidin-6-yl)methyl)-1-ethylimidazolidine-2,4-dione. The title compound was prepared by General Procedures B, F and G. ¹H NMR (400 MHz, Methanol-d4) δ 9.18 (s, 1H), 7.58 (d, J=1.2 Hz, 1H), 7.46 (d, J=2.2 Hz, 1H), 7.37 (d, J=2.3 Hz, 1H), 5.02 (d, J=0.9 Hz, 2H), 4.07 (s, 2H), 3.73-3.61 (m, 2H), 3.50-3.40 (m, 3H), 3.15-2.78 (m, 4H), 2.69 (t, J=11.9 Hz, 1H), 2.47 (s, 3H), 1.18 (t, J=7.3 Hz, 3H). [M+H] 500.1

Example 189

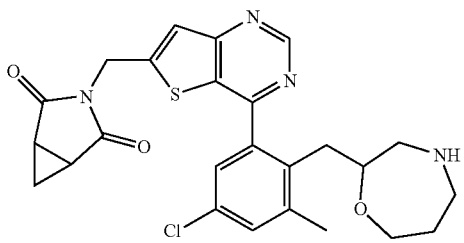 [SMILES: Cc1cc(Cl)cc(-c2ncnc3cc(CN4C(=O)C5CC5C4=O)sc23)c1CC1CNCCCO1]

3-((4-(2-((1,4-oxazepan-2-yl)methyl)-5-chloro-3-methylphenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. ¹H NMR (400 MHz, Methanol-d4) δ 9.17 (s, 1H), 7.51 (s, 1H), 7.48 (s, 1H), 7.40 (s, 1H), 4.86 (s, 2H), 3.78 (t, J=9.0, 8.3 Hz, 1H), 3.51 (dt, J=11.9, 5.5 Hz, 1H), 3.27-3.04 (m, 5H), 2.89 (t, J=12.6, 11.2 Hz, 1H), 2.77 (d, J=14.4 Hz, 1H), 2.59 (ddt, J=8.0, 3.6, 2.0 Hz, 2H), 2.48 (s, 3H), 1.87-1.79 (m, 2H), 1.62 (td, J=7.9, 4.0 Hz, 1H), 1.45 (t, J=3.2 Hz, 1H). [M+H] 497.0

Example 190

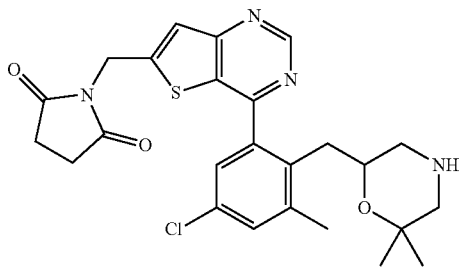 [SMILES: Cc1cc(Cl)cc(-c2ncnc3cc(CN4C(=O)CCC4=O)sc23)c1CC1CNCC(C)(C)O1]

1-((4-(5-chloro-2-((6,6-dimethylmorpholin-2-yl)methyl)-3-methylphenyl)thieno[3,2-d]pyrimidin-6-yl)methyl)pyrrolidine-2,5-dione. The title compound was prepared by General Procedures B, F and G. ¹H NMR (400 MHz, Methanol-d4) δ 9.32 (s, 1H), 7.70 (s, 1H), 7.53 (d, J=2.0 Hz, 1H), 7.47 (d, J=2.2 Hz, 1H), 5.06 (s, 2H), 3.86 (s, 1H), 3.21-2.83 (m, 4H), 2.77 (s, 4H), 2.62 (d, J=12.2 Hz, 2H), 2.49 (s, 3H), 1.06 (s, 3H), 0.72 (s, 3H). [M+H] 499.1

Example 191

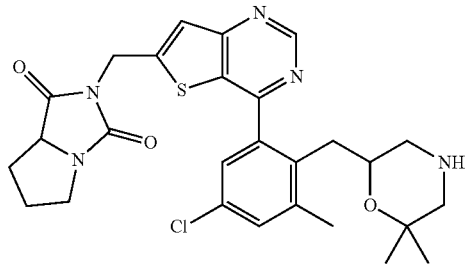 [SMILES: Cc1cc(Cl)cc(-c2ncnc3cc(CN4C(=O)C5CCCN5C4=O)sc23)c1CC1CNCC(C)(C)O1]

2-((4-(5-chloro-2-((6,6-dimethylmorpholin-2-yl)methyl)-3-methylphenyl)thieno[3,2-d]pyrimidin-6-yl)methyl)tetrahydro-1H-pyrrolo[1,2-c]imidazole-1,3(2H)-dione. The title compound was prepared by General Procedures B, F and G. ¹H NMR (400 MHz, Methanol-d4) δ 9.36 (s, 1H), 7.72 (s, 1H), 7.55 (d, J=1.9 Hz, 1H), 7.50 (d, J=2.2 Hz, 1H), 5.06 (t, J=3.1 Hz, 2H), 4.29 (t, J=8.2 Hz, 1H), 3.87 (t, J=9.0 Hz, 1H), 3.71-3.55 (m, 1H), 3.32-3.21 (m, 1H), 3.20-2.85 (m, 4H), 2.78-2.56 (m, 2H), 2.49 (s, 3H), 2.32-2.03 (m, 3H), 1.80-1.64 (m, 1H), 1.05 (s, 3H), 0.70 (s, 3H). [M+H] 540.2

Example 192

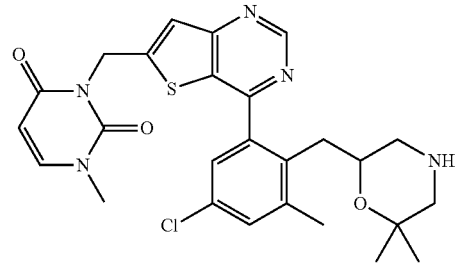 [SMILES: Cc1cc(Cl)cc(-c2ncnc3cc(Cn4c(=O)ccn(C)c4=O)sc23)c1CC1CNCC(C)(C)O1]

3-((4-(5-chloro-2-((6,6-dimethylmorpholin-2-yl)methyl)-3-methylphenyl)thieno[3,2-d]pyrimidin-6-yl)methyl)-1-methylpyrimidine-2,4(1H,3H)-dione. The title compound was prepared by General Procedures B, F and G. ¹H NMR (400 MHz, Methanol-d4) δ 9.25 (s, 1H), 7.69 (d, J=0.9 Hz, 1H), 7.59 (d, J=7.8 Hz, 1H), 7.50 (d, J=2.3 Hz, 1H), 7.44 (d, J=2.3 Hz, 1H), 5.75 (d, J=7.9 Hz, 1H), 5.54-5.38 (m, 2H), 3.81 (dd, J=11.4, 8.8 Hz, 1H), 3.38 (s, 3H), 3.15-3.03 (m, 2H), 2.97 (d, J=12.7 Hz, 1H), 2.87 (dd, J=14.6, 3.0 Hz, 1H), 2.66-2.53 (m, 2H), 2.47 (s, 3H), 0.99 (s, 3H), 0.63 (s, 3H). [M+H] 526.2

Example 193

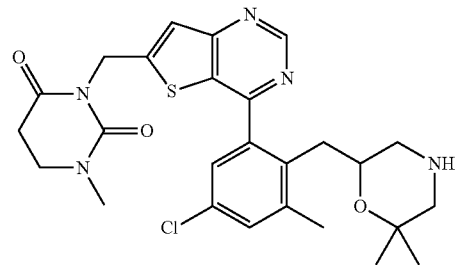 [SMILES: Cc1cc(Cl)cc(-c2ncnc3cc(CN4C(=O)CCN(C)C4=O)sc23)c1CC1CNCC(C)(C)O1]

3-((4-(5-chloro-2-((6,6-dimethylmorpholin-2-yl)methyl)-3-methylphenyl)thieno[3,2-d]pyrimidin-6-yl)methyl)-1-methyldihydropyrimidine-2,4(1H,3H)-dione. The title compound was prepared by General Procedures B, F and G. $^1$H NMR (400 MHz, Methanol-d4) δ 9.36 (s, 1H), 7.72 (s, 1H), 7.56 (d, J=2.0 Hz, 1H), 7.50 (d, J=2.2 Hz, 1H), 5.31 (d, J=2.3 Hz, 2H), 3.86 (t, J=9.7 Hz, 1H), 3.46 (t, J=6.9 Hz, 2H), 3.23-2.87 (m, 7H), 2.79 (t, J=6.5 Hz, 2H), 2.68-2.56 (m, 2H), 2.49 (s, 3H), 1.06 (s, 3H), 0.70 (s, 3H). [M+H] 528.2

Example 194

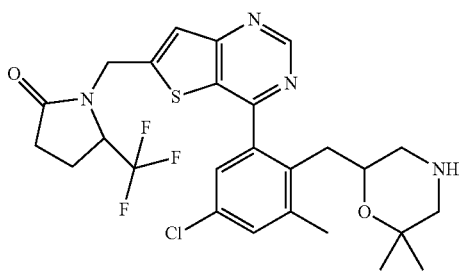 [SMILES: Cc1cc(Cl)cc(-c2ncnc3cc(CN4C(=O)CCC4C(F)(F)F)sc23)c1CC1CNCC(C)(C)O1]

1-((4-(5-chloro-2-((6,6-dimethylmorpholin-2-yl)methyl)-3-methylphenyl)thieno[3,2-d]pyrimidin-6-yl)methyl)-5-(trifluoromethyl)pyrrolidin-2-one. The title compound was prepared by General Procedures B, F and G. $^1$H NMR (400 MHz, Methanol-d4) δ 9.25 (s, 1H), 7.60 (d, J=2.2 Hz, 1H), 7.50 (d, J=2.2 Hz, 1H), 7.46 (t, J=2.2 Hz, 1H), 5.11 (d, J=16.5 Hz, 1H), 4.88 (d, J=16.5 Hz, 1H), 4.50-4.33 (m, 1H), 3.87 (t, J=9.9 Hz, 1H), 3.11 (dd, J=13.8, 8.7 Hz, 2H), 3.01 (d, J=12.5 Hz, 1H), 2.95-2.82 (m, 1H), 2.72-2.53 (m, 3H), 2.48 (s, 3H), 2.47-2.14 (m, 3H), 1.06 (s, 3H), 0.81 (d, J=6.6 Hz, 3H). [M+H] 553.2

Example 195

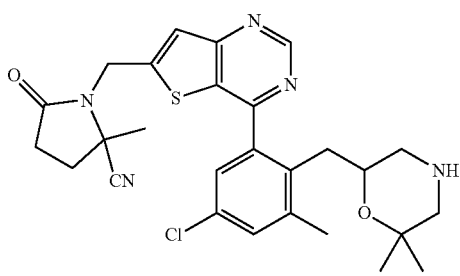 [SMILES: Cc1cc(Cl)cc(-c2ncnc3cc(CN4C(=O)CCC4(C)C#N)sc23)c1CC1CNCC(C)(C)O1]

1-((4-(5-chloro-2-((6,6-dimethylmorpholin-2-yl)methyl)-3-methylphenyl)thieno[3,2-d]pyrimidin-6-yl)methyl)-2-methyl-5-oxopyrrolidine-2-carbonitrile. The title compound was prepared by General Procedures B, F and G. $^1$H NMR (400 MHz, Methanol-d4) δ 9.19 (s, 1H), 7.68 (q, J=1.1 Hz, 1H), 7.46 (s, 1H), 7.40 (t, J=2.5 Hz, 1H), 5.10-4.92 (m, 2H), 3.89-3.80 (m, 1H), 3.16-2.78 (m, 4H), 2.72-2.51 (m, 5H), 2.47 (s, 3H), 2.30-2.18 (m, 1H), 1.76 (s, 3H), 1.07 (s, 3H), 0.87 (d, J=3.0 Hz, 3H). [M+H] 524.2

Example 196

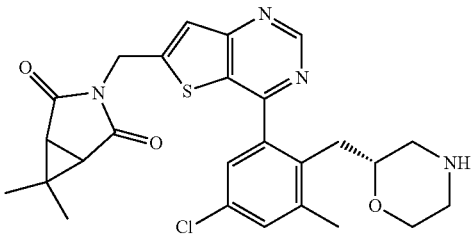 [SMILES: Cc1cc(Cl)cc(-c2ncnc3cc(CN4C(=O)C5C(C4=O)C5(C)C)sc23)c1C[C@@H]1CNCCO1]

3-((4-(5-chloro-3-methyl-2-(((R)-morpholin-2-yl)methyl)phenyl)thieno[3,2-d]pyrimidin-6-yl)methyl)-6,6-dimethyl-3-azabicyclo[3.1.0]hexane-2,4-dione. The title compound was prepared by General Procedures A, F and G. $^1$H NMR (400 MHz, Methanol-d4) δ 9.30 (s, 1H), 7.67 (s, 1H), 7.53 (d, J=2.3 Hz, 1H), 7.41 (d, J=2.3 Hz, 1H), 4.98-4.93 (m, 2H), 3.77-3.68 (m, 1H), 3.64 (dd, J=13.1, 3.7 Hz, 1H), 3.47 (td, J=12.6, 2.3 Hz, 1H), 3.21-3.15 (m, 1H), 3.08 (d, J=12.8 Hz, 1H), 2.96-2.81 (m, 3H), 2.70 (t, J=11.8 Hz, 1H), 2.53 (s, 2H), 2.49 (s, 3H), 1.25 (s, 3H), 1.15 (s, 3H). [M+H] 511.0

Example 197

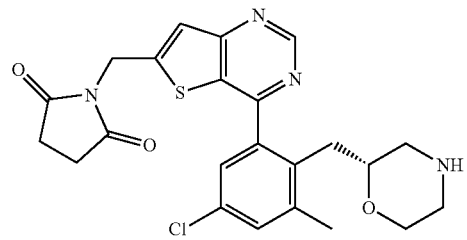 [SMILES: Cc1cc(Cl)cc(-c2ncnc3cc(CN4C(=O)CCC4=O)sc23)c1C[C@@H]1CNCCO1]

(R)-1-((4-(5-chloro-3-methyl-2-(morpholin-2-ylmethyl)phenyl)thieno[3,2-d]pyrimidin-6-yl)methyl)pyrrolidine-2,5-dione. The title compound was prepared by General Procedures A, F and G. $^1$H NMR (400 MHz, Methanol-d4) δ 9.26 (s, 1H), 7.66 (s, 1H), 7.52 (s, 1H), 7.41 (s, 1H), 5.05 (s, 2H), 3.76-3.61 (m, 2H), 3.46 (t, J=12.4 Hz, 1H), 3.17 (d, J=12.7 Hz, 1H), 3.08 (d, J=12.9 Hz, 1H), 2.99-2.82 (m, 3H), 2.78 (s, 4H), 2.71 (t, J=11.8 Hz, 1H), 2.49 (s, 3H). [M+H]471.0

Example 198

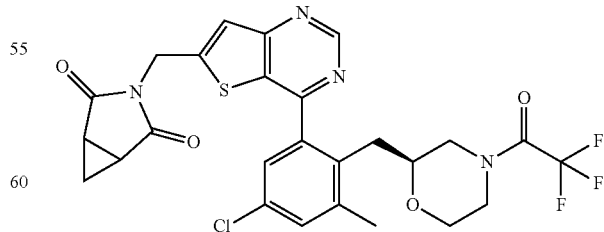

3-((4-(5-chloro-3-methyl-2-(((S)-4-(2,2,2-trifluoroacetyl)morpholin-2-yl)methyl)phenyl)thieno[3,2-d]pyrimidin-6-yl)methyl)-3-azabicyclo[3.1.0]hexane-2,4-dione. The title compound was prepared by General Procedures A, F and G.

¹H NMR (400 MHz, Methanol-d4) δ 9.15 (d, J=7.6 Hz, 1H), 7.51 (d, J=4.6 Hz, 1H), 7.43 (s, 1H), 7.34 (s, 1H), 4.85 (s, 3H), 4.10-4.04 (m, 1H), 3.64-2.75 (m, 8H), 2.56-2.42 (m, 2H), 2.41 (s, 3H), 1.63-1.57 (m, 1H), 1.46-1.36 (m, 1H). [M+H] 579.0

Example 199

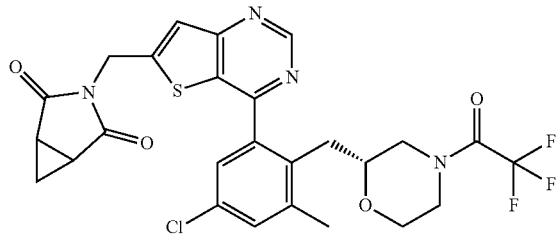 [SMILES: Cc1cc(Cl)cc(-c2ncnc3cc(CN4C(=O)C5CC5C4=O)sc23)c1C[C@@H]1CN(C(=O)C(F)(F)F)CCO1]

3-((4-(5-chloro-3-methyl-2-(((R)-4-(2,2,2-trifluoro-acetyl)morpholin-2-yl)methyl)phenyl)thieno[3,2-d]pyrimidin-6-yl)methyl)-3-azabicyclo[3.1.0]hexane-2,4-dione. The title compound was prepared by General Procedures A, F and G. ¹H NMR (400 MHz, Methanol-d4) δ 9.15 (d, J=7.6 Hz, 1H), 7.51 (d, J=4.6 Hz, 1H), 7.43 (s, 1H), 7.34 (s, 1H), 4.85 (s, 3H), 4.10-4.04 (m, 1H), 3.64-2.75 (m, 8H), 2.56-2.42 (m, 2H), 2.41 (s, 3H), 1.63-1.57 (m, 1H), 1.46-1.36 (m, 1H). [M+H] 579.0

Example 200

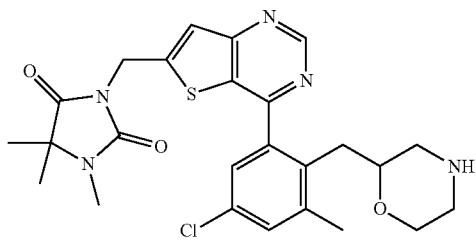 [SMILES: Cc1cc(Cl)cc(-c2ncnc3cc(CN4C(=O)N(C)C(C)(C)C4=O)sc23)c1CC1CNCCO1]

3-((4-(5-chloro-3-methyl-2-(morpholin-2-ylmethyl)phenyl)thieno[3,2-d]pyrimidin-6-yl)methyl)-1,5,5-trimethyl-imidazolidine-2,4-dione. The title compound was prepared by General Procedures B, F and G. ¹H NMR (400 MHz, Methanol-d4) δ 9.29 (s, 1H), 7.65 (s, 1H), 7.52 (d, J=2.1 Hz, 1H), 7.43 (d, J=2.2 Hz, 1H), 5.08 (s, 2H), 3.72 (s, 1H), 3.63 (d, J=12.9 Hz, 1H), 3.52-3.41 (m, 1H), 3.18 (d, J=12.8 Hz, 1H), 3.07 (d, J=12.5 Hz, 1H), 3.00-2.80 (m, 6H), 2.71 (t, J=11.3 Hz, 1H), 2.48 (s, 3H), 1.40 (s, 6H). [M+H] 514.2

Example 201

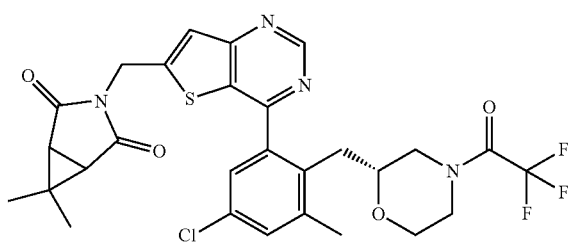 [SMILES: Cc1cc(Cl)cc(-c2ncnc3cc(CN4C(=O)C5C(C4=O)C5(C)C)sc23)c1C[C@@H]1CN(C(=O)C(F)(F)F)CCO1]

3-((4-(5-chloro-3-methyl-2-(((R)-4-(2,2,2-trifluoro-acetyl)morpholin-2-yl)methyl)phenyl)thieno[3,2-d]pyrimidin-6-yl)methyl)-6,6-dimethyl-3-azabicyclo[3.1.0]hexane-2,4-dione. The title compound was prepared by General Procedures A, F and G. ¹H NMR (400 MHz, Methanol-d4) δ 9.17 (d, J=7.6 Hz, 1H), 7.55 (d, J=4.8 Hz, 1H), 7.44 (s, 1H), 7.32 (s, 1H), 4.90 (s, 3H), 4.07 (t, J=12.4 Hz, 1H), 3.65-3.38 (m, 3H), 3.24-2.72 (m, 5H), 2.47 (s, 2H), 2.46 (s, 3H), 1.23 (s, 3H), 1.10 (s, 3H). [M+H] 607.0

Example 202

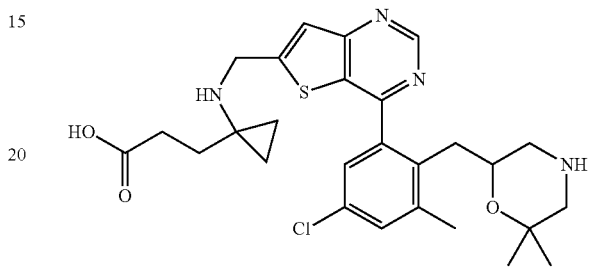

3-(1-(((4-(5-chloro-2-((6,6-dimethylmorpholin-2-yl)methyl)-3-methylphenyl)thieno[3,2-d]pyrimidin-6-yl)methyl)amino)cyclopropyl)propanoic acid. Isolated along with 4-((4-(5-chloro-2-((6,6-dimethylmorpholin-2-yl)methyl)-3-methylphenyl)thieno[3,2-d]pyrimidin-6-yl)methyl)-4-azaspiro[2.4]heptan-5-one. [M+H]529.2

Example 203

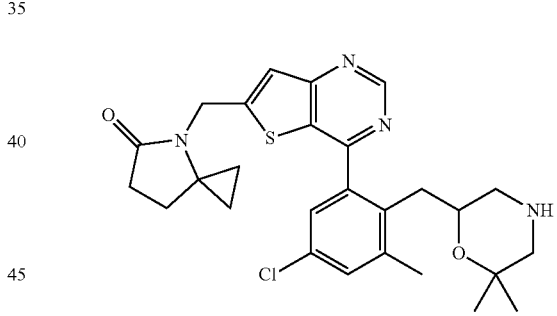

4-((4-(5-chloro-2-((6,6-dimethylmorpholin-2-yl)methyl)-3-methylphenyl)thieno[3,2-d]pyrimidin-6-yl)methyl)-4-azaspiro[2.4]heptan-5-one. The title compound was prepared by General Procedures B, F and G. [M+H] 511.1

Example 204

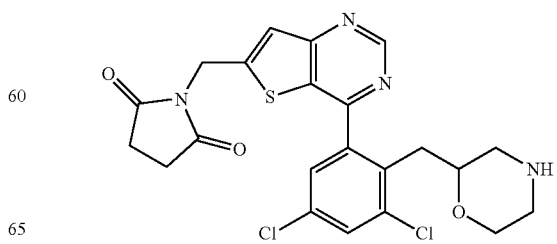

1-((4-(3,5-dichloro-2-(morpholin-2-ylmethyl)phenyl)thieno[3,2-d]pyrimidin-6-yl)methyl)pyrrolidine-2,5-dione. The title compound was prepared by General Procedures B, F and G. ¹H NMR (400 MHz, Methanol-d4) δ 9.18 (s, 1H), 7.77 (s, 1H), 7.56 (s, 2H), 5.02 (s, 2H), 3.78 (m, 1H), 3.46 (m, 2H), 3.10 (m, 2H), 2.78 (s, 4H), 1.87 (s, 1H), 1.31 (s, 4H). [M+H] 491.0

Example 205

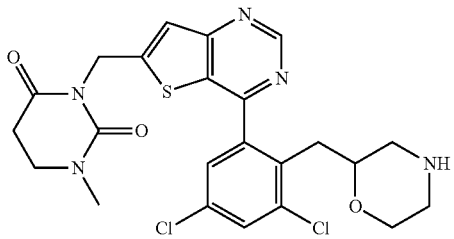 [SMILES: CN1CCC(=O)N(Cc2cc3ncnc(-c4cc(Cl)cc(Cl)c4CC4CNCCO4)c3s2)C1=O]

3-((4-(3,5-dichloro-2-(morpholin-2-ylmethyl)phenyl)thieno[3,2-d]pyrimidin-6-yl)methyl)-1-methyldihydropyrimidine-2,4(1H,3H)-dione. The title compound was prepared by General Procedures B, F and G. ¹H NMR (400 MHz, Methanol-d4) δ 9.18 (s, 1H), 7.77 (s, 1H), 7.56 (s, 2H), 5.25 (s, 2H), 3.78 (m, 1H), 3.44 (m, 2H), 3.08 (m, 2H), 3.02 (s, 3H), 2.78 (m, 4H), 1.90 (s, 1H), 1.32 (s, 4H). [M+H] 520.0

Example 206

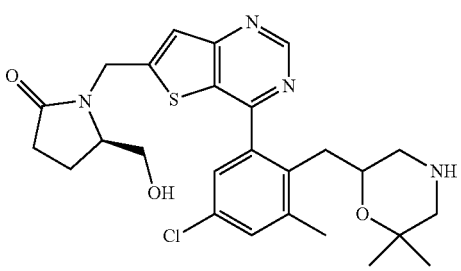 [SMILES: Cc1cc(Cl)cc(-c2ncnc3cc(CN4C(=O)CC[C@@H]4CO)sc23)c1CC1CNCC(C)(C)O1]

(5R)-1-((4-(5-chloro-2-((6,6-dimethylmorpholin-2-yl)methyl)-3-methylphenyl)thieno[3,2-d]pyrimidin-6-yl)methyl)-5-(hydroxymethyl)pyrrolidin-2-one. The title compound was prepared by General Procedures B, F and G (using LiHMDS in place of cesium carbonate). ¹H NMR (400 MHz, Methanol-d4) δ 9.17 (s, 1H), 7.58 (s, 1H), 7.47 (s, 1H), 7.42 (s, 1H), 5.10 (d, J=16.1 Hz, 1H), 4.76 (d, J=16.1 Hz, 1H), 3.94-3.68 (m, 3H), 3.68-3.54 (m, 1H), 3.21-2.54 (m, 5H), 2.47 (s, 3H), 2.43-2.25 (m, 1H), 2.25-2.03 (m, 1H), 2.03-1.83 (m, 1H), 1.05 (s, 3H), 0.82 (d, J=11.6 Hz, 3H). [M+H] 515.2

Example 207

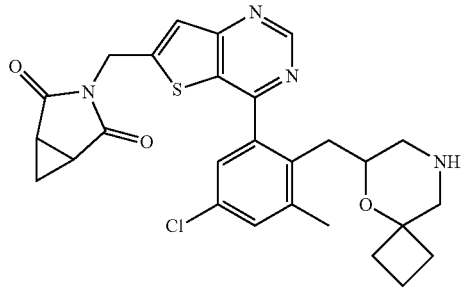

3-((4-(2-((5-oxa-8-azaspiro[3.5]nonan-6-yl)methyl)-5-chloro-3-methylphenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. ¹H NMR (400 MHz, Methanol-d4) δ 9.17 (s, 1H), 7.53 (s, 1H), 7.49 (d, J=2.3 Hz, 1H), 7.44 (d, J=2.3 Hz, 1H), 4.85 (s, 2H), 3.61 (tt, J=9.9, 3.0 Hz, 1H), 3.33-3.28 (m, 1H), 3.16 (dd, J=14.6, 8.9 Hz, 1H), 3.04 (d, J=12.4 Hz, 1H), 2.92 (dd, J=14.6, 3.4 Hz, 1H), 2.66 (d, J=12.2 Hz, 2H), 2.58 (dd, J=8.1, 3.6 Hz, 2H), 2.47 (s, 3H), 2.04-1.97 (m, 1H), 1.72-1.45 (m, 7H). [M+H] 523.0

Example 208

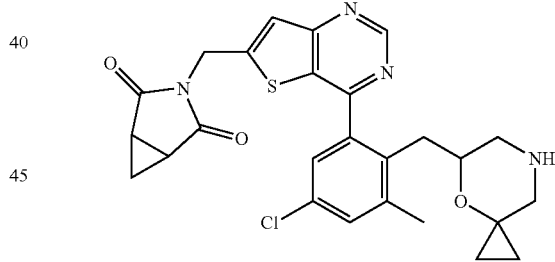

3-((4-(2-((4-oxa-7-azaspiro[2.5]octan-5-yl)methyl)-5-chloro-3-methylphenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. ¹H NMR (400 MHz, Methanol-d4) δ 9.17 (s, 1H), 7.53 (s, 1H), 7.46 (d, J=2.3 Hz, 1H), 7.40 (d, J=2.3 Hz, 1H), 4.86 (d, J=2.5 Hz, 2H), 3.75 (td, J=10.0, 8.6, 3.0 Hz, 1H), 3.32-3.29 (m, 1H), 3.21 (d, J=13.1 Hz, 1H), 3.14 (dd, J=14.7, 8.8 Hz, 1H), 2.91 (dd, J=14.8, 3.4 Hz, 1H), 2.79 (t, J=12.3, 11.6 Hz, 1H), 2.62 (d, J=13.1 Hz, 1H), 2.59 (dd, J=8.1, 3.6 Hz, 2H), 2.44 (s, 3H), 1.62 (td, J=8.1, 4.6 Hz, 1H), 1.49 (dt, J=4.6, 3.6 Hz, 1H), 0.51 (t, J=2.4 Hz, 2H), 0.34 (dd, J=30.9, 11.1 Hz, 2H). [M+H] 509.0

Example 209

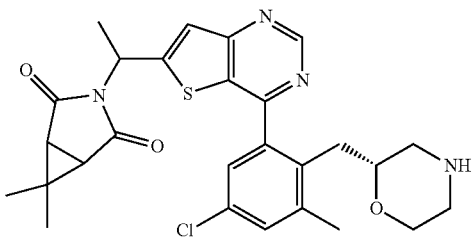 [SMILES: Cc1cc(Cl)cc(-c2ncnc3cc(C(C)N4C(=O)C5C(C4=O)C5(C)C)sc23)c1C[C@@H]1CNCCO1]

3-(1-(4-(5-chloro-3-methyl-2-(((R)-morpholin-2-yl)methyl)phenyl)thieno[3,2-d]pyrimidin-6-yl)ethyl)-6,6-dimethyl-3-azabicyclo[3.1.0]hexane-2,4-dione. The title compound was prepared by General Procedures A and F using 3-(1-(4-chlorothieno[3,2-d]pyrimidin-6-yl)ethyl)-6,6-dimethyl-3-azabicyclo[3.1.0]hexane-2,4-dione. $^1$H NMR (400 MHz, Methanol-d4) δ 9.17 (s, 1H), 7.55 (dd, J=3.8, 1.2 Hz, 1H), 7.46 (d, J=2.3 Hz, 1H), 7.35 (s, 1H), 5.65 (dtd, J=7.4, 6.3, 3.3 Hz, 1H), 3.73-3.60 (m, 2H), 3.43 (td, J=12.7, 2.0 Hz, 1H), 3.17-2.95 (m, 3H), 2.85 (dddd, J=18.0, 14.2, 10.8, 3.7 Hz, 2H), 2.68 (t, J=11.9 Hz, 1H), 2.50 (dd, J=5.2, 1.8 Hz, 1H), 2.47 (s, 3H), 2.43 (t, J=5.6 Hz, 1H), 1.84 (d, J=7.2 Hz, 3H), 1.25-1.21 (m, 6H). [M+H]525.0

Example 210

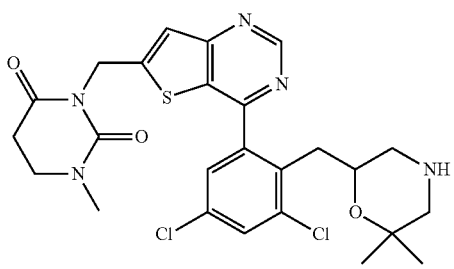

3-((4-(3,5-dichloro-2-((6,6-dimethylmorpholin-2-yl)methyl)phenyl)thieno[3,2-d]pyrimidin-6-yl)methyl)-1-methyldihydropyrimidine-2,4(1H,3H)-dione. The title compound was prepared by General Procedures B, F and G. $^1$H NMR (400 MHz, Chloroform-d) δ 9.24 (s, 1H), 8.08 (s, 1H), 7.57 (s, 2H), 5.30 (s, 2H), 5.26 (s, 2H), 4.10 (m, 1H), 3.04 (s, 3H), 2.78 (m, 2H), 1.80 (s, 6H), 1.34 (s, 4H), 0.70 (m, 2H). [M+H] 548.0

Example 211

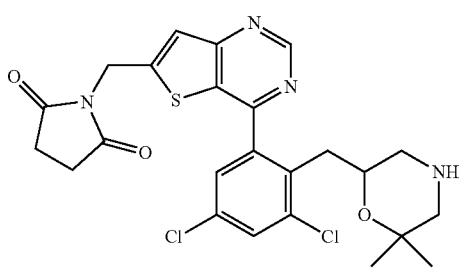 [SMILES: CC1(C)CNCC(Cc2c(Cl)cc(Cl)cc2-c2ncnc3cc(CN4C(=O)CCC4=O)sc23)O1]

1-((4-(3,5-dichloro-2-((6,6-dimethylmorpholin-2-yl)methyl)phenyl)thieno[3,2-d]pyrimidin-6-yl)methyl)pyrrolidine-2,5-dione. The title compound was prepared by General Procedures B, F and G. $^1$H NMR (400 MHz, Chloroform-d) δ 9.29 (s, 1H), 7.57 (s, 2H), 7.42 (s, 1H), 5.30 (s, 2H), 4.99 (s, 2H), 3.20 (m, 1H), 3.02 (m, 1H), 2.80 (m, 2H), 1.63 (s, 6H), 1.33 (s, 4H), 0.71 (m, 2H). [M+H] 519.0

Example 212

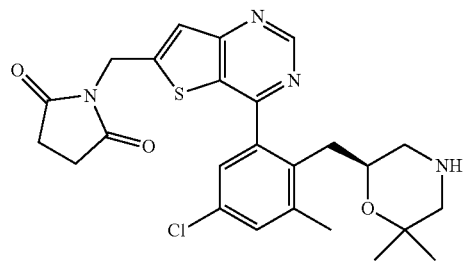 [SMILES: Cc1cc(Cl)cc(-c2ncnc3cc(CN4C(=O)CCC4=O)sc23)c1C[C@H]1CNCC(C)(C)O1]

(S)-1-((4-(5-chloro-2-((6,6-dimethylmorpholin-2-yl)methyl)-3-methylphenyl)thieno[3,2-d]pyrimidin-6-yl)methyl)pyrrolidine-2,5-dione. The title compound was prepared by General Procedures A, F and G. $^1$H NMR (400 MHz, Methanol-d4) δ 9.34 (s, 1H), 7.72 (s, 1H), 7.54 (s, 1H), 7.48 (s, 1H), 5.07 (s, 2H), 3.86 (t, J=7.9 Hz, 1H), 3.21-2.85 (m, 4H), 2.77 (s, 4H), 2.62 (d, J=11.8 Hz, 2H), 2.48 (s, 3H), 1.06 (s, 3H), 0.72 (s, 3H). [M+H] 499.1

Example 213

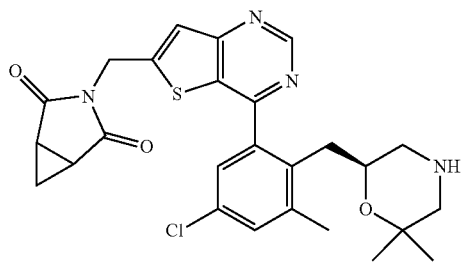 [SMILES: Cc1cc(Cl)cc(-c2ncnc3cc(CN4C(=O)C5CC5C4=O)sc23)c1C[C@H]1CNCC(C)(C)O1]

3-((4-(5-chloro-2-(((S)-6,6-dimethylmorpholin-2-yl)methyl)-3-methylphenyl)thieno[3,2-d]pyrimidin-6-yl)methyl)-3-azabicyclo[3.1.0]hexane-2,4-dione. The title compound was prepared by General Procedures A, F and G. $^1$H NMR (400 MHz, Methanol-d4) δ 9.30 (s, 1H), 7.64 (s, 1H), 7.53 (d, J=2.2 Hz, 1H), 7.48 (d, J=2.2 Hz, 1H), 4.88 (s, 2H), 3.85 (t, J=9.7 Hz, 1H), 3.22-3.04 (m, 2H), 3.00 (d, J=12.6 Hz, 1H), 2.95-2.87 (m, 1H), 2.70-2.53 (m, 4H), 2.48 (s, 3H), 1.70-1.56 (m, 1H), 1.50 (q, J=3.8 Hz, 1H), 1.05 (s, 3H), 0.70 (s, 3H). [M+H]511.2

Example 214

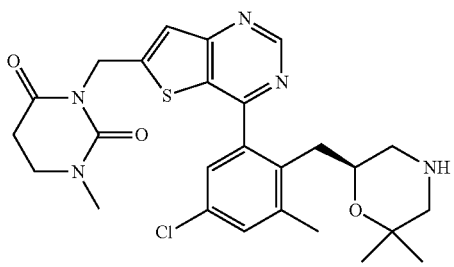 [SMILES: Cc1cc(Cl)cc(-c2ncnc3cc(CN4C(=O)CCN(C)C4=O)sc23)c1C[C@H]1CNCC(C)(C)O1]

(S)-3-((4-(5-chloro-2-((6,6-dimethylmorpholin-2-yl)methyl)-3-methylphenyl)thieno[3,2-d]pyrimidin-6-yl)methyl)-1-methyldihydropyrimidine-2,4(1H,3H)-dione. The title compound was prepared by General Procedures A, F and G. $^1$H NMR (400 MHz, Methanol-d4) δ 9.32 (s, 1H), 7.69 (s, 1H), 7.54 (d, J=2.1 Hz, 1H), 7.48 (d, J=2.2 Hz, 1H), 5.30 (d, J=2.3 Hz, 2H), 3.85 (t, J=9.6 Hz, 1H), 3.45 (t, J=6.7 Hz, 2H), 3.20-2.86 (m, 7H), 2.78 (t, J=6.6 Hz, 2H), 2.62 (d, J=11.6 Hz, 2H), 2.48 (s, 3H), 1.05 (s, 3H), 0.70 (s, 3H). [M+H] 528.2

Example 215

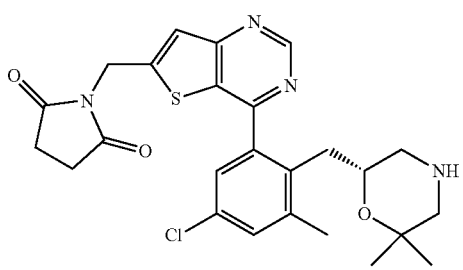 [SMILES: Cc1cc(Cl)cc(-c2ncnc3cc(CN4C(=O)CCC4=O)sc23)c1C[C@@H]1CNCC(C)(C)O1]

(R)-1-((4-(5-chloro-2-((6,6-dimethylmorpholin-2-yl)methyl)-3-methylphenyl)thieno[3,2-d]pyrimidin-6-yl)methyl)pyrrolidine-2,5-dione. The title compound was prepared by General Procedures A, F and G. $^1$H NMR (400 MHz, Methanol-d4) δ 9.34 (s, 1H), 7.72 (s, 1H), 7.54 (s, 1H), 7.48 (s, 1H), 5.07 (s, 2H), 3.86 (t, J=7.9 Hz, 1H), 3.21-2.85 (m, 4H), 2.77 (s, 4H), 2.62 (d, J=11.8 Hz, 2H), 2.48 (s, 3H), 1.06 (s, 3H), 0.72 (s, 3H). [M+H] 499.1

Example 216

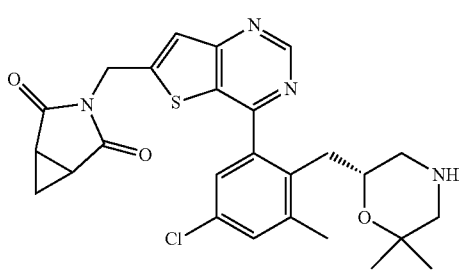

3-((4-(5-chloro-2-(((R)-6,6-dimethylmorpholin-2-yl)methyl)-3-methylphenyl)thieno[3,2-d]pyrimidin-6-yl)methyl)-3-azabicyclo[3.1.0]hexane-2,4-dione. The title compound was prepared by General Procedures A, F and G. $^1$H NMR (400 MHz, Methanol-d4) δ 9.30 (s, 1H), 7.64 (s, 1H), 7.53 (d, J=2.2 Hz, 1H), 7.48 (d, J=2.2 Hz, 1H), 4.88 (s, 2H), 3.85 (t, J=9.7 Hz, 1H), 3.22-3.04 (m, 2H), 3.00 (d, J=12.6 Hz, 1H), 2.95-2.87 (m, 1H), 2.70-2.53 (m, 4H), 2.48 (s, 3H), 1.70-1.56 (m, 1H), 1.50 (q, J=3.8 Hz, 1H), 1.05 (s, 3H), 0.70 (s, 3H). [M+H]511.2

Example 217

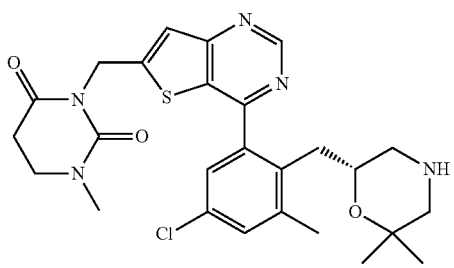 [SMILES: Cc1cc(Cl)cc(-c2ncnc3cc(CN4C(=O)CCN(C)C4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)-1-methyldihydropyrimidine-2,4(1H,3H)-dione. The title compound was prepared by General Procedures A, F and G. $^1$H NMR (400 MHz, Methanol-d4) δ 9.32 (s, 1H), 7.69 (s, 1H), 7.54 (d, J=2.1 Hz, 1H), 7.48 (d, J=2.2 Hz, 1H), 5.30 (d, J=2.3 Hz, 2H), 3.85 (t, J=9.6 Hz, 1H), 3.45 (t, J=6.7 Hz, 2H), 3.20-2.86 (m, 7H), 2.78 (t, J=6.6 Hz, 2H), 2.62 (d, J=11.6 Hz, 2H), 2.48 (s, 3H), 1.05 (s, 3H), 0.70 (s, 3H). [M+H] 528.2

Example 218

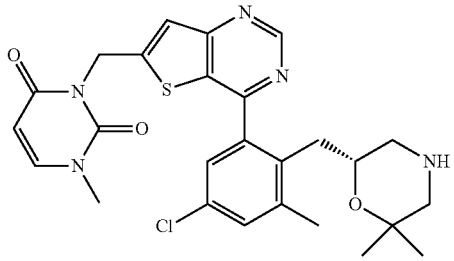

(R)-3-((4-(5-chloro-2-((6,6-dimethylmorpholin-2-yl)methyl)-3-methylphenyl)thieno[3,2-d]pyrimidin-6-yl)methyl)-1-methylpyrimidine-2,4(1H,3H)-dione. The title compound was prepared by General Procedures A, F and G. $^1$H NMR (400 MHz, Methanol-d4) δ 9.25 (s, 1H), 7.69 (d, J=0.9 Hz, 1H), 7.59 (d, J=7.8 Hz, 1H), 7.50 (d, J=2.3 Hz, 1H), 7.44 (d, J=2.3 Hz, 1H), 5.75 (d, J=7.9 Hz, 1H), 5.54-5.38 (m, 2H), 3.81 (dd, J=11.4, 8.8 Hz, 1H), 3.38 (s, 3H), 3.15-3.03 (m, 2H), 2.97 (d, J=12.7 Hz, 1H), 2.87 (dd, J=14.6, 3.0 Hz, 1H), 2.66-2.53 (m, 2H), 2.47 (s, 3H), 0.99 (s, 3H), 0.63 (s, 3H). [M+H] 526.2

Example 219

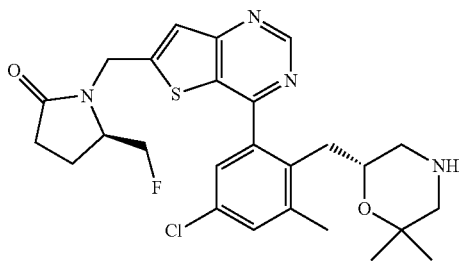 [SMILES: Cc1cc(Cl)cc(-c2ncnc3cc(CN4C(=O)CC[C@@H]4CF)sc23)c1C[C@@H]1CNCC(C)(C)O1]

(R)-1-((4-(5-chloro-2-(((R)-6,6-dimethylmorpholin-2-yl)methyl)-3-methylphenyl)thieno[3,2-d]pyrimidin-6-yl)methyl)-5-(fluoromethyl)pyrrolidin-2-one. The title compound was prepared by General Procedures A, F and G (using LiHMDS in place of cesium carbonate). $^1$H NMR (400 MHz, Methanol-d4) δ 9.23 (s, 1H), 7.61 (s, 1H), 7.49 (d, J=2.2 Hz, 1H), 7.45 (d, J=2.3 Hz, 1H), 5.05 (d, J=16.3 Hz, 1H), 4.82 (d, J=15.5 Hz, 1H), 4.67 (dd, J=48.3, 10.8 Hz, 1H), 4.48 (ddd, J=47.0, 10.4, 4.7 Hz, 1H), 4.02 (d, J=23.6 Hz, 1H), 3.93-3.76 (m, 1H), 3.17-3.04 (m, 2H), 3.04-2.95 (m, 1H), 2.95-2.81 (m, 1H), 2.72-2.56 (m, 2H), 2.45-2.16 (m, 2H), 2.01-1.85 (m, 1H), 1.06 (s, 3H), 0.81 (s, 3H). [M+H] 517.2

Example 220

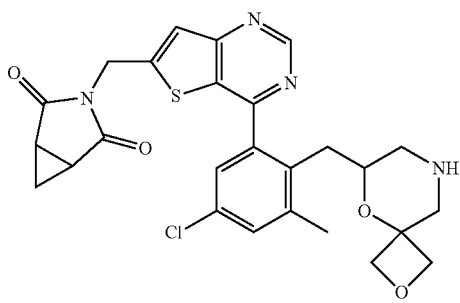 [SMILES: Cc1cc(Cl)cc(-c2ncnc3cc(CN4C(=O)C5CC5C4=O)sc23)c1CC1CNCC2(COC2)O1]

3-((4-(2-((2,5-dioxa-8-azaspiro[3.5]nonan-6-yl)methyl)-5-chloro-3-methylphenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. $^1$H NMR (400 MHz, Methanol-d4) δ 9.17 (s, 1H), 7.55 (s, 1H), 7.51 (d, J=2.3 Hz, 1H), 7.47 (d, J=2.3 Hz, 1H), 4.85 (d, J=5.8 Hz, 2H), 4.41 (d, J=7.0 Hz, 1H), 4.15 (d, J=7.0 Hz, 1H), 4.09 (d, J=7.4 Hz, 1H), 3.69-3.59 (m, 2H), 3.50 (d, J=7.5 Hz, 1H), 3.25 (dd, J=14.7, 8.9 Hz, 1H), 3.17 (d, J=12.4 Hz, 1H), 2.93 (dd, J=14.7, 2.9 Hz, 1H), 2.86 (dd, J=13.0, 1.5 Hz, 1H), 2.73 (dd, J=12.8, 11.2 Hz, 1H), 2.53 (dd, J=8.1, 3.6 Hz, 2H), 2.47 (s, 3H), 1.59 (td, J=8.1, 4.6 Hz, 1H), 1.49 (dt, J=4.5, 3.6 Hz, 1H). [M+H] 525.1

Example 221

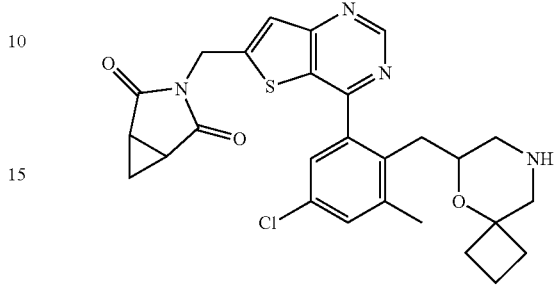

3-((4-(2-((5-oxa-8-azaspiro[3.5]nonan-6-yl)methyl)-5-chloro-3-methylphenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. $^1$H NMR (400 MHz, Methanol-d4) δ 9.17 (s, 1H), 7.58 (s, 1H), 7.48 (d, J=2.3 Hz, 1H), 7.43 (d, J=2.3 Hz, 1H), 5.01 (s, 2H), 3.63 (tt, J=9.8, 9.4, 2.6 Hz, 1H), 3.33-3.28 (m, 1H), 3.14 (dd, J=14.6, 8.7 Hz, 1H), 3.04 (d, J=12.8 Hz, 1H), 2.90 (dd, J=14.6, 3.5 Hz, 1H), 2.76 (s, 4H), 2.64 (t, J=12.2 Hz, 2H), 2.47 (s, 3H), 2.02 (dd, J=12.6, 4.9 Hz, 1H), 1.72-1.45 (m, 5H). [M+H] 511.1

Example 222

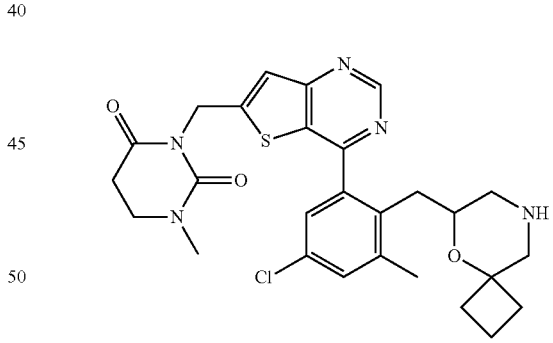

3-((4-(2-((5-oxa-8-azaspiro[3.5]nonan-6-yl)methyl)-5-chloro-3-methylphenyl)thieno[3,2-d]pyrimidin-6-yl)methyl)-1-methyldihydropyrimidine-2,4(1H,3H)-dione. The title compound was prepared by General Procedures B, F and G. $^1$H NMR (400 MHz, Methanol-d4) δ 9.16 (s, 1H), 7.55 (s, 1H), 7.48 (d, J=2.3 Hz, 1H), 7.43 (d, J=2.3 Hz, 1H), 5.25 (s, 2H), 3.60 (tt, J=10.2, 2.1 Hz, 1H), 3.44 (t, J=6.8 Hz, 2H), 3.33-3.28 (m, 1H), 3.14 (dd, J=14.5, 8.8 Hz, 1H), 3.06-3.00 (m, 1H), 3.02 (s, 3H), 2.91 (dd, J=14.6, 3.4 Hz, 1H), 2.77 (t, J=6.9 Hz, 2H), 2.64 (t, J=12.6 Hz, 2H), 2.47 (s, 3H), 2.04-1.96 (m, 1H), 1.72-1.48 (m, 5H). [M+H] 540.2

Example 223

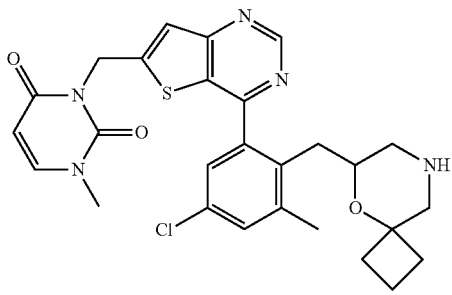 [SMILES: Cc1cc(Cl)cc(-c2ncnc3cc(Cn4c(=O)ccn(C)c4=O)sc23)c1CC1CNCC2(CCC2)O1]

3-((4-(2-((5-oxa-8-azaspiro[3.5]nonan-6-yl)methyl)-5-chloro-3-methylphenyl)thieno[3,2-d]pyrimidin-6-yl)methyl)-1-methylpyrimidine-2,4(1H,3H)-dione. The title compound was prepared by General Procedures B, F and G. $^1$H NMR (400 MHz, Methanol-d4) δ 9.16 (s, 1H), 7.63 (s, 1H), 7.57 (d, J=7.9 Hz, 1H), 7.47 (d, J=2.3 Hz, 1H), 7.43 (d, J=2.2 Hz, 1H), 5.74 (d, J=7.9 Hz, 1H), 5.43 (s, 2H), 3.58 (tt, J=10.0, 8.5, 2.9 Hz, 1H), 3.37 (s, 3H), 3.27 (d, J=12.7 Hz, 1H), 3.16 (dd, J=14.6, 8.9 Hz, 1H), 3.03 (d, J=12.8 Hz, 1H), 2.91 (dd, J=14.6, 3.3 Hz, 1H), 2.61 (dt, J=12.2, 5.5 Hz, 2H), 2.46 (s, 3H), 2.01-1.94 (m, 1H), 1.63-1.36 (m, 5H). [M+H] 538.2

Example 224

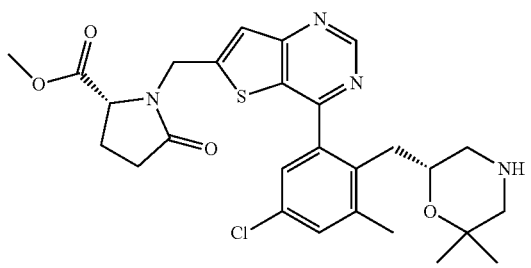 [SMILES: COC(=O)[C@H]1CCC(=O)N1Cc1cc2ncnc(-c3cc(Cl)cc(C)c3C[C@@H]3CNCC(C)(C)O3)c2s1]

methyl (R)-1-((4-(5-chloro-2-(((R)-6,6-dimethylmorpholin-2-yl)methyl)-3-methylphenyl)thieno[3,2-d]pyrimidin-6-yl)methyl)-5-oxopyrrolidine-2-carboxylate. The title compound was prepared by General Procedures B, F and G (using LiHMDS in place of cesium carbonate). $^1$H NMR (400 MHz, Methanol-d4) δ 9.18 (s, 1H), 7.54 (dt, J=2.0, 1.0 Hz, 1H), 7.46 (d, J=2.3 Hz, 1H), 7.42 (d, J=2.0 Hz, 1H), 5.09 (d, J=16.2 Hz, 1H), 4.65 (dd, J=16.2, 4.7 Hz, 1H), 4.39 (td, J=9.1, 2.9 Hz, 1H), 3.85 (t, J=9.7 Hz, 1H), 3.74 (d, J=2.5 Hz, 3H), 3.18-2.95 (m, 3H), 2.85 (dt, J=14.5, 3.7 Hz, 1H), 2.70-2.31 (m, 8H), 2.23-2.09 (m, 1H), 1.05 (s, 3H), 0.82 (d, J=10.3 Hz, 3H). [M+H] 543.2

Example 225

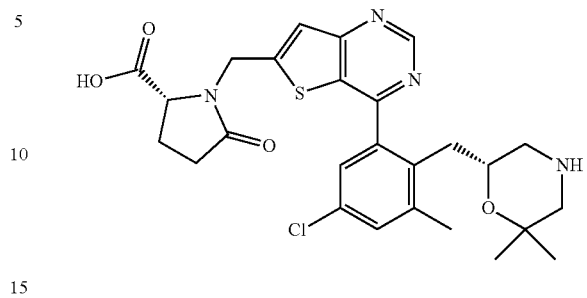

(R)-1-((4-(5-chloro-2-(((R)-6,6-dimethylmorpholin-2-yl)methyl)-3-methylphenyl)thieno[3,2-d]pyrimidin-6-yl)methyl)-5-oxopyrrolidine-2-carboxylic acid. The title compound was prepared by General Procedures B, F and G (using LiHMDS in place of cesium carbonate). $^1$H NMR (400 MHz, Methanol-d4) δ 9.18 (s, 1H), 7.55 (d, J=3.1 Hz, 1H), 7.46 (d, J=2.2 Hz, 1H), 7.42 (d, J=2.3 Hz, 1H), 5.18-5.07 (m, 1H), 4.66 (dd, J=16.2, 11.0 Hz, 1H), 4.37-4.25 (m, 1H), 3.89-3.76 (m, 1H), 3.19-2.95 (m, 3H), 2.86 (ddd, J=14.3, 6.1, 3.6 Hz, 1H), 2.71-2.33 (m, 8H), 2.25-2.11 (m, 1H), 1.05 (d, J=3.5 Hz, 3H), 0.83 (d, J=6.0 Hz, 3H). [M+H] 529.2

Example 226

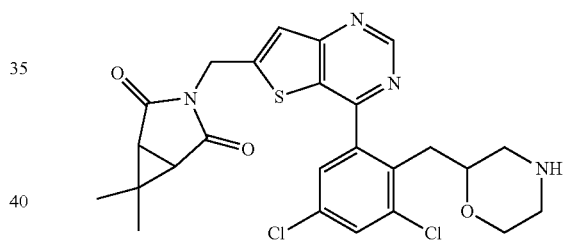

3-((4-(3,5-dichloro-2-(morpholin-2-ylmethyl)phenyl)thieno[3,2-d]pyrimidin-6-yl)methyl)-6,6-dimethyl-3-azabicyclo[3.1.0]hexane-2,4-dione. The title compound was prepared by General Procedures B, F and G. $^1$H NMR (400 MHz, Methanol-d4) δ 9.19 (s, 1H), 7.77 (s, 1H), 7.55 (s, 2H), 4.92 (s, 2H), 3.78 (m, 1H), 3.46 (m, 2H), 3.11 (m, 2H), 2.52 (s, 2H), 1.87 (s, 1H), 1.31 (s, 6H), 1.24 (s, 2H), 1.14 (s, 2H). [M+H] 531.0

Example 227

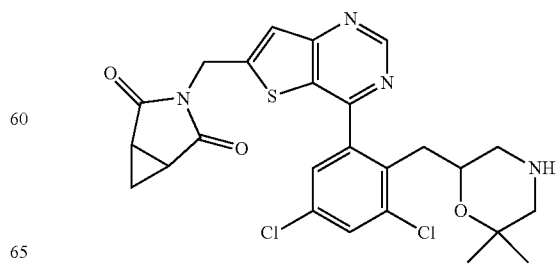

3-((4-(3,5-dichloro-2-((6,6-dimethylmorpholin-2-yl)methyl)phenyl)thieno[3,2-d]pyrimidin-6-yl)methyl)-3-azabicyclo[3.1.0]hexane-2,4-dione. The title compound was prepared by General Procedures B, F and G. ¹H NMR (400 MHz, Methanol-d4) δ 9.19 (s, 1H), 7.78 (s, 1H), 7.54 (s, 2H), 4.92 (s, 2H), 3.96 (m, 1H), 3.11 (m, 2H), 2.58 (m, 2H), 1.89 (s, 1H), 1.62 (m, 1H), 1.48 (m, 1H), 1.31 (s, 6H), 1.03 (s, 2H), 0.54 (s, 2H). [M+H] 531.0

Example 228

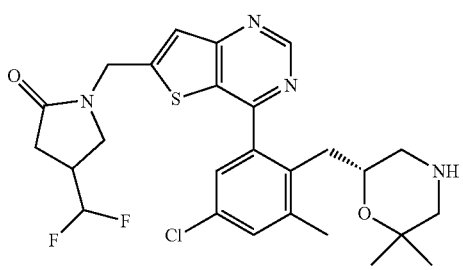 [SMILES: Cc1cc(Cl)cc(-c2ncnc3cc(CN4CC(C(F)F)CC4=O)sc23)c1C[C@@H]1CNCC(C)(C)O1]

1-((4-(5-chloro-2-(((R)-6,6-dimethylmorpholin-2-yl)methyl)-3-methylphenyl)thieno[3,2-d]pyrimidin-6-yl)methyl)-4-(difluoromethyl)pyrrolidin-2-one. The title compound was prepared by General Procedures B, F and G (using LiHMDS in place of cesium carbonate). ¹H NMR (400 MHz, Methanol-d4) δ 9.18 (s, 1H), 7.56 (d, J=1.0 Hz, 1H), 7.47 (d, J=2.3 Hz, 1H), 7.43 (s, 1H), 5.97 (t, J=56.3 Hz, 1H), 4.86-4.77 (m, 2H), 3.93-3.79 (m, 1H), 3.74-3.60 (m, 1H), 3.59-3.49 (m, 1H), 3.23-2.81 (m, 4H), 2.74-2.49 (m, 5H), 2.47 (s, 3H), 1.05 (s, 3H), 0.79 (s, 3H). [M+H] 535.2

Example 229

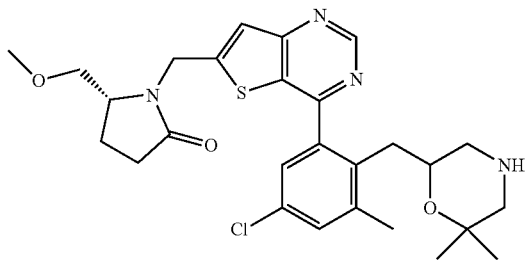 [SMILES: COC[C@H]1CCC(=O)N1Cc1cc2ncnc(-c3cc(Cl)cc(C)c3CC3CNCC(C)(C)O3)c2s1]

(5R)-1-((4-(5-chloro-2-((6,6-dimethylmorpholin-2-yl)methyl)-3-methylphenyl)thieno[3,2-d]pyrimidin-6-yl)methyl)-5-(methoxymethyl)pyrrolidin-2-one. The title compound was prepared by General Procedures B, F and G (using LiHMDS in place of cesium carbonate). ¹H NMR (400 MHz, Methanol-d4) δ 9.20 (d, J=1.1 Hz, 1H), 7.58 (d, J=1.0 Hz, 1H), 7.48 (d, J=2.0 Hz, 1H), 7.43 (t, J=2.5 Hz, 1H), 5.00 (d, J=16.2 Hz, 1H), 4.83 (d, J=16.3 Hz, 1H), 3.95-3.76 (m, 2H), 3.59 (dd, J=10.3, 2.9 Hz, 1H), 3.52-3.41 (m, 1H), 3.30 (s, 3H), 3.20-2.95 (m, 3H), 2.87 (ddd, J=14.4, 10.8, 3.5 Hz, 1H), 2.72-2.49 (m, 3H), 2.47 (s, 3H), 2.44-2.27 (m, 1H), 2.25-2.11 (m, 1H), 1.95-1.78 (m, 1H), 1.10-1.01 (m, 3H), 0.81 (d, J=21.4 Hz, 3H). [M+H] 529.2

Example 230

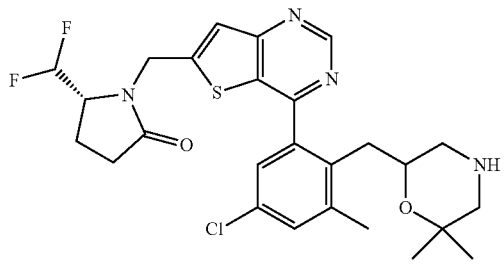

(5R)-1-((4-(5-chloro-2-((6,6-dimethylmorpholin-2-yl)methyl)-3-methylphenyl)thieno[3,2-d]pyrimidin-6-yl)methyl)-5-(difluoromethyl)pyrrolidin-2-one. The title compound was prepared by General Procedures B, F and G (using LiHMDS in place of cesium carbonate). ¹H NMR (400 MHz, Methanol-d4) δ 9.25 (s, 1H), 7.61 (s, 1H), 7.50 (d, J=2.2 Hz, 1H), 7.46 (d, J=2.3 Hz, 1H), 6.07 (t, J=55.0 Hz, 1H), 5.09 (d, J=16.3 Hz, 1H), 4.83 (d, J=16.3 Hz, 1H), 4.16-3.98 (m, 1H), 3.86 (t, J=10.0 Hz, 1H), 3.20-2.83 (m, 4H), 2.71-2.50 (m, 2H), 2.48 (s, 3H), 2.45-2.07 (m, 3H), 1.06 (s, 3H), 0.81 (d, J=2.1 Hz, 3H). [M+H] 535.2

Example 231

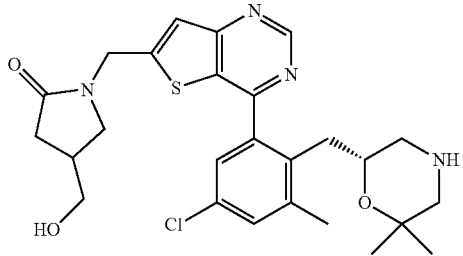 [SMILES: Cc1cc(Cl)cc(-c2ncnc3cc(CN4CC(CO)CC4=O)sc23)c1C[C@@H]1CNCC(C)(C)O1]

1-((4-(5-chloro-2-(((R)-6,6-dimethylmorpholin-2-yl)methyl)-3-methylphenyl)thieno[3,2-d]pyrimidin-6-yl)methyl)-4-(hydroxymethyl)pyrrolidin-2-one. The title compound was prepared by General Procedures B, F and G (using LiHMDS in place of cesium carbonate). ¹H NMR (400 MHz, Methanol-d4) δ 9.22 (s, 1H), 7.60 (s, 1H), 7.48 (d, J=2.2 Hz, 1H), 7.45 (d, J=2.0 Hz, 1H), 4.84 (s, 2H), 3.92-3.79 (m, 1H), 3.68-3.42 (m, 4H), 3.20-2.95 (m, 3H), 2.88 (d, J=14.2 Hz, 1H), 2.72-2.50 (m, 4H), 2.47 (s, 3H), 2.28 (t, J=11.1 Hz, 1H), 1.05 (s, 3H), 0.80 (d, J=8.8 Hz, 3H). [M+H] 515.2

Example 232

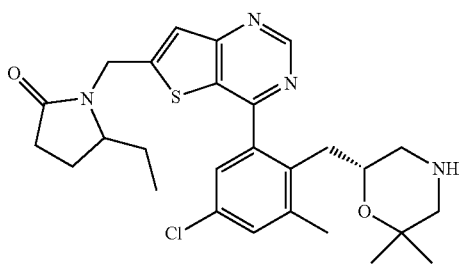 [SMILES: CCC1CCC(=O)N1Cc1cc2ncnc(-c3cc(Cl)cc(C)c3C[C@@H]3CNCC(C)(C)O3)c2s1]

1-((4-(5-chloro-2-(((R)-6,6-dimethylmorpholin-2-yl)methyl)-3-methylphenyl)thieno[3,2-d]pyrimidin-6-yl)methyl)-5-ethylpyrrolidin-2-one. The title compound was prepared by General Procedures B, F and G (using LiHMDS in place of cesium carbonate). [M+H] 513.0

Example 233

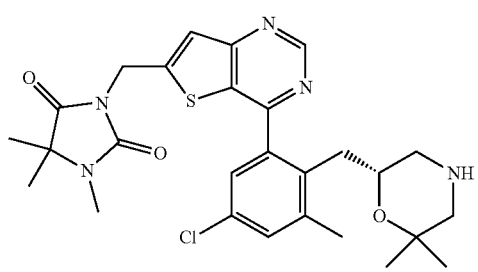 [SMILES: Cc1cc(Cl)cc(-c2ncnc3cc(CN4C(=O)N(C)C(C)(C)C4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)-1,5,5-trimethylimidazolidine-2,4-dione. The title compound was prepared by General Procedures B, F and G. $^1$H NMR (400 MHz, Methanol-d4) δ 9.33 (s, 1H), 7.69 (s, 1H), 7.53 (s, 1H), 7.50 (s, 1H), 5.09 (s, 2H), 3.86 (t, J=12.0 Hz, 1H), 3.15-2.93 (m, 3H), 2.90 (s, 3H), 2.63-2.60 (m, 1H), 2.48 (s, 3H), 1.40 (s, 6H), 1.04 (s, 3H), 0.70 (s, 3H). [M+H]542.0

Example 234

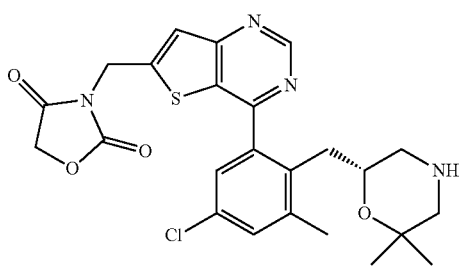 [SMILES: Cc1cc(Cl)cc(-c2ncnc3cc(CN4C(=O)COC4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)oxazolidine-2,4-dione. The title compound was prepared by General Procedures B, F and G. $^1$H NMR (400 MHz, Methanol-d4) δ 9.24 (s, 1H), 7.70 (s, 1H), 7.50 (s, 1H), 7.46 (s, 1H), 5.09 (s, 2H), 3.84 (t, J=12.0 Hz, 1H), 3.15-2.52 (m, 5H), 2.47 (s, 3H), 1.04 (s, 3H), 0.74 (s, 3H). [M+H] 501.0

Example 235

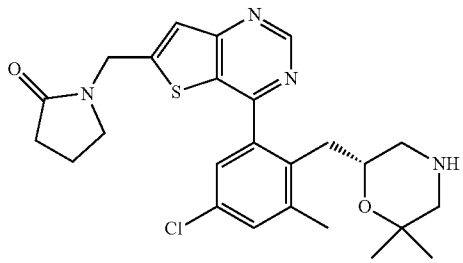 [SMILES: Cc1cc(Cl)cc(-c2ncnc3cc(CN4CCCC4=O)sc23)c1C[C@@H]1CNCC(C)(C)O1]

(R)-1-((4-(5-chloro-2-((6,6-dimethylmorpholin-2-yl)methyl)-3-methylphenyl)thieno[3,2-d]pyrimidin-6-yl)methyl)pyrrolidin-2-one. The title compound was prepared by General Procedures B, F and G (using LiHMDS in place of cesium carbonate). $^1$H NMR (400 MHz, Methanol-d4) δ 9.20 (s, 1H), 7.60 (s, 1H), 7.48 (s, 1H), 7.44 (s, 1H), 4.84 (s, 2H), 3.83 (t, J=12.0 Hz, 1H), 3.51-2.06 (m, 11H), 2.48 (s, 3H), 1.04 (s, 3H), 0.79 (s, 3H). [M+H] 485.0

Example 236

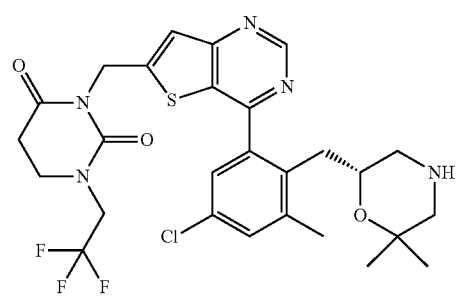 [SMILES: Cc1cc(Cl)cc(-c2ncnc3cc(CN4C(=O)CCN(CC(F)(F)F)C4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)-1-(2,2,2-trifluoroethyl)dihydropyrimidine-2,4(1H,3H)-dione. The title compound was prepared by General Procedures B, F and G. $^1$H NMR (400 MHz, Methanol-d4) δ 9.32 (s, 1H), 7.70 (s, 1H), 7.55 (s, 1H), 7.49 (s, 1H), 5.33 (s, 2H), 4.18 (q, J=9.2 Hz, 2H), 3.84 (t, J=8.8 Hz, 1H), 3.64 (t, J=6.4 Hz, 2H), 3.17-2.58 (m, 8H), 2.49 (s, 3H), 1.05 (s, 3H), 0.69 (s, 3H). [M+H] 596.0

225

Example 237

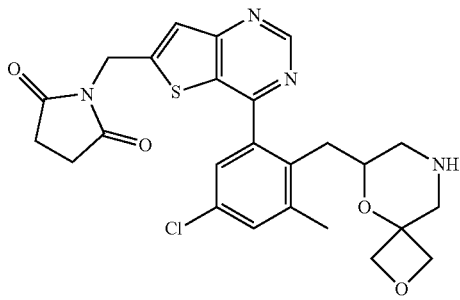 [SMILES: Cc1cc(Cl)cc(-c2ncnc3cc(CN4C(=O)CCC4=O)sc23)c1CC1CNCC2(COC2)O1]

1-((4-(2-((2,5-dioxa-8-azaspiro[3.5]nonan-6-yl)methyl)-5-chloro-3-methylphenyl)thieno[3,2-d]pyrimidin-6-yl)methyl)pyrrolidine-2,5-dione. The title compound was prepared by General Procedures B, F and G. $^1$H NMR (400 MHz, Methanol-d4) δ 9.16 (s, 1H), 7.62 (s, 1H), 7.51 (d, J=2.0 Hz, 1H), 7.48 (d, J=2.3 Hz, 1H), 4.93 (s, 2H), 4.37 (d, J=7.0 Hz, 1H), 4.07 (d, J=6.9 Hz, 1H), 3.98 (d, J=7.3 Hz, 1H), 3.63-3.53 (m, 2H), 3.35-3.27 (m, 1H), 3.19 (d, J=12.5 Hz, 1H), 2.90 (dd, J=14.9, 2.3 Hz, 1H), 2.81 (dd, J=13.0, 1.5 Hz, 1H), 2.77-2.69 (m, 2H), 2.67 (s, 4H), 2.45 (s, 3H). [M+H] 513.0

Example 238

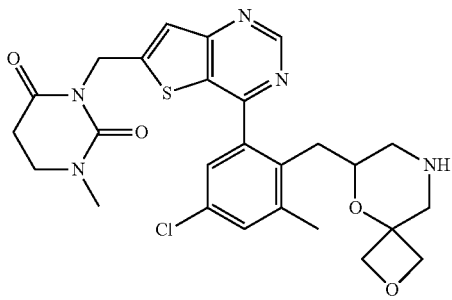 [SMILES: Cc1cc(Cl)cc(-c2ncnc3cc(CN4C(=O)CCN(C)C4=O)sc23)c1CC1CNCC2(COC2)O1]

3-((4-(2-((2,5-dioxa-8-azaspiro[3.5]nonan-6-yl)methyl)-5-chloro-3-methylphenyl)thieno[3,2-d]pyrimidin-6-yl)methyl)-1-methyldihydropyrimidine-2,4(1H,3H)-dione. The title compound was prepared by General Procedures B, F and G. $^1$H NMR (400 MHz, Methanol-d4) δ 9.15 (s, 1H), 7.57 (s, 1H), 7.51 (d, J=2.2 Hz, 1H), 7.47 (d, J=2.3 Hz, 1H), 5.33-5.20 (m, 2H), 4.37 (d, J=6.9 Hz, 1H), 4.12 (d, J=7.0 Hz, 1H), 4.04 (d, J=7.5 Hz, 1H), 3.65-3.43 (m, 3H), 3.40 (t, J=6.9 Hz, 2H), 3.35-3.26 (m, 1H), 3.20-3.10 (m, 2H), 2.99 (s, 3H), 2.95-2.79 (m, 2H), 2.74 (t, J=6.9 Hz, 2H), 2.46 (s, 3H). [M+H] 542.1

226

Example 239

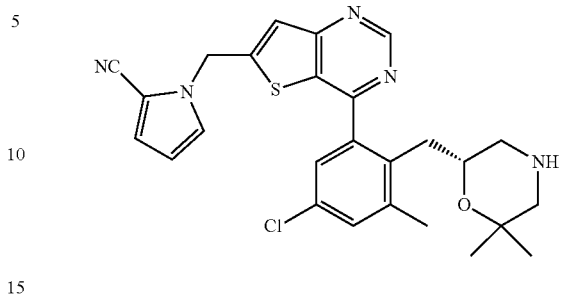

(R)-1-((4-(5-chloro-2-((6,6-dimethylmorpholin-2-yl)methyl)-3-methylphenyl)thieno[3,2-d]pyrimidin-6-yl)methyl)-1H-pyrrole-2-carbonitrile. The title compound was prepared by General Procedures B, F and G. $^1$H NMR (400 MHz, Methanol-d4) δ 9.29 (s, 1H), 8.07 (s, 1H), 7.72 (s, 1H), 7.51 (s, 1H), 7.48 (s, 1H), 6.85 (s, 1H), 5.93 (d, J=7.2 Hz, 2H), 3.82 (t, J=8.4 Hz, 1H), 3.18-2.56 (m, 6H), 2.47 (s, 2H), 0.97 (s, 3H), 0.55 (s, 3H). [M+H] 493.0

Example 240

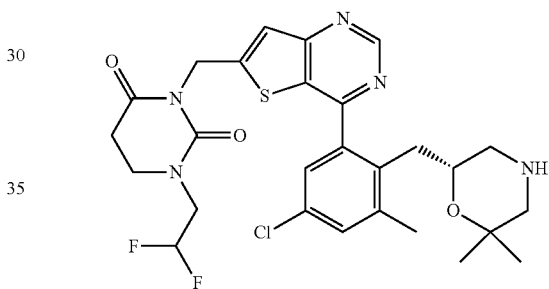

(R)-3-((4-(5-chloro-2-((6,6-dimethylmorpholin-2-yl)methyl)-3-methylphenyl)thieno[3,2-d]pyrimidin-6-yl)methyl)-1-(2,2-difluoroethyl)dihydropyrimidine-2,4(1H,3H)-dione. The title compound was prepared by General Procedures B, F and G. $^1$H NMR (400 MHz, Methanol-d4) δ 9.24 (s, 1H), 7.63 (s, 1H), 7.51 (s, 1H), 7.47 (s, 1H), 7.45 (s, 1H), 5.28 (s, 2H), 3.86-3.77 (m, 2H), 3.58 (t, J=6.4 Hz, 1H), 3.18-2.56 (m, 6H), 3.14-2.57 (m, 10H), 2.48 (s, 3H), 1.04 (s, 3H), 0.72 (s, 3H). [M+H] 578.0

Example 241

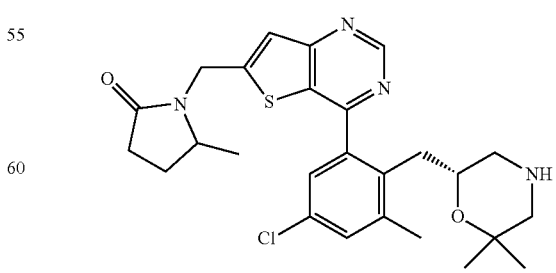

1-((4-(5-chloro-2-(((R)-6,6-dimethylmorpholin-2-yl)methyl)-3-methylphenyl)thieno[3,2-d]pyrimidin-6-yl)

methyl)-5-methylpyrrolidin-2-one. The title compound was prepared by General Procedures B, F and G (using LiHMDS in place of cesium carbonate). ¹H NMR (400 MHz, Methanol-d4) δ 9.29 (s, 1H), 7.67 (s, 1H), 7.52 (s, 1H), 7.47 (s, 1H), 5.03 (d, J=16.8 Hz, 1H), 4.77 (d, J=16.8 Hz, 1H), 3.85-3.80 (m, 2H), 3.09-2.28 (m, 9H), 2.46 (s, 3H), 1.69 (bs, 1H), 1.30 (d, J=6.0 Hz, 3H), 1.06 (s, 3H), 0.77 (s, 3H). [M+H] 499.0

Example 242

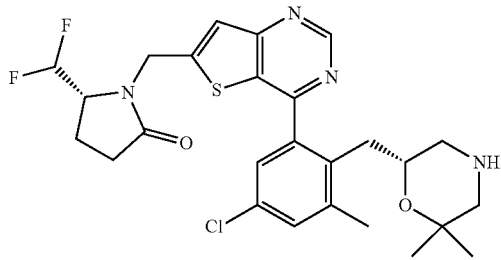 [SMILES: Cc1cc(Cl)cc(-c2ncnc3cc(CN4C(=O)CC[C@@H]4C(F)F)sc23)c1C[C@@H]1CNCC(C)(C)O1]

(R)-1-((4-(5-chloro-2-(((R)-6,6-dimethylmorpholin-2-yl)methyl)-3-methylphenyl)thieno[3,2-d]pyrimidin-6-yl)methyl)-5-(difluoromethyl)pyrrolidin-2-one. The title compound was prepared by General Procedures B, F and G (using LiHMDS in place of cesium carbonate). [M+H] 535.2

Example 243

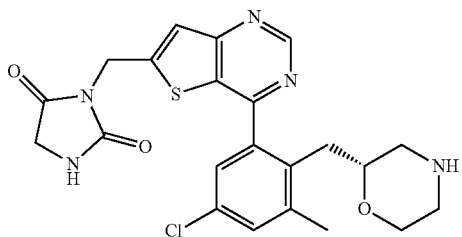 [SMILES: Cc1cc(Cl)cc(-c2ncnc3cc(CN4C(=O)CNC4=O)sc23)c1C[C@@H]1CNCCO1]

(R)-3-((4-(5-chloro-3-methyl-2-(morpholin-2-ylmethyl)phenyl)thieno[3,2-d]pyrimidin-6-yl)methyl)imidazolidine-2,4-dione. The title compound was prepared by General Procedures A, F and G. ¹H NMR (400 MHz, Methanol-d4) δ 9.22 (s, 1H), 7.63 (d, J=1.1 Hz, 1H), 7.49 (s, 1H), 7.40 (s, 1H), 5.04 (s, 2H), 4.05 (s, 2H), 3.73-3.61 (m, 2H), 3.43 (t, J=13.1 Hz, 1H), 3.13 (d, J=12.3 Hz, 1H), 3.06 (d, J=12.8 Hz, 1H), 3.01-2.79 (m, 3H), 2.69 (s, 1H), 2.48 (s, 3H). [M+H] 472.0

Example 244

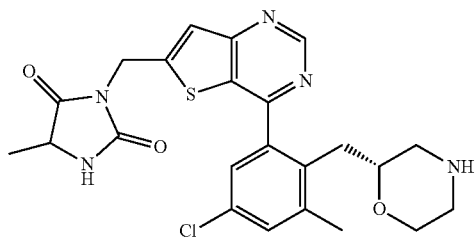 [SMILES: Cc1cc(Cl)cc(-c2ncnc3cc(CN4C(=O)NC(C)C4=O)sc23)c1C[C@@H]1CNCCO1]

3-((4-(5-chloro-3-methyl-2-(((R)-morpholin-2-yl)methyl)phenyl)thieno[3,2-d]pyrimidin-6-yl)methyl)-5-methylimidazolidine-2,4-dione. The title compound was prepared by General Procedures A, F and G. ¹H NMR (400 MHz, Methanol-d4) δ 9.24 (s, 1H), 7.61 (s, 1H), 7.50 (s, 1H), 7.41 (s, 1H), 5.04 (s, 2H), 4.21 (q, J=6.9 Hz, 1H), 3.75-3.61 (m, 2H), 3.44 (t, J=12.8 Hz, 1H), 3.15 (d, J=12.8 Hz, 1H), 3.06 (d, J=12.8 Hz, 1H), 3.01-2.81 (m, 3H), 2.70 (t, J=11.9 Hz, 1H), 2.48 (s, 3H), 1.40-1.34 (m, 3H). [M+H] 486.0

Example 245

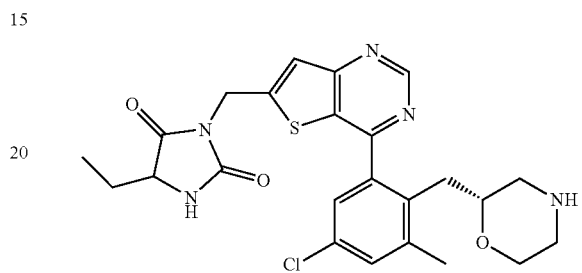

3-((4-(5-chloro-3-methyl-2-(((R)-morpholin-2-yl)methyl)phenyl)thieno[3,2-d]pyrimidin-6-yl)methyl)-5-ethylimidazolidine-2,4-dione. The title compound was prepared by General Procedures A, F and G. [M+H] 500.0

Example 246

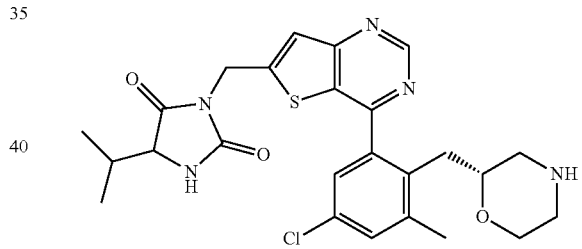

3-((4-(5-chloro-3-methyl-2-(((R)-morpholin-2-yl)methyl)phenyl)thieno[3,2-d]pyrimidin-6-yl)methyl)-5-isopropylimidazolidine-2,4-dione. The title compound was prepared by General Procedures A, F and G. [M+H] 514.0

Example 247

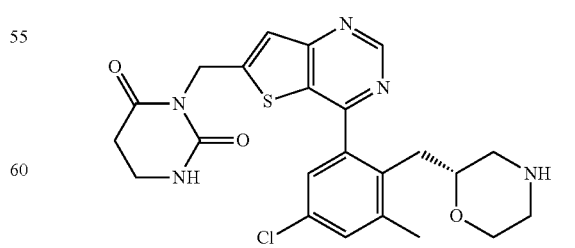

(R)-3-((4-(5-chloro-3-methyl-2-(morpholin-2-ylmethyl)phenyl)thieno[3,2-d]pyrimidin-6-yl)methyl)dihydropyrimidine-2,4(1H,3H)-dione. The title compound was prepared by General Procedures A, F and G. $^1$H NMR (400 MHz, Methanol-d4) δ 9.25 (s, 1H), 7.63 (s, 1H), 7.51 (s, 1H), 7.42 (s, 1H), 5.28 (s, 2H), 3.74-3.56 (m, 2H), 3.46 (d, J=12.3 Hz, 1H), 3.37 (t, J=6.9 Hz, 2H), 3.15 (d, J=13.2 Hz, 1H), 3.06 (d, J=12.6 Hz, 1H), 2.98-2.81 (m, 3H), 2.78-2.64 (m, 2H), 2.58 (t, J=6.8 Hz, 1H), 2.48 (s, 3H). [M+H] 486.0

Example 248

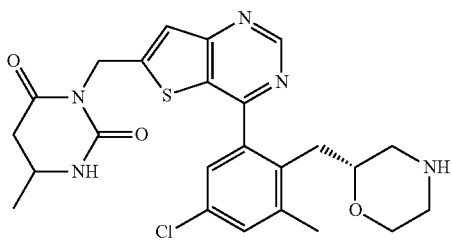 [SMILES: Cc1cc(Cl)cc(-c2ncnc3cc(CN4C(=O)CC(C)NC4=O)sc23)c1C[C@@H]1CNCCO1]

3-((4-(5-chloro-3-methyl-2-(((R)-morpholin-2-yl)methyl)phenyl)thieno[3,2-d]pyrimidin-6-yl)methyl)-6-methyldihydropyrimidine-2,4(1H,3H)-dione. The title compound was prepared by General Procedures A, F and G. $^1$H NMR (400 MHz, Methanol-d4) δ 9.29 (s, 1H), 7.65 (s, 1H), 7.53 (d, J=2.3 Hz, 1H), 7.43 (d, J=2.4 Hz, 1H), 5.33 (d, J=15.9 Hz, 1H), 5.26 (d, J=15.8 Hz, 1H), 3.76-3.54 (m, 2H), 3.45 (t, J=12.3 Hz, 1H), 3.18 (d, J=12.5 Hz, 1H), 3.07 (d, J=12.8 Hz, 1H), 2.96-2.82 (m, 2H), 2.78 (dd, J=16.6, 4.4 Hz, 1H), 2.70 (t, J=11.8 Hz, 1H), 2.62 (dd, J=16.6, 4.7 Hz, 1H), 2.56-2.44 (m, 4H), 2.35 (dd, J=16.6, 9.6 Hz, 1H), 1.24 (d, J=6.4 Hz, 3H). [M+H] 514.0

Example 249

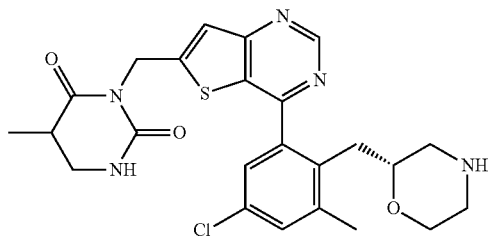 [SMILES: Cc1cc(Cl)cc(-c2ncnc3cc(CN4C(=O)NCC(C)C4=O)sc23)c1C[C@@H]1CNCCO1]

3-((4-(5-chloro-3-methyl-2-(((R)-morpholin-2-yl)methyl)phenyl)thieno[3,2-d]pyrimidin-6-yl)methyl)-5-methyldihydropyrimidine-2,4(1H,3H)-dione. The title compound was prepared by General Procedures A, F and G. $^1$H NMR (400 MHz, Methanol-d4) δ 9.23 (s, 1H), 7.59 (s, 1H), 7.50 (s, 1H), 7.40 (d, J=2.3 Hz, 1H), 5.31 (d, J=15.8 Hz, 1H), 5.22 (d, J=15.5 Hz, 1H), 3.75-3.61 (m, 2H), 3.50-3.37 (m, 2H), 3.18-3.02 (m, 2H), 2.98-2.82 (m, 2H), 2.82-2.56 (m, 3H), 2.48 (s, 3H), 2.40-2.33 (m, 1H), 1.26-1.17 (m, 3H). [M+H] 500.0

Example 250

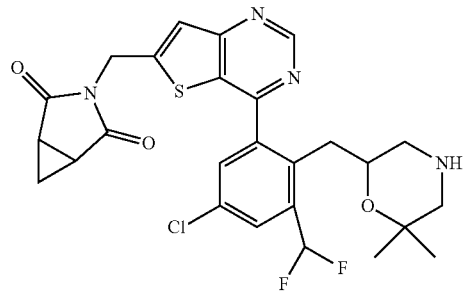 [SMILES: CC1(C)CNCC(Cc2c(-c3ncnc4cc(CN5C(=O)C6CC6C5=O)sc34)cc(Cl)cc2C(F)F)O1]

3-((4-(5-chloro-3-(difluoromethyl)-2-((6,6-dimethylmorpholin-2-yl)methyl)phenyl)thieno[3,2-d]pyrimidin-6-yl)methyl)-3-azabicyclo[3.1.0]hexane-2,4-dione. The title compound was prepared by General Procedures B and F using 3-((4-chlorothieno[3,2-d]pyrimidin-6-yl)methyl)-3-azabicyclo[3.1.0]hexane-2,4-dione. [M+H] 547.1

Example 251

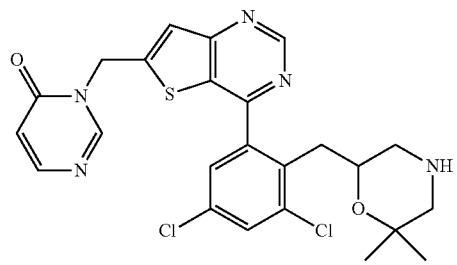 [SMILES: CC1(C)CNCC(Cc2c(Cl)cc(Cl)cc2-c2ncnc3cc(Cn4cnccc4=O)sc23)O1]

3-((4-(3,5-dichloro-2-((6,6-dimethylmorpholin-2-yl)methyl)phenyl)thieno[3,2-d]pyrimidin-6-yl)methyl)pyrimidin-4(3H)-one. The title compound was prepared by General Procedures B, F and G. $^1$H NMR (400 MHz, Methanol-d4) δ 9.21 (s, 1H), 8.81 (s, 1H), 7.98 (d, J=4 Hz, 1H), 7.77 (d, J=4 Hz, 1H), 7.75 (s, 1H), 7.65 (s, 1H), 6.65 (s, 1H), 5.57 (d, J=4 Hz, 2H), 3.92 (m, 1H), 3.11 (m, 2H), 2.91 (m, 1H), 2.55 (m, 2H), 1.30 (s, 2H), 0.94 (s, 3H), 0.38 (s, 3H). [M+H] 516.0

Example 252

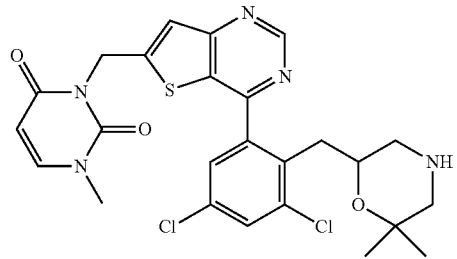 [SMILES: Cn1ccc(=O)n(Cc2cc3ncnc(-c4cc(Cl)cc(Cl)c4CC4CNCC(C)(C)O4)c3s2)c1=O]

3-((4-(3,5-dichloro-2-((6,6-dimethylmorpholin-2-yl)methyl)phenyl)thieno[3,2-d]pyrimidin-6-yl)methyl)-1-methylpyrimidine-2,4(1H,3H)-dione. The title compound was prepared by General Procedures B, F and G. $^1$H NMR (400 MHz, Methanol-d4) δ 9.19 (s, 1H), 7.77 (s, 1H), 7.63 (s, 1H), 7.62 (s, 1H), 7.58-7.56 (m, 1H), 5.74 (d, J=8 Hz, 1H), 5.44 (d, J=8 Hz, 1H), 3.94 (m, 1H), 3.37 (s, 3H), 3.10 (m, 2H), 2.56 (m, 2H), 2.01 (m, 1H), 1.30 (m, 2H), 0.97 (s, 3H), 0.45 (s, 3H). [M+H] 546.0

Example 253

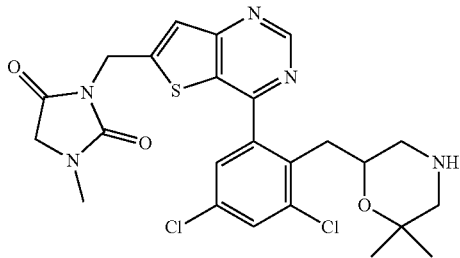

3-((4-(3,5-dichloro-2-((6,6-dimethylmorpholin-2-yl) methyl)phenyl)thieno[3,2-d]pyrimidin-6-yl)methyl)-1-methylimidazolidine-2,4-dione. The title compound was prepared by General Procedures B, F and G. $^1$H NMR (400 MHz, Methanol-d4) δ 9.19 (s, 1H), 7.77 (s, 1H), 7.63 (s, 1H), 7.60 (s, 1H), 5.02 (s, 2H), 4.02 (s, 2H), 3.96 (m, 1H), 3.12 (m, 2H), 2.96 (s, 3H), 2.58 (m, 2H), 2.02 (m, 1H), 1.30 (s, 2H), 1.01 (s, 3H), 0.54 (s, 3H). [M+H] 534.0

Example 254

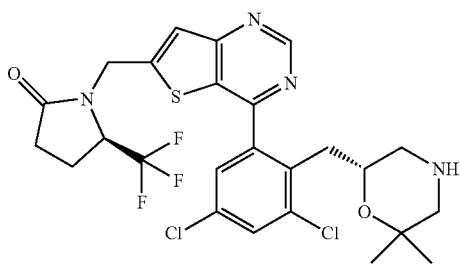 [SMILES: CC1(C)CNC[C@@H](Cc2c(Cl)cc(Cl)cc2-c2ncnc3cc(CN4C(=O)CC[C@@H]4C(F)(F)F)sc23)O1]

(R)-1-((4-(3,5-dichloro-2-(((R)-6,6-dimethylmorpholin-2-yl)methyl)phenyl)thieno[3,2-d]pyrimidin-6-yl)methyl)-5-(trifluoromethyl)pyrrolidin-2-one. The title compound was prepared by General Procedures B, F and G (LiHMDS was used in place of cesium carbonate). $^1$H NMR (400 MHz, Methanol-d4) δ 9.23 (s, 1H), 7.58 (s, 1H), 7.49 (s, 1H), 7.44 (s, 1H), 5.12 (d, J=16.4 Hz, 1H), 4.82 (d, J=16.4 Hz, 1H), 4.16 (t, J=6.5 Hz, 1), 3.85 (t, J=8.0 Hz, 1H), 3.16-2.19 (m, 9H), 2.47 (s, 3H), 1.06 (s, 3H), 0.80 (s, 3H). [M+H] 553.0

Example 255

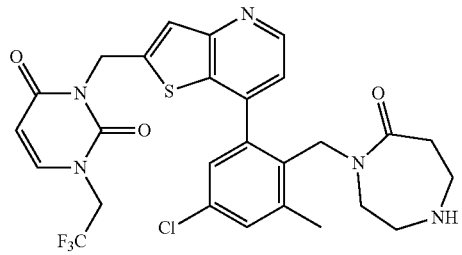 [SMILES: Cc1cc(Cl)cc(-c2ccnc3cc(Cn4c(=O)ccn(CC(F)(F)F)c4=O)sc23)c1CN1CCNCCC1=O]

3-((7-(5-chloro-3-methyl-2-((7-oxo-1,4-diazepan-1-yl) methyl)phenyl)thieno[3,2-b]pyridin-2-yl)methyl)-1-(2,2,2-trifluoroethyl)pyrimidine-2,4(1H,3H)-dione. The title compound was prepared by General Procedures C and E using 3-((7-(4,4,5,5-tetramethyl-1,3,2-dioxaborolan-2-yl)thieno [3,2-b]pyridin-2-yl)methyl)-1-(2,2,2-trifluoroethyl)pyrimidine-2,4(1H,3H)-dione.

Example 256

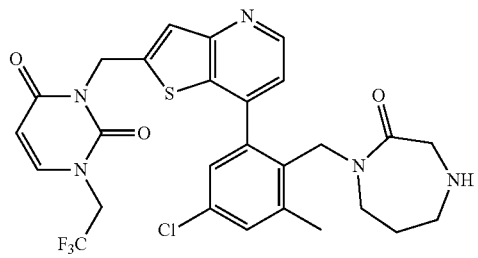 [SMILES: Cc1cc(Cl)cc(-c2ccnc3cc(Cn4c(=O)ccn(CC(F)(F)F)c4=O)sc23)c1CN1CCCNCC1=O]

3-((7-(5-chloro-3-methyl-2-((2-oxo-1,4-diazepan-1-yl) methyl)phenyl)thieno[3,2-b]pyridin-2-yl)methyl)-1-(2,2,2-trifluoroethyl)pyrimidine-2,4(1H,3H)-dione. The title compound was prepared by General Procedures C and E using 3-((7-(4,4,5,5-tetramethyl-1,3,2-dioxaborolan-2-yl)thieno [3,2-b]pyridin-2-yl)methyl)-1-(2,2,2-trifluoroethyl)pyrimidine-2,4(1H,3H)-dione.

Example 257

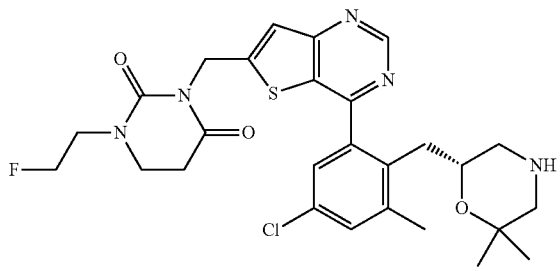 [SMILES: Cc1cc(Cl)cc(-c2ncnc3cc(CN4C(=O)CCN(CCF)C4=O)sc23)c1C[C@@H]1CNCC(C)(C)O1]

3-[[4-[5-chloro-2-[[(2R)-6,6-dimethylmorpholin-2-yl] methyl]-3-methyl-phenyl]thieno[3,2-d]pyrimidin-6-yl] methyl]-1-(2-fluoroethyl)hexahydropyrimidine-2,4-dione. The title compound was prepared by General Procedures A, F, and G.

Example 258

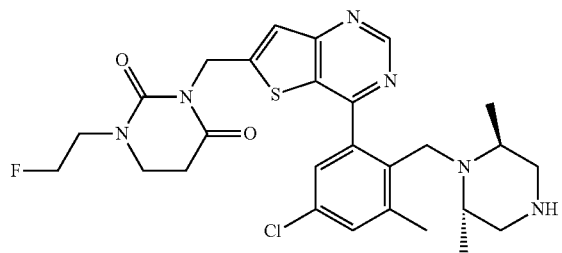 [SMILES: Cc1cc(Cl)cc(-c2ncnc3cc(CN4C(=O)CCN(CCF)C4=O)sc23)c1CN1[C@@H](C)CNC[C@@H]1C]

3-((4-(5-chloro-2-(((2S,6S)-2,6-dimethylpiperazin-1-yl)methyl)-3-methylphenyl)thieno[3,2-d]pyrimidin-6-yl)methyl)-1-(2-fluoroethyl)dihydropyrimidine-2,4(1H,3H)-dione. The title compound was prepared by General Procedures C, F, and G.

Example 259

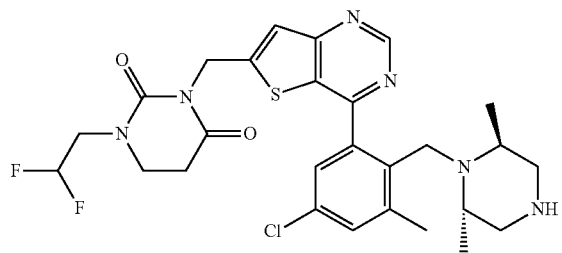 [SMILES: Cc1cc(Cl)cc(-c2ncnc3cc(CN4C(=O)CCN(CC(F)F)C4=O)sc23)c1CN1[C@@H](C)CNC[C@@H]1C]

3-((4-(5-chloro-2-(((2S,6S)-2,6-dimethylpiperazin-1-yl)methyl)-3-methylphenyl)thieno[3,2-d]pyrimidin-6-yl)methyl)-1-(2,2-difluoroethyl)dihydropyrimidine-2,4(1H,3H)-dione. The title compound was prepared by General Procedures C, F, and G.

Example 260

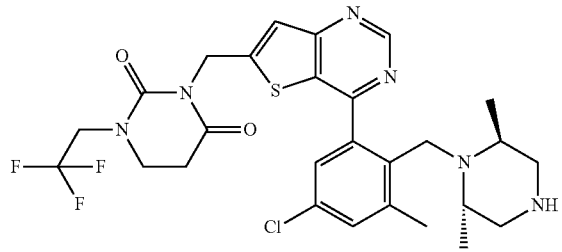 [SMILES: Cc1cc(Cl)cc(-c2ncnc3cc(CN4C(=O)CCN(CC(F)(F)F)C4=O)sc23)c1CN1[C@@H](C)CNC[C@@H]1C]

3-((4-(5-chloro-2-(((2S,6S)-2,6-dimethylpiperazin-1-yl)methyl)-3-methylphenyl)thieno[3,2-d]pyrimidin-6-yl)methyl)-1-(2,2,2-trifluoroethyl)dihydropyrimidine-2,4(1H,3H)-dione. The title compound was prepared by General Procedures C, F, and G.

Example 261

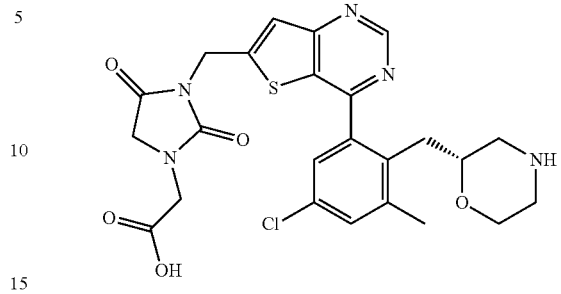

(R)-2-(3-((4-(5-chloro-3-methyl-2-(morpholin-2-ylmethyl)phenyl)thieno[3,2-d]pyrimidin-6-yl)methyl)-2,4-dioxoimidazolidin-1-yl)acetic acid. The title compound was prepared by alkylation of the Boc-protected title compound of Example 243 with sodium hydride and t-butyl-bromoacetate, followed by global deprotection with TFA.

Example 262

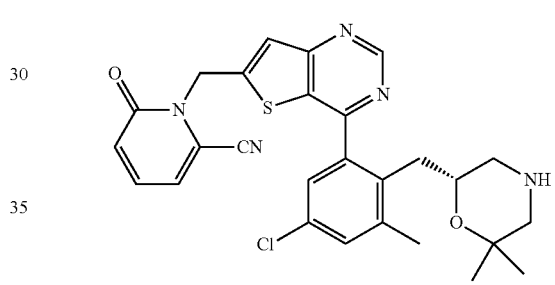

(R)-1-((4-(5-chloro-2-(((6,6-dimethylmorpholin-2-yl)methyl)-3-methylphenyl)thieno[3,2-d]pyrimidin-6-yl)methyl)-6-oxo-1,6-dihydropyridine-2-carbonitrile. The title compound was prepared by General Procedures A, F, and G.

Example 263

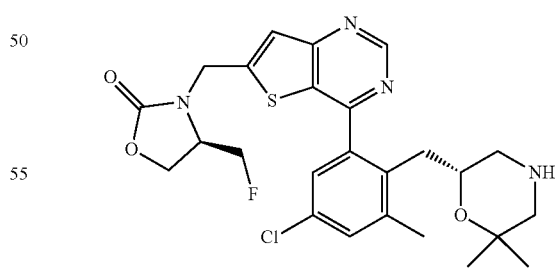

(R)-3-((4-(5-chloro-2-(((R)-6,6-dimethylmorpholin-2-yl)methyl)-3-methylphenyl)thieno[3,2-d]pyrimidin-6-yl)methyl)-4-(fluoromethyl)oxazolidin-2-one. The title compound was prepared by General Procedures A, F, and G using (R)-4-(((tert-butyldimethylsilyl)oxy)methyl)oxazolidin-2-one. TBS deprotection with TBAF was followed by treatment with DAST.

Example 264

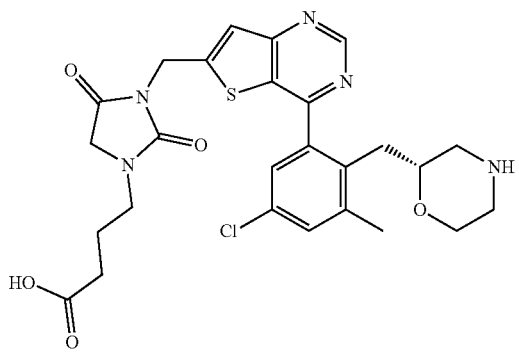 [SMILES: Cc1cc(Cl)cc(-c2ncnc3cc(CN4C(=O)CN(CCCC(=O)O)C4=O)sc23)c1C[C@@H]1CNCCO1]

(R)-4-(3-((4-(5-chloro-3-methyl-2-(morpholin-2-ylmethyl)phenyl)thieno[3,2-d]pyrimidin-6-yl)methyl)-2,4-dioxoimidazolidin-1-yl)butanoic acid. The title compound was prepared by alkylation of the Boc-protected title compound of Example 243 with sodium hydride and t-butyl-bromobutyrate, followed by global deprotection with TFA.

Example 265

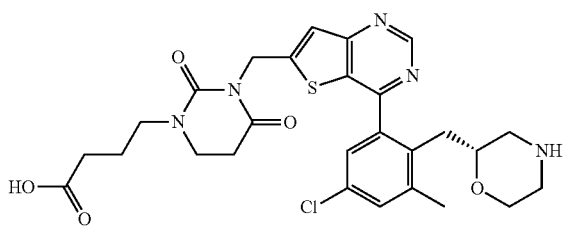 [SMILES: Cc1cc(Cl)cc(-c2ncnc3cc(CN4C(=O)CCN(CCCC(=O)O)C4=O)sc23)c1C[C@@H]1CNCCO1]

(R)-4-(3-((4-(5-chloro-3-methyl-2-(morpholin-2-ylmethyl)phenyl)thieno[3,2-d]pyrimidin-6-yl)methyl)-2,4-dioxotetrahydropyrimidin-1(2H)-yl)butanoic acid. The title compound was prepared by alkylation of the Boc-protected title compound of Example 247 with sodium hydride and t-butyl-bromobutyrate, followed by global deprotection with TFA.

Example 266

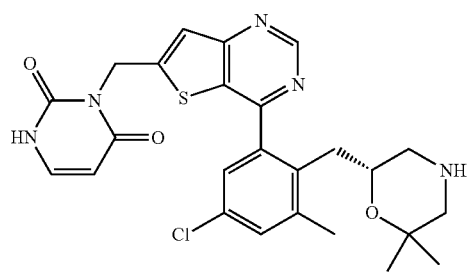 [SMILES: Cc1cc(Cl)cc(-c2ncnc3cc(Cn4c(=O)cc[nH]c4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)pyrimidine-2,4(1H,3H)-dione. The title compound was prepared by General Procedures A, F, and G.

Example 267

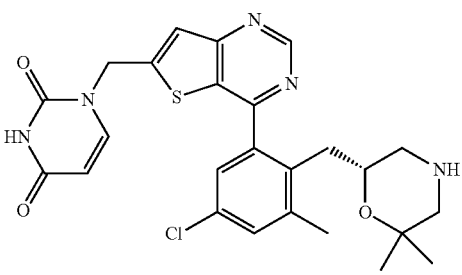 [SMILES: Cc1cc(Cl)cc(-c2ncnc3cc(Cn4ccc(=O)[nH]c4=O)sc23)c1C[C@@H]1CNCC(C)(C)O1]

(R)-1-((4-(5-chloro-2-((6,6-dimethylmorpholin-2-yl)methyl)-3-methylphenyl)thieno[3,2-d]pyrimidin-6-yl)methyl)pyrimidine-2,4(1H,3H)-dione. Regioisomer isolated from Example 266.

Example 268

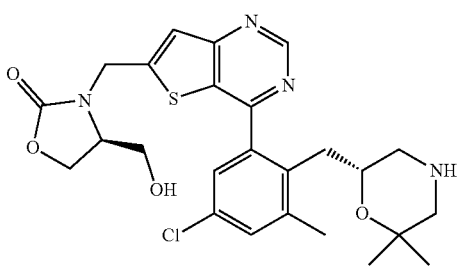 [SMILES: Cc1cc(Cl)cc(-c2ncnc3cc(CN4C(=O)OC[C@@H]4CO)sc23)c1C[C@@H]1CNCC(C)(C)O1]

(S)-3-((4-(5-chloro-2-(((R)-6,6-dimethylmorpholin-2-yl)methyl)-3-methylphenyl)thieno[3,2-d]pyrimidin-6-yl)methyl)-4-(hydroxymethyl)oxazolidin-2-one. The title compound was prepared by global deprotection of the TBS ether in Example 263.

Example 269

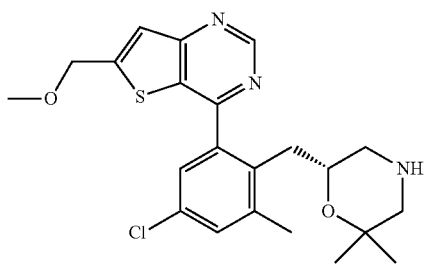 [SMILES: COCc1cc2ncnc(-c3cc(Cl)cc(C)c3C[C@@H]3CNCC(C)(C)O3)c2s1]

(R)-6-(4-chloro-2-(6-(methoxymethyl)thieno[3,2-d]pyrimidin-4-yl)-6-methylbenzyl)-2,2-dimethylmorpholine. Byproduct isolated from Example 268.

Example 270

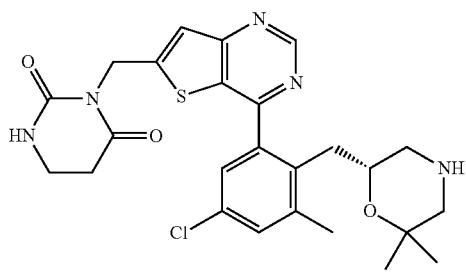 [SMILES: Cc1cc(Cl)cc(-c2ncnc3cc(CN4C(=O)CCNC4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)dihydropyrimidine-2,4(1H,3H)-dione. The title compound was prepared by General Procedures A, F, and G.

Example 271

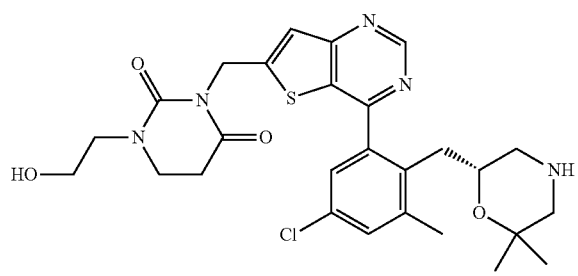 [SMILES: Cc1cc(Cl)cc(-c2ncnc3cc(CN4C(=O)CCN(CCO)C4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)-1-(2-hydroxyethyl)dihydropyrimidine-2,4(1H,3H)-dione. The title compound was prepared by General Procedures A, F, and G using 1-(2-((tert-butyldimethylsilyl)oxy)ethyl)dihydropyrimidine-2,4(1H,3H)-dione.

Example 272

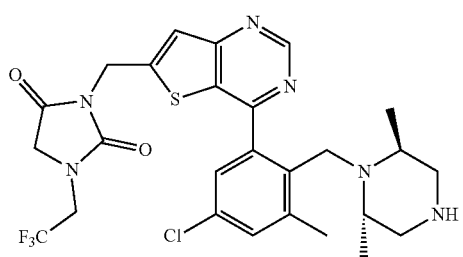 [SMILES: Cc1cc(Cl)cc(-c2ncnc3cc(CN4C(=O)CN(CC(F)(F)F)C4=O)sc23)c1CN1[C@@H](C)CNC[C@@H]1C]

3-((4-(5-chloro-2-(((2S,6S)-2,6-dimethylpiperazin-1-yl)methyl)-3-methylphenyl)thieno[3,2-d]pyrimidin-6-yl)methyl)-1-(2,2,2-trifluoroethyl)imidazolidine-2,4-dione. The title compound was prepared by General Procedures C, F, and G followed by alkylation of the hydantoin with sodium hydride and trifluoroethyl triflate and deprotection with TFA.

Example 273

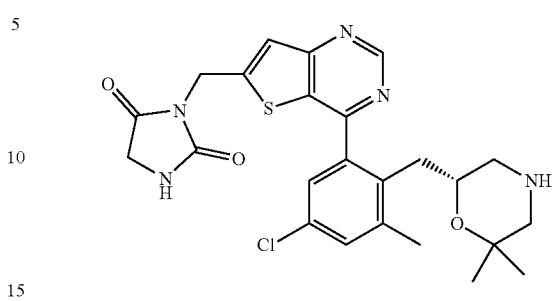

(R)-3-((4-(5-chloro-2-((6,6-dimethylmorpholin-2-yl)methyl)-3-methylphenyl)thieno[3,2-d]pyrimidin-6-yl)methyl)imidazolidine-2,4-dione. The title compound was prepared by General Procedures A, F, and G.

Example 274

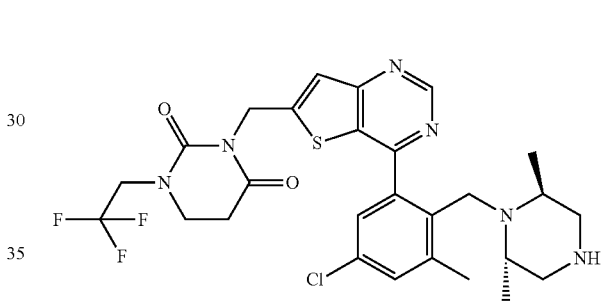

3-((4-(5-chloro-2-(((2S,6S)-2,6-dimethylpiperazin-1-yl)methyl)-3-methylphenyl)thieno[3,2-d]pyrimidin-6-yl)methyl)-1-(2,2,2-trifluoroethyl)pyrimidine-2,4(1H,3H)-dione. The title compound was prepared by General Procedures C, F, and G.

Example 275

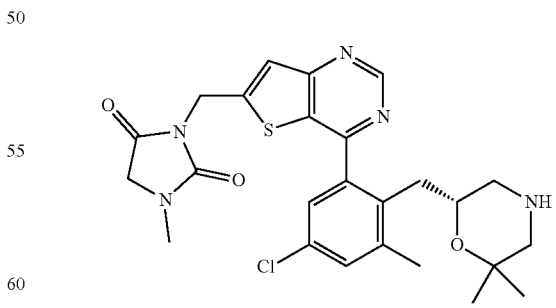

(R)-3-((4-(5-chloro-2-((6,6-dimethylmorpholin-2-yl)methyl)-3-methylphenyl)thieno[3,2-d]pyrimidin-6-yl)methyl)-1-methylimidazolidine-2,4-dione. The title compound was prepared by General Procedures A, F, and G.

Example 276

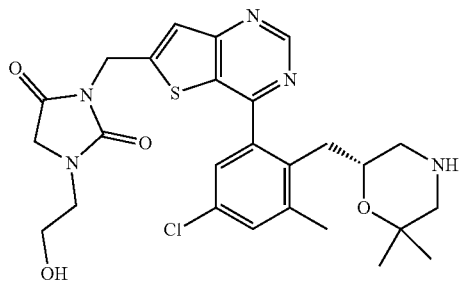 [SMILES: Cc1cc(Cl)cc(-c2ncnc3cc(CN4C(=O)CN(CCO)C4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)-1-(2-hydroxyethyl)imidazolidine-2,4-dione. The title compound was prepared by General Procedures A, F, and G using 1-(2-((tert-butyldimethylsilyl)oxy)ethyl)imidazolidine-2,4-dione followed by global deprotection with TFA.

Example 277

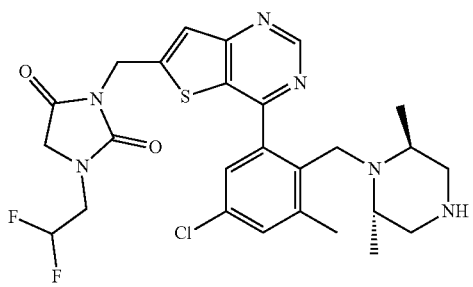 [SMILES: Cc1cc(Cl)cc(-c2ncnc3cc(CN4C(=O)CN(CC(F)F)C4=O)sc23)c1CN1[C@@H](C)CNC[C@@H]1C]

3-((4-(5-chloro-2-(((2S,6S)-2,6-dimethylpiperazin-1-yl)methyl)-3-methylphenyl)thieno[3,2-d]pyrimidin-6-yl)methyl)-1-(2,2-difluoroethyl)imidazolidine-2,4-dione. The title compound was prepared by General Procedures C, F, and G followed by alkylation of the hydantoin with cesium carbonate and 2-iodo-1,1-difluoroethane and deprotection with HCl.

Example 278: Biological Activity

Activity for compounds described herein is provided in Table 2, wherein potency levels are provided as follows: (Potency: USP7 $IC_{50}$: A<0.01 μM; B=0.01-0.1 μM; C=>0.1 μM.

TABLE 2

| Example No. | Potency |
|---|---|
| 1 | C |
| 2 | A |
| 3 | A |
| 4 | C |
| 5 | B |
| 6 | B |
| 7 | B |
| 8 | A |
| 9 | A |
| 10 | A |

TABLE 2-continued

| Example No. | Potency |
|---|---|
| 11 | A |
| 12 | A |
| 13 | A |
| 14 | A |
| 15 | A |
| 16 | B |
| 17 | A |
| 18 | A |
| 19 | B |
| 20 | A |
| 21 | A |
| 22 | A |
| 23 | A |
| 24 | A |
| 25 | A |
| 26 | A |
| 27 | B |
| 28 | A |
| 29 | A |
| 30 | A |
| 31 | A |
| 32 | A |
| 33 | A |
| 34 | A |
| 35 | B |
| 36 | B |
| 37 | A |
| 38 | A |
| 39 | A |
| 40 | B |
| 41 | B |
| 42 | NM* |
| 43 | A |
| 44 | A |
| 45 | A |
| 46 | A |
| 47 | A |
| 48 | A |
| 49 | A |
| 50 | A |
| 51 | A |
| 52 | B |
| 53 | B |
| 54 | A |
| 55 | B |
| 56 | B |
| 57 | A |
| 58 | B |
| 59 | B |
| 60 | B |
| 61 | B |
| 62 | C |
| 63 | C |
| 64 | B |
| 65 | A |
| 66 | A |
| 67 | A |
| 68 | B |
| 69 | A |
| 70 | B |
| 71 | C |
| 72 | C |
| 73 | A |
| 74 | C |
| 75 | A |
| 76 | B |
| 77 | A |
| 78 | A |
| 79 | A |
| 80 | A |
| 81 | C |
| 82 | C |
| 83 | A |
| 84 | A |
| 85 | A |
| 86 | A |
| 87 | A |
| 88 | A |

TABLE 2-continued

| Example No. | Potency |
|---|---|
| 89 | A |
| 90 | C |
| 91 | C |
| 92 | A |
| 93 | A |
| 94 | A |
| 95 | A |
| 96 | B |
| 97 | A |
| 98 | A |
| 99 | A |
| 100 | B |
| 101 | B |
| 102 | A |
| 103 | A |
| 104 | A |
| 105 | C |
| 106 | A |
| 107 | A |
| 108 | A |
| 109 | A |
| 110 | A |
| 111 | A |
| 112 | A |
| 113 | A |
| 114 | B |
| 115 | C |
| 116 | A |
| 117 | A |
| 118 | A |
| 119 | A |
| 120 | A |
| 121 | A |
| 122 | C |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | B |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | B |
| 147 | B |
| 148 | B |
| 149 | B |
| 150 | A |
| 151 | A |
| 152 | A |
| 153 | A |
| 154 | A |
| 155 | A |
| 156 | B |
| 157 | B |
| 158 | B |
| 159 | B |
| 160 | A |
| 161 | B |
| 162 | A |
| 163 | A |
| 164 | A |
| 165 | A |
| 166 | A |

TABLE 2-continued

| Example No. | Potency |
|---|---|
| 167 | A |
| 168 | A |
| 169 | A |
| 170 | A |
| 171 | A |
| 172 | C |
| 173 | C |
| 174 | C |
| 175 | C |
| 176 | A |
| 177 | A |
| 178 | A |
| 179 | A |
| 180 | A |
| 181 | B |
| 182 | A |
| 183 | A |
| 184 | A |
| 185 | B |
| 186 | A |
| 187 | A |
| 188 | A |
| 189 | A |
| 190 | A |
| 191 | A |
| 192 | A |
| 193 | A |
| 194 | A |
| 195 | B |
| 196 | A |
| 197 | A |
| 198 | C |
| 199 | A |
| 200 | A |
| 201 | B |
| 202 | B |
| 203 | B |
| 204 | A |
| 205 | A |
| 206 | B |
| 207 | A |
| 208 | A |
| 209 | A |
| 210 | A |
| 211 | A |
| 212 | B |
| 213 | B |
| 214 | B |
| 215 | A |
| 216 | A |
| 217 | A |
| 218 | A |
| 219 | A |
| 220 | A |
| 221 | A |
| 222 | A |
| 223 | A |
| 224 | A |
| 225 | C |
| 226 | A |
| 227 | A |
| 228 | B |
| 229 | B |
| 230 | A |
| 231 | B |
| 232 | B |
| 233 | A |
| 234 | A |
| 235 | B |
| 236 | A |
| 237 | A |
| 238 | A |
| 239 | C |
| 240 | A |
| 241 | B |
| 242 | A |
| 243 | A |
| 244 | A |

TABLE 2-continued

| Example No. | Potency |
|---|---|
| 245 | A |
| 246 | A |
| 247 | A |
| 248 | A |
| 249 | A |
| 250 | A |
| 251 | C |
| 252 | A |
| 253 | A |
| 254 | NM* |
| 255 | B |
| 256 | B |
| 257 | A |
| 258 | A |
| 259 | A |
| 260 | A |
| 261 | B |
| 262 | C |
| 263 | A |
| 264 | B |
| 265 | B |
| 266 | B |
| 267 | A |
| 268 | A |
| 269 | C |
| 270 | A |
| 271 | A |
| 272 | A |
| 273 | A |
| 274 | A |
| 275 | A |
| 276 | A |
| 277 | A |

*NM indicates that the potency was not measured

Materials and Methods Used in Examples 279-285

Cell Culture, Cell Treatments, and Viability Assays.

CHP-134 was purchased from Sigma Aldrich, MOLM-13 was purchased from AddexBio, and NB-1 was purchased from Sekisui XenoTech. All other cell lines were purchased from American Type Culture Collection. For all cell lines, identity was confirmed by short tandem repeat profiling and culturing was performed in recommended growth medium. For studies evaluating cellular effects of compound treatment, 250 to 2,000 cells in 40 µl of recommended medium were seeded per well in 384-well plates (Corning 3764). DMSO-solubilized compounds were added in duplicate in a two-fold dilution series using a D300e Digital Dispenser (Hewlett-Packard). Following a 5-day incubation, cell viability was measured using CellTiter-Glo (Promega) following the manufacturer's instructions. Luminescence was measured using a CLARIOstar plate reader (BMG LABTECH) and normalized to that of DMSO-treated cells. IC50 values were determined by non-linear regression using a 4-parameter fit in Prism (GraphPad Software). Inhibitor profiling of the 430-cell line panel was conducted and analyzed similarly.

RNASeq Analysis.

RNA was extracted from approximately 1 million cells using the Allprep DNA/RNA Mini Kit (Qiagen). Whole transcriptome non-stranded libraries were prepared using the TruSeq RNA Library Prep Kit v2 (Illumina). Sequencing was performed on Illumina NovaSeq using paired-end mode, 200 cycles, targeting 40 million reads per sample, by MedGenome. Sequencing results were processed on the Seven Bridges Genomics platform through Kallisto Quant (version 0.43.1) aligning to the gencode.v27 transcript reference. Aligned reads were imported by tximport (version 1.10.1) and Treatment fold change and significance were calculated with DESeq2 (version 1.22.2) with an experimental design of "~Time+Treatment+Time: Treatment" on genes with at least 10 counts. Shrunk log 2 fold changes (lfcShrink function, type="apeglm") were used for significance calculation. For gene set enrichment analysis, genes with at least 2-fold up or down change and adjusted p<0.01 were considered significantly differentially expressed. Gene sets were downloaded from MSigDB v6.2 (http://software-.broadinstitute.org/gsea/msigdb) and those with at least 4 overlapping genes with the significantly regulated genes were used for hypergeometric test calculation.

Statistical Analysis.

Cancer Cell Line Encyclopedia (CCLE) mutation data was downloaded from https://data.broadinstitute.org/ccleiCCLE_DepMap_18Q2_maf_20180502.txt.gz. Genes were considered mutated if they were annotated in CCLE as containing variants that were either a TCGA Hotspot, a COSMIC Hotspot, or a deleterious variant. Genes with at least 6 mutated cell lines out of the 397 cell lines that overlapped with the cell line screening panel were tested one gene at a time in linear models or coordinately in multivariate models where the fraction cell signal at 1 µM compound was the dependent variable. For compound synergy analysis, a Bliss-independence model was used. Briefly, the products of the fraction of maximal cell signal for each of the tested compounds alone were calculated as the expected signal in the absence of any compound interaction. The $\log_2$ of the ratio of expected:observed signal was calculated to indicate synergy (positive) or interference (negative) interactions. For in vivo studies, interval-censored survival analysis was performed using the icenReg package (reference: https://cran.r-project.org/web/packages/icenReg/citation.html), using the "ic_par" parametric regression model with proportional hazards and a Weibull distribution.

Western blotting, caspase activation, γ-H2AX and phospho-S6 assays.

For Western blotting, compound-treated cells were lysed in RIPA lysis buffer (ThermoScientific) containing Halt Protease and Phosphatase Inhibitor Cocktail (Life Technologies). Lysates were quantified using the BCA protein assay (Pierce) and equivalent protein was separated by SDS-PAGE (4-12%, ThermoScientific). Following electrophoresis, proteins were transferred to PVDF membranes. Membranes were blocked with 5% milk or BSA in TBS+0.05% Tween-20 (TBST) and subjected to Western blot analysis using the following primary antibodies, diluted in blocking solution and incubated overnight at 4° C.: GAPDH (14C10, Cell Signaling, 1:1000), p53 (DO1, Santa Cruz, 1:200), p21 (12D1, Cell Signaling, 1:500), UHRF1 (H-8, Santa Cruz, 1:100), MYCN (Cell Signaling, 1:1000). Blots were then incubated for 1 hour at room temperature in secondary antibodies, diluted 1:10,000, and imaged using SuperSignal West chemiluminescent reagents (Life Technologies). Caspase activation assays were performed on compound-treated cells using the Caspase-Glo 3/7 Assay Kit (Promega) according to the manufacturer's protocol, and luminescence was measured using a CLARIOstar plate reader (BMG LABTECH). For γ-H2AX measurement, compound-treated cells were harvested, fixed and stained using the H2A.X Phosphorylation Assay Kit (Sigma) according to the manufacturer's protocol. Data were collected using FACSCanto (Becton Dickinson) and Attune (Thermo Fisher Scientific) flow cytometers and analyzed with FlowJo software (FlowJo LLC). For phospho-S6 ELISA assays, compound-treated cells were lysed in PathScan Sandwich ELISA Lysis Buffer (Cell Signaling) containing Halt Protease and Phosphatase Inhibitor Cocktail (Life Technologies). Lysates were quantified using the BCA protein assay (Pierce) and equivalent protein was used in the PathScan Phospho-S6 Ribosomal Protein (Ser235/236) Sandwich ELISA Kit (Cell Signaling) according to the manufacturer's protocol. Absorbance was measured using the Spectramax 300 plate reader (Molecular Devices).

Animal Experiments.

MM. 1S and H526 xenograft studies were conducted according to the guidelines approved by the Applicant's Institutional Animal Care and Use Committee (IACUC). MM.1S cells were inoculated in PBS into irradiated NOD/SCID mice, while H526 cells were inoculated in PBS/Matrigel (Corning) into Nu/Nu mice (Jackson Laboratories). Mice were randomized into groups when mean tumor size reached 150 mm$^3$ (MM.1S) or 50-100 mm$^3$ (H526), respectively, and drug administration by oral gavage was started on day of randomization. Tumor volumes and body weights were subsequently measured twice per week. Tumor volumes were calculated using the formula: $V=0.5(A \times B^2)$, where A and B are the long and short diameters of the tumor, respectively.

Example 279

Figure 1B:
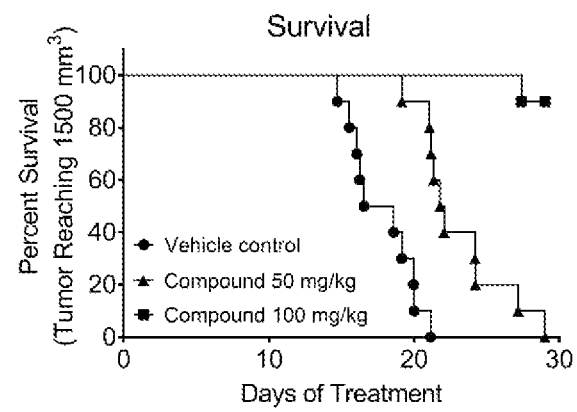

The effects of USP7 inhibition were assessed in vivo in the MM.1S xenograft model in NOD-SCID mice via daily oral dosing of the USP7 inhibitor 3-((7-(5-chloro-2-(((2S,6S)-2,6-dimethylpiperazin-1-yl)methyl)-3-methylphenyl)thieno[3,2-b]pyridin-2-yl)methyl)-3-azabicyclo[3.1.0]hexane-2,4-dione (the compound of Example 31) at 50 mg/kg and 100 mg/kg. These doses were well tolerated in preliminary experiments in tumor-free NOD-SCID mice. In the longer-term xenograft study in tumor-bearing mice we observed dose-dependent body weight loss in a fraction of mice. However, brief dosing holidays allowed the mice to recover and dosing to continue. The compound effectively inhibited MM.1S tumor growth and prolonged survival in a dose-dependent manner as shown in FIG. 1A and FIG. 1B.

Example 280

USP7 inhibition by the compounds of Examples 31 and 124 reduced the viability of several p53-wild type blood cancer cell lines, including M07e, OCI-AML5 and MOLM13, in vitro as shown in the following Table 3. Idasanutlin was used as a positive control, and as expected these cell lines were also sensitive to this compound.

TABLE 3

Cytotoxicity concentrations of USP7 inhibitors and idasanutlin in p53 wild-type blood cancer cell lines ($CC_{50}$ is the concentration of the tested compound at which half of the cells die; AML refers to acute myeloid leukemia; MM refers to multiple myeloma; nd means not determined).

| Cell Line | Cancer Type | Idasanutlin $CC_{50}$ (μM) | Example 31 Compound $CC_{50}$ (μM) | Example 124 Compound $CC_{50}$ (μM) |
|---|---|---|---|---|
| M07e | AML | 0.03 | 0.1 | 0.2 |
| OCI-AML5 | AML | 0.04 | 0.2 | 0.2 |
| MOLM13 | AML | 0.02 | 0.1 | 0.4 |
| EOL-1 | AML | 0.05 | 0.04 | nd |
| MOLP8 | MM | 0.3 | 0.2 | nd |
| NCI-H929 | MM | 0.2 | 0.4 | nd |
| MM.1S | MM | 0.02 | 0.1 | 0.1 |

Example 281

USP7 has been reported to stabilize MYCN (also referred to as MYCN proto-oncogene, a gene that is a member of the MYC family which is over-expressed in a variety of tumors). Since MYCN amplification is an established driver mutation in neuroblastoma, the effect of USP7 inhibition on a panel of p53 wild-type, MYCN- or MYC-amplified neuroblastoma cell lines was tested. The USP7 inhibitors of Examples 31 and 124 reduced viability of all three MYCN-amplified and two MYC-amplified neuroblastoma cell lines tested as shown in Table 4. Idasanutlin was used as a positive control, and as expected these cell lines were also sensitive to this compound.

TABLE 4

Cytotoxicity of USP7 inhibitors and idasanutlin in p53 wild-type neuroblastoma cell lines (nd means not determined).

| Cell Line | MYC/MYCN Amplification Status | Idasanutlin $CC_{50}$ (μM) | Example 31 Compound $CC_{50}$ (μM) | Example 124 Compound $CC_{50}$ (μM) |
|---|---|---|---|---|
| SH-SY5Y | MYC amplified | 0.1-0.5 | 1.8 | 1.9 |
| SK-N-SH | MYC amplified | 0.2 | nd | nd |
| IMR-32 | MYCN amplified | 0.24 | nd | nd |
| CHP-134 | MYCN amplified | 0.01 | 0.5 | 0.6 |
| NB-1 | MYCN amplified | 0.1 | 0.6 | 0.5 |

Example 282

In addition to the many p53 wild-type cell lines in the cell line panel that were sensitive to USP7 inhibition, a subset of p53 mutant cell lines that were inhibited by our USP7 inhibitors were identified and are shown in Table 5.

TABLE 5

Cytotoxicity of USP7 inhibitors and idasanutlin in p53-mutant cancer cell lines (nd means not determined).

| Cell Line | Cancer Type | Idasanutlin $CC_{50}$ (μM) | Example 31 Compound $CC_{50}$ (μM) | Example 124 Compound $CC_{50}$ (μM) |
|---|---|---|---|---|
| H526 | lung, small cell | 6.5 | 0.5 | 0.5 |
| EBC-1 | lung, squamous cell carcinoma | 16.2 | nd | nd |
| NCI-H820 | lung, papillary adenocarcinoma | 9.7 | nd | nd |
| NCI-H2009 | lung, adenocarcinoma | >25 | nd | nd |

TABLE 5-continued

Cytotoxicity of USP7 inhibitors and idasanutlin in p53-mutant cancer cell lines (nd means not determined).

| Cell Line | Cancer Type | Idasanutlin CC$_{50}$ (μM) | Example 31 Compound CC$_{50}$ (μM) | Example 124 Compound CC$_{50}$ (μM) |
|---|---|---|---|---|
| HUH-7 | hepatocellular carcinoma | >25 | nd | nd |
| MHCC97-H | hepatocellular carcinoma | >25 | nd | nd |
| NCI-N87 | gastric | 8.6 | nd | nd |
| JJN-3 | multiple myeloma | >25 | nd | nd |
| HCC1806 | breast, triple-negative | 7.5 | nd | nd |
| HCC1937 | breast, triple-negative, BRCA1 mutant | 7.1 | 0.1 | nd |
| LA-N-2 | neuroblastoma, MYCN-amplified | 5.3 | 0.6 | 0.2 |
| SK-N-DZ | neuroblastoma, MYCN-amplified | >12.5 | 0.2 | 0.2 |

Figure 2A:
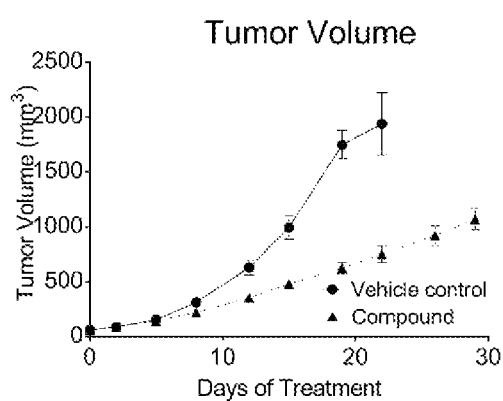
FIGS. 2A-2B Depicts the effects of USP7 inhibition in vivo (using 3-((7-(5-chloro-3-methyl-2-(((R)-morpholin-2-yl)methyl)phenyl)thieno[3,2-b]pyridin-2-yl)methyl)-6,6-dimethyl-3-azabicyclo[3.1.0]hexane-2,4-dione).
Figure 2B:
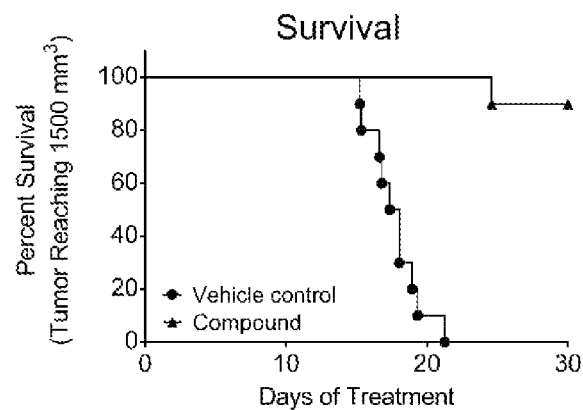

The effect of pharmacological inhibition of USP7 on the viability of the p53 mutant small cell lung cancer cell line, H526 was further evaluated. The USP7 inhibitors of Examples 31 and 124 significantly inhibited viability of H526 in vitro with a CC$_{50}$ of 500 nM using the CellTiter-Glo assay. In contrast, idasanutlin, whose inhibitory effect is dependent on a functional p53 pathway, had no effect. The Example 124 compound, 3-((7-(5-chloro-3-methyl-2-(((R)-morpholin-2-yl)methyl)phenyl)thieno[3,2-b]pyridin-2-yl)methyl)-6,6-dimethyl-3-azabicyclo[3.1.0]hexane-2,4-dione, did not induce any change in p21 level after 2, 8 or 24 hours of treatment, confirming that the p53 pathway is non-functional in this cell line. Similarly, USP7 inhibition did not reduce MYCN protein levels after 2, 8 or 24 hours of treatment, indicating that although MYCN is amplified in H526 cells, the killing of these cells by USP7 inhibitor was not due to destabilization of MYCN. In vivo, 3-((7-(5-chloro-3-methyl-2-(((R)-morpholin-2-yl)methyl)phenyl)thieno[32-b]pyridin-2-yl)methyl)-6,6-dimethyl-3-azabicyclo[3.1.0]hexane-2,4-dione inhibited tumor growth and prolonged survival in the H526 xenograft model in athymic nude mice, when administered via twice-daily oral dosing at 50 mg/kg (see FIG. 2) or daily oral dosing at 100 mg/kg (data not shown). These doses were well tolerated both in preliminary testing in tumor-free mice and in the tumor-bearing mice used in the study.

Example 283

Tests were conducted to determine whether the USP7 inhibitor 3-((7-(5-chloro-3-methyl-2-(((R)-morpholin-2-yl)methyl)phenyl)thieno[3,2-b]pyridin-2-yl)methyl)-6,6-dimethyl-3-azabicyclo[3.1.0]hexane-2,4-dione potentiates the activity of DNA-damaging agents commonly used for small cell lung cancer chemotherapy, namely carboplatin, doxorubicin, and the PARP inhibitor olaparib. We found modest synergy between the tested USP7 inhibitor and these agents in H526 cells. While the tested USP7 inhibitor alone did not increase levels of phosphorylated histone H2AX (γ-H2AX), a marker of DNA damage, treatment with a combination of this USP7 inhibitor and carboplatin increased γ-H2AX, suggesting that USP7 inhibition could hinder the repair of DNA damage induced by this agent.

Example 284

The effect of combining the USP7 inhibitor 3-((7-(5-chloro-3-methyl-2-(((R)-morpholin-2-yl)methyl)phenyl)thieno[3,2-b]pyridin-2-yl)methyl)-6,6-dimethyl-3-azabicyclo[3.1.0]hexane-2,4-dione with the PIM kinase inhibitor AZD 1208, the PI3K inhibitor pictilisib and the PI3K inhibitor taselisib in the p53 mutant H526 cell line was tested. This USP7 inhibitor strongly synergized with each of AZD 1208, pictilisib and taselisib, suggesting that USP7 functions in a related pathway in these cells. As expected, no synergy was observed when 3-((7-(5-chloro-3-methyl-2-(((R)-morpholin-2-yl)methyl)phenyl)thieno[3,2-b]pyridin-2-yl)methyl)-6,6-dimethyl-3-azabicyclo[3.1.0]hexane-2,4-dione was dosed with itself. Both PIM and PI3K promote the activity of mammalian target of rapamycin (mTOR), which regulates cellular protein translation and controls phosphorylation of S6 at the Ser235/236 site. Treatment with 3-((7-(5-chloro-3-methyl-2-(((R)-morpholin-2-yl)methyl)phenyl)thieno[3,2-b]pyridin-2-yl)methyl)-6,6-dimethyl-3-azabicyclo[3.1.0]hexane-2,4-dione alone decreased levels of phosphorylated S6 (Ser235/236) suggesting that USP7 inhibition might directly affect this pathway.

Example 285

In order to identify pathways impacted by USP7 inhibition, RNASeq was used to profile transcriptomic changes in H526 cells following treatment with the USP7 inhibitor 3-((7-(5-chloro-3-methyl-2-(((R)-morpholin-2-yl)methyl)phenyl)thieno[3,2-b]pyridin-2-yl)methyl)-6,6-dimethyl-3-azabicyclo[3.1.0]hexane-2,4-dione for 24 or 48 hours. These time points were informed by the observation that this USP7 inhibitor induced apoptosis in H526 cells in a dose-dependent manner starting 72 hours post treatment, as measured by caspase-3/7 induction and an increase in the sub-G1 population upon propidium iodide labeling (data not shown). Measurement of transcriptional changes prior to 72 hours should thus uncover programs triggered by USP7 inhibition without being confounded by apoptosis pathways themselves. USP7 inhibitor treatment resulted in upregulation of a large number of genes normally silenced by the polycomb repressive complex 2 (PRC2). PRC2, whose components include the proteins EZH2, SUZ12 and EED, trimethylates histone H3 at lysine 27 (H3K27me3). Gene set enrichment analysis showed that the gene sets listed in Table 5 were all regulated by this pathway.

TABLE 6

Gene sets significantly upregulated upon USP7 inhibitor treatment of H526 cells.

| Pathway | FDR p-value | Number of differentially expressed genes found within gene set |
|---|---|---|
| MEISSNER_BRAIN_HCP_WITH_H3K4ME3_AND_H3K27ME3 | 1.04E−54 | 226 |
| BENPORATH_ES_WITH_H3K27ME3 | 1.75E−47 | 213 |
| BENPORATH_SUZ12_TARGETS | 2.82E−46 | 201 |
| BENPORATH_EED_TARGETS | 2.30E−35 | 185 |
| BENPORATH_PRC2_TARGETS | 1.72E−31 | 131 |
| MEISSNER_NPC_HCP_WITH_H3K4ME2 | 2.40E−28 | 113 |
| MIKKELSEN_MCV6_HCP_WITH_H3K27ME3 | 3.72E−28 | 102 |
| MIKKELSEN_MEF_HCP_WITH_H3K27ME3 | 9.98E−24 | 110 |
| MEISSNER_NPC_HCP_WITH_H3_UNMETHYLATED | 1.46E−23 | 105 |
| MEISSNER_NPC_HCP_WITH_H3K4ME2_AND_H3K27ME3 | 3.68E−23 | 83 |

VI. Embodiments

Embodiment P1

A compound of structural formula I or a pharmaceutically acceptable salt thereof:

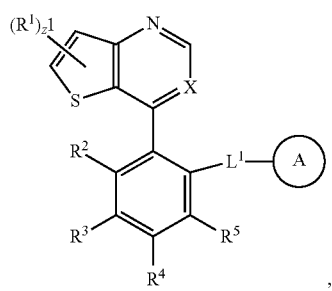

(I)

wherein:

$z^1$ is 0 to 2;

X is N or CH;

$L^1$ is an substituted or unsubstituted alkylene;

Ring A is substituted or unsubstituted cycloalkyl, substituted or unsubstituted heterocycloalkyl, substituted or unsubstituted aryl, or substituted or unsubstituted heteroaryl;

$R^1$ is independently halogen, $-CF_3$, $-CCl_3$, $-CBr_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-CN$, $-N_3$, $-S(O)_{n1}R^{1A}$, $-S(O)_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCH_2R^{1A}$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

wherein if $z^1$ is 2, then the two $R^1$ substituents optionally join together to form a substituted or unsubstituted cycloalkyl, substituted or unsubstituted heterocycloalkyl, substituted or unsubstituted aryl, or or substituted or unsubstituted heteroaryl;

$R^2$ is hydrogen, halogen, $-CF_3$, $-CCl_3$, $-CBr_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-CN$, $-N_3$, $-S(O)_{n2}R^{2A}$, $-S(O)_{v2}NR^{2B}R^{2C}$, $-NHNR^{2B}R^{2C}$, $-ONR^{2B}R^{2C}$, $-NHC(O)NHNR^{2B}R^{2C}$, $-NHC(O)NR^{2B}R^{2C}$, $-N(O)_{m2}$, $-NR^{2B}R^{2C}$, $-C(O)R^{2D}$, $-C(O)OR^{2D}$, $-C(O)NR^{2B}R^{2C}$, $-OR^{2A}$, $-NR^{2B}SO_2R^{2A}$, $-NR^{2B}C(O)R^{2D}$, $-NR^{2B}C(O)OR^{2D}$, $-NR^{2B}OR^{3D}$, $-OCH_2R^{2A}$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-CF_3$, $-CCl_3$, $-CBr_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-CN$, $-N_3$, $-S(O)_{n3}R^{3A}$, $-S(O)_{v3}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m3}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3A}$, $-NR^3BC(O)R^{3D}$, $-NR^3BC(O)OR^{3D}$, $-NR^{3B}OR^{3D}$, $-OCH_2R^{3A}$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, $-CF_3$, $-CCl_3$, $-CBr_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-CN$, $-N_3$, $-S(O)_{n4}R^{4A}$, $-S(O)_{v4}NR^{4B}R^{4C}$, $-NHNR^{4B}R^{4C}$, $-ONR^{4B}R^{4C}$, $-NHC(O)NHNR^{4B}R^{4C}$, $-NHC(O)NR^{4B}R^{4C}$, $-N(O)_{m4}$, $-NR^{4B}R^{4C}$, $-C(O)R^{4D}$, $-C(O)OR^{4D}$, $-C(O)NR^{4B}R^{4C}$, $-OR^{4A}$, $-NR^{4B}SO_2R^{4A}$, $-NR^{4B}C(O)R^{4D}$, $-NR^{4B}C(O)OR^{4D}$, $-NR^{4B}OR^{4D}$, $-OCH_2R^{4A}$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, $-CF_3$, $-CCl_3$, $-CBr_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-CN$, $-N_3$, $-S(O)_{n5}R^{5A}$, $-S(O)_{v5}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m5}$, $-NR^{5B}R^{5D}$, $-C(O)R^{5D}$, $-C(O)OR^{5D}$, $-C(O)NR^{5B}R^{5C}$, —OR$^{5A}$, —NR$^{5B}$SO$_2$R$^{5A}$, —NR$^{5B}$C(O)R$^{5D}$, —NR$^{5B}$C(O)OR$^{5D}$, —NR$^{5B}$OR$^{5D}$, —OCF$_3$, —OCH$_2$R$^{5A}$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, and R$^{5D}$ are independently hydrogen, halogen, —N$_3$, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n1, n2, n3, n4, and n5 are independently an integer from 0 to 4;

v1, v2, v3, v4, and v5 are independently 1 or 2; and m1, m2, m3, m4, and m5 are independently 1 or 2.

Embodiment P2

The compound of embodiment P1, or a pharmaceutically acceptable salt thereof, wherein the compound has the structural formula (Ia):

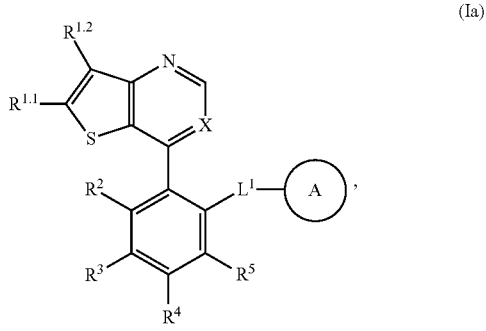

(Ia)

wherein:

R$^{1.1}$ is —CR$^{1A}$R$^{1B}$, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —S(O)$_{n1.1}$R$^{1A}$, —S(O)$_{v1.1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1.1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1.2}$ is hydrogen, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —S(O)$_{n1.2}$R$^{2A}$, —S(O)$_{v1.2}$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m1.2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, and R$^{2D}$ are independently hydrogen, halogen, —N$_3$, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n$^{1.1}$ and n$^{1.2}$ are independently an integer from 0 to 4;

v$^{1.1}$ and v$^{1.2}$ are independently 1 or 2; and m$^{1.1}$ and m$^{1.2}$ are independently 1 or 2.

Embodiment P3

The compound of embodiment P2, or a pharmaceutically acceptable salt thereof, wherein the compound has the structural formula (Ib):

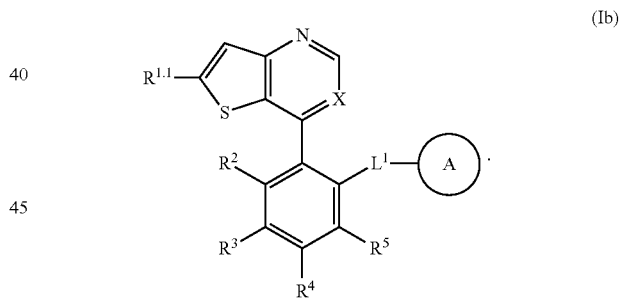

(Ib)

Embodiment P4

The compound of any one of embodiment P1 to P3, wherein R$^1$ is independently —CR$^{1A}$R$^{1B}$.

Embodiment P5

The compound of any one of embodiments P1 to P4, or a pharmaceutically acceptable salt thereof, wherein L$^1$ is a substituted or unsubstituted C$_1$-C$_4$ alkylene.

Embodiment P6

The compound of any one of embodiments P1 to P5, wherein L$^1$ is unsubstituted methylene.

Embodiment P7

The compound of any one of embodiments P1 to P5, wherein $L^1$ is substituted methylene.

Embodiment P8

The compound of embodiment P1 or P3, or a pharmaceutically acceptable salt thereof, wherein $R^1$ is independently

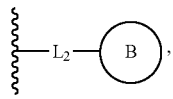

wherein:
$L^2$ is a substituted or unsubstituted alkylene or a bond; and
Ring B is a substituted or unsubstituted cycloalkyl, substituted or unsubstituted heterocycloalkyl, substituted or unsubstituted aryl, or substituted or unsubstituted heteroaryl.

Embodiment P9

The compound of embodiment P8, or a pharmaceutically acceptable salt thereof,
wherein:
Ring B is

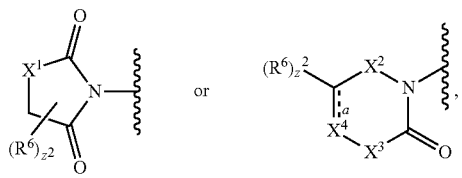

wherein:
a is a bond;
$X^1$ is $CH_2$, $CHR^{11}$, $C(R^{11})_2$, NH, $NR^{11}$, S, or O;
$X^2$ is $CH_2$, $CHR^{11}$, $C(R^{11})_2$, NH, $NR^{11}$, or C=O;
$X^3$ is $CH_2$, $CHR^{11}$, $C(R^{11})_2$, NH, or $NR^{11}$;
$X^4$ is CH, $C(R^{11})$, N, $CH_2$, $CHR^{11}$, $C(R^{11})_2$, O, S, NH or $NR^{10}$;
$z^2$ is an integer from 0 to 2;
$R^6$ is independently halogen, $-N_3$, $-CF_3$, $-CCl_3$, $-CBr_3$, $-CI_3$, $-CN$, $-CHO$, $-OR^{6A}$, $-NR^{6B}R^{6C}$, $-COOR^{6A}$, $-CONR^{6B}R^{6C}$, $-NR^{1B}C(O)R^{1A}$, $-NO_2$, $-S(O)_{n6}R^{6B}$, $-S(O)_{v6}NR^{6B}R^{6C}$, $-NHNR^{6B}R^{6C}$, $-ONR^{6B}R^{6C}$, $-NHC(O)NHNR^{6B}R^{6C}$, $-N(O)_{m6}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two $R^6$ substituents which are bonded to the 5-membered Ring B optionally join together to form a substituted or unsubstituted cycloalkyl, a substituted or unsubstituted heterocycloalkyl, a substituted or unsubstituted aryl or a substituted or unsubstituted heteroaryl; $R^{6B}$ and $R^{6C}$ substituents optionally join together to form a substituted or unsubstituted heterocycloalkyl or substituted or unsubstituted heteroaryl;
$n^6$ is an integer from 0 to 4;
$v^6$ is 1 or 2;
$m^6$ is 1 or 2;
$R^{10}$ is hydrogen or substituted or unsubstituted alkyl; and
$R^{11}$ is hydrogen or substituted or unsubstituted alkyl.

Embodiment P10

The compound of embodiment P8 or P9, or a pharmaceutically acceptable salt thereof, wherein:
Ring B is

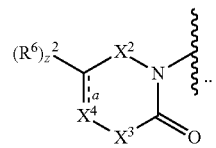

Embodiment P11

The compound of any one of embodiments P8 to P10, or a pharmaceutically acceptable salt thereof, wherein $L^2$ is a substituted $C_1$-$C_4$ alkylene, an unsubstituted $C_1$-$C_4$ alkylene, or a bond.

Embodiment P12

The compound of any one of embodiments P8 to P11, or a pharmaceutically acceptable salt thereof, wherein $L^2$ is a substituted or unsubstituted methylene.

Embodiment P13

The compound of any one of embodiment P8 to P11, or a pharmaceutically acceptable salt thereof, wherein $L^2$ is a bond.

Embodiment P14

The compound of any one of embodiments P8 to P13, or a pharmaceutically acceptable salt thereof, wherein the compound has the structural formula (IIa) or (IIb):

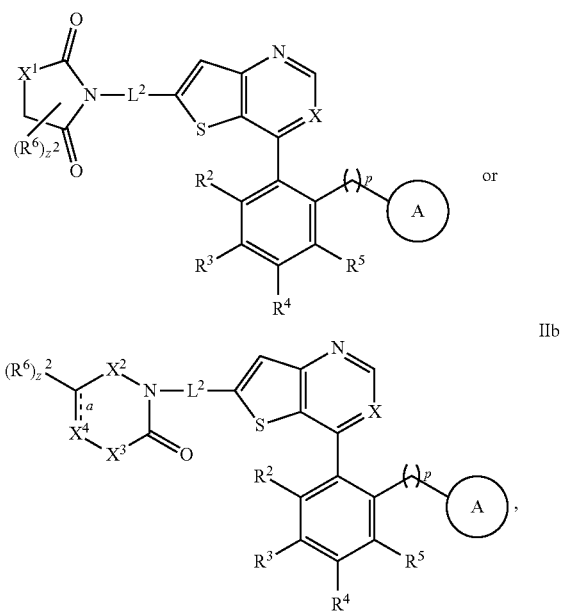

wherein:
  p is an integer from 0 to 2; and
  $L^2$ is a substituted or unsubstituted methylene.

Embodiment P15

The compound of embodiment P14, or a pharmaceutically acceptable salt thereof, wherein:
  $R^2$ is hydrogen;
  $R^3$ is substituted or unsubstituted $C_1$-$C_8$ alkyl, halogen, or CN;
  $R^4$ is hydrogen or halogen;
  $R^5$ is substituted or unsubstituted $C_1$-$C_8$ alkyl, unsubstituted $C_3$-$C_8$ cycloalkyl, halogen or CN; and
  $R^6$ is independently halogen, substituted or unsubstituted $C_1$-$C_8$ alkyl, unsubstituted $C_3$-$C_8$ cycloalkyl, unsubstituted 3 to 7 membered heterocycloalkyl, unsubstituted $C_5$-$C_6$ aryl, unsubstituted 5 to 6 membered heteroaryl, or two $R^6$ substituents optionally join together to form a substituted or unsubstituted cycloalkyl, a substituted or unsubstituted heterocycloalkyl, a substituted or unsubstituted aryl, or a substituted or unsubstituted heteroaryl.

Embodiment P16

The compound of embodiment P14 or P15, wherein p is 1.

Embodiment P17

The compound of any one of embodiments P0 to P14 having structural formula (IIc) or (IId):

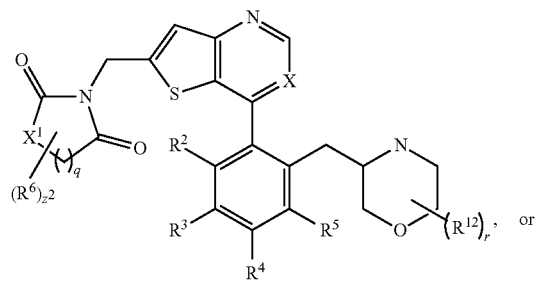

(IIc)

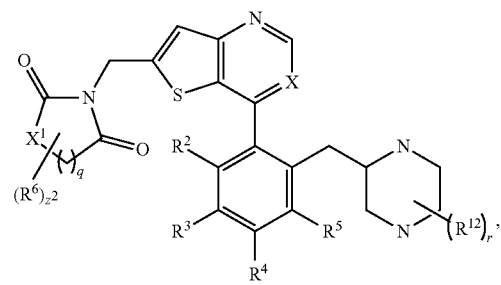

(IId)

wherein:
  $R^{12}$ is hydrogen or substituted or unsubstituted alkyl;
  q is 1 or 2; and
  r is 1 or 2.

Embodiment P18

The compound of any one of embodiments P8 to P17, or a pharmaceutically acceptable salt thereof, wherein $R^3$ is a halogen and $R^5$ is unsubstituted $C_1$-$C_5$ alkyl.

Embodiment P19

The compound of any one of embodiment P8 to P18, or a pharmaceutically acceptable salt thereof, wherein $R^3$ is a halogen and $R^5$ is unsubstituted $C_1$-$C_3$ alkyl.

Embodiment P20

The compound of any one of embodiments P8 to P19, or a pharmaceutically acceptable salt thereof, wherein $R^3$ is Cl.

Embodiment P21

The compound of any one of embodiments P8 to P20, or a pharmaceutically acceptable salt thereof, wherein $R^5$ is unsubstituted $C_1$-$C_8$ alkyl or unsubstituted $C_3$-$C_8$ cycloalkyl.

Embodiment P22

The compound of any one of embodiments P8 to P21, or a pharmaceutically acceptable salt thereof, wherein $R^5$ is independently halogen, unsubstituted methyl, unsubstituted ethyl, or unsubstituted cyclopropyl.

Embodiment P23

The compound of any one of embodiments P8 to P22, or a pharmaceutically acceptable salt thereof, wherein $R^3$ is CN.

Embodiment P24

The compound of any one of embodiment P8 to P23, or a pharmaceutically acceptable salt thereof, wherein $R^4$ is hydrogen.

Embodiment P25

The compound of any one of embodiments P8 to P24, or a pharmaceutically acceptable salt thereof, wherein each $R^6$ is independently halogen.

Embodiment P26

The compound of any one of embodiments P9 to P24, or a pharmaceutically acceptable salt thereof, wherein each $R^6$ is independently F, Cl, or Br.

Embodiment P27

The compound of any one of embodiments P8 to P24, or a pharmaceutically acceptable salt thereof, wherein each $R^6$ is independently substituted or unsubstituted $C_1$-$C_8$ alkyl.

Embodiment P28

The compound of any one of embodiments P8 to P24, or a pharmaceutically acceptable salt thereof, wherein each $R^6$ is independently unsubstituted methyl or substituted ethyl.

Embodiment P29

The compound of any one of embodiments P8 to P24, or a pharmaceutically acceptable salt thereof, wherein two $R^6$ moieties bonded to adjacent carbon atoms on the B ring join to form a substituted or unsubstituted cycloalkyl.

Embodiment P30

The compound of any one of embodiments P8 to P24, or a pharmaceutically acceptable salt thereof, wherein the two $R^6$ moieties are joined to form a substituted or unsubstituted $C_3$-$C_4$ cycloalkyl.

Embodiment P31

The compound of any one of embodiments P8 to P24, or a pharmaceutically acceptable salt thereof, wherein $R^6$ is independently an unsubstituted $C_3$-$C_8$ cycloalkyl, unsubstituted 3 to 7 membered heterocycloalkyl, or unsubstituted 5 to 6 membered heteroaryl, or two $R^6$ substituents optionally join together to form a substituted or unsubstituted cycloalkyl, a substituted or unsubstituted heterocycloalkyl, a substituted or unsubstituted aryl, or a substituted or unsubstituted heteroaryl.v

Embodiment P32

The compound of any one of embodiments P8 to P24, or a pharmaceutically acceptable salt thereof, wherein $R^6$ is independently unsubstituted cyclopropyl, unsubstituted cyclopentyl, unsubstituted cyclohexyl, unsubstituted piperidinyl, unsubstituted pyrrolidinyl, unsubstituted oxetanyl, or unsubstituted phenyl.

Embodiment P33

The compound of any one of embodiments P1 to P32, or a pharmaceutically acceptable salt thereof, wherein each $R^1$ is independently substituted alkyl.

Embodiment P34

The compound of any one of embodiments P1 to P33 or a pharmaceutically acceptable salt thereof, wherein each $R^1$ is independently substituted $C_1$-$C_8$ alkyl.

Embodiment P35

The compound of any one of embodiments P1 to P34, or a pharmaceutically acceptable salt thereof, wherein each $R^1$ is independently hydroxyl-substituted methyl, hydroxyl-substituted ethyl, or hydroxyl-substituted propyl.

Embodiment P36

The compound of any one of embodiments P1 to P35, or a pharmaceutically acceptable salt thereof, wherein each $R^1$ is independently methyl substituted with —NH—$SO_2CH_3$ or ethyl substituted with —NH—$SO_2CH_3$.

Embodiment P37

The compound of any one of embodiments P1 to P36, or a pharmaceutically acceptable salt thereof, wherein each $R^1$ is independently methyl substituted with —NH—C(O)$CH_3$ or ethyl substituted with —NH—C(O)$CH_3$.

Embodiment P38

The compound of any one of embodiments P1 to P37, or a pharmaceutically acceptable salt thereof, wherein:
Ring A is $R^7$-substituted or unsubstituted $C_3$-$C_8$ cycloalkyl or $R^7$-substituted or unsubstituted 3 to 7 membered heterocycloalkyl;
$R^7$ is halogen, —$CF_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^8$-substituted or unsubstituted $C_1$-$C_8$ alkyl, $R^8$-substituted or unsubstituted 2 to 8 membered heteroalkyl, $R^8$-substituted or unsubstituted $C_3$-$C_8$ cycloalkyl, $R^8$-substituted or unsubstituted 3 to 7 membered heterocycloalkyl, $R^8$-substituted or unsubstituted $C_5$-$C_6$ aryl, or $R^8$-substituted or unsubstituted 5 to 6 membered heteroaryl; and
$R^8$ is halogen, —$CF_3$, $CCl_3$, $CBr3$, $Cl3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_5$ alkyl, unsubstituted 2 to 8 membered heteroalkyl, unsubstituted $C_3$-$C_8$ cycloalkyl, unsubstituted 3 to 7 membered heterocycloalkyl, unsubstituted $C_5$-$C_6$ aryl, or unsubstituted 5 to 6 membered heteroaryl.

Embodiment P39

The compound of any one of embodiments P1 to P38, or a pharmaceutically acceptable salt thereof, wherein ring A is $R^7$-substituted or unsubstituted $C_3$-$C_8$ cycloalkyl.

Embodiment P40

The compound of any one of embodiments P1 to P39, or a pharmaceutically acceptable salt thereof, wherein:
ring A is $R^7$-substituted or unsubstituted cyclopentyl or $R^7$-substituted or unsubstituted cyclohexyl; and
$R^7$ is —$NH_2$ or unsubstituted azetidinyl.

Embodiment P41

The compound of any one of embodiments P1 to P40, or a pharmaceutically acceptable salt thereof, wherein ring A is $R^7$-substituted or unsubstituted 3 to 7 membered heterocycloalkyl.

Embodiment P42

The compound of any one of embodiments P1 to P40, or a pharmaceutically acceptable salt thereof, wherein:
ring A is $R^7$-substituted or unsubstituted azetidinyl, $R^7$-substituted or unsubstituted pyrrolidinyl, unsubstituted piperazinyl, $R^7$-substituted or unsubstituted piperidinyl, unsubstituted morpholinyl, unsubstituted azepanyl, or unsubstituted oxoazepanyl; and
$R^7$ is unsubstituted methyl, unsubstituted ethyl, unsubstituted isopropyl, unsubstituted cyclopropyl, F, —$CF_3$, $N_3$, —NH₂, —NHC(O), —OH, —CHF₂, —CH₂F, —O—CH₃, —O—CH₂CH₃, —CH₂CH₂CH₂OH, —CH₂OH, unsubstituted azetidinyl, or unsubstituted oxetanyl.

Embodiment P43

A compound selected from:

3-((7-(5-chloro-2-(((2S,6S)-2,6-dimethylpiperazin-1-yl)methyl)-3-methylphenyl)thieno[3,2-b]pyridin-2-yl)methyl)-3-azabicyclo[3.1.0]hexane-2,4-dione having the structure:

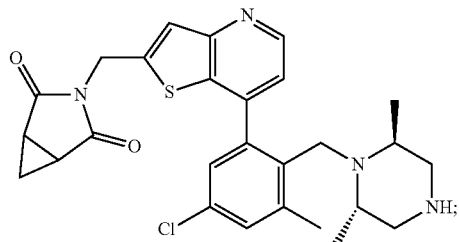

3-((4-(5-chloro-2-(((2S,6S)-2,6-dimethylpiperazin-1-yl)methyl)-3-methylphenyl)thieno[3,2-d]pyrimidin-6-yl)methyl)-3-azabicyclo[3.1.0]hexane-2,4-dione having the structure:

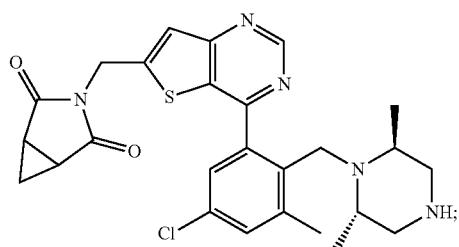

3-((7-(5-chloro-3-methyl-2-(((R)-morpholin-2-yl)methyl)phenyl)thieno[3,2-b]pyridin-2-yl)methyl)-6,6-dimethyl-3-azabicyclo[3.1.0]hexane-2,4-dione having the structure:

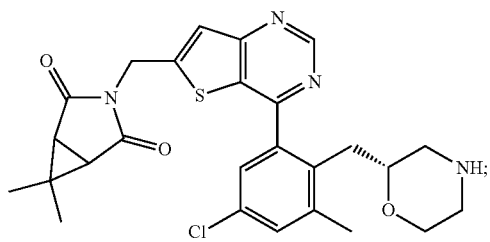 [SMILES: Cc1cc(Cl)cc(-c2ncnc3cc(CN4C(=O)C5C(C4=O)C5(C)C)sc23)c1C[C@@H]1CNCCO1]

3-((4-(5-chloro-2-(((R)-6,6-dimethylmorpholin-2-yl)methyl)-3-methylphenyl)thieno[3,2-d]pyrimidin-6-yl)methyl)-3-azabicyclo[3.1.0]hexane-2,4-dione having the structure:

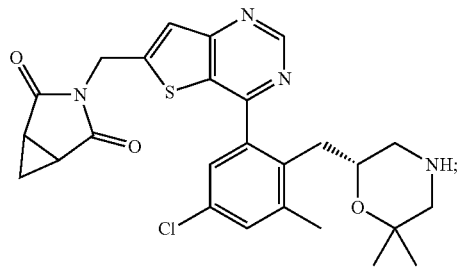 [SMILES: Cc1cc(Cl)cc(-c2ncnc3cc(CN4C(=O)C5CC5C4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)-1-methylpyrimidine-2,4(1H,3H)-dione having the structure:

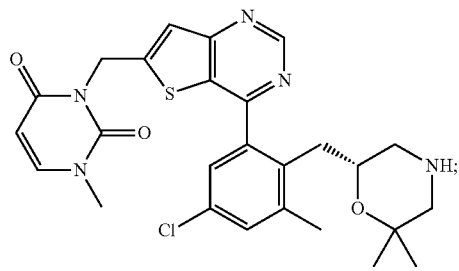 [SMILES: Cc1cc(Cl)cc(-c2ncnc3cc(Cn4c(=O)ccn(C)c4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)-1-(2,2,2-trifluoroethyl)dihydropyrimidine-2,4(1H,3H)-dione having the structure:

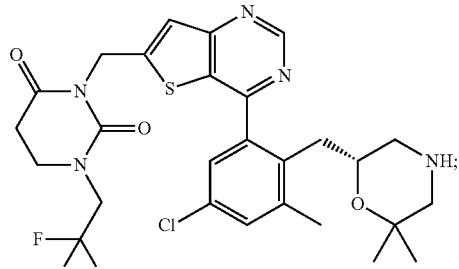

(R)-3-((4-(5-chloro-2-((6,6-dimethylmorpholin-2-yl)methyl)-3-methylphenyl)thieno[3,2-d]pyrimidin-6-yl)methyl)-1-(2,2-difluoroethyl)dihydropyrimidine-2,4(1H,3H)-dione having the structure:

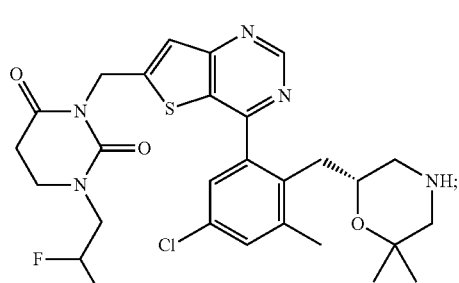

3-((4-(3,5-dichloro-2-((6,6-dimethylmorpholin-2-yl)methyl)phenyl)thieno[3,2-d]pyrimidin-6-yl)methyl)-1-methylpyrimidine-2,4(1H,3H)-dione having the structure:

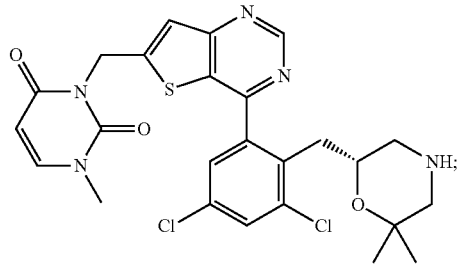 [SMILES: Cn1ccc(=O)n(Cc2cc3ncnc(-c4cc(Cl)cc(Cl)c4C[C@@H]4CNCC(C)(C)O4)c3s2)c1=O]

3-[[4-[5-chloro-2-[[(2R)-6,6-dimethylmorpholin-2-yl]methyl]-3-methyl-phenyl] thieno[3,2-d]pyrimidin-6-yl]methyl]-1-(2-fluoroethyl)hexahydropyrimidine-2,4-dione having the structure:

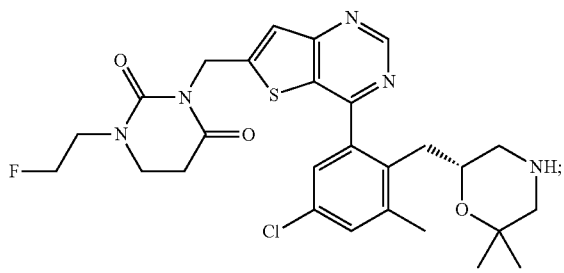 [SMILES: Cc1cc(Cl)cc(-c2ncnc3cc(CN4C(=O)CCN(CCF)C4=O)sc23)c1C[C@@H]1CNCC(C)(C)O1]

3-[[4-[5-chloro-2-[[(2S,6S)-2,6-dimethylpiperazin-1-yl]methyl]-3-methyl-phenyl] thieno[3,2-d]pyrimidin-6-yl]methyl]-1-(2-fluoroethyl)hexahydropyrimidine-2,4-dione having the structure:

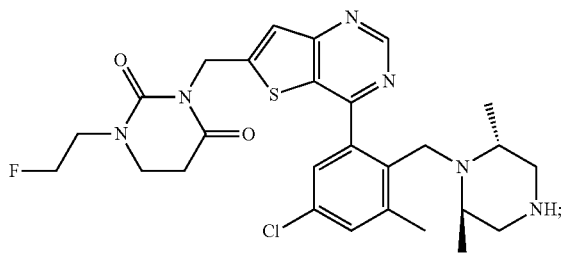 [SMILES: Cc1cc(Cl)cc(-c2ncnc3cc(CN4C(=O)CCN(CCF)C4=O)sc23)c1CN1[C@H](C)CNC[C@H]1C]

3-[[4-[5-chloro-2-[[(2S,6S)-2,6-dimethylpiperazin-1-yl]methyl]-3-methyl-phenyl] thieno[3,2-d]pyrimidin-6-yl]methyl]-1-(2,2-difluoroethyl)hexahydropyrimidine-2,4-dione having structure:

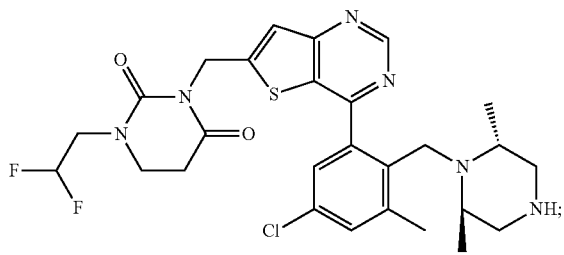

3-[[4-[5-chloro-2-[[(2S,6S)-2,6-dimethylpiperazin-1-yl]methyl]-3-methyl-phenyl] thieno[3,2-d]pyrimidin-6-yl]methyl]-1-(2,2,2-trifluoroethyl)hexahydropyrimidine-2,4-dione having the structure:

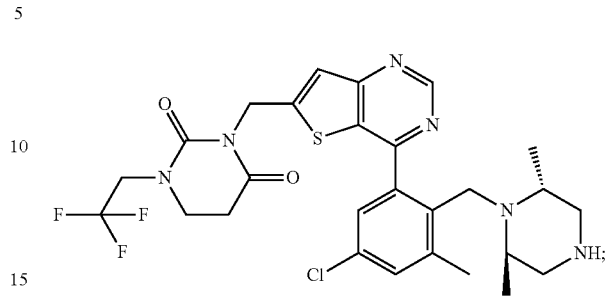

3-((7-(5-chloro-2-(((R)-6,6-dimethylmorpholin-2-yl)methyl)-3-methylphenyl)thieno[3,2-b]pyridin-2-yl)methyl)-3-azabicyclo[3.1.0]hexane-2,4-dione having the structure:

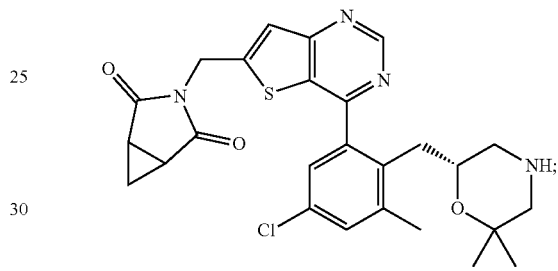

(R)-1-((4-(5-chloro-2-((6,6-dimethylmorpholin-2-yl)methyl)-3-methylphenyl)thieno[3,2-d]pyrimidin-6-yl)methyl)pyrrolidine-2,5-dione having the structure:

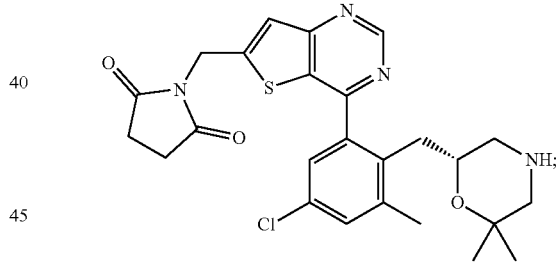

and (R)-3-((4-(5-chloro-2-((6,6-dimethylmorpholin-2-yl)methyl)-3-methylphenyl)thieno[3,2-d]pyrimidin-6-yl)methyl)-1-methyldihydropyrimidine-2,4(1H,3H)-dione having the structure:

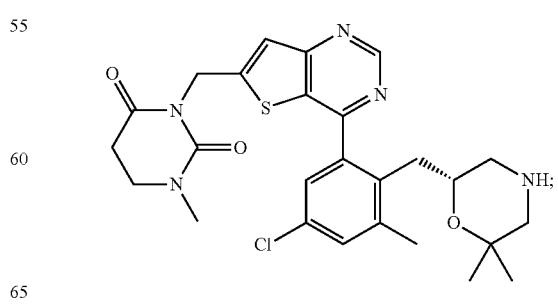

or a pharmaceutically acceptable salt thereof.

263

Embodiment P44

A pharmaceutical composition comprising a compound of any one of embodiments 1-43, and a pharmaceutically acceptable excipient.

Embodiment P45

The pharmaceutical composition of embodiment P44 for use in treating cancer, wherein the cancer is a cancer modulated by ubiquitin specific protease 7 (USP7) inhibitors.

Embodiment P46

The pharmaceutical composition of embodiment P44 or P45 for use in treating solid and/or blood cancer, including ovarian cancer, breast cancer, lung cancer, pancreatic cancer, kidney cancer, melanoma, liver cancer, colon cancer, sarcoma, brain cancer, prostate cancer, leukemia, lymphoma, or multiple myeloma.

Embodiment P47

A method of treating cancer comprising administering to a subject in need thereof a therapeutically effective amount of a compound of any one of embodiments 1 to 43.

Embodiment P48

The method of embodiment P47 comprising administering to the subject in need thereof an anti-cancer therapeutic agent.

Embodiment P49

The method of embodiment P46, wherein the cancer is a solid tumor or a blood cancer.

Embodiment P50

The method of embodiment P49, wherein the solid tumor is ovarian cancer, breast cancer, lung cancer, pancreatic cancer, kidney cancer, melanoma, liver cancer, colon cancer, sarcoma, brain cancer, or prostate cancer.

Embodiment P51

The method of embodiment P49, wherein the blood cancer is leukemia, lymphoma, or multiple myeloma.

Embodiment P52

The pharmaceutical composition of embodiment P44 for use in treating cancer, wherein the cancer is a cancer experiencing gene silencing via polycomb repressive complex 2 (PRC2).

Embodiment P53

A method of treating a patient having a cancer experiencing gene silencing via polycomb repressive complex 2 (PRC2), comprising administering to the patient a therapeutically effective amount of a ubiquitin specific protease 7 (USP7) inhibitor.

Embodiment P54

The method of embodiment 53, wherein the USP7 inhibitor is a compound of embodiment 1.

Embodiment P55

The method of embodiment 54, wherein the USP7 inhibitor is co-administered with at least one of a histone deacetylase (HDAC) inhibitor, a proteasome inhibitor, a BET inhibitor and/or a B-cell lymphoma 2 (Bcl-2) inhibitor.

What is claimed is:
1. A compound of structural formula I:

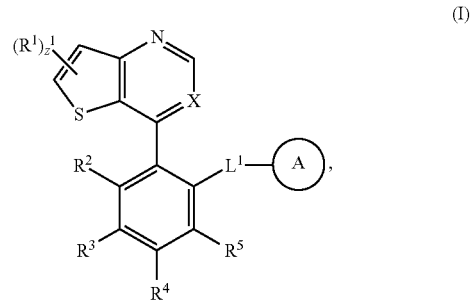

(I)

or a pharmaceutically acceptable salt thereof:
wherein:
$z^1$ is 0 to 2;
X is N or CH;
$L^1$ is an substituted or unsubstituted alkylene;
Ring A is substituted or unsubstituted cycloalkyl, substituted or unsubstituted heterocycloalkyl, substituted or unsubstituted aryl, or substituted or unsubstituted heteroaryl;
$R^1$ is independently halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —$S(O)_{n1}R^{1A}$, —$S(O)_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCH_2R^{1A}$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein if $z^1$ is 2, then the two $R^1$ substituents optionally join together to form a substituted or unsubstituted cycloalkyl, substituted or unsubstituted heterocycloalkyl, substituted or unsubstituted aryl, or substituted or unsubstituted heteroaryl;
$R^2$ is hydrogen, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —$S(O)_{n2}R^{2A}$, —$S(O)_{v2}NR^{2B}R^{2C}$, —$NHNR^{2B}R^{2C}$, —$ONR^{2B}R^{2C}$, —$NHC(O)NHNR^{2B}R^{2C}$, —NHC(O)

NR²ᴮR²ᶜ, —N(O)ₘ₂, —NR²ᴮR²ᶜ, —C(O)R²ᴰ, —C(O)OR²ᴰ, —C(O)NR²ᴮR²ᶜ, —OR²ᴬ, —NR²ᴮSO₂R²ᴬ, —NR²ᴮC(O)R²ᴰ, —NR²ᴮC(O)OR²ᴰ, —NR²ᴮOR³ᴰ, —OCH₂R²ᴬ, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R³ is hydrogen, halogen, —CF₃, —CCl₃, —CBr₃, —CI₃, —CHF₂, —CHCl₂, —CHBr₂, —CHI₂, —CH₂F, —CH₂Cl, —CH₂Br, —CH₂I, —CN, —N₃, —S(O)ₙ₃R³ᴬ, —S(O)ᵥ₃NR³ᴮR³ᶜ, —NHNR³ᴮR³ᶜ, —ONR³ᴮR³ᶜ, —NHC(O)NHNR³ᴮR³ᶜ, —NHC(O)NR³ᴮR³ᶜ, —N(O)ₘ₃, —NR³ᴮR³ᶜ, —C(O)R³ᴰ, —C(O)OR³ᴰ, —C(O)NR³ᴮR³ᶜ, —OR³ᴬ, —NR³ᴮSO₂R³ᴬ, —NR³ᴮC(O)R³ᴰ, —NR³ᴮC(O)OR³ᴰ, —NR³ᴮOR³ᴰ, —OCH₂R³ᴬ, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁴ is hydrogen, halogen, —CF₃, —CCl₃, —CBr₃, —CI₃, —CHF₂, —CHCl₂, —CHBr₂, —CHI₂, —CH₂F, —CH₂Cl, —CH₂Br, —CH₂I, —CN, —N₃, —S(O)ₙ₄R⁴ᴬ, —S(O)ᵥ₄NR⁴ᴮR⁴ᶜ, —NHNR⁴ᴮR⁴ᶜ, —ONR⁴ᴮR⁴ᶜ, —NHC(O)NHNR⁴ᴮR⁴ᶜ, —NHC(O)NR⁴ᴮR⁴ᶜ, —N(O)ₘ₄, —NR⁴ᴮR⁴ᶜ, —C(O)R⁴ᴰ, —C(O)OR⁴ᴰ, —C(O)NR⁴ᴮR⁴ᶜ, —OR⁴ᴬ, —NR⁴ᴮSO₂R⁴ᴬ, —NR⁴ᴮC(O)R⁴ᴰ, —NR⁴ᴮC(O)OR⁴ᴰ, —NR⁴ᴮOR⁴ᴰ, —OCH₂R⁴ᴬ, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, substituted or unsubstituted alkyl, substituted or unsubstituted heteroalkyl, substituted or unsubstituted Response to Communication with Examiner cycloalkyl, substituted or unsubstituted heterocycloalkyl, substituted or unsubstituted aryl, or substituted or unsubstituted heteroaryl;

R⁵ is hydrogen, halogen, —CF₃, —CCl₃, —CBr₃, —CI₃, —CHF₂, —CHCl₂, —CHBr₂, —CHI₂, —CH₂F, —CH₂Cl, —CH₂Br, —CH₂I, —CN, —N₃, —S(O)ₙ₅R⁵ᴬ, —S(O)₅NR⁵ᴮR⁵ᶜ, —NHNᴿᴮR⁵ᶜ, —ONR⁵ᴮR⁵ᶜ, —NHC(O)NHNR⁵ᴮR⁵ᶜ, —NHC(O)NR⁵ᴮR⁵ᶜ, —N(O)ₘ₅, —NR⁵ᴮR⁵ᶜ, —C(O)R⁵ᴰ, —C(O)OR⁵ᴰ, —C(O)NR⁵ᴮR⁵ᶜ, —OR⁵ᴬ, —NR⁵ᴮSO₂R⁵ᴬ, —NR⁵ᴮC(O)R⁵ᴰ, —NR⁵ᴮC(O)OR⁵ᴰ, —NR⁵ᴮOR⁵ᴰ, —OCF₃, —OCH₂R⁵ᴬ, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, and $R^{5D}$ are independently hydrogen, halogen, —N₃, —CF₃, —CCl₃, —CBr₃, —CI₃, —CH₂Cl, —CH₂Br, —CH₂F, —CH₂I, —CHCl₂, —CHBr₂, —CHF₂, —CHI₂, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n1, n2, n3, n4, and n5 are independently an integer from 0 to 4;

v1, v2, v3, v4, and v5 are independently 1 or 2; and m1, m2, m3, m4, and m5 are independently 1 or 2.

2. The compound of claim 1, wherein the compound has the structural formula (Ia):

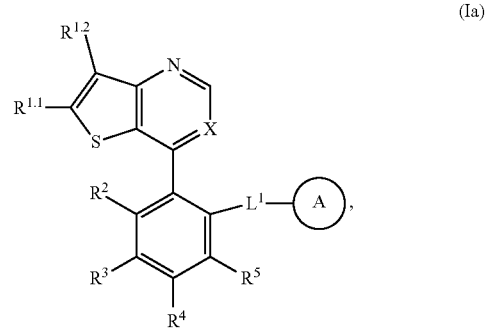

(Ia)

wherein:

$R^{1.1}$ is —CR$^{1A}$R$^{1B}$, halogen, —CF₃, —CCl₃, —CBr₃, —CI₃, —CHF₂, —CHCl₂, —CHBr₂, —CHI₂, —CH₂F, —CH₂Cl, —CH₂Br, —CH₂I, —CN, —N₃, —S(O)$_{m1.1}$R$^{1A}$, —S(O)$_{v1.1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1.1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO₂R$^{1A}$, —NR$^{1B}$C(O)R$^{1D}$, —NR$^{1B}$C(O)OR$^{1D}$, —NR$^{1B}$OR$^{1D}$, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1.2}$ is hydrogen, halogen, —CF₃, —CCl₃, —CBr₃, —CI₃, —CHF₂, —CHCl₂, —CHBr₂, —CHI₂, —CH₂F, —CH₂Cl, —CH₂Br, —CH₂I, —CN, —N₃, —S(O)$_{m1.2}$R$^{2A}$, —S(O)$_{v1.2}$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m1.2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO₂R$^{2A}$, —NR$^{2B}$C(O)R$^{2D}$, —NR$^{2B}$C(O)OR$^{2D}$, —NR$^{2B}$OR$^{2D}$, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, and $R^{2D}$ are independently hydrogen, halogen, —N₃, —CF₃, —CCl₃, —CBr₃, —CI₃, —CH₂Cl, —CH₂Br, —CH₂F, —CH₂I, —CHCl₃, —CHBr₂, —CHF₂, —CHI₂, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHSO₂H, —NHC(O)H, —NHC(O)—OH, —NHOH, —OCF₃, —OCCl₃, —OCBr₃, OCI₃, —OCHF₂, —OCHCl₂, —OCHBr₂, —OCHI₂, —OCH₂F, —OCH₂Cl, —OCH₂Br, —OCH₂I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n1.1 and n1.2 are independently an integer from 0 to 4;

v1.1 and v1.2 are independently 1 or 2; and m1.1 and m1.2 are independently 1 or 2.

3. The compound of claim 2, wherein the compound has the structural formula (Ib):

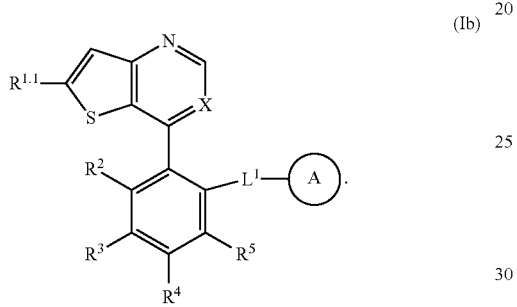

4. The compound of claim 1, wherein R¹ is —CR^{1A}R^{1B}.

5. The compound of claim 1, wherein L¹ is a substituted or unsubstituted C₁-C₄ alkylene.

6. The compound of claim 5, wherein L¹ is unsubstituted methylene.

7. The compound of claim 5, wherein L¹ is substituted methylene.

8. The compound of claim 1, wherein R¹ is independently

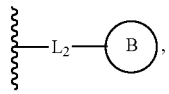

wherein:

L² is a substituted or unsubstituted alkylene or a bond; and

Ring B is a substituted or unsubstituted cycloalkyl, substituted or unsubstituted heterocycloalkyl, substituted or unsubstituted aryl, or substituted or unsubstituted heteroaryl.

9. The compound of claim 8, wherein:

Ring B is

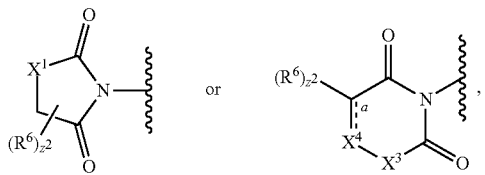

wherein:

a is a bond;

X¹ is CH₂, CHR¹¹, C(R¹¹)₂, NH, NR¹¹, S, or O;

X² is CH₂, CHR¹¹, C(R¹¹)₂, NH, NR¹¹, or C═O;

X³ is CH₂, CHR¹¹, C(R¹¹)₂, NH, or NR¹¹;

X⁴ is CH, C(R¹¹), N, CH₂, CHR¹¹, C(R¹¹)₂, O, S, NH or NR¹¹;

z² is an integer from 0 to 2;

R⁶ is independently halogen, —N₃, —CF₃, —CCl₃, —CBr₃, —CI₃, —CN, —CHO, —OR^{6A}, —NR^{6B}R^{6C}, —COOR^{6A}, —CONR^{6B}R^{6C}, —NR^{6AB}C(O)R^{6AA}, —NO₂, —S(O)_{n6}R^{6B}, —S(O)_{v6}NR^{6B}R^{6C}, —NHNR^{6B}R^{6C}, —ONR^{6B}R^{6C}, —NHC(O)NHNR^{6B}R^{6C}, —N(O)_{m6}, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two R⁶ substituents which are bonded to the 5-membered Ring B optionally join together to form a substituted or unsubstituted cycloalkyl, a substituted or unsubstituted heterocycloalkyl, a substituted or unsubstituted aryl or a substituted or unsubstituted heteroaryl; R^{6B} and R^{6C} substituents optionally join together to form a substituted or unsubstituted heterocycloalkyl or substituted or unsubstituted heteroaryl;

n6 is an integer from 0 to 4;

v6 is 1 or 2;

m6 is 1 or 2; and

R¹¹ is hydrogen or substituted or unsubstituted alkyl.

10. The compound of claim 9, wherein:

Ring B is

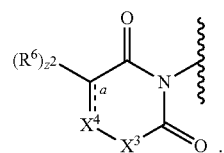

11. The compound of claim 8, wherein L² is a substituted C₁-C₄ alkylene, an unsubstituted C₁-C₄ alkylene, or a bond.

12. The compound of claim 11, wherein L² is a substituted or unsubstituted methylene.

13. The compound of claim 11, wherein L² is a bond.

14. The compound of claim 9, wherein the compound has the structural formula (IIa) or (IIb):

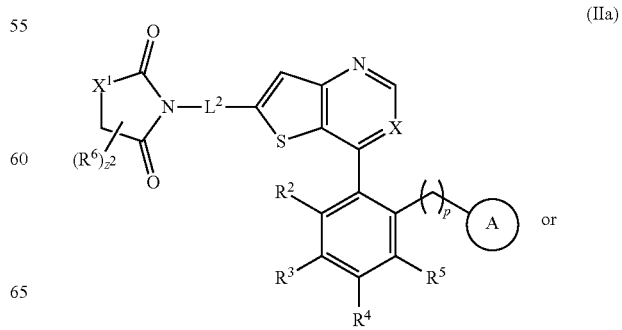

(IIb)

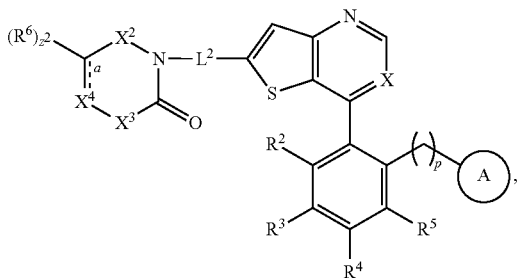

wherein:
p is an integer from 0 to 2; and
$L^2$ is a substituted or unsubstituted methylene.

15. The compound of claim 14, wherein:
$R^2$ is hydrogen;
$R^3$ is substituted or unsubstituted $C_1$-$C_8$ alkyl, halogen, or CN;
$R^4$ is hydrogen or halogen;
$R^5$ is substituted or unsubstituted $C_1$-$C_8$ alkyl, unsubstituted $C_3$-$C_8$ cycloalkyl, halogen or CN; and
$R^6$ is independently halogen, substituted or unsubstituted $C_1$-$C_8$ alkyl, unsubstituted $C_3$-$C_8$ cycloalkyl, unsubstituted 3 to 7 membered heterocycloalkyl, unsubstituted $C_5$-$C_6$ aryl, unsubstituted 5 to 6 membered heteroaryl, or two $R^6$ substituents optionally join together to form a substituted or unsubstituted cycloalkyl, a substituted or unsubstituted heterocycloalkyl, a substituted or unsubstituted aryl or a substituted or unsubstituted heteroaryl.

16. The compound of claim 14, wherein p is 1.
17. The compound of claim 9 having structural formula (IIc) or (IId):

(IIc)

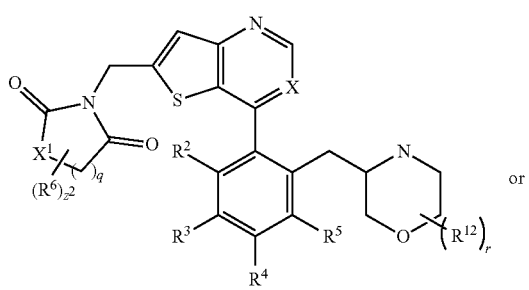

or (IId)

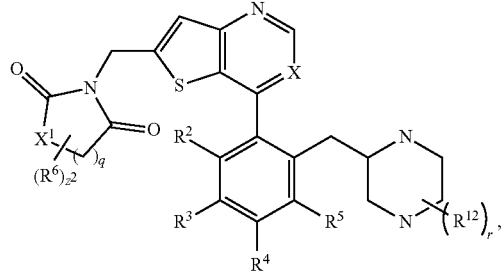

wherein:
$R^{12}$ is hydrogen or substituted or unsubstituted alkyl;
q is 1 or 2; and
r is 1 or 2.

18. The compound of claim 15, wherein $R^3$ is a halogen and $R^5$ is unsubstituted $C_1$-$C_5$ alkyl.
19. The compound of claim 18, wherein $R^3$ is a halogen and $R^5$ is unsubstituted $C_1$-$C_3$ alkyl.
20. The compound of claim 19, wherein $R^3$ is Cl.
21. The compound of claim 15, wherein $R^5$ is unsubstituted $C_1$-$C_8$ alkyl or unsubstituted $C_3$-$C_8$ cycloalkyl.
22. The compound of claim 15, wherein $R^5$ is independently halogen, unsubstituted methyl, unsubstituted ethyl, or unsubstituted cyclopropyl.
23. The compound of claim 15, wherein $R^3$ is CN.
24. The compound of claim 15, wherein $R^4$ is hydrogen.
25. The compound of claim 15, wherein each $R^6$ is independently halogen.
26. The compound of claim 25, wherein each $R^6$ is independently F, Cl, or Br.
27. The compound of claim 15, wherein each $R^6$ is independently substituted or unsubstituted $C_1$-$C_8$ alkyl.
28. The compound of claim 27, wherein each $R^6$ is independently unsubstituted methyl or substituted ethyl.
29. The compound of claim 15, wherein two $R^6$ moieties bonded to adjacent carbon atoms on the B ring join to form a substituted or unsubstituted cycloalkyl.
30. The compound of claim 29, wherein the two $R^6$ moieties are joined to form a substituted or unsubstituted $C_3$-$C_4$ cycloalkyl.
31. The compound of claim 15, wherein $R^6$ is independently an unsubstituted $C_3$-$C_8$ cycloalkyl, unsubstituted 3 to 7 membered heterocycloalkyl, unsubstituted 5 to 6 membered heteroaryl, or two $R^6$ substituents optionally join together to form a substituted or unsubstituted cycloalkyl, a substituted or unsubstituted heterocycloalkyl, a substituted or unsubstituted aryl or a substituted or unsubstituted heteroaryl.
32. The compound of claim 31, wherein $R^6$ is independently unsubstituted cyclopropyl, unsubstituted cyclopentyl, unsubstituted cyclohexyl, unsubstituted piperidinyl, unsubstituted pyrrolidinyl, unsubstituted oxetanyl, or unsubstituted phenyl.
33. The compound of claim 1, wherein each $R^1$ is independently substituted alkyl.
34. The compound of claim 33, wherein each $R^1$ is independently substituted $C_1$-$C_8$ alkyl.
35. The compound of claim 34, wherein each $R^1$ is independently hydroxyl-substituted methyl, hydroxyl-substituted ethyl, or hydroxyl-substituted propyl.
36. The compound of claim 34, wherein each $R^1$ is independently methyl substituted with —NH—$SO_2CH_3$ or ethyl substituted with —NH—$SO_2CH_3$.
37. The compound of claim 34, wherein each $R^1$ is independently methyl substituted with —NH—C(O)$CH_3$ or ethyl substituted with —NH—C(O)$CH_3$.
38. The compound of claim 14, wherein:
Ring A is $R^7$-substituted or unsubstituted $C_3$-$C_8$ cycloalkyl or $R^7$-substituted or unsubstituted 3 to 7 membered heterocycloalkyl;
$R^7$ is halogen, —$CF_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^8$-substituted or unsubstituted $C_1$-$C_8$ alkyl, $R^8$-substituted or unsubstituted 2 to 8 membered heteroalkyl, $R^8$-substituted or unsubstituted $C_3$-$C_8$ cycloalkyl, $R^8$-substituted or unsubstituted 3 to 7 membered heterocycloalkyl, $R^8$-substituted or unsubstituted $C_5$-$C_6$ aryl, or $R^8$-substituted or unsubstituted 5 to 6 membered heteroaryl; and $R^8$ is halogen, —$CF_3$, $CCl_3$, $CBr_3$, $CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_8$ alkyl, unsubstituted 2 to 8 membered heteroalkyl, unsubstituted $C_3$-$C_8$ cycloalkyl, unsubstituted 3 to 7 membered heterocycloalkyl, unsubstituted $C_5$-$C_6$ aryl, or unsubstituted 5 to 6 membered heteroaryl.

39. The compound of claim 38, wherein ring A is $R^7$-substituted or unsubstituted $C_3$-$C_8$ cycloalkyl.

40. The compound of claim 39, wherein:
ring A is $R^7$-substituted or unsubstituted cyclopentyl or $R^7$-substituted or unsubstituted cyclohexyl; and
$R^7$ is —$NH_2$ or unsubstituted azetidinyl.

41. The compound of claim 38, wherein ring A is $R^7$-substituted or unsubstituted 3 to 7 membered heterocycloalkyl.

42. The compound of claim 41, wherein:
ring A is $R^7$-substituted or unsubstituted azetidinyl, $R^7$-substituted or unsubstituted pyrrolidinyl, unsubstituted piperazinyl, $R^7$-substituted or unsubstituted piperidinyl, unsubstituted morpholinyl, unsubstituted azepanyl, or unsubstituted oxoazepanyl; and
$R^7$ is unsubstituted methyl, unsubstituted ethyl, unsubstituted isopropyl, unsubstituted cyclopropyl, F, —$CF_3$, $N_3$, —$NH_2$, —NHC(O), —OH, —$CHF_2$, —$CH_2F$, —O—$CH_3$, —O—$CH_2CH_3$, —$CH_2CH_2CH_2OH$, —$CH_2OH$, unsubstituted azetidinyl, or unsubstituted oxetanyl.

43. A compound selected from:
3-((7-(5-chloro-2-(((2S,6S)-2,6-dimethylpiperazin-1-yl)methyl)-3-methylphenyl)thieno[3,2-b]pyridin-2-yl)methyl)-3-azabicyclo[3.1.0]hexane-2,4-dione having the structure:

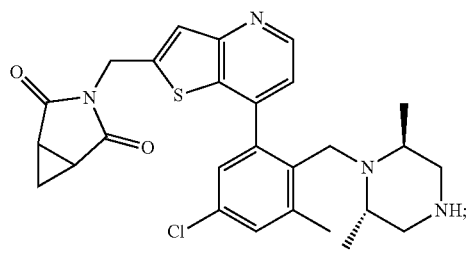 [SMILES: Cc1cc(Cl)cc(-c2ccnc3cc(CN4C(=O)C5CC5C4=O)sc23)c1CN1[C@@H](C)CNC[C@@H]1C]

3-((4-(5-chloro-2-(((2S,6S)-2,6-dimethylpiperazin-1-yl)methyl)-3-methylphenyl)thieno[3,2-d]pyrimidin-6-yl)methyl)-3-azabicyclo[3.1.0]hexane-2,4-dione having the structure:

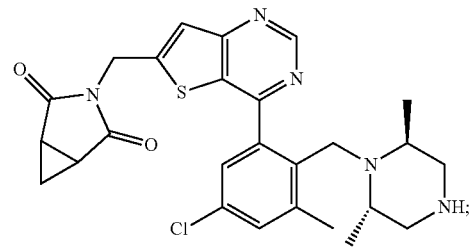 [SMILES: Cc1cc(Cl)cc(-c2ncnc3cc(CN4C(=O)C5CC5C4=O)sc23)c1CN1[C@@H](C)CNC[C@@H]1C]

3-((7-(5-chloro-3-methyl-2-(((R)-morpholin-2-yl)methyl)phenyl)thieno[3,2-b]pyridin-2-yl)methyl)-6,6-dimethyl-3-azabicyclo[3.1.0]hexane-2,4-dione having the structure:

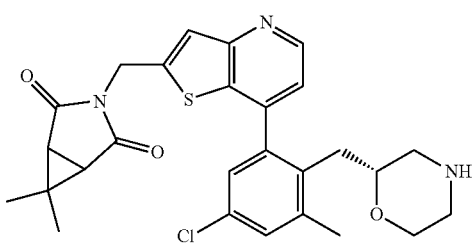

3-((4-(5-chloro-2-(((R)-6,6-dimethylmorpholin-2-yl)methyl)-3-methylphenyl)thieno[3,2-d]pyrimidin-6-yl)methyl)-3-azabicyclo[3.1.0]hexane-2,4-dione having the structure:

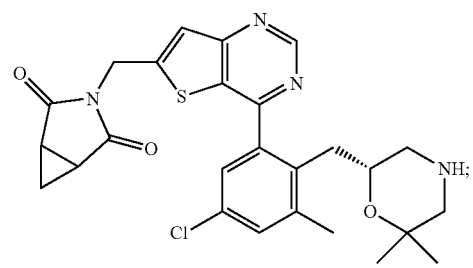 [SMILES: Cc1cc(Cl)cc(-c2ncnc3cc(CN4C(=O)C5CC5C4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)-1-methylpyrimidine-2,4(1H,3H)-dione having the structure:

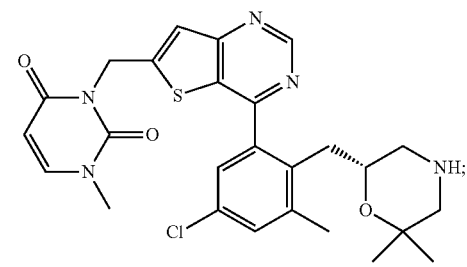 [SMILES: Cc1cc(Cl)cc(-c2ncnc3cc(Cn4c(=O)ccn(C)c4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)-1-(2,2,2-trifluoroethyl)dihydropyrimidine-2,4(1H,3H)-dione having the structure:

273

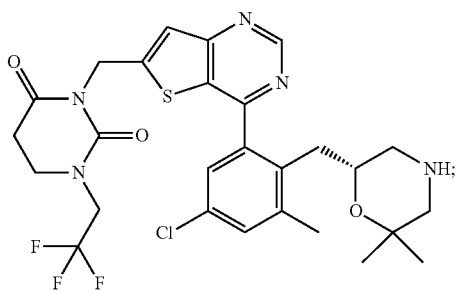 [SMILES: Cc1cc(Cl)cc(-c2ncnc3cc(CN4C(=O)CCN(CC(F)(F)F)C4=O)sc23)c1C[C@@H]1CNCC(C)(C)O1]

(R)-3-((4-(5-chloro-2-((6,6-dimethylmorpholin-2-yl)
methyl)-3-methylphenyl)thieno[3,2-d]pyrimidin-6-yl)
methyl)-1-(2,2-difluoroethyl)dihydropyrimidine-2,4
(1H,3H)-dione having the structure:

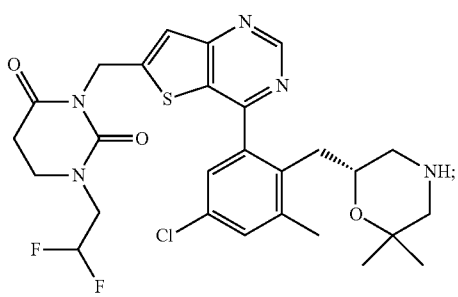 [SMILES: Cc1cc(Cl)cc(-c2ncnc3cc(CN4C(=O)CCN(CC(F)F)C4=O)sc23)c1C[C@@H]1CNCC(C)(C)O1]

3-((4-(3,5-dichloro-2-((6,6-dimethylmorpholin-2-yl)
methyl)phenyl)thieno[3,2-d]pyrimidin-6-yl)methyl)-1-
methylpyrimidine-2,4(1H,3H)-dione having the structure:

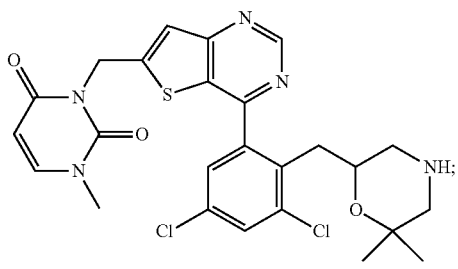 [SMILES: Cn1ccc(=O)n(Cc2cc3ncnc(-c4cc(Cl)cc(Cl)c4CC4CNCC(C)(C)O4)c3s2)c1=O]

3-[[4-[5-chloro-2-[[(2R)-6,6-dimethylmorpholin-2-yl]
methyl]-3-methyl-phenyl]thieno[3,2-d]pyrimidin-6-yl]
methyl]-1-(2-fluoroethyl)hexahydropyrimidine-2,4-di-
one having the structure:

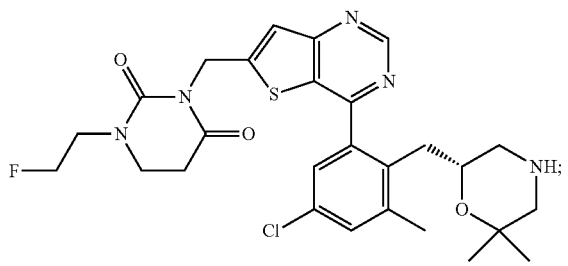 [SMILES: Cc1cc(Cl)cc(-c2ncnc3cc(CN4C(=O)CCN(CCF)C4=O)sc23)c1C[C@@H]1CNCC(C)(C)O1]

274

3-[[4-[5-chloro-2-[[(2S,6S)-2,6-dimethylpiperazin-1-yl]
methyl]-3-methyl-phenyl]thieno[3,2-d]pyrimidin-6-yl]
methyl]-1-(2-fluoroethyl)hexahydropyrimidine-2,4-di-
one having the structure:

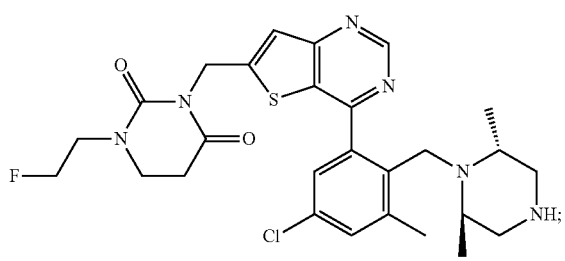 [SMILES: Cc1cc(Cl)cc(-c2ncnc3cc(CN4C(=O)CCN(CCF)C4=O)sc23)c1CN1[C@H](C)CNC[C@H]1C]

3-[[4-[5-chloro-2-[[(2S,6S)-2,6-dimethylpiperazin-1-yl]
methyl]-3-methyl-phenyl]thieno[3,2-d]pyrimidin-6-yl]
methyl]-1-(2,2-difluoroethyl)hexahydropyrimidine-2,
4-dione having structure:

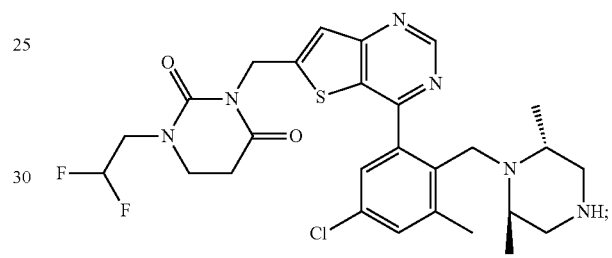

3-[[4-[5-chloro-2-[[(2S,6S)-2,6-dimethylpiperazin-1-yl]
methyl]-3-methyl-phenyl]thieno[3,2-d]pyrimidin-6-yl]
methyl]-1-(2,2,2-trifluoroethyl)hexahydropyrimidine-
2,4-dione having the structure:

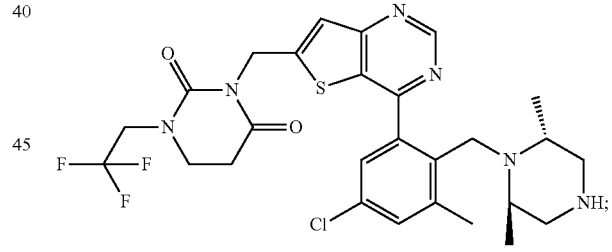

3-((7-(5-chloro-2-(((R)-6,6-dimethylmorpholin-2-yl)
methyl)-3-methylphenyl)thieno[3,2-b]pyridin-2-yl)
methyl)-3-azabicyclo[3.1.0]hexane-2,4-dione having
the structure:

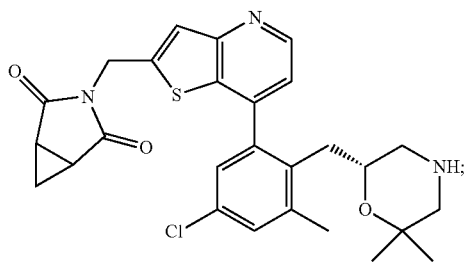 [SMILES: Cc1cc(Cl)cc(-c2ccnc3cc(CN4C(=O)C5CC5C4=O)sc23)c1C[C@@H]1CNCC(C)(C)O1]

(R)-1-((4-(5-chloro-2-((6,6-dimethylmorpholin-2-yl)methyl)-3-methylphenyl)thieno[3,2-d]pyrimidin-6-yl)methyl)pyrrolidine-2,5-dione having the structure:

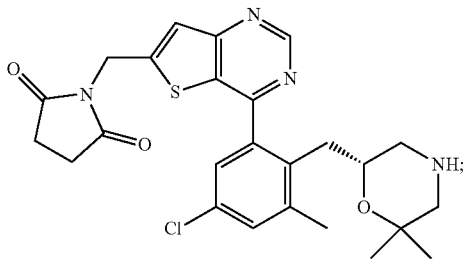 [SMILES: Cc1cc(Cl)cc(-c2ncnc3cc(CN4C(=O)CCC4=O)sc23)c1C[C@@H]1CNCC(C)(C)O1]

(R)-3-((4-(5-chloro-2-((6,6-dimethylmorpholin-2-yl)methyl)-3-methylphenyl)thieno[3,2-d]pyrimidin-6-yl)methyl)-1-methyldihydropyrimidine-2,4(1H,3H)-dione having the structure:

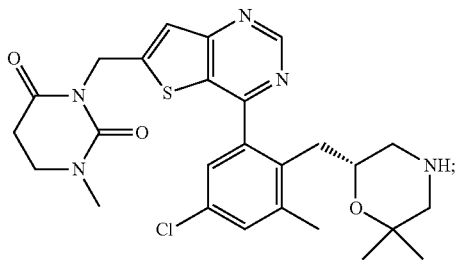 [SMILES: Cc1cc(Cl)cc(-c2ncnc3cc(CN4C(=O)CCN(C)C4=O)sc23)c1C[C@@H]1CNCC(C)(C)O1]

or a pharmaceutically acceptable salt thereof.

44. A pharmaceutical composition comprising a compound of claim 1, and a pharmaceutically acceptable excipient.

45. The pharmaceutical composition of claim 44 for use in treating cancer in a patient suffering from cancer, and wherein the cancer is a cancer modulated by ubiquitin specific protease 7 (USP7) inhibitors.

46. The pharmaceutical composition of claim 45 for use in treating solid cancer or blood cancer.

47. A method of treating cancer comprising administering to a subject suffering from cancer a therapeutically effective amount of the compound of claim 1.

48. The method of claim 47, further comprising administering to the subject an anti-cancer therapeutic agent.

49. The method of claim 47, wherein the cancer is solid cancer or blood cancer.

50. The method of claim 49, wherein the solid cancer is ovarian cancer, breast cancer, lung cancer, pancreatic cancer, kidney cancer, melanoma, liver cancer, colon cancer, sarcoma, brain cancer, or prostate cancer.

51. The method of claim 49, wherein the blood cancer is leukemia, lymphoma, or multiple myeloma.

52. The pharmaceutical composition of claim 44 for use in treating cancer in a patient suffering from cancer, and wherein the cancer is a cancer experiencing gene silencing via polycomb repressive complex 2 (PRC2).

53. A method of treating a patient suffering from a cancer experiencing gene silencing via polycomb repressive complex 2 (PRC2), comprising administering to the patient a therapeutically effective amount of a ubiquitin specific protease 7 (USP7) inhibitor, wherein the USP7 inhibitor is the compound of claim 1.

54. The method of claim 53, wherein the USP7 inhibitor is co-administered with at least one of a histone deacetylase (HDAC) inhibitor, a proteasome inhibitor, a BET inhibitor and/or a B-cell lymphoma 2 (Bcl-2) inhibitor.

55. The pharmaceutical composition of claim 46, wherein the cancer is breast cancer, lung cancer, pancreatic cancer, kidney cancer, melanoma, liver cancer, colon cancer, sarcoma, brain cancer, prostate cancer, leukemia, lymphoma, or multiple myeloma.

* * * * *